(12) United States Patent
Howard

(10) Patent No.: US 11,504,038 B2
(45) Date of Patent: Nov. 22, 2022

(54) EARLY DETECTION OF NEURODEGENERATIVE DISEASE

(71) Applicant: Newton Howard, Providence, RI (US)

(72) Inventor: Newton Howard, Providence, RI (US)

( * ) Notice: Subject to any disclaimer, the term of this patent is extended or adjusted under 35 U.S.C. 154(b) by 92 days.

(21) Appl. No.: 16/584,654

(22) Filed: Sep. 26, 2019

(65) Prior Publication Data

US 2020/0037942 A1 Feb. 6, 2020

Related U.S. Application Data

(63) Continuation-in-part of application No. 15/431,283, filed on Feb. 13, 2017, now abandoned.

(60) Provisional application No. 62/294,435, filed on Feb. 12, 2016, provisional application No. 62/831,575, filed on Apr. 9, 2019.

(51) Int. Cl.
*A61B 5/00* (2006.01)
*A61B 5/16* (2006.01)

(52) U.S. Cl.
CPC .............. *A61B 5/162* (2013.01); *A61B 5/165* (2013.01); *A61B 5/167* (2013.01)

(58) Field of Classification Search
CPC ... A61B 5/4076; A61B 5/4082; A61B 5/4088; A61B 5/4094; A61B 5/0476; A61B 4/048; A61B 5/0478; A61B 5/0482
See application file for complete search history.

(56) References Cited

U.S. PATENT DOCUMENTS

| | | | |
|---|---|---|---|
| 6,468,210 B1 | 10/2002 | Iliff | |
| 7,285,090 B2* | 10/2007 | Stivoric | A61B 5/4866 600/300 |
| 7,299,088 B1* | 11/2007 | Thakor | A61B 5/4094 600/544 |
| 7,539,533 B2* | 5/2009 | Tran | A61B 5/681 600/509 |
| 7,558,622 B2* | 7/2009 | Tran | A61B 5/1113 600/509 |
| 7,733,224 B2* | 6/2010 | Tran | A61B 7/04 340/540 |
| 7,756,575 B2 | 7/2010 | Park | |
| 7,959,567 B2* | 6/2011 | Stivoric | A61B 5/411 600/300 |

(Continued)

FOREIGN PATENT DOCUMENTS

| | | |
|---|---|---|
| WO | 2007062519 A1 | 6/2007 |
| WO | 2011127424 A1 | 10/2011 |

OTHER PUBLICATIONS

Uhlhaas, P. J. & Singer, W. 2010. Abnormal neural oscillations and synchrony in schizophrenia. Nat Rev Neurosci, 11, 100-13.

(Continued)

*Primary Examiner* — Shirley X Jian
(74) *Attorney, Agent, or Firm* — Michael A. Schwartz

(57) ABSTRACT

Embodiments of the present systems and methods may provide a non-invasive system to measure and integrate behavioral and cognitive features enabling early detection and progression tracking of degenerative disease. For example, a method of detecting neurodegenerative disease may comprise measuring functioning of at least one of the motor system, cognitive function, and brain activity of a subject during everyday life and analyzing the gathered at least one motor system data, cognitive function data, and brain activity data of the subject.

3 Claims, 56 Drawing Sheets

(56) References Cited

U.S. PATENT DOCUMENTS

| | | | |
|---|---|---|---|
| 8,036,736 B2* | 10/2011 | Snyder | A61B 5/0205 600/544 |
| 8,103,333 B2* | 1/2012 | Tran | A61B 5/01 600/509 |
| 8,108,036 B2* | 1/2012 | Tran | A61B 5/4806 600/509 |
| 8,157,731 B2* | 4/2012 | Teller | A61B 5/1118 |
| 8,323,188 B2* | 12/2012 | Tran | A61B 8/4472 600/300 |
| 8,323,189 B2* | 12/2012 | Tran | A61B 5/1112 600/300 |
| 8,449,471 B2* | 5/2013 | Tran | A61B 5/1117 600/485 |
| 8,461,988 B2* | 6/2013 | Tran | A61B 8/565 340/540 |
| 8,475,368 B2* | 7/2013 | Tran | A61B 5/14542 600/300 |
| 8,525,673 B2* | 9/2013 | Tran | A61B 5/389 340/540 |
| 8,525,687 B2* | 9/2013 | Tran | A61B 5/0008 340/669 |
| 8,531,291 B2* | 9/2013 | Tran | A61B 5/0008 340/540 |
| 8,543,199 B2* | 9/2013 | Snyder | A61B 5/01 600/544 |
| 8,641,612 B2* | 2/2014 | Teller | A61B 5/4866 600/300 |
| 8,652,038 B2* | 2/2014 | Tran | G16H 40/67 600/300 |
| 8,680,991 B2* | 3/2014 | Tran | G16H 80/00 340/540 |
| 8,684,900 B2* | 4/2014 | Tran | A61B 5/002 600/3 |
| 8,684,922 B2* | 4/2014 | Tran | A61B 5/6887 600/300 |
| 8,708,904 B2* | 4/2014 | Stivoric | A61B 5/01 600/301 |
| 8,747,336 B2* | 6/2014 | Tran | G16H 40/67 600/587 |
| 8,750,971 B2* | 6/2014 | Tran | A61B 5/1117 600/509 |
| 8,838,565 B2 | 9/2014 | Bradshaw | |
| 8,958,882 B1* | 2/2015 | Hagedorn | A61B 5/0006 607/45 |
| 9,028,405 B2* | 5/2015 | Tran | G06Q 30/0269 600/300 |
| 9,204,796 B2* | 12/2015 | Tran | G06F 19/00 |
| 9,399,144 B2 | 7/2016 | Howard | |
| 9,445,730 B2* | 9/2016 | Snyder | A61B 5/14552 |
| 9,613,188 B2 | 4/2017 | Bradshaw | |
| 9,622,675 B2* | 4/2017 | Leyde | A61B 5/0031 |
| 9,643,019 B2* | 5/2017 | Higgins | A61B 5/4094 |
| 9,652,996 B2 | 5/2017 | Chen | |
| 9,782,122 B1* | 10/2017 | Pulliam | A61B 5/1112 |
| 9,898,656 B2* | 2/2018 | Snyder | G06K 9/00496 |
| 10,176,299 B2 | 1/2019 | Torres | |
| 10,463,271 B2 | 11/2019 | Intrator | |
| 10,799,186 B2 | 10/2020 | Howard | |
| 2004/0133118 A1 | 7/2004 | Llinas | |
| 2005/0032219 A1 | 2/2005 | Aubourg | |
| 2005/0273890 A1 | 12/2005 | Flaherty | |
| 2006/0184485 A1 | 8/2006 | Horvitz | |
| 2007/0038307 A1 | 2/2007 | Webster | |
| 2007/0100251 A1 | 5/2007 | Prichep | |
| 2007/0100666 A1* | 5/2007 | Stivoric | A61B 5/6833 705/3 |
| 2007/0265533 A1* | 11/2007 | Tran | A61B 5/7264 600/481 |
| 2007/0276270 A1* | 11/2007 | Tran | A61B 5/002 600/508 |
| 2008/0007154 A1 | 1/2008 | Wei | |
| 2008/0234598 A1* | 9/2008 | Snyder | A61B 5/374 600/545 |
| 2008/0275309 A1* | 11/2008 | Stivoric | G16H 15/00 600/300 |
| 2008/0294019 A1* | 11/2008 | Tran | A61B 5/4875 600/301 |
| 2009/0024050 A1* | 1/2009 | Jung | G16H 40/67 600/544 |
| 2009/0048530 A1* | 2/2009 | Sarkela | A61B 5/374 600/544 |
| 2009/0182391 A1 | 7/2009 | Fowler | |
| 2009/0318779 A1* | 12/2009 | Tran | A61B 5/026 600/301 |
| 2010/0098113 A1 | 4/2010 | Nicholson | |
| 2010/0280403 A1 | 11/2010 | Erdogmus | |
| 2011/0150964 A1 | 6/2011 | Borck | |
| 2011/0201944 A1* | 8/2011 | Higgins | A61B 5/4094 600/483 |
| 2012/0235819 A1 | 9/2012 | Watkins | |
| 2012/0330109 A1* | 12/2012 | Tran | A61B 5/411 600/301 |
| 2013/0046358 A1 | 2/2013 | Leyde | |
| 2013/0138357 A1 | 5/2013 | Watson | |
| 2013/0231574 A1* | 9/2013 | Tran | A61B 5/11 600/479 |
| 2013/0237906 A1 | 9/2013 | Park | |
| 2013/0338526 A1 | 12/2013 | Howard | |
| 2014/0146211 A1 | 5/2014 | Mori | |
| 2014/0148872 A1 | 5/2014 | Goldwasser | |
| 2014/0249429 A1* | 9/2014 | Tran | A61B 5/1117 600/483 |
| 2014/0303508 A1 | 10/2014 | Plotnik-Peleg | |
| 2014/0336539 A1 | 11/2014 | Torres | |
| 2015/0359467 A1* | 12/2015 | Tran | A61B 5/1113 600/301 |
| 2016/0029946 A1 | 2/2016 | Simon | |
| 2016/0120432 A1 | 5/2016 | Sridhar | |
| 2016/0242699 A1 | 8/2016 | Das | |
| 2016/0253917 A1 | 9/2016 | Tinjust | |
| 2016/0262680 A1 | 9/2016 | Martucci | |
| 2017/0039045 A1* | 2/2017 | Abrahami | A61P 25/16 |
| 2017/0095193 A1 | 4/2017 | Shin | |
| 2017/0164852 A1 | 6/2017 | Jackson | |
| 2017/0164895 A1 | 6/2017 | Howard | |
| 2017/0251985 A1 | 9/2017 | Howard | |
| 2017/0258389 A1 | 9/2017 | Howard | |
| 2017/0258390 A1 | 9/2017 | Howard | |
| 2018/0093092 A1 | 4/2018 | Howard | |
| 2018/0168459 A1* | 6/2018 | Tran | H04B 1/3827 |
| 2018/0184964 A1* | 7/2018 | Simon | A61B 5/002 |
| 2018/0260486 A1 | 9/2018 | Howard | |
| 2018/0333587 A1 | 11/2018 | Howard | |
| 2018/0338715 A1 | 11/2018 | Howard | |
| 2019/0333629 A1 | 10/2019 | Torres | |
| 2020/0037942 A1 | 2/2020 | Howard | |
| 2020/0060566 A1 | 2/2020 | Howard | |

OTHER PUBLICATIONS

Uswatte, G., Taub, E., Morris, D., Vignolo, M. & Mcculloch, K. 2005. Reliability and Validity of the Upper-Extremity Motor Activity Log-14 for Measuring Real-World Arm Use. Stroke, 36, 2493-2496.

Vacha, L. & Barunik, J. 2012. Co-movement of energy commodities revisited: Evidence from wavelet coherence analysis Energy Economics, 34, 241-247.

Valderrama-Gama, E., Damian, J., Pérez Del Molino, J., López, M. R., Pérez, M. L. & Iglesias, F. 2000. Association of individual activities of daily living with self-rated health in older people. Age and Ageing, 29, 267-270.

Van Lancker Sidtis, D., Rogers, T., Godier, V., Tagliati, M. & Sidtis, J. J. 2010. Voice and fluency changes as a function of speech task and deep brain stimulation. J Speech Lang Hear Res, 53, 1167-77.

Vanello, N., Guidi, A., Gentili, C., Werner, S., Bertschy, G., Valenza, G., Lanata, A. & Scilingo, E. P. Speech analysis for mood state characterization in bipolar patients. Engineering in Medicine and Biology Society (EMBC), 2012 Annual International Conference of the IEEE, 2012. IEEE, 2104-2107.

(56) References Cited

OTHER PUBLICATIONS

Vazey, E. M. & Aston-Jones, G. 2012. The emerging role of norepinephrine in cognitive dysfunctions of Parkinson's disease. Front Behav Neurosci, 6, 48.
Veltink, P. H., Bussmann, H. B., De Vries, W., Martens, W. L. & Van Lummel, R. C. 1996. Detection of static and dynamic activities using uniaxial accelerometers. Rehabilitation Engineering, IEEE Transactions on, 4, 375-385.
Veltink, P. H. & De Rossi, D. 2010. Wearable technology for biomechanics: e-textile or micromechanical sensors? [Conversations in BME]. Engineering in Medicine and Biology Magazine, IEEE, 29, 37-43.
Verloigne, M., Van Lippevelde, W., Maes, L., Yildirim, M., Chinapaw, M., Manios, Y., Androutsos, O., Kovács, É., Bringolf-Isler, B. & Brug, J. 2012. Levels of physical activity and sedentary time among 10-to 12-year-old boys and girls across 5 European countries using accelerometers: an observational study within the ENERGY-project. Int J Behav Mutr Phys Act, 9, 34.
Walsh, K. & Bennett, G. 2001. Parkinson's disease and anxiety. Postgraduate medical journal, 77, 89-93.
Wang, H.-C., Lees, A. J. & Brown, p. 1999. Impairment of EEG desynchronisation before and during movement and its relation to bradykinesia in Parkinson's disease. Journal of Neurology, Neurosurgery & Psychiatry, 66, 442-446.
Wang, Y. 2007. The OAR model of neural informatics for internal knowledge representation in the brain. International Journal of Cognitive Informatics and Natural Intelligence (IJCINI), 1, 66-77.
Wang, Y., Gao, S. & Gao, X. Common spatial pattern method for channel selection in motor imagery based brain-computer interface. Engineering in Medicine and Biology Society, 2005. IEEE-EMBS 2005. 27th Annual International Conference of the, 2006. IEEE, 5392-5395.
Ward, L. M. 2003. Synchronous neural oscillations and cognitive processes. Trends in cognitive sciences, 7, 553-559.
Weinberger, M., Mahant, N., Hutchison, W. D., Lozano, A. M., Moro, E., Hodaie, M., Lang, A. E. & Dostrovsky, J. O. 2006. Beta oscillatory activity in the subthalamic nucleus and its relation to dopaminergic response in Parkinson's disease. Journal of neurophysiology, 96, 3248-3256.
Welch, P. D. 1967. The use of fast Fourier transform for the estimation of power spectra: A method based on time averaging over short, modified periodograms. Audio and Electroacoustics, IEEE Transactions on, 15, 70-73.
Who 2007. Neurological Disorders affect millions globally: WHO report. World Health Organization.
Williams, Jr, G. R., Rockwood, Jr, C. A., Bigliani, L. U., Iannotti, J. P. & Stanwood, W. 2004. Rotator Cuff Tears: Why Do We Repair Them?*. The Journal of Bone & Joint Surgery, 86, 2764-2776.
Winter, D. A. 2009. Biomechanics and motor control of human movement, Wiley.com.
Winter, W. R., Nunez, P. L., Ding, J. & Srinivasan, R. 2007. Comparison of the effect of volume conduction on EEG coherence with the effect of field spread on MEG coherence Statistics in medicine, 26, 3946-3957.
Woollacott, M. & Shumway-Cook, A. 2002. Attention and the control of posture and gait: a review of an emerging area of research Gait & posture, 16, 1-14.
Wu, G., Van Der Helm, F. C., Veeger, H., Makhsous, M., Van Roy, P., Anglin, C., Nagels, J., Karduna, A. R., Mcquade, K. & Wang, X. 2005. ISB recommendation on definitions of joint coordinate systems of various joints for the reporting of human joint motion—Part II: shoulder, elbow, wrist and hand. Journal of biomechanics, 38, 981-992.
Wu, T. & Hallett, M. 2005. A functional MRI study of automatic movements in patients with Parkinson's disease. Brain, 128, 2250-2259.
Yang, C.-C. & Hsu, Y.-L. 2010. A review of accelerometry-based wearable motion detectors for physical activity monitoring. Sensors, 10, 7772-7788.

Yekhlef, F., Ballan, G., Macia, F., Delmer, O., Sourgen, C. & Tison, F. 2003. Routine MRI for the differential diagnosis of Parkinson's disease, MSA, PSP, and CBD. Journal of neural transmission, 110, 151-169.
Yener, G. G. & Basar, E. 2013. Brain oscillations as biomarkers in neuropsychiatric disorders: following an interactive panel discussion and synopsis. Suppl Clin Neurophysiol, 62, 343-63.
Zajicek, M. 2006. Aspects of HCI research for older people. Universal Access in the Information Society, 5, 279-286.
Zhang, Z. G., Hu, L., Hung, Y. S., Mouraux, A. & Iannetti, G. D. 2012. Gamma-band oscillations in the primary somatosensory cortex—a direct and obligatory correlate of subjective pain intensity. The Journal of Neuroscience, 32, 7429-7438.
Zhao, Y. J., Wee, H. L., Chan, Y. H., Seah, S. H., Au, W. L., Lau, P. N., Pica, E. C., Li, S. C., Luo, N. & Tan, L. 2010. Progression of Parkinson's disease as evaluated by Hoehn and Yahr stage transition times. Movement Disorders, 25, 710-716.
Zhou, H. & Hu, H. 2008. Human motion tracking for rehabilitation—A survey. Biomedical Signal Processing and Control, 3, 1-18.
Zhou, H., Stone, T., Hu, H. & Harris, N. 2008. Use of multiple wearable inertial sensors in upper limb motion tracking. Medical Engineering & Physics, 30, 123-133.
Zijlstra, W. & Hof, A. L. 2003. Assessment of spatio-temporal gait parameters from trunk accelerations during human walking. Gait & posture, 18, 1-10.
Zoia, S., Pezzetta, E., Blason, L., Scabar, A., Carrozzi, M., Bulgheroni, M. & Castiello, U. 2006. A comparison of the reach-to-grasp movement between children and adults: a kinematic study. Developmental neuropsychology, 30, 719-738.
Abbott, R. D., Petrovitch, H., White, L. R., Masaki, K. H., Tanner, C. M., Curb, J. D., Grandinetti, A., Blanchette, P. L., Popper, J. S. & Ross, G. W. 2001. Frequency of bowel movements and the future risk of Parkinson's disease. Neurology, 57, 456-62.
Ashby, F. G. & Isen, A. M. 1999. A neuropsychological theory of positive affect and its influence on cognition. Psychological review, 106, 529.
Barra, J., Bray, A., Sahni, V., Golding, J. & Gresty, M. 2006. Increasing cognitive load with increasing balance challenge: recipe for catastrophe. Experimental Brain Research, 174, 734-745.
Bellizzi, J., Crowley, A. & Hasty, R. 1983. The Effects of Color in Store Design. Journal of Retailing, 59, 21-47.
Bergmann, J., Goodier, H., Anastasova, S., Spulber, L, Georgiou, P. & Mcgregor, A. 2012. An integrated clothing sensing system for measuring Knee Joint Angles. Bioengineering Conference. Oxford, UK.
Caballol, N., Marti, M. J. & Tolosa, E. 2007. Cognitive dysfunction and dementia in Parkinson disease. Movement Disorders, 22, S358-S366.
Caraceni, T. & Musicco, M. 2001. Levodopa or dopamine agonists, or deprenyl as initial treatment for Parkinson's disease. A randomized multicenter study. Parkinsonism Relat Disord, 7, 107-114.
Drachman, D. A. 2005. Do we have brain to spare? Neurology, 64, 2004-2005.
Foster, H. D. & Hoffer, A. 2004. The two faces of L-DOPA: benefits and adverse side effects in the treatment of Encephalitis lethargica, Parkinson's disease, multiple sclerosis and amyotrophic lateral sclerosis. Medical Hypotheses, 62, 177-181.
Levine, C. B., Fahrbach, K. R., Siderowf, A. D., Estok, R. P., Ludensky, V. M. & Ross, S. D. 2003. Diagnosis and Treatment of Parkinson's Disease: A Systematic Review of the Literature: Summary.
Lewitt, P. A. 2008. Levodopa for the treatment of Parkinson's disease. New England Journal of Medicine, 359, 2468-2476.
Maasen, S. & Weingart, p. 1995. Metaphors: Messengers of meaning. Science Communication, 17.
Olanow, C. W., Hauser, R. A., Jankovic, J., Langston, W., Lang, A., Poewe, W., Tolosa, E., Stocchi, F., Melamed, E. & Eyal, E. 2008. A randomized, double-blind, placebo-controlled, delayed start study to assess rasagiline as a disease modifying therapy in Parkinson's disease (the ADAGIO study): Rationale, design, and baseline characteristics. Movement Disorders, 23, 2194-2201.

(56) References Cited

OTHER PUBLICATIONS

Roetenberg, D. 2005. 3D Motion Analysis Applying Inertial Sensing. Measuring Behavior 2005. Wageningen, The Netherlands: Noldus Information Technology.

Smith, S. W. 1998. The Scientist and Engineer's Guide to Digital Signal Processing. California Technical Publishing.

Horak, F., Nutt, J. & Nashner, L. 1992. Postural inflexibility in parkinsonian subjects. Journal of the neurological sciences, 111, 46-58.

Howard, N. Mar. 2012. Brain Language: The Fundamental Code Unit. The Brain Sciences Journal, 1, 6-34.

Howard, N. Mar. 2012. Energy Paradox of the Brain The Brain Sciences Journal, 1, 35-44.

Howard, N. 2013. Approach Towards a Natural Language Analysis for Diagnosing Mood Disorders and Comorbid Conditions. Lecture Notes in Computer Science, MICAI 2013.

Howard, N. 2013. The Twin Hypotheses: Brain Code and the Fundamental Code Unit: Towards Understanding the Computational Primitive Elements of Cortical Computing. Springer Lecture Notes in Artificial Intelligence, MICAI 2013.

Howard, N. & Bergmann, J. 2012. Combining Computational Neuroscience and Body Sensor Networks to Investigate Alzheimer's Disease. . Journal of Functional Neurology, Rehabilitation and Ergonomics, 2, 29-38.

Howard, N., Bergmann, J. & Howard, R. 2013. Exploring the Relationship Between Everyday Speech and Motor Symptoms of Parkinson's Disease as Prerequisite Analysis for Tool Development. Lecture Notes in Computer Science, MICAI 2013.

Howard, N. & Guidere, M. 2011. Computational Methods for Clinical Applications: An Introduction. Functional Neurology, Rehabilitation, and Ergonomics. vol. 1, 237-250.

Howard, N. & Guidere, M. 2012. LXIO: The Mood Detection Robopsych. The Brain Sciences Journal, 1, 98-109.

Howard, N., Pollock, R., Prinold, J., Sinha, J., Newham, D. & Bergmann, J. 2013. Effect of Impairment on Upper Limb Performance in an Ageing Sample Population. In: Stephanidis, C. & Antona, M. (eds.) Universal Access in Human-Computer Interaction. User and Context Diversity. Springer Berlin Heidelberg.

Hsu, J. 2009. How Much Power Does the Human Brain Require to Operate. Popular Science, November.

Hu, M., Cooper, J., Beamish, R., Jones, E., Butterworth, R., Catterall, L. & Ben-Shlomo, Y. 2011. How well do we recognise non-motor symptoms in a British Parkinson's disease population? J Neurol, 258, 1513-7.

Hubbard, M. 2009. Safer Ski Jump Landing Surface Design Limits Normal Impact Velocity. Journal of ASTM International, 6.

Hughes, A. J., Daniel, S. E., Kilford, L. & Lees, A. J. 1992. Accuracy of clinical diagnosis of idiopathic Parkinson's disease: a clinico-pathological study of 100 cases Journal of Neurology, Neurosurgery & Psychiatry, 55,181-184.

Huxhold, O., Li, S.-C., Schmiedek, F. & Lindenberger, U. 2006. Dual-tasking postural control: aging and the effects of cognitive demand in conjunction with focus of attention. Brain research bulletin, 69, 294-305.

Iannetti, G. D. & Mouraux, A. 2010. From the neuromatrix to the pain matrix (and back). Experimental Brain Research, 205, 1-12.

Iannetti, G. D., Zambreanu, L., Cruccu, G. & Tracey, I. 2005. Operculoinsular cortex encodes pain intensity at the earliest stages of cortical processing as indicated by amplitude of laser-evoked potentials in humans. Neuroscience, 131, 199-208.

I Sturkenboom IHWM, et al. 2008. Guidelines for Occupational Therapy in Parkinson's Disease Rehabilitation. In Parkinson Centre Nijmegen, T. N. M. F., U.S.A.: (ed.) ParkinsonNet/ National Parkinson Foundation (NPF).

Illes, J., Metter, E. J., Hanson, W. R. & Iritani, S. 1988. Language production in Parkinson's disease: Acoustic and inguistic considerations Brain and Language, 33, 146-160.

Ioannides, A. A. 2006. Magnetoencephalography as a research tool in neuroscience: state of the art. The Neuroscientist, 12, 524-544.

Ioannides, A. A. 2007. Dynamic functional connectivity. Current opinion in neurobiology, 17, 161-170.

Ioannides, A. A., Dimitriadis, S. I., Saridis, G. A., Voultsidou, M., Poghosyan, V., Liu, L. & Laskaris, N. A. 2012. Source Space Analysis of Event-Related Dynamic Reorganization of Brain Networks. Computational and Mathematical Methods in Medicine, 2012, 15.

Isenberg, C. & Conrad, B. 1994. Kinematic properties of slow arm movements in Parkinson's disease. J Neurol, 241, 323-330.

Jacobs, D. H., Shuren, J., Bowers, D. & Heilman, K. M. 1995. Emotional facial imagery, perception, and expression in Parkinson's disease Neurology, 45, 1696-1702.

Jankovic, J. 2008. Parkinson's disease: clinical features and diagnosis. Journal of Neurology, Neurosurgery & Psychiatry, 79, 368-376.

Jankovic, J. & Aguilar, L. G. 2008. Current approaches to the treatment of Parkinson's disease. Neuropsychiatric disease and treatment, 4, 743.

Jette, A. M. & Branch, L. G. 1981. The Framingham Disability Study II: Physical disability among the aging. American Journal of Public Health, 71, 1211-1216.

Karduna, A., Mcclure, P., Michener, L. & Sennett, B. 2001a. Dynamic measurements of three-dimensional scapular kinematics: a validation study. Journal of biomechanical engineering, 123, 184-190.

Katsikitis, M. & Pilowsky, I. 1988. A study of facial expression in Parkinson's disease using a novel microcomputer-based method. Journal of Neurology, Neurosurgery & Psychiatry, 51, 362-366.

Kee, D. W., Bathurst, K. & Hellige, J. B. 1983. Lateralized interference of repetitive finger tapping: influence of familial handedness, cognitive load and verbal production. Neuropsychologia, 21, 617-24.

Kelly, V. E., Eusterbrock, A. J. & Shumway-Cook, A. 2012. A review of dual-task walking deficits in people with Parkinson's disease: motor and cognitive contributions, mechanisms, and clinical implications. Parkinsons Dis, 2012, 918719.

Keltner, D., Ekman, P., Gonzaga, G. C. & Beer, J. 2003. Facial expression of emotion. In M.Lewis and J Haviland-Jones ( eds) Handbook of emotions, 2nd edition. New York: Guilford Publications, Inc .

Kety, S. S. 1957. The general metabolism of the brain in vivo. Metabolism of the nervous system, 221-237.

Kircher, T., Leube, D., Erb, M., Grodd, W. & Rapp, A. 2007. Neural correlates of metaphor processing in schizophrenia. Neuroimage, 34, 281-290.

Kish, S. J., Shannak, K. S., Rajput, A. H., Gilbert, J. J. & Hornykiewicz, O. 1984. Cerebellar norepinephrine in patients with Parkinson's disease and control subjects. Archives of neurology, 41, 612.

Klassen, B. T., Hentz, J. G., Shill, H. A., Driver-Dunckley, E., Evidente, V. G. H., Sabbagh, M. N., Adler, C. H. & Caviness, J. N. 2011. Quantitative EEG as a predictive biomarker for Parkinson disease dementia. Neurology, 77, 118-124.

Klein, C., Schneider, S. A. & Lang, A. E. 2009. Hereditary Parkinsonism: Parkinson disease look-alikes—An algorithm for clinicians to "PARK" genes and beyond Movement Disorders, 24, 2042-2058.

Koenig, T., Prichep, L., Dierks, T., Hubl, D., Wahlund, L. O., John, E. R. & Jelic, V. 2005. Decreased EEG synchronization in Alzheimer's disease and mild cognitive impairment. Neurobiology of aging, 26, 165-171.

Konczak, J., Corcos, D. M., Horak, F., Poizner, H., Shapiro, M., Tuite, P., Volkmann, J. & Maschke, M. 2009. Proprioception and motor control in Parkinson's disease. Journal of motor behavior, 41, 543-552.

Krohn, A., Beigl, M., Decker, C., Kochendörfer, U., Robinson, P. & Zimmer, T. 2005. Inexpensive and automatic calibration for acceleration sensors. Ubiquitous computing systems Springer.

Kronland-Martinet, R., Morlet, J. & Grossmann, A. 1987. Analysis of sound patterns through wavelet transforms. International Journal of Pattern Recognition and Artificial Intelligence, 1, 273-302.

Kulkarni, S. S., Reddy, N. P. & Hariharan, S. I. 2009. Facial expression (mood) recognition from facial images using committee neural networks. Biomedical engineering online, 10, 16.

(56) References Cited

OTHER PUBLICATIONS

Lachaux, J.-P., Lutz, A., Rudrauf, D., Cosmelli, D., Le Van Quyen, M., Martinerie, J. & Varela, F. 2002. Estimating the time-course of coherence between single-trial brain signals: an introduction to wavelet coherence. Neurophysiologie Clinique/Clinical Neurophysiology, 32, 157-174.

Lakoff, G. & Johnson, M. 1980. Metaphors we live by Chicago. Chicago University.

Lalkhen, A. G. & Mccluskey, A. 2008. Clinical tests: sensitivity and specificity. Continuing Education in Anaesthesia, Critical Care & Pain, 8, 221-223.

Larson, D. R. 2007. Unitary systems, wavelet sets, and operator-theoretic interpolation of wavelets and frames. In GOH, S. S., Ron, A. & Shen, Z. (eds.) Gabor and wavelet frames. Singapore: World Scientific Publishing.

Laughlin, S. B. & Sejnowski, T. J. 2003. Communication in Neuronal Networks. Science, 301, 1870-1874.

Leardini, A., Chiari, L., Croce, U. D. & Cappozzo, A. 2005. Human movement analysis using stereophotogrammetry. Part 3. Soft tissue artifact assessment and compensation. Gait & Posture, 21, 212-225.

Lee, C. M., Narayanan, S. S. & Pieraccini, R. 1999. Combining acoustic and language information for emotion recognition. Neural Computation, 11, 1155-1182.

Lee, J. M., Koh, S. B., Chae, S. W. Seo, W. K. Kwon Do, Y., Kim, J. H. Oh, K. Baik, J. S. & Park, K. W. 2012. Postural instability and cognitive dysfunction in early Parkinson's disease. Can J Neurol Sci, 39, 473-82.

Neuman, Y., Cohen, Y., Assaf, D. & Kedma, G. 2012. Proactive screening for depression through metaphorical and automatic text analysis. Artificial Intelligence in Medicine.

Niazmand, K., Tonn, K., Zhao, Y., Fietzek, U., Schroeteler, F., Ziegler, K., Ceballos-Baumann, A. & Lueth, T. Freezing of Gait detection in Parkinson's disease using accelerometer based smart clothes. Biomedical Circuits and Systems Conference (BioCAS), 2011 IEEE, 2011. IEEE, 201-204.

Niedermeyer, E. 1997. Alpha rhythms as physiological and abnormal phenomena. International Journal of Psychophysiology, 26, 31-49.

NIMH 2013. The Numbers Count: Mental Disorders in America. National Institute of Mental Health.

Nocera, J. & Hass, C. 2012. Should gait speed be included in the clinical evaluation of Parkinson's disease? Advances in Parkinson's Disease vol. 1, No. 1, 1-4 (2012).

Nocera, J. R., Buckley, T., Waddell, D., Okun, M. S. & Hass, C. J. 2010. Knee Extensor Strength, Dynamic Stability, and Functional Ambulation: Are They Related in Parkinson's Disease? Archives of physical medicine and rehabilitation, 91, 589-595.

O'Shea, S., Morris, M. E. & Iansek, R. 2002. Dual task interference during gait in people with Parkinson disease affects of motor versus cognitive secondary tasks. Physical Therapy, 82, 888-897.

O'Donovan, K. J., Kamnik, R., O'Keeffe, D. T. & Lyons, G. M. 2007. An inertial and magnetic sensor based technique for joint angle measurement. Journal of biomechanics, 40, 2604-2611.

O'Sullivan, M., Blake, C., Cunningham, C., Boyle, G. & Finucane, C. 2009. Correlation of accelerometry with clinical balance tests in older fallers and non-fallers. Age and ageing, 38, 308-313.

Ohgi, S., Morita, S., Loo, K. K. & Mizuike, C. 2008. Time series analysis of spontaneous upper-extremity movements of premature infants with brain injuries. Phys Ther, 88, 1022-1033.

Olanow, C. W., Rascol, O., Hauser, R., Feigin, P. D., Jankovic, J., Lang, A., Langston, W., Melamed, E., Poewe, W., Stocchi, F. & Tolosa, E. 2009. A Double-Blind, Delayed-Start Trial of Rasagiline in Parkinson's Disease. New England Journal of Medicine, 361, 1268-1278.

Ooi, K. E. B., Lech, M. & Allen, N. B. 2013a. Multichannel Weighted Speech Classification System for Prediction of Major Depression in Adolescents. Biomedical Engineering, IEEE Transactions on, 60, 497-506.

Pagan, F. L. 2012. Improving outcomes through early diagnosis of Parkinson's disease. The American journal of managed care, 18, S176-82.

Pahwa, R. & Lyons, K. E. 2010. Early diagnosis of Parkinson's disease: recommendations from diagnostic clinical guidelines. Am J Manag Care, 16 Suppl Implications, S94-9.

Pantic, M. & Rothkrantz, L. J. M. 2000. Automatic analysis of facial expressions: the state of the art. Pattern Analysis and Machine Intelligence, IEEE Transactions on, 22, 1424-1445.

Park, D. C., Polk, T. A., Mikels, J. A., Taylor, S. F. & Marshuetz, C. 2001. Cerebral aging: integration of brain and behavioral models of cognitive function. Dialogues in clinical neuroscience, 3, 151.

Pascual-Leone, A., Freitas, C., Oberman, L., Horvath, J. C., Halko, M., Eldaief, M., Bashir, S., Vernet, M., Shafi, M. & Westover, B. 2011. Characterizing brain cortical plasticity and network dynamics across the age-span in health and disease with TMS-EEG and TMS-fMRI. Brain topography, 24, 302-315.

Paulis, W. D., Horemans, H. L. D., Brouwer, B. S. & Stam, H. J. 2011. Excellent test-retest and inter-rater reliability for Tardieu Scale measurements with inertial sensors in elbow flexors of stroke patients. Gait & posture, 33, 185-189.

Paulsen, J. S., Nance, M., Kim, J.-I., Carlozzi, N. E., Panegyres, P. K., Erwin, C., Goh, A., Mccusker, E. & Williams, J. K. 2013. A Review of Quality of Life after Predictive Testing for and Earlier Identification of Neurodegenerative Diseases. Progress in Neurobiology.

Parkinson's Disease Foundation 2013. Statistics on Parkinson's Disease. Parkinson's Disease Foundation. http://www.pdf.org/en/parkinson_statistics.

Peelle, J. E. & Davis, M. H. 2012. Neural Oscillations Carry Speech Rhythm through to Comprehension. Front Psychol 3, 320.

Péron, J., Dondaine, T., Le Jeune, F., Grandjean, D. & Vérin, M. 2012. Emotional processing in Parkinson's disease: a systematic review. Movement Disorders, 27, 186-199.

Pezard, L., Jech, R. & Ruzicka, E. 2001. Investigation of non-linear properties of multichannel EEG in the early stages of Parkinson's disease Clinical neurophysiology, 112, 38-45.

Plotnik, M., Flash, T., Inzelberg, R., Schechtman, E. & Korczyn, A. D. 1998. Motor switching abilities in Parkinson's Disease and old age: temporal aspects. Journal of Neurology, Neurosurgery & Psychiatry, 65, 328-337.

Polzin, T. S. & Waibel, A. Detecting emotions in speech. Proceedings of the CMC, 1998. Citeseer.

Portney, L. & Watkins, M. 2000. Validity of measurements. Foundations of clinical research: Applications to practice, 69-86.

Prinold, J. A., Shaheen, A. F. & Bull, A. M. 2011. Skin-fixed scapula trackers: A comparison of two dynamic methods across a range of calibration positions Journal of biomechanics, 44, 2004-2007.

Rahn Iii, D. A., Chou, M., Jiang, J. J. & Zhang, Y. 2007. Phonatory impairment in Parkinson's disease: evidence from nonlinear dynamic analysis and perturbation analysis Journal of Voice, 21, 64-71.

Ramaker, C., Marinus, J., Stiggelbout, A. M. & Van Hilten, B. J. 2002. Systematic evaluation of rating scales for impairment and disability in Parkinson's disease Movement Disorders, 17, 867-876.

Rapcan, V., D'arcy, S., Penard, N., Robertson, I. H. & Reilly, R. B. The use of telephone speech recordings for assessment and monitoring of cognitive function in elderly people. Interspeech, 2009. 943-946.

Rascol, O., Brooks, D. J., Korczyn, A. D., De Deyn, P. P., Clarke, C. E. & Lang, A. E. 2000. A five-year study of the incidence of dyskinesia in patients with early Parkinson's disease who were treated with ropinirole or levodopa. New England Journal of Medicine, 342, 1484-1491.

Ravina, B., Eidelberg, D., Ahlskog, J. E., Albin, R. L., Brooks, D. J., Carbon, M., Dhawan, V., Feigin, A., Fahn, S. & Guttman, M. 2005. The role of radiotracer imaging in Parkinson disease Neurology, 64, 208-215.

Ray, N. J., Jenkinson, N., Brittain, J., Holland, P., Joint, C., Nandi, D., Bain, P. G., Yousif, N., Green, A., Stein, J. S. & Aziz, T. Z. 2009. The role of the subthalamic nucleus in response inhibition: evidence from deep brain stimulation for Parkinson's disease. Neuropsychologia, 47, 2828-2834.

(56) References Cited

OTHER PUBLICATIONS

Resch, J. E., May, B., Tomporowski, P. D. & Ferrara, M. S. 2011. Balance performance with a cognitive task: a continuation of the dual-task testing paradigm. Journal of athletic training, 46,170.
Richards, J. G. 1999. The measurement of human motion: A comparison of commercially available systems. Human Movement Science, 18, 589-602.
Riedel, O., Klotsche, J., Spottke, A., Deuschi, G., Forstl, H., Henn, F., Heuser, L, Oertel, W., Reichmann, H. & Riederer, P. 2008. Cognitive impairment in 873 patients with idiopathic Parkinson's disease. Journal of neurology, 255, 255-264.
Riley, D., Lang, A. E., Blair, R. D., Birnbaum, A. & Reid, B. 1989. Frozen shoulder and other shoulder disturbances in Parkinson's disease. Journal of Neurology, Neurosurgery & Psychiatry, 52, 63-66.
Rissanen, S., Kankaanpaa, M., Tarvainen, M. P., Nuutinen, J., Tarkka, I. M., Airaksinen, O. & Karjalainen, P. A. 2007. Analysis of surface EMG signal morphology in Parkinson's disease Physiological measurement, 28, 1507.
Roberts, B. W. & Delvecchio, W. F. 2000. The rank-order consistency of personality traits from childhood to old age: a quantitative review of longitudinal studies. Psychol Bull, 126, 3-25.
Roberts, J. E. & Kassel, J. D. 1996. Mood-state dependence in cognitive vulnerability to depression: The roles of positive and negative affect Cognitive Therapy and Research, 20, 1-12.
Roberts, S. & Roberts, p. 1996. Tournament water skiing trauma. British journal of sports medicine, 30, 90-93.
Rochester, L., Hetherington, V., Jones, D., Nieuwboer, A., Willems, A.-M., Kwakkel, G. & Van Wegen, E. 2004. Attending to the task: interference effects of functional tasks on walking in Parkinson's disease and the roles of cognition, depression, fatigue, and balance. Archives of physical medicine and rehabilitation, 85, 1578-1585.
Rochford, I., Rapcan, V., D'arcy, S. & Reilly, R. B. Dynamic minimum pause threshold estimation for speech analysis in studies of cognitive function in ageing. Engineering in Medicine and Biology Society (EMBC), 2012 Annual International Conference of the IEEE, 2012. IEEE, 3700-3703.
Roetenberg, D., Luinge, H. & Veltink, P. Inertial and magnetic sensing of human movement near ferromagnetic materials. Mixed and Augmented Reality, 2003. Proceedings. The Second IEEE and ACM International Symposium on, 2003. IEEE, 268-269.
Rolfe, D. F. & Brown, G. C. 1997. Cellular energy utilization and molecular origin of standard metabolic rate in mammals. Physiological reviews, 77, 731-758.
Rom, D. M. 1990. A sequentially rejective test procedure based on a modified Bonferroni inequality. Biometrika, 77, 363-665.
Rosin, R., Topka, H. & Dichgans, J. 1997. Gait initiation in Parkinson's disease. Movement disorders, 12, 682-690.
Sande De Souza, L. A., Dionisio, V. C. & Almeida, G. L. 2011. Multi-joint movements with reversal in Parkinson's disease: Kinematics and electromyography. Journal of Electromyography and Kinesiology, 21, 376-383.
Sankari, Z., Adeli, H. & Adeli, A. 2012. Wavelet coherence model for diagnosis of Alzheimer disease. Clinical EEG and Neuroscience, 43, 268-278.
Samthein, J., Stern, J., Aufenberg, C., Rousson, V. & Jeanmonod, D. 2006. Increased EEG power and slowed dominant frequency in patients with neurogenic pain. Brain, 129, 55-64.
Bower, J. H., Grossardt, B. R., Maraganore, D. M., Ahlskog, J. E., Colligan, R. C., Geda, Y. E., Themeau, T. M. & Rocca, W. A. 2010. Anxious personality predicts an increased risk of Parkinson's disease. Movement disorders, 25, 2105-2113.
Bowers, D., Miller, K., Bosch, W., Gokcay, D., Pedraza, O., Springer, U. & Okun, M. 2006. Faces of emotion in Parkinsons disease: micro-expressivity and bradykinesia during voluntary facial expressions. J Int Neuropsychol Soc, 12, 765-73.
Braak, H., Del Tredici, K., Rub, U., De Vos, R. A., Jansen Steur, E. N. & Braak, E. 2003. Staging of brain pathology related to sporadic Parkinson's disease. Neurobiol Aging, 24, 197-211.

Braak, H., Ghebremedhin, E., Rub, U., Bratzke, H. & Del Tredici, K. 2004. Stages in the development of Parkinson's disease-related pathology Cell Tissue Res, 318, 121-34.
Branch, L. G. & Jette, A. M. 1982. A Prospective study of long-term care institutionalization among the aged. American Journal of Public Health, 1373-1374.
Brooks, D. J. 2010. Imaging Approaches to Parkinson Disease. Journal of Nuclear Medicine, 51, 596-609.
Brown, P., Oliviero, A., Mazzone, P., Insola, A., Tonali, P. & Di Lazzaro, V. 2001. Dopamine dependency of oscillations between subthalamic nucleus and pallidum in Parkinson's disease. The Journal of neuroscience, 21, 1033-1038.
Brown, R. & Marsden, C. 1991. Dual task performance and processing resources in normal subjects and patients with Parkinson's disease Brain, 114, 215-231.
Burn, D. J., Rowan, E. N., Allan, L. M., Molloy, S., O'brien, J. T. & Mckeith, I. G. 2006. Motor subtype and cognitive decline in Parkinson's disease, Parkinson's disease with dementia, and dementia with Lewy bodies. Journal of Neurology, Neurosurgery & Psychiatry, 77, 585-589.
Butz, M. & Van Ooyen, A. 2013. A Simple Rule for Dendritic Spine and Axonal Bouton Formation Can Account for Cortical Reorganization after Focal Retinal Lesions. PLoS computational biology, 9, e1003259.
Calne, D. B., Snow, B. J. & Lee, C. 1992. Criteria for diagnosing Parkinson's disease. Annals of neurology, 32, S125-S127.
Cappozzo, A., Catani, F., Leardini, A., Benedetti, M. G. & Della Croce, U. 1996. Position and orientation in space of Sones during movement: experimental artefacts Clinical biomechanics, 11, 90-100.
Cardona, J. F., Gershanik, O., Gelormini-Lezama, C., Houck, A. L., Cardona, S., Kargieman, L., Trujillo, N., Arevalo, A., Amoruso, L., Manes, F. & Ibanez, A. 2013. Action-verb processing in Parkinson's disease: new pathways for motor-language coupling. Brain Struct Funct, 218, 1355-73.
Catarino, A., Andrade, A., Churches, O., Wagner, A., Baron-Cohen, S. & Ring, H. 2013. Task-related functional connectivity in autism spectrum conditions: an EEG study using wavelet transform coherence. Molecular Autism, 4, 1.
Chan, C. H., Poon, C. C. Y., Wong, R. C. S. & Zhang, Y. T. A hybrid body sensor network for continuous and long-term measurement of arterial blood pressure. Medical Devices and Biosensors, 2007. ISSS-MDBS 2007. 4th IEEE/EMBS International Summer School and Symposium on, 2007. IEEE, 121-123.
Chan, H. K. Y., Zheng, H., Wang, H., Gawley, R., Yang, M. & Sterritt, R. Feasibility study on iPhone accelerometer for gait detection. Pervasive Computing Technologies for Healthcare (PervasiveHealth), 2011 5th International Conference on, 2011. IEEE, 184-187.
Chang, P. F., Arendt-Nielsen, L. & Chen, A. C. N. 2002. Dynamic changes and spatial correlation of EEG activities during cold pressor test in man. Brain research bulletin, 57, 667-675.
Chen, A. C. N. & Rappelsberger, p. 1994. Brain and human pain: topographic EEG amplitude and coherence mapping. Brain topography, 7, 129-140.
Chen, E., Widick, P. & Chatterjee, A. 2008. Functional-anatomical organization of predicate metaphor processing. Brain and language, 107, 194-202.
Cheung, V. H., Gray, L. & Karunanithi, M. 2011. Review of accelerometry for determining daily activity among elderly patients. Archives of physical medicine and rehabilitation, 92, 998-1014.
Chiang, J., Wang, Z. J. & Mckeown, M. J. EEG source extraction by autoregressive source separation reveals abnormal synchronization in Parkinson's disease. Engineering in Medicine and Biology Society, 2009. EMBC 2009. Annual International Conference of the IEEE, 2009. IEEE, 1868-1872.
Chomsky, N. & Dinozzi, R. 1972. Language and mind, Harcourt Brace Jovanovich New York.
Chung, W.-Y., Purwar, A. & Sharma, A. Frequency domain approach for activity classification using accelerometer. Engineering in Medicine and Biology Society, 2008. EMBS 2008. 30th Annual International Conference of the IEEE, 2008. IEEE, 1120-1123.

(56) References Cited

OTHER PUBLICATIONS

Collins, F. & Prabhakar, A. 2013. BRAIN Initiative Challenges Researchers to unlock mysteries of human mind. The White House Blog.

Cortes, C. & Vapnik, V. 1995. Support-vector networks. Machine learning, 20, 273-297.

Cummins, N., Epps, J., Breakspear, M. & Goecke, R. An Investigation of Depressed Speech Detection: Features and Normalization. Interspeech, 2011. 2997-3000.

Dai, X. & Larson, D. R. 1998. Wandering vectors for unitary systems and orthogonal wavelets, AMS Bookstore.

Dall, S. R. X., Houston, A. I. & Mcnamara, J. M. 2004. The behavioural ecology of personality: consistent individual differences from an adaptive perspective. Ecology Letters, 7, 734-739.

Datta, P., Shankle, W. R. & Pazzani, M. Applying machine learning to an Alzheimer's database. Artificial Intelligence in Medicine: AAAI-96 Spring Symposium, 1996 Stanford. 26-30.

Dayan, E., Inzelberg, R. & Flash, T. 2012. Altered Perceptual Sensitivity to Kinematic Invariants in Parkinson's Disease PloS one, 7, e30369.

De La Monte, S. M , Wells, S. E., Hedley-Whyte, E. T. & Growdon, J. H. 1989. Neuropathological distinction between Parkinson's dementia and Parkinson's plus Alzheimer's disease. Annals of neurology, 26, 309-320.

Dethier, M., Blairy, S., Rosenberg, H. & Mcdonald, S. 2013. Emotional regulation impairments following severe traumatic brain injury: an investigation of the body and facial feedback effects. J Int Neuropsychol Soc, 19, 367-79.

Dobkin, B. H. & Dorsch, A. 2011. The Promise of mHealth Daily Activity Monitoring and Outcome Assessments by Wearable Sensors Neurorehabilitation and Neural Repair, 25, 788-798.

Dounskaia, N., Fradet, L., Lee, G., Leis, B. C. & Adler, C. H. 2009a. Submovements during pointing movements in Parkinson's disease Experimental brain research, 193, 529-544.

Dounskaia, N., Van Gemmed, A. W., Leis, B. C. & Stelmach, G. E. 2009b. Biased wrist and finger coordination in Parkinsonian patients during pedormance of graphical tasks Neuropsychologia, 47, 2504-2514.

Du, F., Qian, Z.-M., Zhu, L., Wu, X. M., Yung, W.-H., Tsim, T.-Y. & Ke, Y. 2009. L-DOPA neurotoxicity is mediated by up-regulation of DMT1—IRE expression. PLoS One, 4, e4593.

Ebersbach, G., Sojer, M., Valldeoriola, F., Wissel, J., Muller, J., Tolosa, E. A. & Poewe, W. 1999. Comparative analysis of gait in Parkinson's disease, cerebellar ataxia and subcortical arteriosclerotic encephalopathy. Brain, 122, 1349-1355.

Ekman, P. 1992. Are there basic emotions? Psychological Review, vol. 99, No. 3. 550-553.

Ekman, P. 1993. Facial expression and emotion. American Psychologist, 48, 384.

Ekman, P. & Rosenberg, E. L. 1997. What the face reveals: Basic and applied studies of spontaneous expression using the Facial Action Coding System (FACS), Oxford University Press.

El Kaliouby, R. & Robinson, P. 2005. Real-time inference of complex mental states from facial expressions and head gestures. In: Kisacanin, B., Pavlovic, V. & Huang, T. (eds.) Real-time vision for human-computer interaction. United States: Springer.

Elble, R. J. 2005. Gravitational artifact in accelerometric measurements of tremor. Clinical Neurophysiology, 116, 1638-1643.

Elkan, C. 1997. Naive bayesian learning. Department of Computer Science-Harvard University.

Elman, J. L. 1993. Learning and development in neural networks: The impedance of starting small. Cognition, 48, 71-99.

Eriksen, N., Stark, A. K. & Pakkenberg, B. 2009. Age and Parkinson's Disease Related Neuronal Death in the Substantia Nigra Pars Compacta Journal of Neural Transmission, 73, 203-213.

Espina, J., Falck, T., Muehlsteff, J. & Aubert, X. Wireless body sensor network for continuous cuff-less blood pressure monitoring. Medical Devices and Biosensors, 2006. 3rd IEEE/EMBS International Summer School on, 2006. IEEE, 11-15.

Factor, S. A. 2001. Parkinson's disease: initial treatment with levodopa or dopamine agonists. Current treatment options in neurology, 3, 479-493.

Fahn, S. 2003. Description of Parkinson's disease as a clinical syndrome. Annals of the New York Academy of Sciences, 991,1-14.

Fahn, S., Oakes, D., Shoulson, I., Kieburtz, K., Rudolph, A., Lang, A., Olanow, C. W., Tanner, C. & Marek, K. 2004. Levodopa and the progression of Parkinson's disease. The New England journal of medicine, 351, 2498.

Fang, C., Storrs, J., Ralescu, A., Lee, J.-H. & Lu, J. 2011. Detecting Parkinson's brain changes using local feature based regional SVM ensemble on MRI images. Human Brain Mapping. Quebec, Canada.

Leergaard, T. B., Hilgetag, C. C. & Sporns, O. 2012. Mapping the connectome: multi-level analysis of brain connectivity. Frontiers in Neuroinformatics, 6.

Levitis, D. A., Lidicker Jr, W. Z. & Freund, G. 2009. Behavioural biologists do not agree on what constitutes behaviour. Animal Behaviour, 78, 103-110.

Lewis, S. J., Foltynie, T., Blackwell, A. D., Robbins, T. W., Owen, A. M. & Barker, R. A. 2005a. Heterogeneity of Parkinson's disease in the early clinical stages using a data driven approach. J Neurol Neurosurg Psychiatry, 76, 343-8.

Lichtwark, G. A. & Wilson, A. M. 2006. Interactions between the human gastrocnemius muscle and the Achilles tendon during incline, level and decline locomotion Journal of Experimental Biology, 209, 4379-4388.

Lim, L., Van Wegen, E. E. H., De Goede, C. J. T., Jones, D., Rochester, L., Hetherington, V., Nieuwboer, A., Willems, A.-M. & Kwakkel, G. 2005. Measuring gait and gait-related activities in Parkinson's patients own home environment: a reliability, responsiveness and feasibility study. Parkinsonism & related disorders, 11, 19-24.

Lin, J. & Qu, L. 2000. Feature extraction based on Morlet wavelet and its application for mechanical fault diagnosis. Journal of sound and vibration, 234, 135-148.

Lipski, J., Nistico, R., Berretta, N., Guatteo, E., Bernardi, G. & Mercuri, N. B. 2011. L-DOPA: a scapegoat for accelerated neurodegeneration in Parkinson's disease? Progress in neurobiology, 94, 389-407.

Liston, M. B., Bergmann, J. H., Keating, N., Green, D. A. & Pavlou, M. 2013. Postural prioritization is differentially altered in healthy older compared to younger adults during visual and auditory coded spatial multitasking. Gait & posture.

Little, M. A., Mcsharry, P. E., Hunter, E. J., Spielman, J. & Ramig, L. O. 2009. Suitability of Dysphonia Measurements for Telemonitoring of Parkinson's Disease. Biomedical Engineering, IEEE Transactions on, 56, 1015-1022.

Liu, X., Ford-Dunn, H. L., Hayward, G. N., Nandi, D., Miall, R. C., Aziz, T. Z. & Stein, J. F. 2002. The oscillatory activity in the Parkinsonian subthalamic nucleus investigated using the macro-electrodes for deep brain stimulation. Clin Neurophysiol, 113, 1667-1672.

Llinas, R., Ribary, U., Contreras, D. & Pedroarena, C. 1998. The neuronal basis for consciousness. Philosophical Transactions of the Royal Society of London. Series B: Biological Sciences, 353, 1841-1849.

Lo, B., Thiemjarus, S., King, R. & Yang, G.-Z. Body sensor network-a wireless sensor platform for pervasive healthcare monitoring. The 3rd International Conference on Pervasive Computing, 2005. 77-80.

Loseu, V., Ghasemzadeh, H. & Jafari, R. 2012. A Mining Technique Using N n-Grams and Motion Transcripts for Body Sensor Network Data Repository Proceedings of the IEEE, 100, 107-121.

Low, L. S., Maddage, M. C., Lech, M., Sheeber, L. B. & Allen, N. B. 2011. Detection of clinical depression in adolescents' speech during family interactions. Biomedical Engineering, IEEE Transactions on, 58, 574-586.

Lu, H., Yang, J., Liu, Z., Lane, N. D., Choudhury, T. & Campbell, A. T. The jigsaw continuous sensing engine for mobile phone applications. Proceedings of the 8th ACM Conference on Embedded Networked Sensor Systems, 2010. ACM, 71-84.

(56) References Cited

OTHER PUBLICATIONS

Luinge, H. & Veltink, P. H. 2005. Measuring orientation of human body segments using miniature gyroscopes and accelerometers. Medical and Biological Engineering and computing, 43, 273-282.

Lyons, M., Akamatsu, S., Kamachi, M. & Gyoba, J. Coding facial expressions with Gabor wavelets. Automatic Face and Gesture Recognition, 1998. Proceedings. Third IEEE International Conference on, 1998 IEEE, 200-205.

Madler, C., Keller, I., Schwender, D. & Poppel, E. 1991. Sensory information processing during general anaesthesia: effect of isoflurane on auditory evoked neuronal oscillations Br J Anaesth, 66, 81-7.

Maki, Y., Yamaguchi, T., Koeda, T. & Yamaguchi, H. 2013. Communicative Competence in Alzheimer's Disease Metaphor and Sarcasm Comprehension. American Journal of Alzheimer's Disease and other Dementias, 28, 69-74.

Manton, K. G. 1988. A longitudinal study of functional change and mortality in the United States. Journal of Gerontology: Social Sciences, 43, S153-161.

Manu, P., Lane, T. J., Matthews, D. A., Castriotta, R. J., Watson, R. K. & Abeles, M. 1994. Alpha-delta sleep in patients with a chief complaint of chronic fatigue Southern medical journal, 87, 465-470.

Markham, C. H. & Diamond, S. G. 1986 Long-term follow-up of early dopa treatment in Parkinson's disease. Annals of neurology, 19, 365-372.

Mayagoitia, R. E , Lotters, J. C. & Veltink, P. H. Standing stability evaluation using a triaxial accelerometer. Engineering in Medicine and Biology Society, 1996. Bridging Disciplines for Biomedicine. Proceedings of the 18th Annual International Conference of the IEEE, 1996. IEEE, 573-574.

Mayagoitia, R. E., Letters, J. C., Veltink, P. H. & Hermens, H. 2002. Standing balance evaluation using a triaxial accelerometer Gait & posture, 16, 55-59.

Mayagoitia, R. E., Nene, A. V. & Veltink, P. H. 2002b. Accelerometer and rate gyroscope measurement of kinematics an inexpensive alternative to optical motion analysis systems. Journal of biomechanics, 35, 537-542.

Mazilu, S., Calatroni, A., Gazit, E., Roggen, D., Hausdorff, J. M. & Troster, G. 2013. Feature Learning for Detection and Prediction of Freezing of Gait in Parkinson's Disease. Machine Learning and Data Mining in Pattern Recognition. Springer.

Mcdonald, S. & Pearce, S. 1998. Requests that overcome listener reluctance: impairment associated with executive Tysfunction in brain injury. Brain Lang, 61, 88-104.

Mcghee, D. J. M., Royle, P. L., Thompson, P. A., Wright, D. E., Zajicek, J. P. & Counsell, C. E. 2013. A systematic review of biomarkers for disease progression in Parkinson's disease BMC neurology, 13, 35.

Meara, J., Bhowmick, B. K. & Hobson, P. 1999. Accuracy of diagnosis in patients with presumed Parkinson's disease. Age and ageing, 28, 99-102.

Menke, R. A., Scholz, J., Miller, K. L., Deoni, S., Jbabdi, S., Matthews, P. M. & Zarei, M. 2009. MRI characteristics of the substantia nigra in Parkinson's disease: A combined quantitative T1 and DTI study. NeuroImage, 47,435-441.

Menke, R. A., Szewczyk-Krolikowski, K., Jbabdi, S., Jenkinson, M., Talbot, K., Mackay, C. E. & Hu, M. 2013. Comprehensive morphometry of subcortical grey matter structures in early-stage Parkinson's disease. Hum Brain Mapp.

Meydan, T. 1997. Recent trends in linear and angular accelerometers. Sensors and Actuators A: Physical, 59, 43-50.

Mielke, M. M., Roberts, R. O., Savica, R., Cha, R., Drubach, D. I., Christianson, M., Pankratz, V. S., Geda, Y. E., Machulda, M. M., Ivnik, R. J., Knopman, D. S., Boeve, B. F., Rocca, W. A. & Petersen, R. C. 2013. Assessing the temporal relationship between cognition and gait: slow gait predicts cognitive decline in the mayo clinic study of aging. J Gerontol A Biol Sci Med Sci, 68, 929-37.

Mioshi, E., Kipps, C. M. & Hodges, J. R. 2009. Activities of daily living in behavioral variant frontotemporal dementia: differences in caregiver and performance-based assessments. Alzheimer Dis Assoc Disord, 23, 70-6.

Mitchell, R. L. C. & Phillips, L. H. 2007. The psychological, neurochemical and functional neuroanatomical mediators of the effects of positive and negative mood on executive functions Neuropsychologia, 45, 617-629.

Mitchell, S., Collin, J., De Luca, C., Burrows, A. & Lipsitz, L. 1995. Open-loop and closed-loop postural control mechanisms in Parkinson's disease: increased mediolateral activity during quiet standing. Neuroscience letters, 197, 133-136.

Mittal, V. A., Walker, E. F., Bearden, C. E., Walder, D., Trottman, H., Daley, M., Simone, A. & Cannon, T. D. 2010. Markers of basal ganglia dysfunction and conversion to psychosis: neurocognitive deficits and dyskinesias in the prodromal period. Biological psychiatry, 68, 93-99.

Moisello, C., Perfetti, B., Marinelli, L., Sanguineti, V., Bove, M., Feigin, A., Di Rocco, A., Eidelberg, D. & Ghilardi, M. F. 2011. Basal ganglia and kinematics modulation: insights from Parkinson's and Huntington's diseases. Parkinsonism Relat Disord, 17, 642-4.

Monetta, L. & Pell, M. D. 2007. Effects of verbal working memory deficits on metaphor comprehension in patients with Parkinson's disease Brain and Language, 101, 80-89.

Moore, S. T., Macdougall, H. G., Gracies, J.-M., Cohen, H. S. & Ondo, W. G. 2007. Long-term monitoring of gait in Parkinson's disease Gait & Posture, 26, 200-207.

Moran, R. J., Mallet, N., Litvak, V., Dolan, R. J., Magill, P. J., Friston, K. J. & Brown, P. 2011. Alterations in Brain Connectivity Underlying Beta Oscillations in Parkinsonism. PLoS Comput Biol, 7, e1002124.

Mountain, G., Wilson, S., Eccleston, C., Mawson, S., Hammerton, J., Ware, T., Zheng, H., Davies, R., Black, N. & Harris, N. 2010. Developing and testing a telerehabilitation system for people following stroke: issues of usability. Journal of Engineering Design, 21, 223-236.

Muir, S. W., Corea, C. L. & Beaupre, L. 2010. Evaluating change in clinical status: reliability and measures of agreement for the assessment of glenohumeral range of motion. North American journal of sports physical therapy NAJSPT, 5, 98.

Munhoz, R. P., Li, J. Y., Kurtinecz, M., Piboolnurak, P., Constantino, A., Fahn, S. & Lang, A. E. 2004. Evaluation of the pull test technique in assessing postural instability in Parkinson's disease. Neurology, 62, 125-127.

Murman, D. L. 2012. Early treatment of Parkinson's disease: opportunities for managed care. The American journal of managed care, 18, S183-8.

Murray, I. A. & Johnson, G. R. 2004. A study of the external forces and moments at the shoulder and elbow while performing every day tasks. Clinical Biomechanics, 19, 586-594.

Nalls, M. A., Plagnol, V., Hernandez, D. G., Sharma, M., Sheerin, U.-M., Saad, M., Simon-Sanchez, J., Schulte, C., Lesage, S. & Sveinbjörnsdóttir, S. 2011. Imputation of sequence variants for identification of genetic risks for Parkinson's disease: a meta-analysis of genome-wide association studies. Lancet, 377, 641-649.

Nandhagopal, R., Kuramoto, L., Schulzer, M., Mak, E., Cragg, J., Mckenzie, J., Mccormick, S., Ruth, T. J., Sossi, V. & De La Fuente-Fernandez, R. 2011. Longitudinal evolution of compensatory changes in striatal dopamine processing in Parkinson's disease. Brain, 134, 3290-3298.

Neel, A. T. 2008. Vowel space characteristics and vowel identification accuracy. J Speech Lang Hear Res, 51, 574-585.

Neuman, Y., Assaf, D., Cohen, Y., Last, M., Argamon, S., Howard, N. & Frieder, O. 2013. Metaphor identification in large texts corpora. PLoS One, 8.

Favre, J., Aissaoui, R., Jolies, B. M., De Guise, J. A. & Aminian, K. 2009. Functional calibration procedure for 3D knee joint angle description using inertial sensors. Journal of biomechanics, 42, 2330-2335.

Fearnley, J. M. & Lees, A. J. 1991. Ageing and Parkinson's disease: substantia nigra regional selectivity. Brain, 114, 2283-2301.

Fehling, C. 1966. Treatment of Parkinson's Syndrome With L-Dopa A Double Blind Study. Acta Neurologica Scandinavica, 42, 367-372.

(56) References Cited

OTHER PUBLICATIONS

Fell, J., Dietl, T., Grunwald, T., Kurthen, M., Klaver, P., Trautner, P., Schaller, C., Elger, C. E. & Fernández, G. 2004. Neural bases of cognitive ERPs: more than phase reset. Journal of cognitive neuroscience, 16, 1595-1604.

Ferguson, L. W., Rajput, M. L., Muhajarine, N., Shah, S. M. & Rajput, A. 2008. Clinical features at first visit and rapid disease progression in Parkinson's disease. Parkinsonism Relat Disord, 14, 431-5.

Flanagan, J. R. & Beltzner, M. A. 2000. Independence of perceptual and sensorimotor predictions in the size-weight illusion. Nat Neurosci, 3, 737-741.

Flash, T., Inzelberg, R., Schechtman, E. & Korczyn, A. D. 1992. Kinematic analysis of upper limb trajectories in Parkinson's disease Experimental neurology, 118, 215-226.

Ford, K. R., Myer, G. D. & Hewett, T. E. 2007. Reliability of landing 3D motion analysis: implications for longitudinal analyses. Medicine and science in sports and exercise, 39, 2021.

Forner-Cordero, A., Mateu-Arce, M., Forner-Cordero, L, Alcantara, E., Moreno, J. & Pons, J. 2008. Study of the motion artefacts of skin-mounted inertial sensors under different attachment conditions. Physiological measurement, 29, N21.

Freed, C. R., Greene, P. E., Breeze, R. E., Tsai, W. Y., Dumouchel, W., Kao, R., Dillon, S., Winfield, H., Culver, S., Trojanowski, J. Q., Eidelberg, D. & Fahn, S. 2001. Transplantation of embryonic dopamine neurons for severe Parkinson's disease. N Engl J Med, 344, 710-719.

Fried, L. P., Kronmal, R. A., Newman, A. B., Bild, D. E., Mittelmark, M. B., Polak, J. F., Robbins, J. A. & Gardin, J. M. 1998. Risk factors for 5-year mortality in older adults. JAMA: the journal of the American Medical Association, 279, 585-592.

Furr, R. M. & Funder, D. C. 2004. Situational similarity and behavioral consistency: Subjective, objective, variable-centered, and person-centered approaches. Journal of Research in Personality, 38, 421-447.

Gamage, S. S. & Lasenby, J. 2002. New least squares solutions for estimating the average centre of rotation and the axis of rotation. Journal of biomechanics, 35, 87-93.

Gandhi, T., Panigrahi, B. K., Bhatia, M. & Anand, S. 2010. Expert model for detection of epileptic activity in EEG signature. Expert Systems with Applications, 37, 3513-3520.

Gandy, L., Allan, N., Attallah, M., Frieder, O., Howard, N., Kanareykin, S., Koppel, M., Last, M., Neuman, Y. & Argamon, S. 2013. Automatic Identification of Conceptual Metaphors with Limited Knowledge. . Association for the Advancement of Artificial Intelligence Conference 2013 (AAAI), . Bellevue, Washington: IEEE.

Ganguli, M., Dodge, H. H. & Mulsant, B. H. 2002. Rates and predictors of mortality in an aging, rural, community-based cohort: the role of depression. Archives of General Psychiatry, 59, 1046.

Garling, E. H., Kaptein, B. L., Mertens, B., Barendregt, W., Veeger, H. E. J., Nelissen, R. & Valstar, E. R. 2007. Soft-tissue artefact assessment during step-up using fluoroscopy and skin-mounted markers. Journal of Biomechanics, 40, S18-S24.

Ghilardi, M.-F., Alberoni, M., Rossi, M., Franceschi, M., Mariani, C. & Fazio, F. 2000. Visual feedback has differential effects on reaching movements in Parkinson's and Alzheimer's disease. Brain research, 876, 112-123.

Gibb, W. R. 1988. Accuracy in the clinical diagnosis of parkinsonian syndromes. Postgraduate medical journal, 64, 345-351.

Gibb, W. R. G. & Lees, A. J. 2008. The Significance of the Lewy Body in the Diagnosis of Idiopathic Parkinson's Disease. Neuropathology and Applied Neurobiology, 15, 27-44.

Gitchel, G. T., Wetzel, P. A. & Baron, M. S. 2012. Pervasive ocular tremor in patients with Parkinson disease. Archives of Neurology, 69, 1011-1017.

Glasheen, J. W. & McMahon, T. A. 1996. Vertical water entry of disks at low Froude numbers. Physics of Fluids, 8, 2078.

Gnädingera, M., Mellinghoff, H.-U. & Kaelin-Lange, A. 2011. Parkinson's disease and the bones. Swiss Med Wkly, 141, w13154.

Goberman, A. M. 2005. Correlation between acoustic speech characteristics and non-speech motor performance in Parkinson Disease Medical science monitor, 11, CR109-CR116.

Godwin, A., Agnew, M. & Stevenson, J. 2009. Accuracy of inertial motion sensors in static, quasistatic, and complex Tynamic motion. Journal of biomechanical engineering, 131, 114501.

Goetz, C. G., Stebbins, G. T., Wolff, D., Deleeuw, W., Bronte-Stewart, H., Elble, R., Hallett, M., Nutt, J., Ramig, L., Sanger, T., Wu, A. D., Kraus, P. H., Blasucci, L. M., Shamim, E. A., Sethi, K. D., Spielman, J., Kubota, K., Grove, A. S., Dishman, E. & Taylor, C. B. 2009. Testing objective measures of motor impairment in early Parkinson's disease: Feasibility study of an at-home testing device. Mov Disord, 24, 551-6.

Green, A. L., Wang, S., Stein, J. F., Pereira, E. a. C., Kringelbach, M. L., Liu, X., Brittain, J. S. & Aziz, T. Z. 2009. Neural signatures in patients with neuropathic pain. Neurology, 72, 569-571.

Greenough, W. T., Black, J. E. & Wallace, C. S. 1993. Experience and brain development. Brain development and cognition: A reader, 290-322.

Groiss, S. J., Wojtecki, L., Südmeyer, M. & Schnitzler, A. 2009. Review: Deep brain stimulation in Parkinson's disease. Therapeutic advances in neurological disorders, 2, 379-391.

Gross, J., Schnitzler, A., Timmermann, L. & Ploner, M. 2007. Gamma oscillations in human primary somatosensory cortex reflect pain perception. PLoS biology, 5, e133.

Grosset, D., Taurah, L., Bum, D. J., Macmahon, D., Forbes, A., Turner, K., Bowron, A., Walker, R., Findley, L. & Foster, O. 2007. A multicentre longitudinal observational study of changes in self-reported health status in people with Parkinson's disease left untreated at diagnosis. Journal of Neurology, Neurosurgery & Psychiatry, 78, 465-469.

Grubbs, F. E. 1969. Procedures for detecting outlying observations in samples. Technometrics, 11, 1-21.

Guo, P.-F., Bhattacharya, P. & Kharma, N. 2010. Advances in detecting Parkinson's disease. Medical Biometrics. Springer.

Halamek, J., Viscor, I. & Kasai, M. 2001. Dynamic range and acquisition system. Measurement Science Review, 1, 71-74.

Hallett, M. & Litvan, I. 1999. Evaluation of surgery for Parkinson's disease A Report of the Therapeutics and Technology Assessment Subcommittee of the American Academy of Neurology Neurology, 53, 1910-1910.

Hammond, C., Bergman, H. & Brown, P. 2007. Pathological synchronization in Parkinson's disease: networks, models and treatments. Trends in neurosciences, 30, 357-364.

Han, C.-X., Wang, J., Yi, G.-S. & Che, Y.-Q. 2013. Investigation of EEG abnormalities in the early stage of Parkinson's Disease Cognitive Neurodynamics, 1-9.

Han, J., Jeon, H. S., Jeon, B. S. & Park, K. S. Gait detection from three dimensional acceleration signals of ankles for the patients with Parkinson's disease. IEEE The International Special Topic Conference on Information Technology in Biomedicine, Ioannina, Epirus, Greece, 2006.

Handojoseno, A. M., Shine, J. M., Nguyen, T. N., Tran, Y., Lewis, S. J. & Nguyen, H. T. 2012. The detection of Freezing of Gait in Parkinson's disease patients using EEG signals based on Wavelet decomposition. Conf Proc IEEE Eng Med Biol Soc, 2012, 69-72.

Hari, R. & Kujala, M. V. 2009. Brain basis of human social interaction: from concepts to brain imaging. Physiol Rev, 89, 153-79.

Harper, D. G. & Blake, R. W. 1989. Short communication: A critical analysis of the use of high-speed film to determine maximum accelerations of fish Journal of Experimental Biology, 142, 465-471.

Hartmann, D. L. 2013. ATMS 552 Notes: Section 9 Wavelets. In: Washington, U. O. (ed.).

Hartmut Traunmuller, A. E. 1994. The frequency range of the voice fundamental in the speech of male and female adults. Department of Linguistics, University of Stockholm.

Hauser, R. A., Lew, M. F., Hurtig, H. I., Ondo, W. G., Wojcieszek, J. & Fitzer-Attas, C. J. 2009. Long-term outcome of early versus delayed rasagiline treatment in early Parkinson's disease. Movement Disorders, 24, 564-573.

(56) References Cited

OTHER PUBLICATIONS

Hayashi, K., Makino, M., Hashizume, M., Nakano, K. & Tsuboi, K. 2010. Electroencephalogram abnormalities in panic disorder patients: a study of symptom characteristics and pathology. BioPsychoSocial medicine, 4, 9-9.
Herculano-Houzel, S. 2009. The human brain in number: a linearly scaled-up primate brain. Frontiers in human neuroscience, 3.
Higashi, H. & Tanaka, T. Optimal design of a bank of spatio-temporal filters for EEG signal classification. Engineering in Medicine and Biology Society, EMBC, 2011 Annual International Conference of the IEEE, Aug. 30, 2011-Sep. 3, 2011 2011. 6100-6103.
Hipp, J. F., Hawellek, D. J., Corbetta, M., Siegel, M. & Engel, A. K. 2012. Large-scale cortical correlation structure of spontaneous oscillatory activity. Nat Neurosci, 15, 884-890.
Hirschmann, J., Hartmann, C. J., Butz, M., Hoogenboom, N., Özkurt, T. E., Elben, S., Vesper, J., Wojtecki, L. & Schnitzler, A. 2013. A direct relationship between oscillatory subthalamic nucleus-cortex coupling and rest tremor in Parkinson's disease. Brain, awt271.
Hong, J. Y., Sunwoo, M. K., Chung, S. J., Ham, J. H., Lee, J. E., Sohn, Y. H. & Lee, P. H. 2013. Subjective cognitive decline predicts future deterioration in cognitively normal patients with Parkinson's disease Neurobiology of Aging.
Aarsland, D., Andersen, K., Larsen, J. P., Lolk, A. & Kragh-Sorensen, P. 2003. Prevalence and characteristics of dementia in Parkinson disease: an 8-year prospective study Arch Neurol, 60, 387-92.
Aarsland, D., Andersen, K., Larsen, J. P., Perry, R., Wentzel-Larsen, T., Lolk, A. & Kragh-Sorensen, P. 2004. The rate of cognitive decline in Parkinson disease. Archives of Neurology, 61, 1906.
Aarsland, D., Brønnick, K., Ehrt, U., De Deyn, P. P., Tekin, S., Emre, M. & Cummings, J. L. 2007. Neuropsychiatric symptoms in patients with Parkinson's disease and dementia: frequency, profile and associated care giver stress. Journal of Neurology, Neurosurgery & Psychiatry, 78, 36-42.
Aarsland, D., Larsen, J. P., Lim, N. G., Janvin, C., Karlsen, K., Tandberg, E. & Cummings, J. L. 1999. Range of neuropsychiatric disturbances in patients with Parkinson's disease. Journal of Neurology, Neurosurgery & Psychiatry, 67, 492-496.
Abosch, A., Lanctin, D., Onaran, I., Eberly, L., Spaniol, M. & Ince, N. F. 2012. Long-term recordings of local field potentials from implanted deep brain stimulation electrodes. Neurosurgery, 71, 804-14.
Adams, B. D., Grosland, N. M., Murphy, D. M. & Mccullough, M. 2003. Impact of impaired wrist motion on hand and upper-extremity performance(1). J Hand Surg Am, 28, 898-903.
Adkin, A. L., Frank, J. S. & Jog, M. S. 2003. Fear of falling and postural control in Parkinson's disease. Movement Disorders, 18, 496-502.
Afza, M. N. 2013. Speech Processing Algorithm For Detection Of Parkinson's Disease. International Journal of Engineering, 2.
Alfaro-Acha, A., Al Snih, S., Raji, M. A., Markides, K. S. & Ottenbacher, K. J. 2007. Does 8-Foot Walk Time Predict Cognitive Decline in Older Mexicans Americans? Journal of the American Geriatrics Society, 55, 245-251.
Allaire, J. C. & Willis, S. L. 2006. Competence in everyday activities as a predictor of cognitive risk and mortality. Aging, Neuropsychology, and Cognition, 13, 207-224.
Allali, G., Van Der Meulen, M. & Assal, F. 2010. Gait and cognition: the impact of executive function. Schweizer Archiv fur Neurologie und Psychiatrie, 161, 195-199.
Alonso-Freeh, F., Zamarbide, I., Alegre, M., Rodriguez-Oroz, M. C., Guridi, J., Manrique, M., Valencia, M., Artieda, J. & Obeso, J. A. 2006. Slow oscillatory activity and levodopa-induced dyskinesias in Parkinson's disease. Brain, 129, 1748-1757.
Ardouin, C., Pillon, B., Peiffer, E., Bejjani, P., Limousin, P., Damier, P., Arnulf, L., Benabid, A., Agid, Y. & Pollak, P. 1999. Bilateral subthalamic or pallidal stimulation for Parkinson's disease affects neither memory nor executive functions: a consecutive series of 62 patients. Annals of neurology, 46, 217-223.

Arle, J. E. & Alterman, R. L. 1999. Surgical options in Parkinson's disease. Medical Clinics of North America, 83, 183-198.
Ashour, R. & Jankovic, J. 2006. Joint and skeletal deformities in Parkinson's disease, multiple system atrophy, and progressive supranuclear palsy. Movement disorders, 21, 1856-1863.
Atallah, L., Aziz, O., Gray, E., Lo, B. & Yang, G.-Z. 2013. An Ear-Worn Sensor for the Detection of Gait Impairment After Abdominal Surgery Surgical Innovation, 20, 86-94.
Aziz, O., Atallah, L., Lo, B., Elhelw, M., Wang, L., Yang, G. Z. & Darzi, A. 2007. A Pervasive Body Sensor Network for Measuring Postoperative Recovery at Home. Surgical Innovation, 14, 83-90.
Baars, B. J. & Gage, N. M. 2010. Cognition, brain, and consciousness: Introduction to cognitive neuroscience, Academic Press.
Baker, S. N. 2007. Oscillatory interactions between sensorimotor cortex and the periphery. Current opinion in neurobiology, 17, 649-655.
Barbeau, A. 1969. L-dopa therapy in Parkinson's disease: a critical review of nine years' experience. Canadian Medical Association Journal, 101, 59.
Barton, B., Grabli, D., Bernard, B., Czemecki, V., Goldman, J. G., Stebbins, G., Dubois, B. & Goetz, C. G. 2012. Clinical validation of movement disorder society-recommended diagnostic criteria for Parkinson's disease with dementia. Movement Disorders, 27, 248-253.
Başar, E. 2012. A review of alpha activity in integrative brain function: Fundamental physiology, sensory coding, cognition and pathology International Journal of Psychophysiology, 86, 1-24.
Baslow, M. H. 2009. The languages of neurons: an analysis of coding mechanisms by which neurons communicate, learn and store information Entropy, 11, 782-797.
Bavelier, D., Newport, E. L., Hall, M. L., Supalla, T. & Boutla, M. 2006. Persistent Difference in Short-Term Memory Span Between Sign and Speech Implications for Cross-Linguistic Comparisons. Psychological Science, 17, 1090-1092.
Bell, A. M., Hankison, S. J. & Laskowski, K. L. 2009. The repeatability of behaviour: a meta-analysis. Animal Behaviour, 77, 771-783.
Belluck, P. 2013. Dementia's Signs May Come Early. The New York Times, Jul. 18.
Berardelli, A., Rothwell, J. C., Thompson, P. D. & Hallett, M. 2001. Pathophysiology of bradykinesia in Parkinson's disease. Brain, 124, 2131-2146.
Berenbaum, H. & Oltmanns, T. F. 1992. Emotional experience and expression in schizophrenia and depression. Journal of abnormal psychology, 101, 37.
Bergmann, J., Chandaria, V. & Mcgregor, A. 2012a. Wearable and Implantable Sensors: The Patient's Perspective. Sensors, 12, 16695-16709.
Bergmann, J., Graham, S., Howard, N. & Mcgregor, A. 2013b. Comparison of median frequency between traditional and functional sensor placements during activity monitoring. Measurement, 46, 2193-2200.
Bergmann, J. & Howard, N. 2012. Combining computational neuroscience and body sensor networks to investigate Alzheimer's disease. BMC Neuroscience, 13, 1-1.
Bergmann, J. & Howard, N. 2013. Design considerations for a wearable sensor network that measures accelerations during jumping. IEEE Body Sensor Network Conference. Cambridge, MA.
Bergmann, J., Langdon, P., Mayagoita, R. & Howard, N. 2013c. Exploring the use of sensors to measure behavioral interactions: An experimental evaluation of using hand trajectories. Plos One, Forthcoming.
Bergmann, J., Mayagoitia, R. & Smith, I. 2009a. A portable system for collecting anatomical joint angles during stair ascent: a comparison with an optical tracking device. Dynamic Medicine, 8, 3.
Bergmann, J., Mayagoitia, R. & Smith, I. 2010. A novel method for determining ground-referenced contacts during stair ascent: Comparing relative hip position to quiet standing hip height Gait & posture, 31, 164-168.
Bergmann, J. & Mcgregor, A. 2011a. Body-Worn Sensor Design: What Do Patients and Clinicians Want? Annals of Biomedical Engineering, 39, 2299-2312.

(56) References Cited

OTHER PUBLICATIONS

Bergmann, J., Smith, I. & Mayagoitia, R. 2012c. Using a body sensor network to measure the effect of fatigue on stair climbing performance. Physiological Measurement, 33, 287.
Bergmann, J. H., De Leeuw, M., Janssen, T. W., Veeger, D. H. & Willems, W. 2008. Contribution of the Reverse Endoprosthesis to Glenohumeral Kinematics. Clinical Orthopaedics and Related Research, 466, 594.
Bigot, J., Longcamp, M., Dal Maso, F. & Amarantini, D. 2011. A new statistical test based on the wavelet cross-spectrum to detect time-frequency dependence between non-stationary signals: Application to the analysis of cortico-muscular interactions. NeuroImage, 55, 1504-1518.
Bland, M. J. & Altman, D. G. 1986. Statistical methods for assessing agreement between two methods of clinical measurement The lancet, 327, 307-310.
Błaszczyk, J. W. & Orawiec, R. 2011. Assessment of postural control in patients with Parkinson's disease: sway ratio analysis Human movement science, 30, 396-404.
Bogdanov, M., Matson, W. R., Wang, L., Matson, T., Saunders-Pullman, R., Bressman, S. S. & Beal, M. F. 2008. Metabolomic profiling to develop blood biomarkers for Parkinson's disease. Brain, 131, 389-396.
Bologna, M., Fabbrini, G., Marsili, L., Defazio, G., Thompson, P. D. & Berardelli, A. 2013. Facial bradykinesia. Journal of Neurology, Neurosurgery & Psychiatry, 84, 681-685.
Bonato, P. 2005. Advances in wearable technology and applications in physical medicine and rehabilitation. Journal of NeuroEngineering and Rehabilitation, 2, 2.
Bond, J. M. & Morris, M. 2000. Goal-directed secondary motor tasks: their effects on gait in subjects with Parkinson disease. Arch Phys Med Rehabil, 81, 110-116.
Bonnard, M., De Graaf, J. & Pailhous, J. 2004. Interactions between cognitive and sensorimotor functions in the motor cortex: evidence from the preparatory motor sets anticipating a perturbation. Rev Neurosci, 15, 371-82.
Bosl, W., Tierney, A., Tager-Flusberg, H. & Nelson, C. 2011. EEG complexity as a biomarker for autism spectrum disorder risk. BMC Medicine, 9, 18.
Bottini Bonfanti, A. 2013. More than movement: the importance of the evolution of mild cognitive impairment in Parkinson's disease Journal of Neurology, Neurosurgery & Psychiatry.
Boulenger, V., Mechtouff, L., Thobois, S., Broussolle, E., Jeannerod, M. & Nazir, T. A. 2008. Word processing in Parkinson's disease is impaired for action verbs but not for concrete nouns. Neuropsychologia, 46, 743-756.
Bourne, D. A., Choo, A. M., Regan, W. D., Macintyre, D. L. & Oxland, T. R. 2009. A New Subject-Specific Skin Correction Factor for Three-Dimensional Kinematic Analysis of the Scapula. Journal of Biomechanical Engineering, 131, 121009.
Ainhi, D. H., Samuel, D. K. & Victor, S. C. F. 2013. Motor features of Parkinson's disease. Clinical Insights: Parkinson's Disease: Diagnosis, Motor Symptoms and Non-Motor Features. Future Medicine Ltd.
Barres, B. A. 2005. Smyelin for glia. Nature Neuroscience, 8, 127-127.
Bertoli-Avella, A. M., Giroud-Benitez, J. L., Akyol, A., Barbosa, E., Schaap, O., Van Der Linde, H. C., Martignoni, E., Lopiano, L., Lamberti, P. & Fincati, E. 2005. Novel parkin mutations detected in patients with early-onset Parkinson's disease Movement disorders, 20, 424-431.
Chaudhuri, K., Healy, D. G. & Schapira, A. H. V. 2006 Non-motor symptoms of Parkinson's disease: diagnosis and management. The Lancet Neurology, 5, 235-245.
Haken, H. 2002. Brain Dynamics: Synchronization and Activity Patterns in Pulse-coupled Neutral Nets with Delays and Noise, Springer.
Hikosaka, O. 2009. Basal Ganglia and Oculomotor Control. In: Editor-in-Chief: Squire, L.R. (ed.) Encyclopedia of Neuroscience Oxford: Academic Press.

Hunt, A. L. & Sethi, K. D. 2006. The pull test: a history. Mov Disord, 21, 894-9.
Lamb, S. M. 1999. Pathways of the Brain: The Neurocognitive Basis of Language, Amsterdam & Philadelphia, John Benjamins Publishing Co.
Nunez, P. L. 2006. Electric fields of the brain: the neurophysics of EEG, Oxford University Press.
Pillon, B., Dubois, B., Ploska, A. & Agid, Y. 1991. Severity and specificity of cognitive impairment in Alzheimer's, Huntington's, and Parkinson's diseases and progressive supranuclear palsy Neurology, 41, 634-643.
Sánchez-Ferro, Á., Benito-León, J., Louis, E. D., Mitchell, A. J., Molina-Arjona, J. A., Trincado, R., Villarejo, A. & Bermejo-Pareja, F. 2012. Rate of cognitive decline in premotor Parkinson's disease: A prospective study (NEDICES). Movement Disorders.
Sioka, C., Fotopoulos, A. & Kyritsis, A. P. 2010. Recent advances in PET imaging for evaluation of Parkinson's disease. European journal of nuclear medicine and molecular imaging, 37, 1594-1603.
Starr, P. A., Vitek, J. L. & Bakay, R. a. E. 1998. Ablative surgery and deep brain stimulation for Parkinson's disease. Neurosurgery, 43, 989-1013.
Tolosa, E., Wenning, G. & Poewe, W. 2006. The diagnosis of Parkinson's disease. The Lancet Neurology, 5, 75-86.
Hawkes, C. H., Del Tredici, K. & Braak, H. 2010. A timeline for Parkinson's disease. Parkinsonism Relat Disord, 16, 79-84.
Howard, N., Bergmann, J. & Stein, J. 2013. Combined Modality of the Brain Code Approach for Early Detection and the Long-term Monitoring of Neurodegenerative Processes. Frontiers Special Issue INCF Course Imaging the Brain at Different Scales.
Abbs, J. H., Hartman, D. E. & Vishwanat, B. 1987. Orofacial motor control impairment in Parkinson's disease. Neurology, 37, 394-8.
Karson, C. N., Burns, R. S., Lewitt, P. A., Foster, N. L. & Newman, R. P. 1984. Blink rates and disorders of movement. Neurology, 34, 677-677.
Machine Learning and Data Mining in Pattern Recognition. In: Perner, P., ed. Machine Learning and Data Mining 2011, New York, NY USA. Springer.
Barnes, G. R., Benson, A. J. & Prior, A. R. 1978. Visual-vestibular interaction in the control of eye movement. Aviat Space Environ Med, 49, 557-564.
Maasen, S., Mendelsohn, E. & Weingart, P. 1995. Biology as society, society as biology : metaphors, Dordrecht; Boston, Kluwer Academic Publishers.
May-Lisowski, T. L. & King, P. M. 2008. Effect of wearing a static wrist orthosis on shoulder movement during feeding. The American Journal of Occupational Therapy, 62, 438-445.
Moffett, S. 2006. The Three-Pound Enigma: The Human Brain and the Quest to Unlock Its Mysteries, Algonquin Books.
Schenck, C. H., Bundlie, S. R. & Mahowald, M. W. 1996. Delayed emergence of a parkinsonian disorder in 38% of 29 older men initially diagnosed with idiopathic rapid eye movement sleep behaviour disorder. Neurology, 46, 388-93.
Sinanovic, O., Kapidzic, A., Kovacevic, L., Hudic, J. & Smajlovic, D. 2005. EEG frequency and cognitive dysfunction in patients with Parkinson's disease. Med Arh, 59, 286-7.
Thies, W. & Bleiler, L. 2011. 2011 Alzheimer's disease facts and figures. Alzheimer's & Dementia, 7, 208-44.
Walter, B. L. & Vitek, J. L. 2004. Surgical treatment for Parkinson's disease. The Lancet Neurology, 3, 719-728.
Wertman, E., Speedie, L., Shemesh, Z., Gilon, D., Raphael, M. & Stessman, J. 1993. Cognitive disturbances in parkinsonian patients with depression. Cognitive and Behavioral Neurology, 6, 31-37.
Howard, N. 2014. "Approach to Study the Brain: towards the Early Detection of Neurodegenerative Disease ." PhD thesis, Oxford University, UK.
Savica, R., Rocca, W. A. & Ahlskog, J. 2010. When does parkinson disease start? Archives of Neurology, 67, 798-801.
Scalzo, P. L., Flores, C. R., Marques, J. R., Robini, S. C. D. O. & Teixeira, A. L. 2012. Impact of changes in balance and walking capacity on the quality of life in patients with Parkinson's disease. Arquivos de neuro-psiquiatria, 70, 119-124.
Schlede, N., Zimmermann, R., Ehrensperger, M. M., Gschwandtner, U., Hardmeier, M., Hatz, F., Monsch, A. U., Naegelin, Y. & Fuhr,

(56) References Cited

OTHER PUBLICATIONS

P. 2011. Clinical EEG in cognitively impaired patients with Parkinson's Disease. J Neurol Sci, 310, 75-8.

Schmidt, G. L., Debuse, C. J. & Seger, C. A. 2007. Right hemisphere metaphor processing? Characterizing the ateralization of semantic processes. Brain Lang, 100,127-41.

Schmidt, G. L. & Seger, C. A. 2009. Neural correlates of metaphor processing: the roles of figurativeness, familiarity and difficulty Brain Cogn, 71, 375-86.

Schneider, K. & Vasilyev, O. V. 2010. Wavelet methods in computational fluid dynamics*. Annual Review of Fluid Mlechanics, 42, 473-503.

Scholz, B., Svensson, M., Alm, H., Sköld, K., Fäith, M., Kultima, K., Guigoni, C., Doudnikoff, E., Li, Q. & Crossman, A. R. 2008. Striatal proteomic analysis suggests that first L-dopa dose equates to chronic exposure PLoS One, 3, e1589.

Schrag, A., Ben-Shlomo, Y. & Quinn, N. 2002. How valid is the clinical diagnosis of Parkinson's disease in the community? Journal of Neurology, Neurosurgery & Psychiatry, 73, 529-534.

Selikhova, M., Williams, D. R., Kempster, P. A., Holton, J. L., Revesz, T. & Lees, A. J. 2009. A clinico-pathological study of subtypes in Parkinson's disease Brain, 132, 2947-57.

Seto, E. Y. W., Giani, A., Shia, V., Wang, C., Yan, P., Yang, A. Y., Jerrett, M. & Bajcsy, R. A wireless body sensor network for the prevention and management of asthma. Industrial Embedded Systems, 2009. SIES'09. IEEE International Symposium on, 2009. IEEE, 120-123.

Shahaf, G., Reches, A., Pinchuk, N., Fisher, T., Ben Bashat, G., Kanter, A., Tauber, I., Kerem, D., Laufer, I. & Aharon-Peretz, J. 2012. Introducing a novel approach of network oriented analysis of ERPs, demonstrated on adult attention deficit hyperactivity disorder. Clinical Neurophysiology, 123, 1568-1580.

Shahed, J. & Jankovic, J. 2007. Exploring the relationship between essential tremor and Parkinson's disease. Parkinsonism & related disorders, 13, 67-76.

Shamoun-Baranes, J., Bom, R., Van Loon, E. E., Ens, B. J., Oosterbeek, K. & Bouten, W. 2012. From sensor data to animal behaviour: an oystercatcher example. PloS one, 7, e37997.

Sheikh, S., Safia, Haque, E. & Mir, S. S. 2013. Neurodegenerative Diseases: Multifactorial Conformational Diseases and Their Therapeutic Interventions Journal of Neurodegenerative Diseases, 2013, 8.

Sheng, M. 2005. Dendritic Spines—Tiny structures in the Brain for Communication Storage. Riken BSI News, 28.

Sheridan, P. L., Solomont, J., Kowall, N. & Hausdorff, J. M. 2003. Influence of Executive Function on Locomotor Function: Divided Attention Increases Gait Variability in Alzheimer's Disease. Journal of the American Geriatrics Society, 51, 1633-1637.

Shi, M., Bradner, J., Hancock, A. M., Chung, K. A., Quinn, J. F., Peskind, E. R., Galasko, D., Jankovic, J., Zabetian, C. P. & Kim, H. M. 2011. Cerebrospinal fluid biomarkers for Parkinson disease diagnosis and progression. Annals of neurology, 69, 570-580.

Shiba, M., Bower, J. H., Maraganore, D. M., Mcdonnell, S. K., Peterson, B. J., Ahlskog, J. E., Schaid, D. J. & Rocca, W. A. 2000. Anxiety disorders and depressive disorders preceding Parkinson's disease: a case-control study. Mov Disord, 15, 669-77.

Shulman, L. M., Pretzer-Aboff, I., Anderson, K. E., Stevenson, R., Vaughan, C. G., Gruber-Baldini, A. L., Reich, S. G. & Weiner, W. J. 2006. Subjective report versus objective measurement of activities of daily living in Parkinson's disease. Movement disorders, 21, 794-799.

Silberstein, P., Pogosyan, A., Kühn, A. A., Hotton, G., Tisch, S., Kupsch, A., Dowsey-Limousin, P., Hariz, M. I. & Brown, P. 2005. Cortico-cortical coupling in Parkinson's disease and its modulation by therapy Brain, 128, 1277-1291.

Silcott, N. A., Bassett, D. R., Thompson, D. L., Fitzhugh, E. C. & Steeves, J. A. 2011. Evaluation of the Omron HJ-720ITC pedometer under free-living conditions Medicine and science in sports and exercise, 43, 1791-1797.

Skodda, S., Gronheit, W. & Schlegel, U. 2011. Intonation and speech rate in Parkinson's disease: General and dynamic aspects and responsiveness to levodopa admission. Journal of Voice, 25, e199-e205.

Skodda, S., Gronheit, W. & Schlegel, U. 2012. Impairment of Vowel Articulation as a Possible Marker of Disease Progression in Parkinson's Disease. PloS one, 7, e32132.

Smith, S. J. M. 2005. EEG in the diagnosis, classification, and management of patients with epilepsy. Journal of Neurology, Neurosurgery & Psychiatry, 76, ii2-ii7.

Soikkeli, R., Partanen, J., Soininen, H., Pääkkönen, A. & Riekkinen, P. 1991a. Slowing of EEG in Parkinson's disease. Electroencephalography and clinical neurophysiology, 79, 159-165.

Sorensen, G., Kempfner, J., Jennum, P. & Sorensen, H. B. Detection of arousals in Parkinson's disease patients. Engineering in Medicine and Biology Society, EMBC, 2011 Annual International Conference of the IEEE, 2011. IEEE, 2764-2767.

Soyel, H. & Demirel, H. 2007. Facial expression recognition using 3D facial feature distances. Image Analysis and Recognition. Springer.

Sponheim, S. R., Clementz, B. A., Iacono, W. G. & Beiser, M. 1994 Resting EEG in first-episode and chronic schizophrenia. Psychophysiology, 31, 37-43.

Sposaro, F. & Tyson, G. iFall: an Android application for fall monitoring and response. Engineering in Medicine and Biology Society, 2009. EMBC 2009. Annual International Conference of the IEEE, 2009. IEEE, 6119-6122.

Starkstein, S., Preziosi, T., Berthier, M., Bolduc, P., Mayberg, H. & Robinson, R. 1989. Depression and cognitive impairment in Parkinson's disease. Brain: a journal of neurology, 112, 1141-1153.

Steffen, T. & Seney, M. 2008. Test-retest reliability and minimal detectable change on balance and ambulation tests, the 36-item short-form health survey, and the unified Parkinson disease rating scale in people with parkinsonism. Physical Therapy, 88, 733-746.

Stern, M. B., Braffman, B. H., Skolnick, B. E., Hurtig, H. I. & Grossman, R. I. 1989. Magnetic resonance imaging in Parkinson's disease and parkinsonian syndromes. Neurology, 39, 1524-1524.

Stikic, M., Johnson, R. R., Levendowski, D. J., Popovic, D. P., Olmstead, R. E. & Berka, C. 2011. EEG-derived estimators of present and future cognitive performance Frontiers in human neuroscience, 5.

Strang, G. 1993. Wavelet Transforms Versus Fourier Transforms. Bull. Amer. Math. Soc., 18, 288-305.

Suzuki, A., Hoshino, T., Shigemasu, K. & Kawamura, M. 2006. Disgust-specific impairment of facial expression recognition in Parkinson's disease. Brain, 129, 707-717.

Tachibana, Y., Iwamuro, H., Kita, H., Takada, M. & Nambu, A. 2011. Subthalamo-pallidal interactions underlying parkinsonian neuronal oscillations in the primate basal ganglia. Eur J Neurosci, 34,1470-84.

Tan, B. T., Minyue, F., Spray, A. & Dermody, P. The use of wavelet transforms in phoneme recognition. Spoken Language, 1996 ICSLP 96. Proceedings., Fourth International Conference on, Oct. 3-6, 1996 1996. 2431-2434 vol. 4.

Tan, H., Pogosyan, A., Anzak, A., Ashkan, K., Bogdanovic, M., Green, A. L., Aziz, T., Foltynie, T., Limousin, P. & Zrinzo, L. 2013. Complementary roles of different oscillatory activities in the subthalamic nucleus in coding motor effort in Parkinsonism. Experimental neurology.

Tanaka, H., Koenig, T., Pascual-Marqui, R. D., Hirata, K., Kochi, K. & Lehmann, D. 2000. Event-related potential and EEG measures in Parkinson's disease without and with dementia Dement Geriatr Cogn Disord, 11, 39-45.

Thatcher, R. W. 2012. Coherence, Phase Differences, Phase Shift, and Phase Lock in EEG/ERP Analyses. Developmental Neuropsychology, 37, 476-496.

Thies, S., Tresadem, P., Kenney, L., Howard, D., Goulermas, J., Smith, C. & Rigby, J. 2007. Comparison of linear accelerations from three measurement systems during "reach & grasp". Medical engineering & physics, 29, 967-972.

Thomas, C., Keselj, V., Cercone, N., Rockwood, K. & Asp, E. Automatic detection and rating of dementia of Alzheimer type

(56) References Cited

OTHER PUBLICATIONS through lexical analysis of spontaneous speech. Mechatronics and Automation, 2005 IEEE International Conference, 2005. IEEE, 1569-1574.

Torrence, C. & Compo, G. P. 1998. A practical guide to wavelet analysis. Bulletin of the American Meteorological society, 79, 61-78.

Trambaiolli, L. R., Lorena, A. C., Fraga, F. J., Kanda, P. A., Anghinah, R. & Nitrini, R. 2011. Improving Alzheimer's disease diagnosis with machine learning techniques Clinical EEG Neuroscience, 42, 160-165.

Traunmüller, H. & Eriksson, A. 1994. The frequency range of the voice fundamental in the speech of male and female adults. Manuscript, Department of Linguistics, University of Stockholm, http://www.ling.su.se/staff/hartmut/aktupub.htm.

Tresilian, J. R., Stelmach, G. E. & Adler, C. H. 1997. Stability of reach-to-grasp movement patterns in Parkinson's disease. Brain, 120, 2093-2111.

Tsanas, A., Little, M. A., Mcsharry, P. E. & Ramig, L. O. 2010. Accurate telemonitoring of Parkinson's disease progression by noninvasive speech tests. Biomedical Engineering, IEEE Transactions on, 57, 884-893.

Tsanas, A., Little, M. A., Mcsharry, P. E. & Ramig, L. O. 2011. Nonlinear speech analysis algorithms mapped to a standard metric achieve clinically useful quantification of average Parkinson's disease symptom severity. Journal of the Royal Society Interface, 8, 842-855.

Tsanas, A., Little, M. A., Mcsharry, P. E., Spielman, J. & Ramig, L. O. 2012. Novel speech signal processing algorithms for high-accuracy classification of Parkinson's disease IEEE Trans Biomed Eng, 59, 1264-1271.

Turner, B. M., Fortsmann, B. U., Wagenmakers, E.-J., Brown, S. D., Sederberg, P. B. & Steyvers, M. 2013. A Bayesiar framework for simultaneously modeling neural and behavioral data. Neuroimage, 72, 193-206.

Locke, E. A. 1986. Generalizing from laboratory to field: Ecological validity or abstraction of essential elements, Lexington, MA, Lexington Books.

Sokoloff, L. 1960. The metabolism of the central nervous system in vivo. Handbook of physiology-neurophysiology, 3, 1843-1864.

Bergmann, J., Fei, J., Green, D. A., Hussain, A., & Howard, N. (2017). A Bayesian Assessment of Real-World Behavior During Multitasking. Cognitive computation, 9(6), 7 49-757. https://doi.org/1 0.1 007/s 12559-017-9500-6 (Year: 20 17).

\* cited by examiner

*Figure 2-1 Animal and human models of PD using neuro-imaging techniques. (Part of image reproduced from Herculano-Houzel (2009) and Sheng (2005).*

*Figure 2-3. Illustrates a surgical device is implanted within the brain that emits electrical impulse treatment which is considered a highly invasive treatment, image from MEMS 2010*

Figure 2-4. Illustrates frequency of most common PD treatment and level of invasiveness

*Figure 2-6. IMU and ICS sensors are currently being developed to measure upper limb data and lower limb stability data. Video/Audio to measure speech data and facial expression will be added in future work. EEG is of interest to add in future work but requires further research and hardware development.*

Fig. 7 for the approach and methods to be developed from.

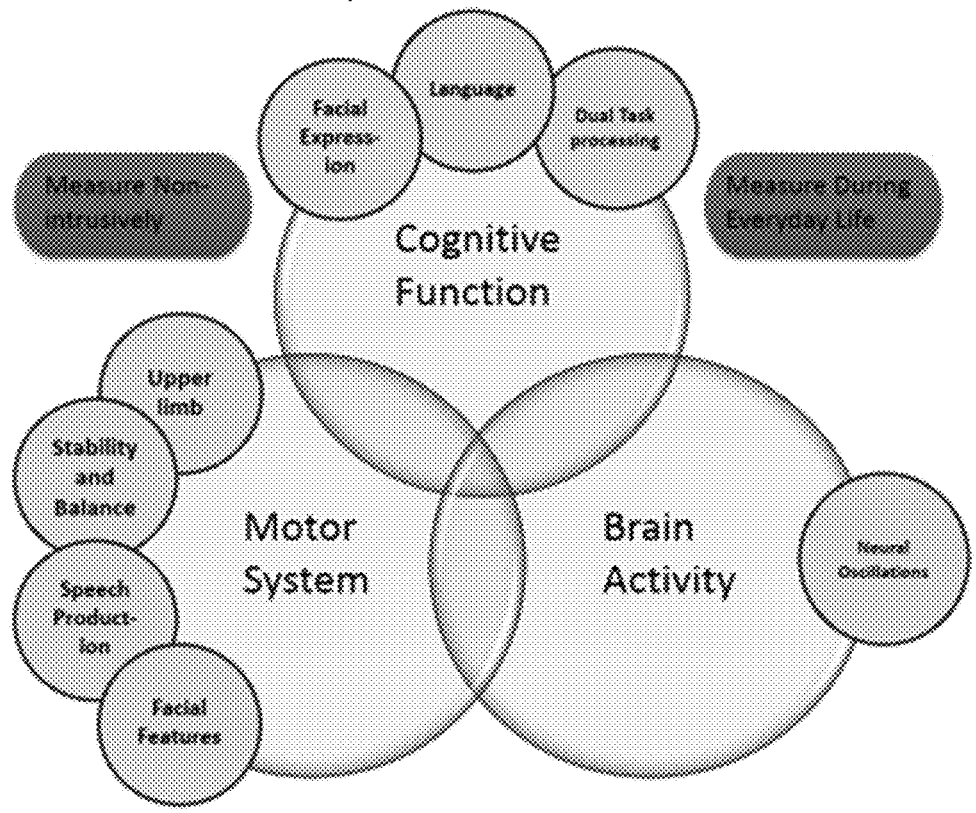

Figure 2-7. Illustrates each measure of interest discussed in this chapter and its associated domain. Notice facial expression is a potential measure of the cognitive function domain, while facial features are a potential measure of the motor system. Speech production is a potential measure of the motor system domain, while language is a potential measure of cognitive function.

Figure 2-8. Abstraction of 3D movement space. (A) Example of "normal" movement space of an individual. (B) Example of restricted space due to loss of certain functions.

Figure 2-9. The top of the figure depicts the gait cycle. The graphs show stride time variance in patients with PD (top row), Huntington's Disease (second row), Amyotrophic Lateral Sclerosis (third row) and healthy controls (bottom row)(physionet). The greatest value range was observed in Huntington's patients.

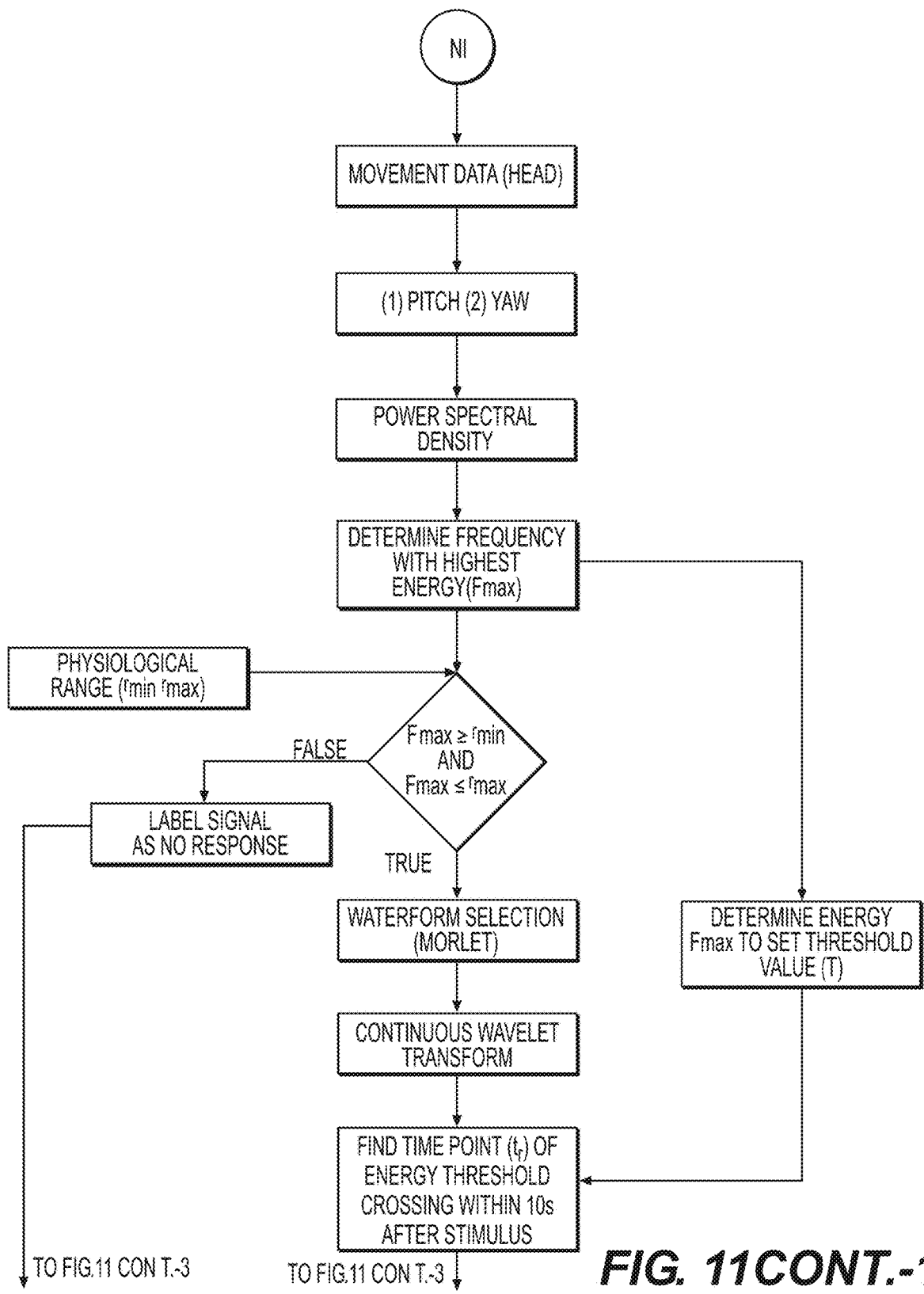
FIG. 11CONT.-1

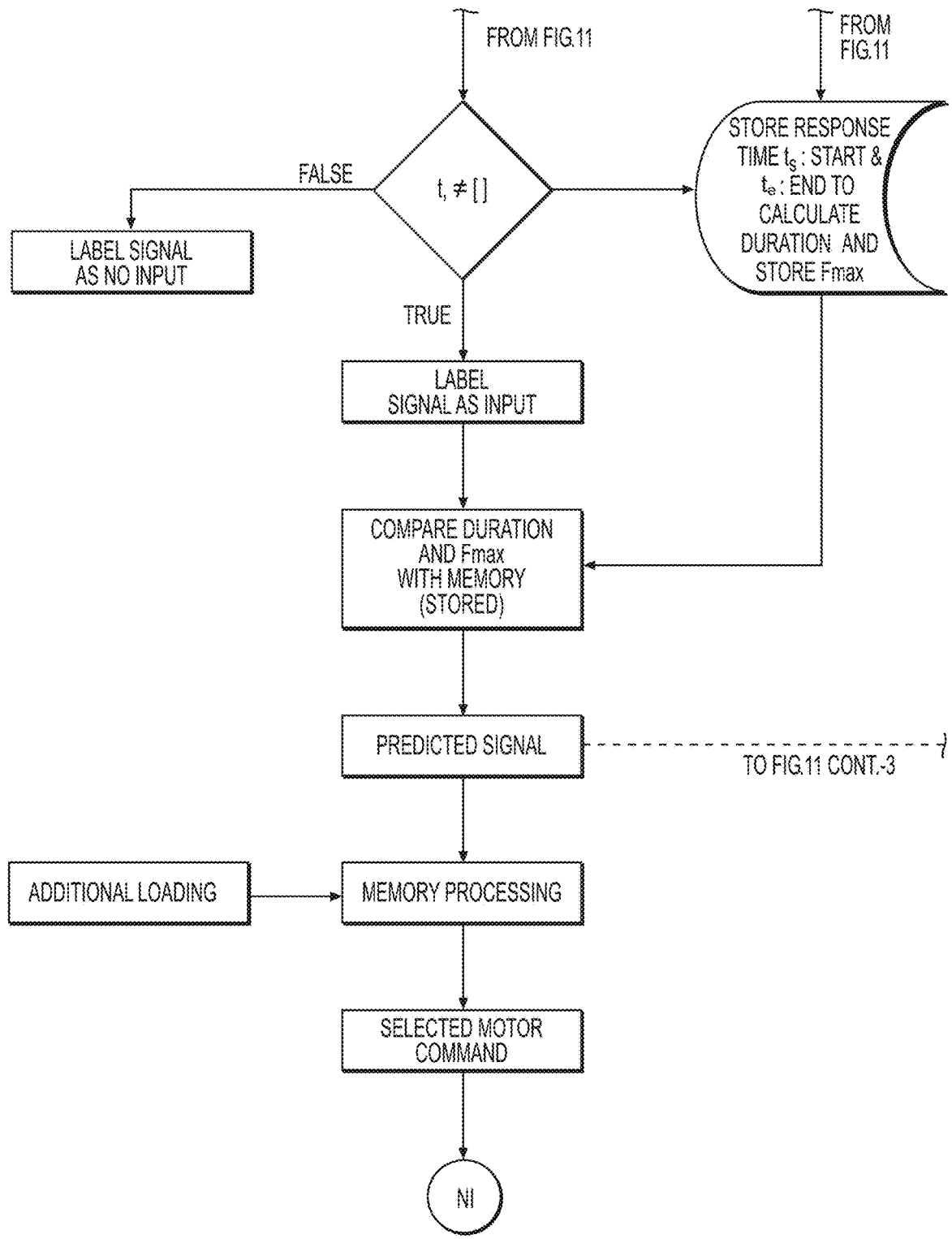
FIG. 11CONT.-2

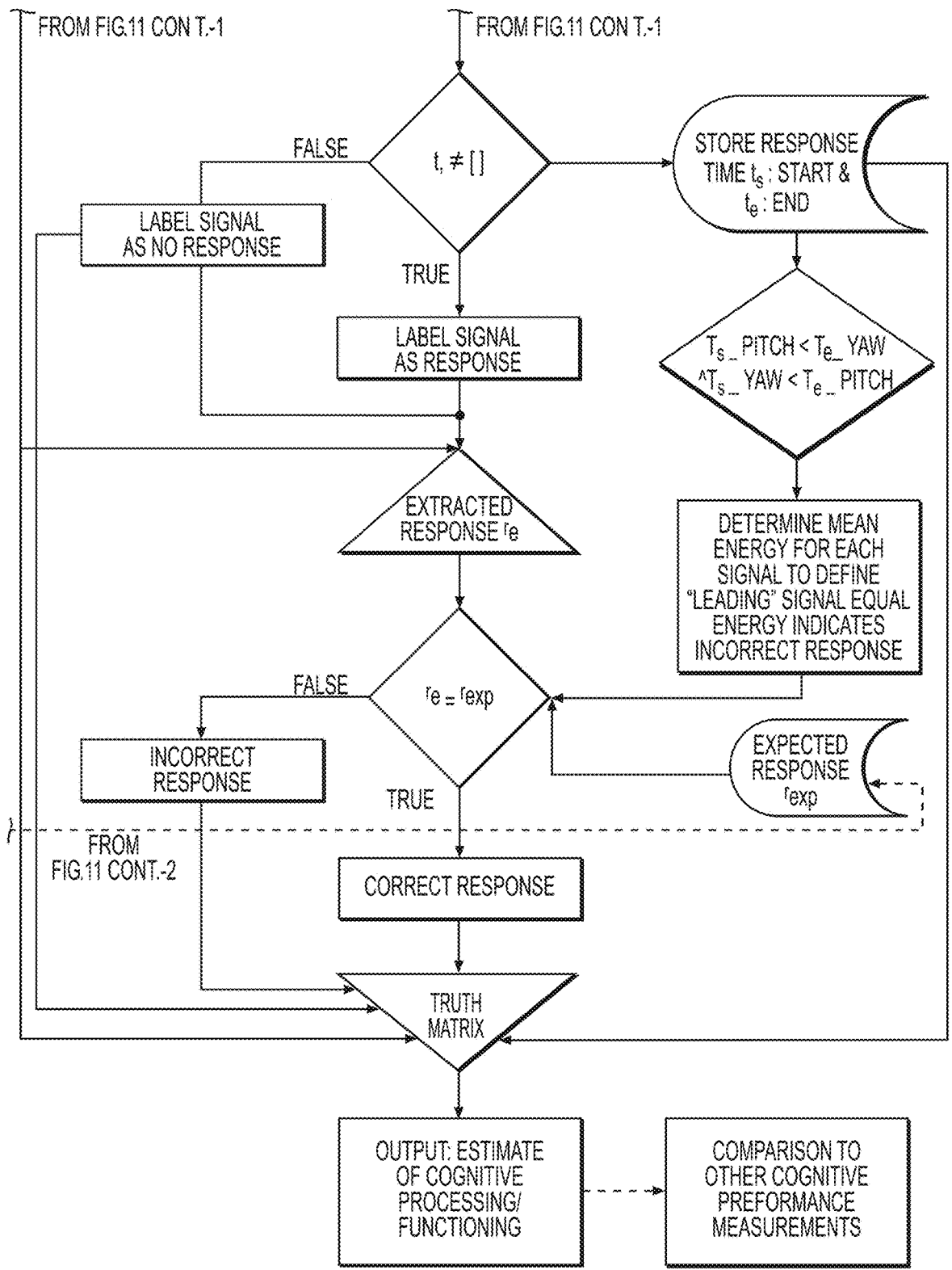
FIG. 11CONT.-3

Fig. 12

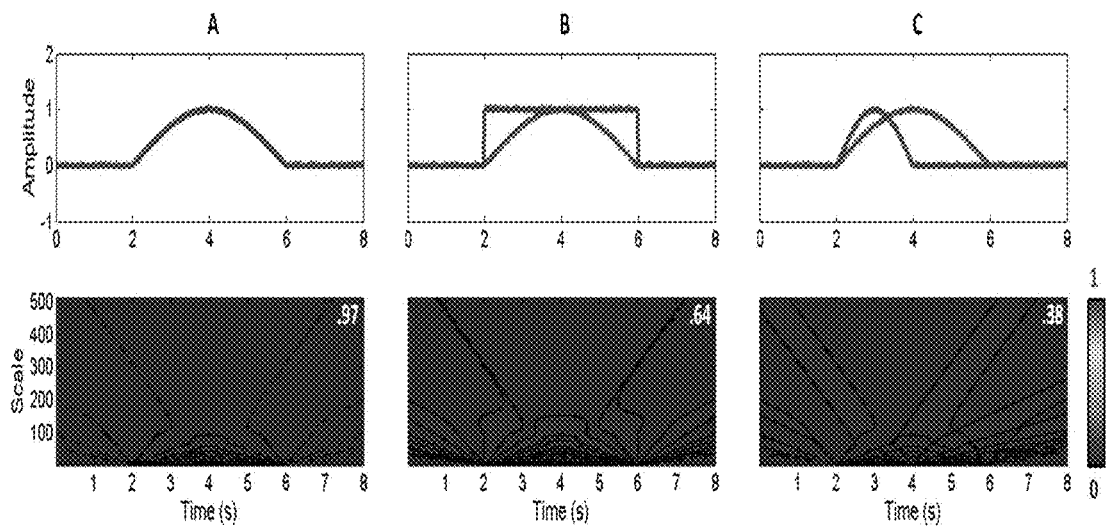

Figure 2-12. Example of how the wavelet coherence changes over a range of three sample wave patterns. Zero-mean Gaussian noise is added to all signals. Top plots: (A) the red signals shows a sine wave with a frequency $f$ and the blue trace has a frequency of $1.001f$. (B) The red signal depicts a sine with a frequency $f$ and the blue is Haar wave with the same frequency $f$, (C)The red signal shows a sine wave with a frequency $f$ and the blue trace has a frequency of $2f$. The bottom plots show the wavelet coherence for each example. The heat map displayed on the side shows the phase, wherein dark blue represents $0°$ and dark red represents $180°$. The mean wavelet cross spectrum value ($\bar{C}$) is displayed in the corner of each wavelet coherence plot.

*Figure 2-13 Detection algorithm flowchart consists of three stages pre-processing, signal-processing and machine learning.*

Figure 2-14. Sensor layout for 256-channel Hydrocele Geodesic Sensor Net (nose at the top of the figure). These figures are modified from (Luu et al 2011). A: represents the pain selection of physiologically relevant electrodes (n=85) given in red. B: shows blank template, which includes all electrodes channels (256).

*Figure 2-15 Gives an overview of measure of interest (first row), specific feature to be measured (second row) data collection method (third row) and analysis method (fourth row)*

Figure 2-16. Sequences A, B and C each with three arm positions

*Figure 2-17 The Optical tracking markers and Inertia Measurement Units (IMUs) attached to 3 points on the left arm.*

Figure 2-18. Initial condition of the two-link model. Segment lengths were taken from anthropometric data (Winter, 1990). The proximal point (p) represents the shoulder; the intermediate point (i) is the elbow and the distal point (d) the hand. All positions are given in (X,Y,Z). ($L_U$) length of the upper arm; ($L_L$) length of the lower arm and hand.

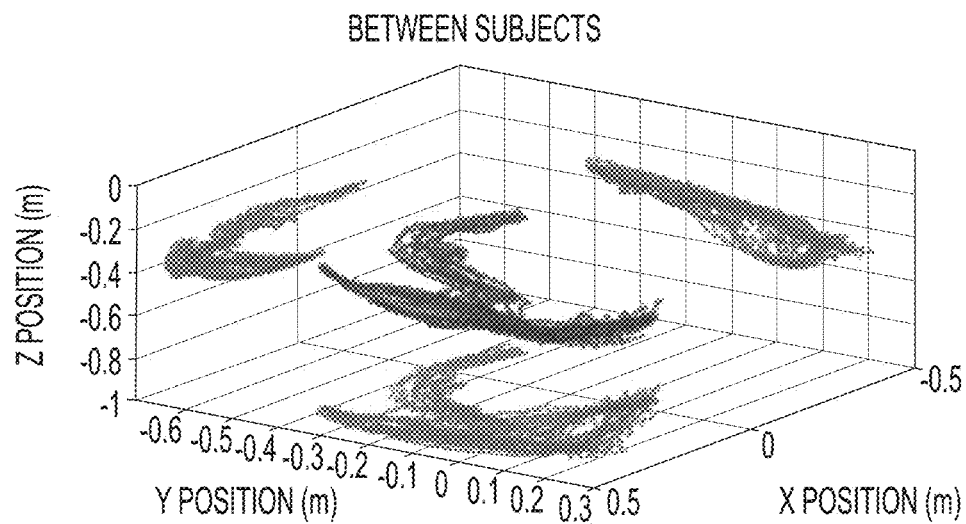
FIG. 20-A1
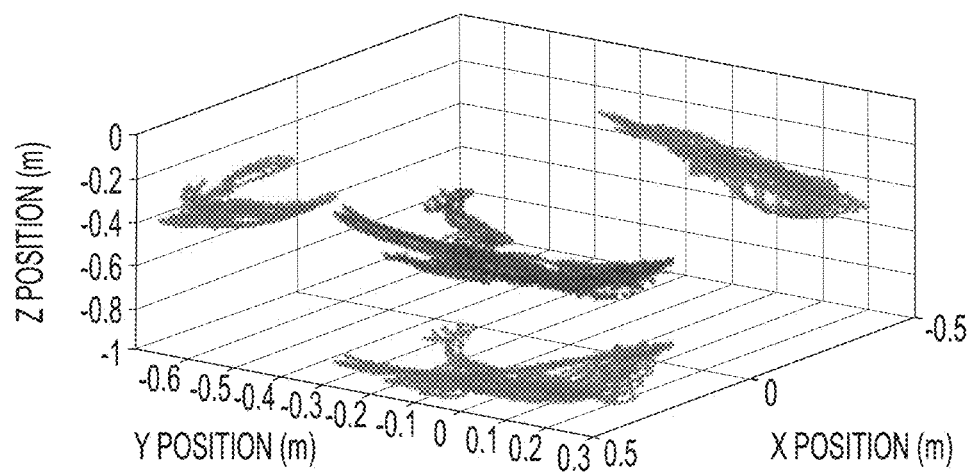
FIG. 20-A2
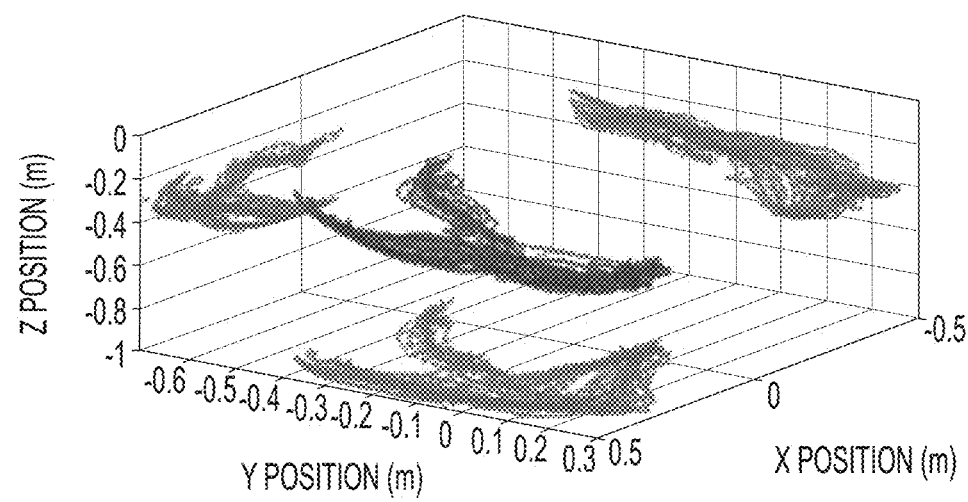
FIG. 20-A3

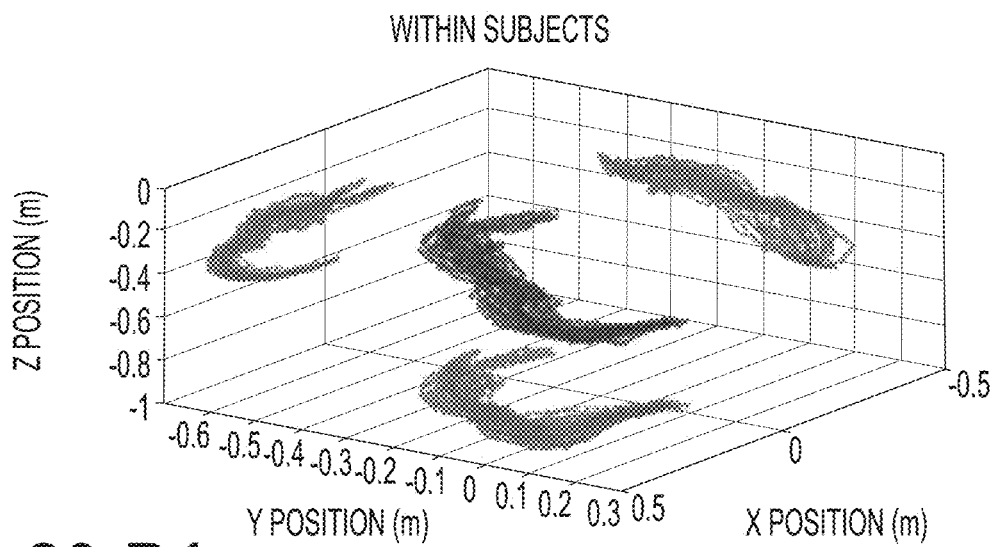
FIG. 20-B1
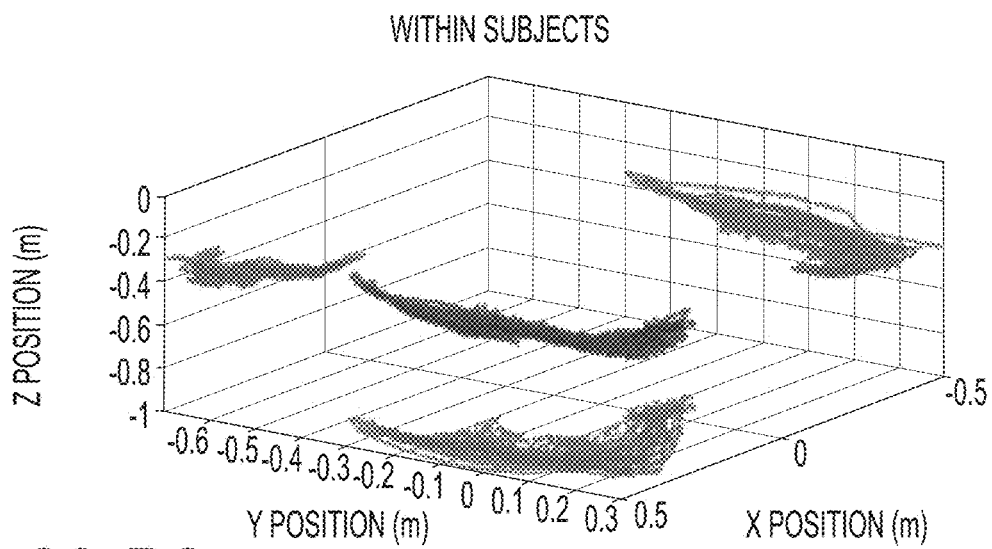
FIG. 20-B2
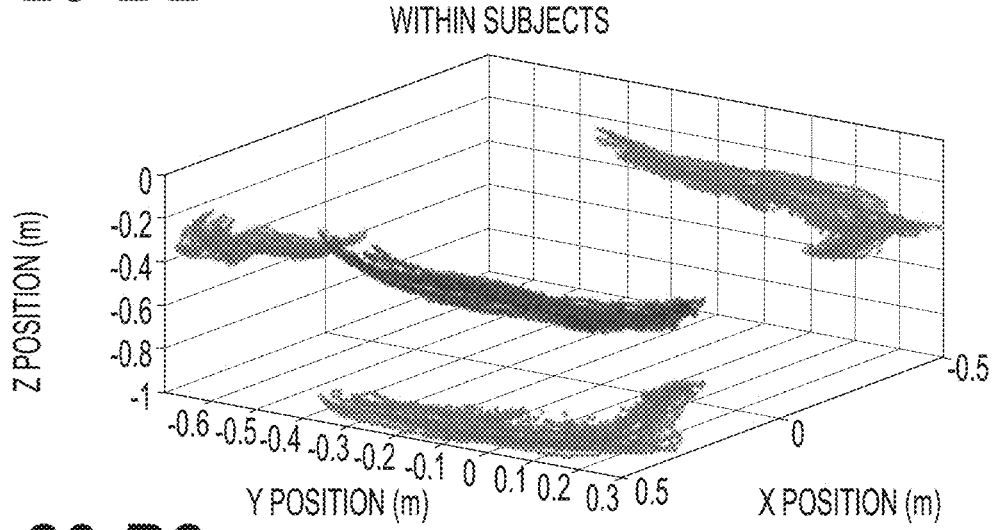
FIG. 20-B3

Fig. 21

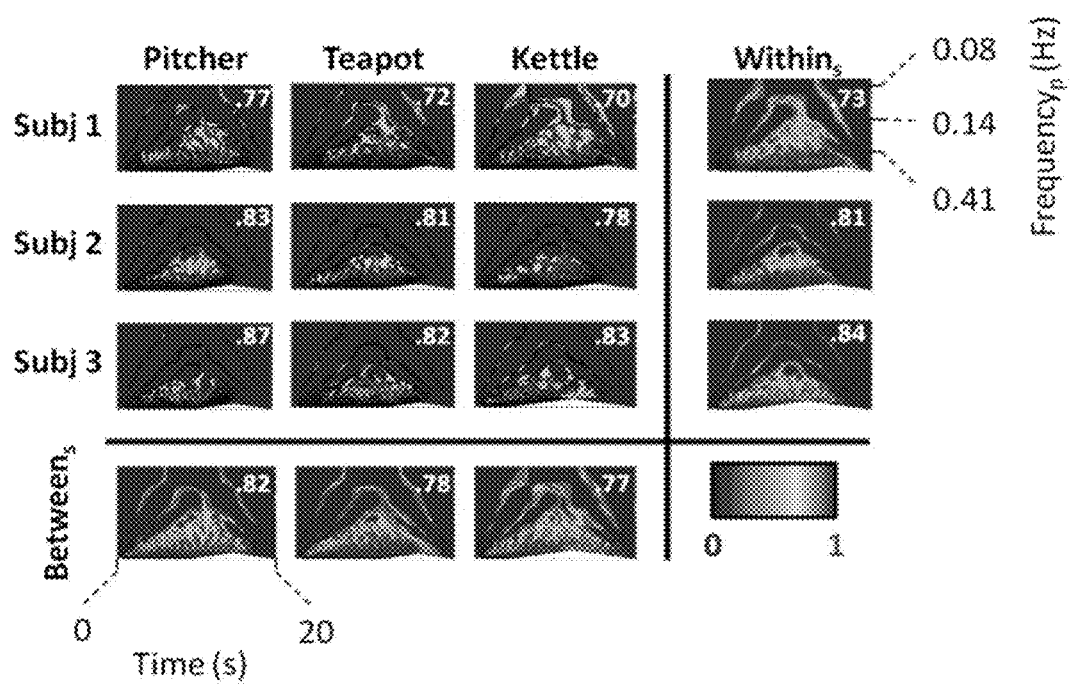

Figure 2-21. Wavelet coherence plots of the Euclidean norm. The mean phase difference across 8 movement repetitions is displayed for each subject utilizing one of three containers. At the end of the rows, all coherences per subject are averaged (Within). At the bottom of each column, all subjects are averaged for each container (Between). The warmer the color of a region, the lower the relative phase difference between the two signals. The full wavelet coherence is subsequently averaged to generate a single value ($\bar{C}$) displayed in the top corner of each plot.

Figure 2-22. Movements performed by participants (A) Starting position for each movement (B) sagittal (forward flexion) plane rotation (C) scapular plane rotation (D) frontal (abduction) plane rotation (E) external rotation and (F) internal rotation.

Figure 2-23. Scapular tracking device used for measuring scapula (shoulder blade) movement.

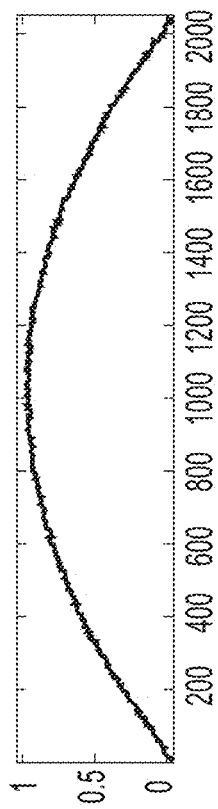
FIG. 24-A1
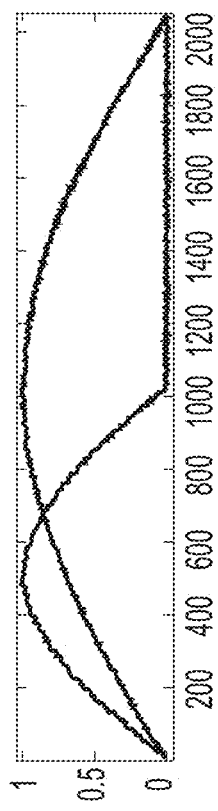
FIG. 24-A2
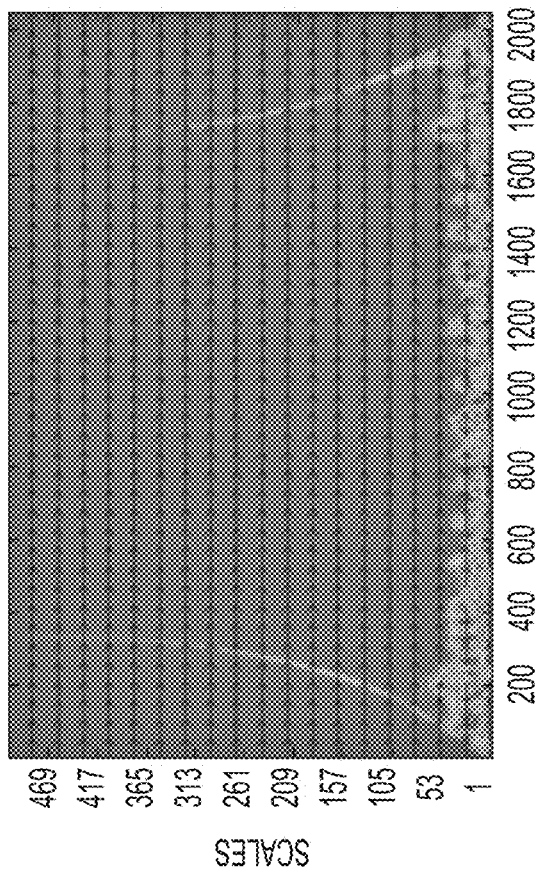
FIG. 24-B1
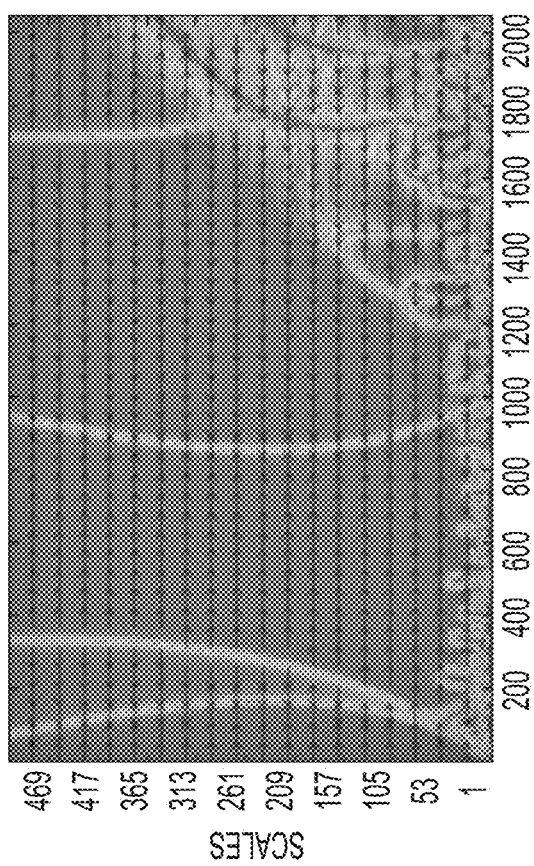
FIG. 24-B2

RANGE OF MOTION
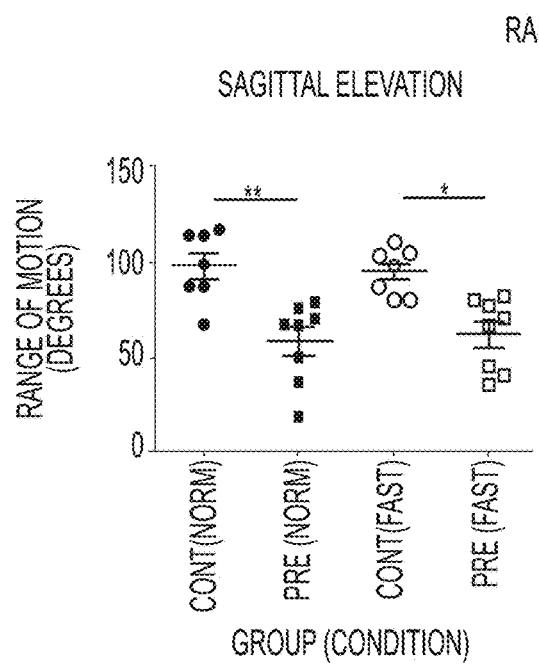
FIG. 25-A1
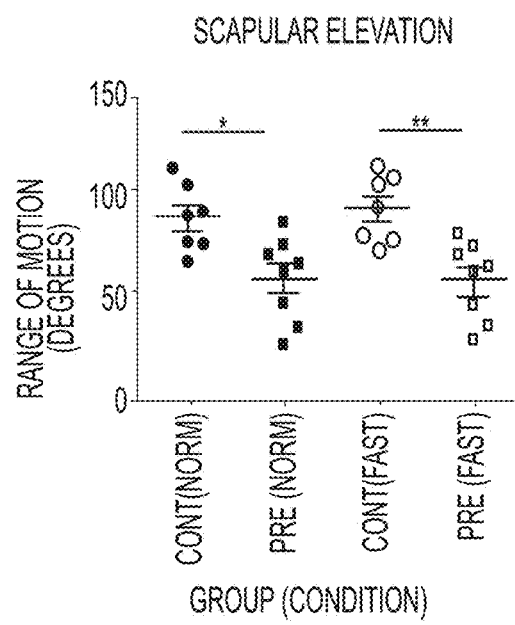
FIG. 25-A2
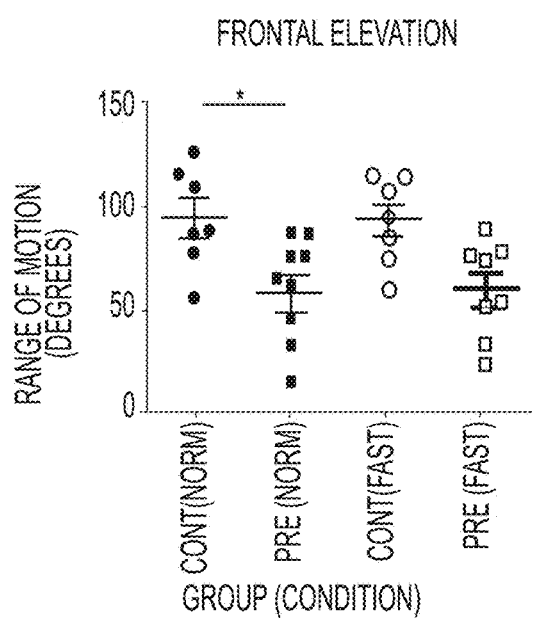
FIG. 25-A3
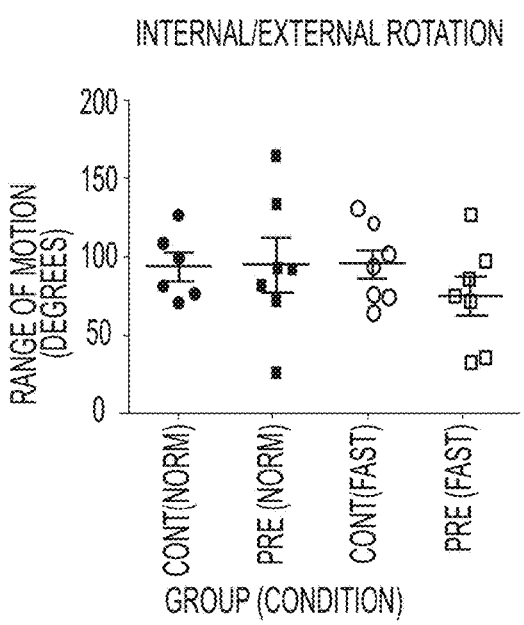
FIG. 25-A4

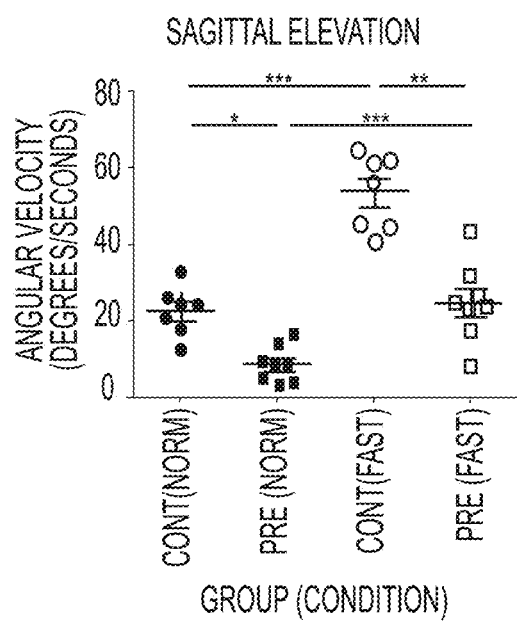
FIG. 25-B1
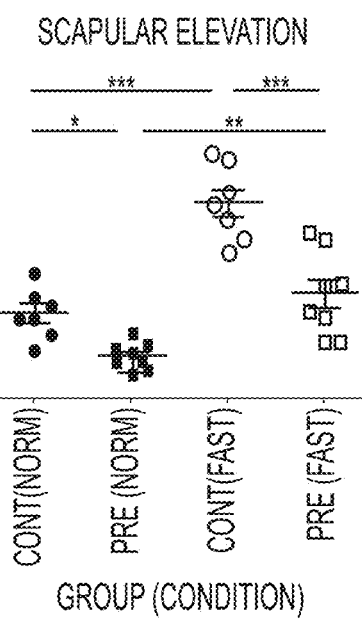
FIG. 25-B2
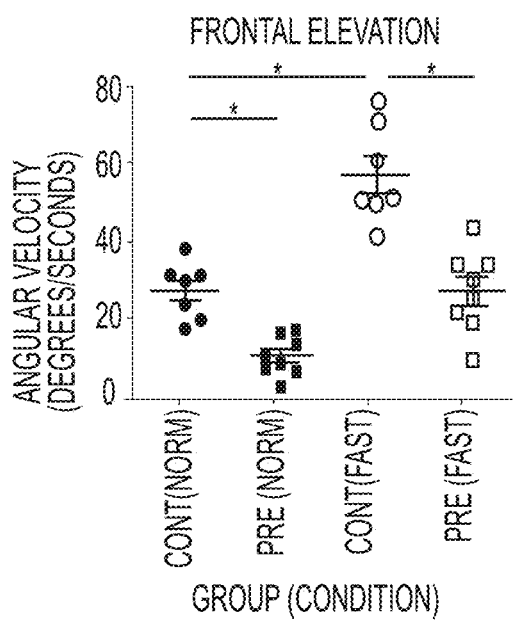
FIG. 25-B3
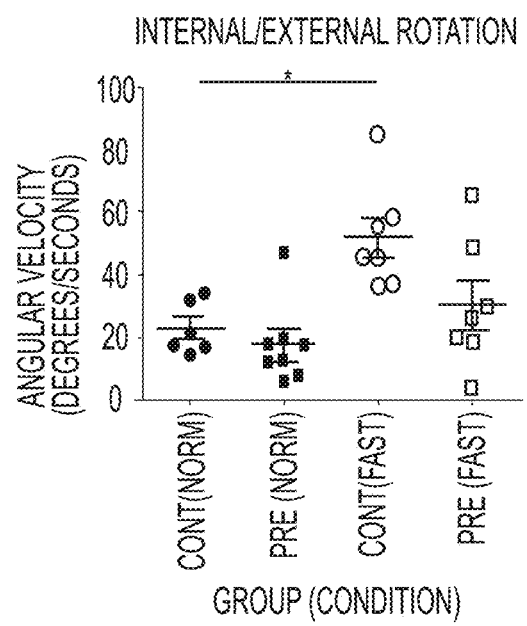
FIG. 25-B4

Fig. 28

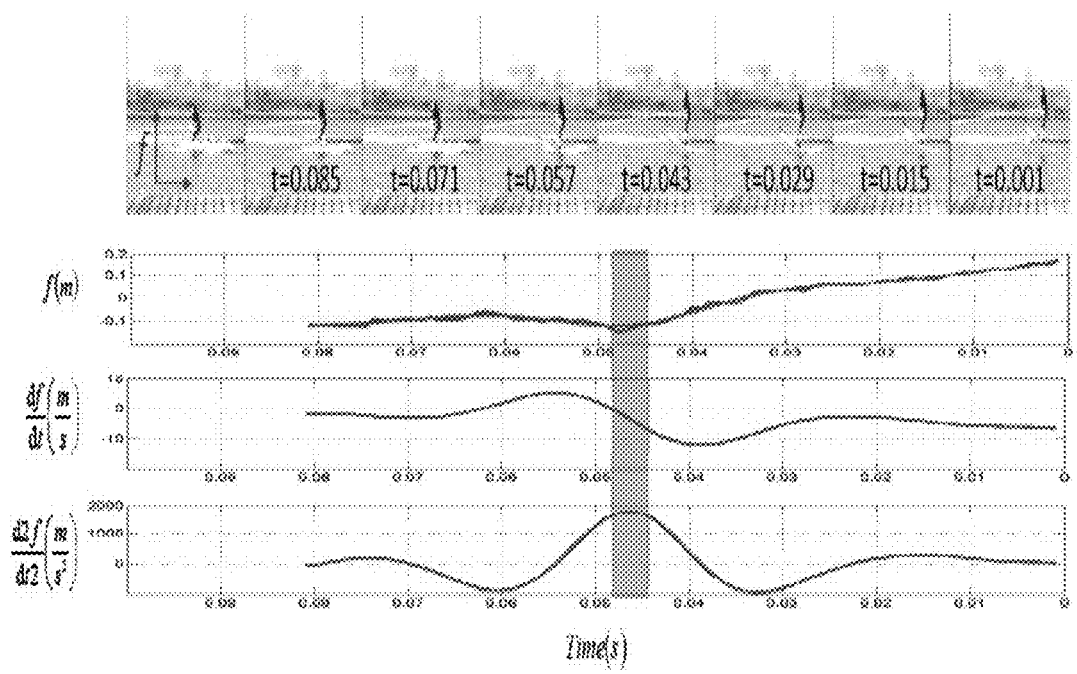

*Figure 2-27. The top row consists of the frames from the high frequency camera showing the landing of a skier entering from the right side of the frame. The subsequent plots show the position f of the ski binding and the two derivatives with m representing meters and s denoting seconds. The red line shows the data low-pass filtered at 50Hz, while blue lines show "non-filtered" data. Peak acceleration occurs during the initial landing period highlighted by the filled blue box.*

*Figure 2-28 Impact of water-skier on water. Mad denotes the total mass of the Skier, ma is mass of water that is being displaced, h is defined as the depth of The ski at the moment of cavity closure and A is the area of both skies.*

*Figure 2-29 Marker cluster placed on the wired accelerometer. The markers were used for the construction of a local coordinate frame*

*Figure 2-30. Experimental setup used including local (sensor based) and global coordinate frames.*

Fig. 32

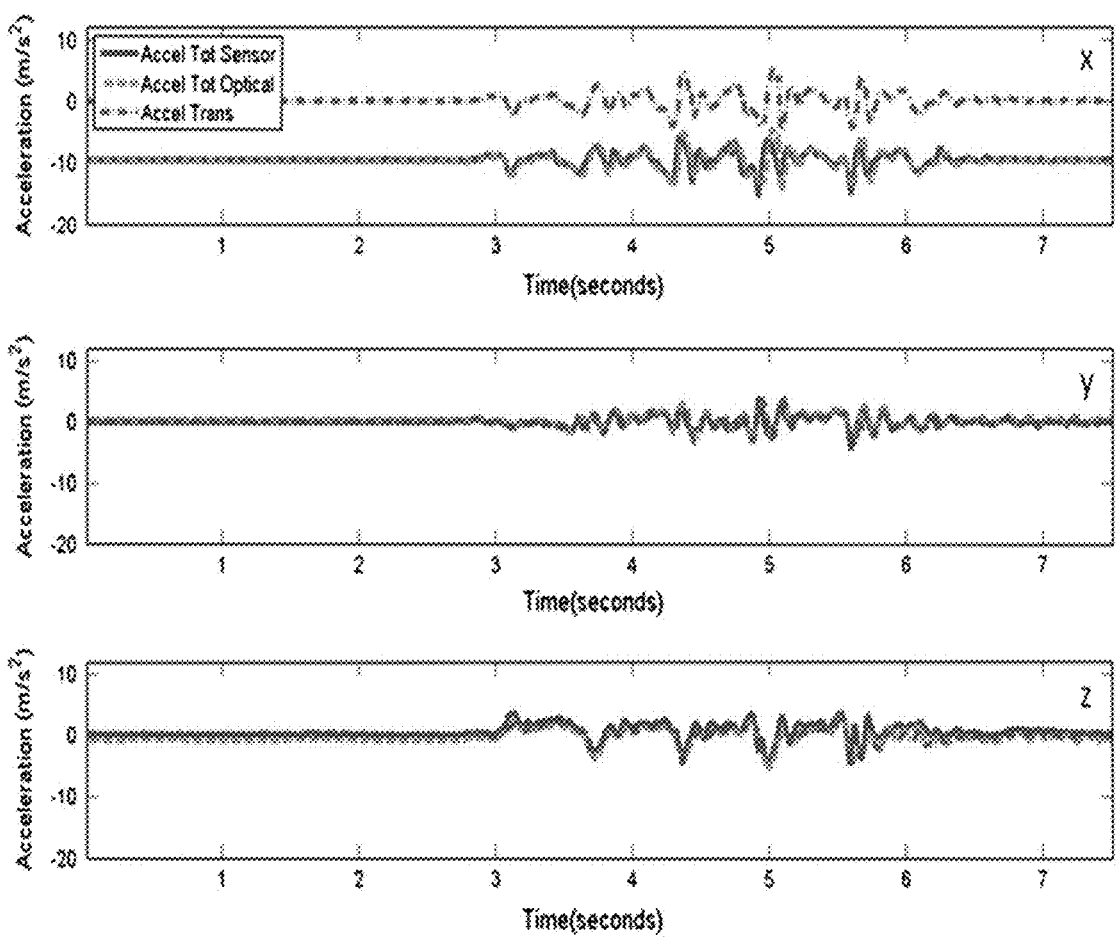

*Figure 2-31. Example data illustrating the acceleration trajectories obtained from the two measurement systems. Data were collected at the pocket during a walking trial. The total accelerations obtained from the sensor (Accel Tot Sensor) and optical tracking systems (Accel Tot Optical), as well as computed translational accelerations (Accel Trans) are shown for each axis (x, y and z).*

*Figure 2-32. Graph represents acceleration recorded from a sensor placed on the back. Data are shown for the x-axis only during a single walking trial. Graph B is the related power/frequency plot using a 3-second moving window.*

*Figure 2-33 Bland and Altman plots given for the total acceleration (Accel Tot), translational (Accel Trans) and gravitational (Accel Grav) acceleration per sensitive axis.*

Fig. 35

| Event | $f_m$ (x-axis) | | | | $f_m$ (y-axis) | | | | $f_m$ (z-axis) | | | |
|---|---|---|---|---|---|---|---|---|---|---|---|---|
| | Accel raw (Hz) | Accel trans (Hz) | Accel grav (Hz) | | Accel raw (Hz) | Accel trans (Hz) | Accel grav (Hz) | | Accel raw (Hz) | Accel trans (Hz) | Accel grav (Hz) | |
| Standing still | Back: 0.46 ± 2.58 Pocket: 9.97 ± 4.00 | Back: 2.35 ± 1.04 Pocket: 7.16 ± 0.98 | Back: 0.22 ± 0.18 Pocket: 0.19 ± 0.26 | | Back: 4.05 ± 2.80 Pocket: 3.70 ± 3.84 | Back: 6.78 ± 0.80 Pocket: 5.40 ± 1.74 | Back: 0.34 ± 0.29 Pocket: 0.21 ± 0.19 | | Back: 0.39 ± 0.61 Pocket: 1.11 ± 2.20 | Back: 6.44 ± 1.43 Pocket: 5.55 ± 2.22 | Back: 0.20 ± 0.15 Pocket: 0.10 ± 0.10 | |
| Walking | Back: 4.79 ± 1.44 Pocket: 5.45 ± 1.30 | Back: 5.27 ± 1.19 Pocket: 6.39 ± 0.89 | Back: 0.44 ± 0.33 Pocket: 0.62 ± 0.21 | | Back: 5.43 ± 1.17 Pocket: 4.04 ± 1.19 | Back: 7.04 ± 2.78 Pocket: 5.18 ± 1.23 | Back: 0.47 ± 0.18 Pocket: 0.41 ± 0.23 | | Back: 1.73 ± 0.48 Pocket: 0.83 ± 0.38 | Back: 1.85 ± 0.58 Pocket: 3.47 ± 0.88 | Back: 0.27 ± 0.15 Pocket: 0.44 ± 0.14 | |
| Stair ascent | Back: 1.68 ± 0.79 Pocket: 0.73 ± 0.44 | Back: 2.13 ± 0.50 Pocket: 2.07 ± 0.84 | Back: 0.39 ± 0.14 Pocket: 0.27 ± 0.09 | | Back: 0.97 ± 0.78 Pocket: 1.34 ± 1.35 | Back: 3.28 ± 1.29 Pocket: 4.36 ± 1.46 | Back: 0.38 ± 0.12 Pocket: 0.44 ± 0.22 | | Back: 0.63 ± 0.27 Pocket: 0.50 ± 0.54 | Back: 2.33 ± 1.00 Pocket: 3.44 ± 1.49 | Back: 0.37 ± 0.15 Pocket: 0.25 ± 0.12 | |
| Stair descent | Back: 3.15 ± 1.28 Pocket: 2.70 ± 1.35 | Back: 3.26 ± 1.00 Pocket: 3.97 ± 1.00 | Back: 0.24 ± 0.08 Pocket: 0.49 ± 0.26 | | Back: 3.54 ± 1.05 Pocket: 2.70 ± 1.87 | Back: 4.75 ± 1.49 Pocket: 4.61 ± 1.28 | Back: 0.39 ± 0.20 Pocket: 0.96 ± 0.20 | | Back: 0.82 ± 0.40 Pocket: 0.34 ± 0.14 | Back: 2.52 ± 1.44 Pocket: 4.69 ± 1.52 | Back: 0.25 ± 0.13 Pocket: 0.31 ± 0.10 | |
| ICC | 0.5350 | 0.8106 0.265 | 0.164 | | 0.3679 | 0.2334 | 0.0224 | | 0.2848 0.0448 | 0.2864 | 0.0001 | |
| ICC corrected | | | | | | | | | | | | |

*Mean median frequency (±standard deviation) over all subjects given for each sensitive axis and activity.*

*Figure 2-34. A depiction of the four tasks performed by the participants. Shown left to right: stand on two legs with eyes open (2LO), stand on two legs eyes closed (2LC), stand only on measured leg eyes open (1LO), stand only on measured leg eyes closed (1LC).*

*Figure 2-35. A subject wearing the ICSS garment and optical tracking markers*

*Figure 2-36. Stability values for the ICSS and optical tracking during 4 different activities. Red square refers to standing only on measured leg with eyes closed (1LC), pink diamond refers to standing on two legs with eyes open (2LO), green circle refers to standing only on measured leg with eyes open (1LO), and purple triangle refers to standing on two legs with eyes closed (2LC).*

*Figure 2-37. Depiction of auditory stroop task design. Stimulus is given over wireless headset into the left or right ear. If stimulus matches side it was delivered to ("left" delivered in left ear), the subject responds by shaking head up and down. If the stimulus does not match the side it was delivered to, the subject responds by shaking the head sideways.*

*Figure 2-38. Example of a scalogram of wavelet coefficients. The plot at the top shows the original yaw signal obtained from subject 1 during a cognitive loaded task. The bottom plot provides the percentage of energy for each coefficient depicted by a heat map that is shown on the side. Dotted green lines show identified crossings of the set threshold.*

Fig. 41

| Test dataset | Stimulus | Yaw | Pitch | Sum yaw and pitch | Tx | Tmx | $t_{onset}(s)$ | $t_{offset}(s)$ |
|---|---|---|---|---|---|---|---|---|
| 1 | 1 | 1 | 0.5 | 1.5 | 1 | 1 | 4.18 | 3.26 |
|   | 2 | 1 | 0.5 | 1.5 | 1 | 1 | 3.02 | 2.96 |
|   | 3 | 1 | 1 | 2 | 1 | 1 | 0 | 2.74 |
| 2 | 1 | 1 | 1 | 2 | 1 | 1 | 0 | 3.24 |
|   | 2 | 1 | 0.5 | 1.5 | 1 | 1 | 2.76 | 2.7 |
|   | 3 | 1 | 0.5 | 1.5 | 1 | 1 | 3.8 | 3.8 |
| 3 | 1 | 1 | 0.5 | 1.5 | 1 | 1 | 3.12 | 3.12 |
|   | 2 | 1 | 1 | 2 | 1 | 1 | 0 | 2.68 |
|   | 3 | 1 | 0.5 | 1.5 | 1 | 1 | 3.08 | 4.84 |
| 4 | 1 | 0 | 0 | 0 | 0 | 0 | | |
|   | 2 | 0 | 0 | 0 | 0 | 0 | | |
|   | 3 | 0 | 0 | 0 | 0 | 0 | | |
| 5 | 1 | 0 | 0 | 0 | 0 | 0 | | |
|   | 2 | 0 | 0 | 0 | 0 | 0 | | |
|   | 3 | 0 | 0 | 0 | 0 | 0 | | |
| 6 | 1 | 0 | 0 | 0 | 0 | 0 | | |
|   | 2 | 0 | 0 | 0 | 0 | 0 | | |
|   | 3 | 0 | 0 | 0 | 0 | 0 | | |

Figure 2-41. 62 Feature Characteristic Points

EARLY DETECTION OF NEURODEGENERATIVE DISEASE

CROSS-REFERENCE TO RELATED APPLICATIONS

This application is a continuation-in-part of U.S. patent application Ser. No. 15/431,283, filed Feb. 13, 2017, which claims the benefit of U.S. Provisional Application No. 62/294,435, filed Feb. 12, 2016, and which claims the benefit of U.S. Provisional Application No. 62/831,575, filed Apr. 9, 2019, the contents of all of which are incorporated herein in their entirety.

BACKGROUND

The present invention relates to techniques for the early detection of neurodegenerative disease.

Neurodegeneration is a progressive loss of neuron function or structure, including death of neurons, and occurs at many different levels of neuronal circuitry. In this thesis I discuss Parkinson's Disease (PD), the second most common neurodegenerative disease (NDD). PD is a devastating progressive NDD often with delayed diagnosis due to detection methods that depend on the appearance of visible motor symptoms. By the time cardinal symptoms manifest, 60 to 80 percent or more of the dopamine-producing cells in the substantia nigra are irreversibly lost. Although there is currently no cure, earlier detection would be highly beneficial to manage treatment and track disease progression. However, today's clinical diagnosis methods are limited to subjective evaluations and observation. Onset, symptoms, and progression significantly vary from patient to patient across stages and subtypes that exceed the scope of a standardized diagnosis.

The goal of this thesis is to provide the basis of a more general approach to study the brain, investigating early detection method for NDD with focus on PD. It details the preliminary development, testing, and validation of tools and methods to objectively quantify and extrapolate motor and non-motor features of PD from behavioral and cognitive output during everyday life. Measures of interest are categorized within three domains: the motor system, cognitive function, and brain activity. This thesis describes the initial development of non-intrusive tools and methods to obtain high-resolution movement and speech data from everyday life and feasibility analysis of facial feature extraction and EEG for future integration. I tested and validated a body sensor system and wavelet analysis to measure complex movements and object interaction in everyday living situations. The sensor system was also tested for differentiating between healthy and impaired movements. Engineering and design criteria of the sensor system were tested for usability during everyday life. Cognitive processing was quantified during everyday living tasks with varying loaded conditions to test methods for measuring cognitive function. Everyday speech was analyzed for motor and non-motor correlations related to the severity of the disease. A neural oscillation detection (NOD) algorithm was tested in pain patients and facial expression was analyzed to measure both motor and non-motor aspects of PD.

Results showed that the wearable sensor system can measure complex movements during everyday living tasks and demonstrates sensitivity to detect physiological differences between patients and controls. Preliminary engineering design supports clothing integration and development of a smartphone sensor platform for everyday use. Early results from loaded conditions suggest that attentional processing is most affected by cognitive demands and could be developed as a method to detect cognitive decline. Analysis of speech symptoms demonstrates a need to collect higher resolution spontaneous speech from everyday living to measure speech motor and non-motor speech features such as language content. Facial expression classifiers and the NOD algorithm indicated feasibility for future integration with additional validation in PD patients.

Thus this thesis describes the initial development of tools and methods towards a more general approach to detecting PD. Measuring speech and movement during everyday life could provide a link between motor and cognitive domains to characterize the earliest detectable features of PD. The approach represents a departure from the current state of detection methods that use single data entities (e.g. one-off imaging procedures), which cannot be easily integrated with other data streams, are time consuming and economically costly. Accordingly, a need arises for a non-invasive system to measure and integrate behavioral and cognitive features enabling early detection and progression tracking of degenerative disease.

SUMMARY

Embodiments of the present systems and methods may provide a non-invasive system to measure and integrate behavioral and cognitive features enabling early detection and progression tracking of degenerative disease.

For example, in an embodiment, a method for detection of neurodegenerative disease may comprise measuring functioning of the motor system, including measuring functioning of upper limb and shoulder movement, cognitive function, including measuring cognitive function during combined physical motion and speech, and brain activity of a subject during everyday life, wherein measuring functioning of the motor system comprises placing a wearable body sensor system on the subject, the wearable body sensor system to measure movements and object interaction of the subject in everyday living situations, the body sensor system comprising an Integrated Clothing Sensing System, an Inertial Measurement Unit, an optical marker tracking system, acceleration sensors, and a Hydrocele Geodesic Sensor Net, and gathering movement data with the wearable body sensor system, wherein measuring functioning of the cognitive function comprises gathering cognitive function data comprising everyday speech data gathered using an audio capture device, and wherein measuring brain activity comprises gathering brain activity data comprising neuronal signals obtained using an implantable probe comprising a microelectrode array of carbon nanotube connections between electronic circuitry and in-vivo human neural tissue; and determining, at a computer system comprising a processor, memory accessible by the processor, and computer program instructions stored in the memory and executable by the processor, the presence of an abnormal condition based on the gathered at least one motor system data, cognitive function data, and brain activity data of the subject, wherein analyzing the gathered motor system data comprises analyzing the gathered movement data to differentiate between movement conditions using wavelet analysis, and generating information indicating movement conditions, wherein analyzing the gathered cognitive function data comprises analyzing the gathered speech data for motor and non-motor correlations related to severity of the neurodegenerative disease data, including determining inability to control voice tone based on jitter of the speech data and determining lack of normal voice modulation based on shimmer of the speech data, and generating information indicating severity of the neurodegenerative disease and the measured motor and non-motor aspects; and wherein analyzing the gathered brain activity comprises analyzing the gathered neural oscillation detection data related to severity of the neurodegenerative disease, including determining spindles in the neural oscillation detection data based on a frequency spectrum of the neural oscillation detection data, and generating information indicating severity of the neurodegenerative disease; and outputting, from the computer system, information indicating severity of the neurodegenerative disease based on the generated information.

In an embodiment, a computer program product for detection of neurodegenerative disease may comprise a non-transitory computer readable storage having program instructions embodied therewith, the program instructions executable by a computer, to cause the computer to perform a method comprising receiving data measuring functioning of at least one of the motor system, cognitive function, and brain activity of a subject during everyday life, wherein measuring functioning of the motor system comprises placing a wearable body sensor system on the subject, the wearable body sensor system adapted to measure movements and object interaction of the subject in everyday living situations, the body sensor system comprising at least one sensor system selected from a group comprising an Integrated Clothing Sensing System, an Inertial Measurement Unit, an optical marker tracking system, acceleration sensors, and a Hydrocele Geodesic Sensor Net, and gathering movement data with the wearable body sensor system, wherein measuring functioning of the cognitive function comprises gathering cognitive function data comprising everyday speech data gathered using an audio capture device, and wherein measuring brain activity comprises gathering brain activity data comprising neuronal signals obtained using an implantable probe comprising a microelectrode array of carbon nanotube connections between electronic circuitry and in-vivo human neural tissue; and determining the presence of an abnormal condition based on the gathered at least one motor system data, cognitive function data, and brain activity data of the subject, wherein analyzing the gathered motor system data comprises analyzing the gathered movement data to differentiate between movement conditions using wavelet analysis, and generating information indicating movement conditions, wherein analyzing the gathered cognitive function data comprises analyzing the gathered speech data for motor and non-motor correlations related to severity of the neurodegenerative disease data, including determining inability to control voice tone based on jitter of the speech data and determining lack of normal voice modulation based on shimmer of the speech data, and generating information indicating severity of the neurodegenerative disease and the measured motor and non-motor aspects, and wherein analyzing the gathered brain activity comprises analyzing the gathered neural oscillation detection data related to severity of the neurodegenerative disease, including determining spindles in the neural oscillation detection data based on a frequency spectrum of the neural oscillation detection data, and generating information indicating severity of the neurodegenerative disease; and outputting information indicating severity of the neurodegenerative disease based on the generated information.

In an embodiment, a system for detection of neurodegenerative disease may comprise at least one of a wearable body sensor system, apparatus for gathering everyday speech data, apparatus for neural oscillation detection, and an electro-encephalogram apparatus, a processor, memory accessible by the processor, computer program instructions stored in the memory and executable by the processor to perform receiving data measuring functioning of at least one of the motor system, cognitive function, and brain activity of a subject during everyday life, wherein measuring functioning of the motor system comprises placing a wearable body sensor system on the subject, the wearable body sensor system adapted to measure movements and object interaction of the subject in everyday living situations, the body sensor system comprising at least one sensor system selected from a group comprising an Integrated Clothing Sensing System, an Inertial Measurement Unit, an optical marker tracking system, acceleration sensors, and a Hydrocele Geodesic Sensor Net, and gathering movement data with the wearable body sensor system, wherein measuring functioning of the cognitive function comprises gathering cognitive function data comprising everyday speech data gathered using an audio capture device, and wherein measuring brain activity comprises gathering brain activity data comprising neuronal signals obtained using an implantable probe comprising a microelectrode array of carbon nanotube connections between electronic circuitry and in-vivo human neural tissue; and determining the presence of an abnormal condition based on the gathered at least one motor system data, cognitive function data, and brain activity data of the subject, wherein analyzing the gathered motor system data comprises analyzing the gathered movement data to differentiate between movement conditions using wavelet analysis, and generating information indicating movement conditions, wherein analyzing the gathered cognitive function data comprises analyzing the gathered speech data for motor and non-motor correlations related to severity of the neurodegenerative disease data, including determining inability to control voice tone based on jitter of the speech data and determining lack of normal voice modulation based on shimmer of the speech data, and generating information indicating severity of the neurodegenerative disease and the measured motor and non-motor aspects, and wherein analyzing the gathered brain activity comprises analyzing the gathered neural oscillation detection data related to severity of the neurodegenerative disease, including determining spindles in the neural oscillation detection data based on a frequency spectrum of the neural oscillation detection data, and generating information indicating severity of the neurodegenerative disease; and outputting information indicating severity of the neurodegenerative disease based on the generated information.

BRIEF DESCRIPTION OF THE DRAWINGS

The details of the present invention, both as to its structure and operation, can best be understood by referring to the accompanying drawings, in which like reference numbers and designations refer to like elements.

FIG. 7 is an exemplary diagram of measure of interests.

FIGS. 11, 11CONT.-1, 11CONT.-2, and 11CONT.-3 are an exemplary flow diagram of a process for measuring cognitive processing during cognitive load tasks.

FIG. 12 is an exemplary diagram of how the wavelet coherence changes over a range of three sample wave patterns.

FIGS. 19 and 19CONT. are an exemplary diagram of positions of the hand in each direction (X, Y and Z) and Euclidean norm for every sequence (A, B, and C).

FIGS. 20-A1, 20-A2, 20-A3, 20B1, 20-B2, and 20-B3 are an exemplary diagram of traces of the hand computed using a two-linked segmental model.

FIG. 21 is an exemplary diagram of wavelet coherence plots of the Euclidean norm.

FIGS. 24-A1, 24-A2, 24-B1, and 24-B2 are exemplary diagrams of wavelet coherence based on two waves with different frequencies.

FIGS. 25-A1, 25-A2, 25-A3, 25-A4, 25-B1, 25-B2, 25-B3, and 25-B4 are exemplary diagrams of a maximum range of glenohumeral motion (A) and mean angular velocity (B) at the shoulder joint.

FIG. 28 is an exemplary diagram of frames from the high frequency camera showing the landing of a skier entering from the right side of the frame and plots showing the position f of the ski binding and the two derivatives with m representing meters and s denoting seconds.

FIG. 32 is an exemplary diagram of data illustrating the acceleration trajectories obtained from the two measurement systems.

FIG. 35 is an exemplary table of mean and median frequency over all subjects given for each sensitive axis and activity.

FIG. 41 is an exemplary diagram of

DETAILED DESCRIPTION

Figure 1:
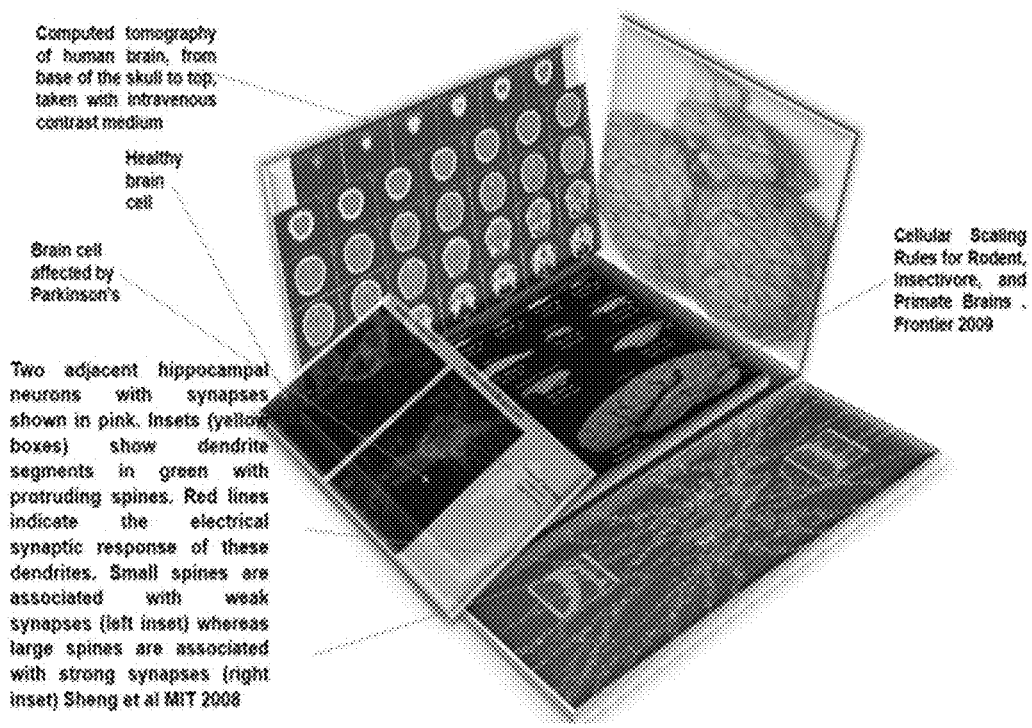
FIG. 1 is an exemplary diagram of animal and human models of PD using neuro-imaging techniques.

Embodiments of the present systems and methods may provide improved electronic stethoscopes that provide diversified diagnosis functionality. For example, embodiments may provide the capability to diagnose a wide range of pathologies by using the device's wireless network capacity to link it to wearable sensors of different kinds, maintaining the traditional use of the stethoscope while enabling it to sense a whole new set of physiological signals.

Section One: Introduction. This section presents an overview of PD and the current state of diagnosis and discusses the need for a new approach. It first describes current diagnosis, known biomarkers, and available treatments of PD and then discusses the deficiencies of detection methods and presents foundations for a new approach. The section concludes with the research statement and specific aims of the thesis.

Section Two: Approach. This section discusses measures of interest within three domains of the approach and the approach design.

Section Three: Methods. This section describes methods for data collection and analyses.

Section Four: Measuring Upper Limb Movement. This section presents testing and validating a BSN to measure arm movements:

Experiment 1: Testing a Body Sensor System to Measure Upper Limb Movements.

Experiment 2: Testing BSN to Measure an Everyday Task Using Continuous Wavelet Transforms. Experiment 3: Measuring Impaired Upper Limb Movements using Wavelet Analysis.

Section Five: BSN Engineering and Design. This section discusses hardware and engineering design criteria for everyday use and integration with everyday objects:

Experiment 4: Testing a Sensor Network to Measure Acceleration during Water-Ski Jumping.

Experiment 5: Comparison of Median Frequency between Traditional and Functional Sensor Placements during Activity Monitoring.

Experiment 6: Testing an Integrated Clothing Sensing System for Measuring Joint Stability.

Section Six: Speech and Movement—Measuring Cognitive Load. This section describes a cognitive load study where everyday tasks are performed simultaneously to measure attentional demand:

Experiment 7: Effect of Everyday Living Behavior on Cognitive Processing.

Section Seven: Everyday Speech and Motor Symptoms. This section looks at correlations between "everyday speech" and motor symptoms then discusses features of phonations and spontaneous speech:

Experiment 8: Examining Everyday Speech and Movement Symptoms.

Section Eight: Brain Activity. This section describes validation of a Neural Oscillation Detection Algorithm in pain patients:

Experiment 9: Neural Oscillation Detection.

Section Nine: Facial Feature Extraction—An Example of Machine Learning. This section presents a 2 part data analysis using machine learning:

Experiment 10: Sentiment Classification and Facial Feature Extraction.

Section Ten: Summary and Conclusions. The approach, aims, and empirical findings of the thesis are summarized and discussed. Plans for future work are briefly described.

ACRONYMS

ACC—Anterior Cingulate Cortex
ACT—Adaptive Control of Thought
AD—Alzheimer's Disease
ADAGIO—A Double-blind, Delayed-start Trial of Rasagiline in Parkinson's
ADL—Activities of Daily Living
ADP—Adenosine Diphosphate
AFR—Audio Affect Recognition
AHRQ—Agency for Healthcare Research and Quality's
AHTD—At Home Telemonitoring Device
AI—Artificial Intelligence
ALS—Amyotrophic Lateral Sclerosis
ANN—Artificial Neutral Networks
ANOVA—Analysis of Variance Software
AP—Anteroposterior
APOE—Apolipoprotein E
APP—Amyloid Precursor Protein
AR—Autoregressive
ARMA—Auto Regressive Movie Average
ASD—Autism Spectrum Disorder
ATP—Adenosine Triphosphate
AUC—Area Under Receiver Operation Characteristics Curve
BC—Brain Code
BDES—Berlin Database of Emotion
BDI—Beck Depression Inventory
BP—Bipolar Disorder
BPM—Backpropagation with Momentum
BSN—Body Sensor Network
CDR—Clinical Dementia Rating Scale
CEAM—Central Amygdala Medical
CGRP—Calcitonin Gene-Related Peptide
CNS—Central Nervous System
COM—Centre of Mass
COMT—Catechol O-Methyl Transferase Inhibitors
CSF—Cerebrospinal fluid
CSP—Common Spatial Pattern
CT—Computer Tomography
CWT—Continuous Wavelet Transform
DA—Dopaminergic
DAT—Dopaminergic Transporter
DBS—Deep Brain Simulation
DCR—Digital Camera Ready
DFA—Detrended Fluctuation Analysis
DLB—Dementia with Lewy Bodies
DNA—DeoxyriboNucleic Acid
DRAM—Dynamic Random Access Memory
DSM—Diagnostic and Statistical Manual
DT/AT—Deceleration time/acceleration time
DTI—Diffusor Tensor Imaging
ECMS—Ego-Centered Mind State
EEG—Electroencephalogram
EFNS—European Federation of the Neurological Societies
EMBS—Engineering in Medicine and Biology Society
EMG—Electromyography
EMNLP—Empirical Methods in Natural Language Processing
ER—Emotion Recognition
ET—Essential Tremor
FCP—Facial Characteristic Points
FCU—Fundamental Code Unit
FFT—Fast Fourier Transforms
FLMP—Fuzzy Logical Model of Perception
$f_m$—Median Frequency
fMRT—Functional Magnetic Resonance Imaging
FOG—Freezing of Gait
GLM—Generalized Linear Models
GMM—Gaussian Mixture Model
GPi—Globus Pallidus
H&Y—Hoehn and Yahr
HMM—Hidden Markov Model
HPC—Hippocampal
HNR—Harmonic-to-noise ratio
Hz—Hertz
IARPA—Intelligence Advance Research Projects Activity
ICAD—International conference on Alzheimer Disease
ICC—Intraclass Correlation Coefficient
ICSS—Integrated Clothing Sensing System
IEEE—Institute of Electrical and Electronics Engineers
IMU—Internal Measurement Unit
IND—Indeterminate
IQ—Intelligence Quotient
IWSF—International Waterski & Wakeboard Federation
kNN—K-Nearest Neighbors
L-DOPA—Levodopa
LDA—Latent Discriminative Analysis
LFP—Local Field Potential
LFPC—Log Frequency Power Coefficients LM—Levenberg-Marquardt
LM—Long-term Memory
LTD—Long-term Depression
LTP—Long-term Potentiation
LXIO—Language/Axiology Input and Output
MAL—Motor Activity Log
MAO-B—Monoamine oxidase B Inhibitors
mBSN—Multimodal Body Sensor Network
MDA—Mind Default Axiology
MDP—Markov Decision Process
ME—Measurement Error
MEG—Magnetoencephalography
MFCC—Mel Frequency Cepstral Coefficient
mg—Milligrams
MIMS—Monthly Index of Medical Specialties
MIT—Massachusetts Institute of Technology
ML—Mediolateral
MLPNN—Multilayered Perceptron Networks
MMSE—Mini Mental State Examination
mPFC—Medical Prefrontal Cortex
MRI—Magnetic resonance imaging
MSI—Mind State Indicator
NDD—Neurological Disorder
NE—Norepinephrinergic
NHR—Noise-to-harmonic ratio
NIMH—National Institute of Mental Health
NINDS—National Institute of Neurological Disorder and Stroke
NIRS—Near Infrared Spectroscopy
NLP—Natural Language Processing
NPT—NeuroPsychologyical Testing
NPT—Normal Pressure and Temperature
NSA—National Security Agency
OAR—Object-Attribute Location
PAG—Periaqueductal Gray
PARK—Gene Family (LRRK2, PARK2, PARK7, PINK', PLA2G6, SNCA, and UCHL1)
PCC—Pearson Correlation Coefficient
PD—Parkinson's Disease
PDQ—Parkinson's Disease Questionnaire
PEA—Phenylethlamine
PET—Positron Emission Tomography
PHNT—Plymouth hospitals NHS Trust
PIGD—Postural Instability Gait Difficulty
PPE—Measure of Fundamental Frequency Variation
PSEN-1—Presenilin-1
PSEN-2—Presenilin-2
PTSD—Posttraumatic Stress Disorder
RAM—Random Access Memory
REM—Rapid Eye Movement
RMSE—Root Mean Square Error
ROC—area under receiver operating characteristics curve
ROM—range of motion
RT—resting tremor
SFFS—Sequential Floating Forward Selection
SNR—Signal to Noise Ratio
SNRI—Serotonin and Norepinephrine Reuptake Inhibitors
SPSS—Statistical Package for the Social Sciences Software
STN—Subthalamic Nucleus
SUVR—Standard Uptake Value Ratio
SVM—Support Vector Machine
TBI—Traumatic Brain Injury
TD—Tremor Dominant
TRAP—tremor at rest, rigidity, akinesia or bradykinesia and impaired postural stability
UPDRS—Unified Parkinson's Disease Rating Scale
VIM—ventrointermediate nucleus of the thalamus Section One: Introduction The human brain, which has been referred to as a "three pound enigma," is considered the grand research challenge of the $21^{st}$ century (Collins and Prabhakar, 2013; Moffett, 2006). We understand the brain as a multidimensional, densely wired matter made of tens of billions of neurons, which interact at the millisecond timescale, connected by trillions of transmission points that generate complex output such as behavior and information processing. Neurons can send and receive signals up to $10^5$ synapses and can combine and process synaptic inputs to implement a rich repertoire of operations that process information (Baars and Gage, 2010; Laughlin and Sejnowski, 2003).

Throughout developmental stages and in adult life, the brain responds to experience by adapting communication via individual synapses (Greenough et al., 1993). In addition, new synapses can be generated, and existing synapses can regenerate or degenerate in response to experience, which can change the spatial pattern of neuron connections. This "plasticity" of synapses and networks is assumed to be the basis of learning and memory (Sheng, 2005). However, neuroplasticity is not only significant for learning and memory; changes in neural pathways and synapses can occur in response to external stimuli (Pascual-Leone et al., 2011). For example limb amputation, traumatic brain injury, neurodegenerative disease, and stroke can yield synaptic changes in order to adapt (Butz and van Ooyen, 2013).

Today neuroscience tools can only record the activity of a few neurons at a time making it difficult to comprehensively understand the human brain which consists of 50-200 billion neurons inter-connected by 100 trillion to 10 quadrillion synaptic junctions (Drachman, 2005). Over a century ago Santiago Ramon y Cajal, known to some as the father of modern neuroscience, said, "the brain is a world consisting of a number of unexplored continents and great stretches of unknown territory" (Barres, 2005). Despite scientific advances, we continue to question how the brain take patterns of light at the eye, sound at the ear, and touch on the skin to determine the properties of the surrounding environment? How does the brain yield emotion and sentiment manifested through expressions, patterns, symbols, and languages? How does the brain support adaptive behavior and produce complex articulated motor function? And how do these computations go awry in disease states?

As a point of departure, some research has attempted to reverse-engineer the brain as a computing system. For example, IBM and Stanford University researchers have modeled a cat's cerebral cortex with the Blue Gene/IP supercomputer, which currently ranks as the world's fourth most powerful supercomputer (Howard, 2012b; Hsu, 2009). Although this machine uses 144 terabytes of RAM the simulated cat brain runs about 100 times slower than a real cat brain. In fact, using just 30 watts of electricity (i.e., enough to power a dim light bulb), the human brains outperform the Blue Gene computer by a factor of a million (Hsu, 2009). Consequently, it is estimated that an artificial processor as smart as the human brain would require at least 10 megawatts to operate (i.e. the amount of energy produced by a small hydroelectric plant) (Howard, 2012b; Kety, 1957; Rolfe and Brown, 1997; Sokoloff, 1960).

Despite recent advances, the brain remains somewhat of a mystery and our understanding of its phenomena remains rudimentary. Over time, the scope of brain science has expanded to include several different approaches to study the functional, structural, molecular, and cellular aspects of the nervous system. Similarly the methods implemented by neuroscientists have also expanded to include microscopy, animal models, brain-imaging, recording electrical activity, and brain stimulation. Mapping the activity of brain function and dysfunction essentially means mapping the neuronal networks, which requires multilevel data from behavioural and cognitive output (Leergaard et al., 2012; Turner et al., 2013).

Better understanding of the human brain would lead to improved detection and treatment of brain dysfunction. Brain disorders are pervasive worldwide; it is estimated that neurological disorders, ranging from brain injury to autism to dementia affect one billion people globally (WHO, 2007). The US National Institute of Mental Health (NIMH) reports that 1 in 4 American adults suffer from a diagnosable mental disorder (NIMH, 2013; WHO, 2007). The Alzheimer's Association estimates that 5.4 million people in the US suffer from Alzheimer's disease (Thies and Bleiler, 2011). It is estimated that 10 million people suffer from PD worldwide, with one million cases the US alone and at least 60,000 new cases diagnosed each year (PDF, 2013). However, the true number of cases of PD is difficult to enumerate, because the disease is typically undiagnosed, misdiagnosed, or diagnosed when the disease has reached an advanced stage. As a result, the actual number of cases of PD is most likely much higher than these numbers suggest.

FIG. 1 illustrates an example of animal and human models of PD using neuro-imaging techniques. (Part of image reproduced from Herculano-Houzel (2009) and Sheng (2005).

Medical practitioners have long relied on clinical observation to diagnose diseases. However, this method is fundamentally subjective and cannot ensure early detection or effective monitoring of brain dysfunction, particularly before symptoms become evident (Belluck, 2013). Diagnosis of neurodegenerative disease (NDD) is often delayed because current detection methods depend on the appearance of outwardly observable symptoms. In contrast, a computational understanding and approach to neurological assessment might provide earlier diagnosis, greater reliability and less obtrusive technologies for monitoring the progression of NDD. NDDs are highly complex and usually feature many levels of symptoms and signs that are not immediately apparent; it is often a combination of factors that contribute to a diagnosis rather than a single indicator (Riess and Kruger, 1999; Sheikh et al., 2013). NDDs and cognitive impairments not only affect the systems of origin (the central nervous system), but also have direct effects on bodily activities and organ systems (Chaudhuri et al., 2006; Hu et al., 2011). For this reason, there exists a multitude of unexploited factors in neurological disorders that might be used to identify and classify diagnosis and treatment as well as aiding scientific comprehension. Many NDDs show similarity to one another. The similarities and relationships between these diseases offer an opportunity to validate diagnostic measurement for early detection and to develop treatment strategies for multiple diseases simultaneously. Neurodegeneration is a progressive loss of neuron function or structure including death of neurons, which occurs at many different levels of neuronal circuitry. In this thesis, I discuss Parkinson's Disease (PD) as one example of NDD, as it is one of the most devastating and currently incurable neurodegenerative diseases. PD diagnosis is often delayed or frequently misdiagnosed because current detection methods rely mainly on the appearance of overt motor symptoms (Barton et al., 2012; Calne et al., 1992; Jankovic, 2008; Meara et al., 1999; Tolosa et al., 2006). Studies have shown that most PD patients lose 60 to 80 percent or more of the dopamine-producing cells in the substantia nigra by the time symptoms appear (NINDS 2013). Early diagnosis is crucial to improve a patient's prognosis, as it allows for the ability to monitor and intervene at an earlier stage. At the moment, there is unprecedented interest in decoding brain activity to help researchers understand complex ailments (ranging from stroke to PD) that affect cognition. The majority of the research focuses on invasive techniques applied to explore cause and effects. This research is extremely important and has already brought many insights to brain function. However, relevant knowledge can also be gained by integration of brain and behavioral models of cognitive function (Park et al., 2001). This understanding follows from the fact that humans and their brains function in and are shaped by continuous interaction with their environments (Hari and Kujala, 2009). This requires a focus on human-environment interaction.

The approach presented here is an attempt to provide a more personalized approach to detection using data fusion from multiple sensors, preferably ones that are unobtrusive and easy to use in an everyday environment. The scope of my research has focused on detecting changes in 3 domains (motor system, cognitive function, and brain activity). Measuring movement, speech, and neural oscillations may provide a more general approach to early diagnosis of PD. Recent studies have shown that early movement impairments can provide insight into underlying neurodegenerative processes (Ghilardi et al., 2000; Mittal et al., 2010). The interaction between cognitive and sensorimotor functions is well established (Bonnard et al., 2004). Speech analysis has also emerged as a potential alternative to clinical tools to assess cognitive function (Rapcan et al., 2009; Rochford et al., 2012). Facial expression analysis has also been explored as a method for assessing motor impairment and emotional states (Bowers et al., 2006; Ekman, 1993; Jacobs et al., 1995; Katsikitis and Pilowsky, 1988; Kellner et al., 2003).

It is widely acknowledged that the brain itself evolved to control movement; on this premise our understanding of the brain should reflect measurements of human movement in everyday environments. Analyzing multiple information streams from multiple modalities may help us to better understand how afferent and efferent information is changing overall cognitive functioning. This approach can also benefit from including physiological measurements of brain activity (Ioannides, 2006; Ioannides, 2007).

The aim of this thesis is, therefore, to explore new methods for measuring changes in movement, speech and brain activity. It provides an overview of current work to develop unobtrusive methods for measuring movement, speech, and brain activity towards the broader goal of early detection and monitoring the progression of PD. With this long-term goal in mind, the next section will provide some background on PD.

Parkinson's Disease

PD is a chronic, progressive NDD usually found in patients over 50 years of age. PD is the most common form of Parkinsonism, a group of conditions that share similar symptoms. Symptoms and severity vary from patient to patient making diagnosis difficult. The classic triad of symptoms comprise tremor at rest, muscle rigidity and bradykinesia (slowing of all movements, particularly walking) (Barton et al., 2012; Calne et al., 1992; Fahn, 2003; Jankovic, 2008; Levine et al., 2003a; Meara et al., 1999; Pahwa and Lyons, 2010; Tolosa et al., 2006). Postural instability, grossly impaired motor skills and general lethargy are also common (Fahn, 2003; Jankovic, 2008). These symptoms are caused by the death of neurons in the substantia nigra pars compacta in the midbrain that control movement by releasing dopamine into the striatum of the basal ganglia; dopamine is a neurotransmitter that modulates neural pathways to select appropriate movements for individual circumstances (Erikson et al., 2009; Jankovic, 2008). Some studies have found that PD patients also exhibit abnormal production of the neurotransmitter norepinephrine (Kish et al., 1984; Vazey and Aston-Jones, 2012; Walsh and Bennett, 2001). Norepinephrine may be linked to non-motor symptoms of PD including fatigue, irregular blood pressure, and anxiety (Vazey and Aston-Jones, 2012; Walsh and Bennett, 2001).

Non-motor symptoms of PD are gaining more awareness, although more research is needed to better understand the onset, cause, and treatment. Often non-motor symptoms are under recognized and under treated in clinical practice (Hu et al., 2011). It is well documented that cognitive impairments and neuropsychological problems, such as depression, dementia-like symptoms, anxiety, hallucinations and excessive daytime sleepiness are associated with PD (Aarsland et al., 2004; Aarsland et al., 2007; Aarsland et al., 1999; Bottini Bonfanti, 2013; Chaudhuri et al., 2006; de la Monte et al., 1989; Hu et al., 2011; Jankovic, 2008; Riedel et al., 2008; Starkstein et al., 1989; Walsh and Bennett, 2001; Wertman et al., 1993). A substantial amount of evidence suggests that non-motor features, such as depression, constipation and fatigue, can predate the better-known somatomotor dysfunctions by as many as 20 years (Braak et al., 2003; Hawkes et al., 2010; Hu et al., 2011; Savica et al., 2010; Tolosa et al., 2006). Cognitive and behavioral changes are usually reflected in detectable changes in speech (Ooi et al., 2013a; Rahn Iii et al., 2007). Hence, speech impairments have been suggested as possible markers for PD detection and progression (Tsanas et al. 2011; Skodda, Gronheit, & Schlegel, 2012). Imprecise vowel articulation has been observed even in mild stages of PD (Skodda, Visser, & Schlegel, 2011) and commonly contributes to reduced speech intelligibility (Neel, 2008; Skodda, et al., 2011).

While there currently exists no way to reverse or stop the progression of the disease, it can be managed with a number of effective treatments. The most common treatment is pharmaceutical intervention using levodopa (L-DOPA), which is converted by surviving neurons into dopamine in order to compensate for the death of the other dopamine-producing cells (Barbeau, 1969; Fahn et al., 2004). Other neurochemical treatments include metabolic inhibitors, which act on cells in the basal ganglia to induce higher dopamine production, and dopamine agonists that have similar clinical effects to L-DOPA. As with many degenerative disorders, PD treatments tend to be most effective when the diagnosis is made early; therefore a high premium is placed on early detection (Shi et al., 2011).

Parkinson's Stages

PD presents a spectrum of motor and non-motor symptoms, with differing age of onset, and rate of progression (Burn et al., 2006; Calne et al., 1992; Chaudhuri et al., 2006; Fahn, 2003; Ferguson et al., 2008; Hawkes et al., 2010; Jankovic, 2008; Riess and Kruger, 1999; Savica et al., 2010; Tolosa et al., 2006). There is no confirmed disease trajectory common to all PD patients. Some begin experiencing symptoms before 40, called early-onset Parkinson's, while in other cases symptoms do not manifest until retirement age. In addition, onset and the severity of individual symptoms vary significantly among patients. For instance, some PD patients have severe tremor while others do not have tremor at all; often these are classified as tremor-dominant and non-tremor dominant (Fahn, 2003; Jankovic, 2008; Lewis et al., 2005b).

Braak et al. (2004) describe Parkinson's as a "multisystem disorder that involves only a few predisposed nerve cell types in specific regions of the human nervous system." Because the autonomic, limbic, and somatomotor systems become damaged as the disease progresses, the authors developed a staggered diagnosis system that acknowledges symptoms associated with the malfunction of each system. In stages 1-2, or the presymptomatic phase, the medulla oblongata/pontine tegmentum and olfactory bulb/anterior olfactory nucleus are the only brain regions that express pathology. In the third and fourth stages, pathological signs of Parkinson's spread to the substantia nigra and other nuclei of the midbrain and forebrain. Stages 3 and 4 encompass the period in which motor symptoms begin to develop. The length of the time from the presymptomatic phase to stages 3-4, when the common Parkinson's symptoms manifest, depends on many factors related to the disease. For instance, Jankovic (2008) shows that younger patients tend to experience significantly longer onset periods, approximately 15 years, whereas patients in the 50+ age group tend to experience symptoms more quickly. In stages 5 and 6, the final stages of PD, the disease affects the mature neocortex, and manifests itself in all its motor and cognitive dimensions, usually including dementia. This is generally considered the end-stage of PD, since it ends with death. Although the length of each stage of Parkinson's is generally dictated by factors unique to the individual, the stages tend to be separated by several years, ranging anywhere from 5 to 20 (Braak et al., 2004; Hawkes et al., 2010; Jankovic, 2008; Savica et al., 2010).

Zhao et al. (2010) use the Hoehn and Yahr (H&Y) scale to evaluate the timeline of disease progression. 1,500 PD patients were evaluated 3-6 times per month over a 2-3 year period. Zhao et al. found the following median transit times between H&Y stages:

Stage 1-2 transition: 20 months
Stage 2-2.5 transition: 62 months
Stage 2.5-3 transition: 25 months
Stage 3-4 transition: 24 months
Stage 4-5 transition: 26 months Factors contributing to faster symptom progression included older diagnosis age, longer disease duration, and high Unified PD Rating Scale (UPDRS) scores at the outset. This suggests that older patients are more vulnerable to dopamine deficiency while early-onset cases tend to be less severe. Their analysis showed that younger patients took much longer to progress from stage 2 to 2.5. Stage 2 was defined as patients with moderate difficulty balancing, and stage 2.5 was defined as patients who were slower to regain their balance than stage 2 patients. To explain the age-onset disparity they suggest that "in older-onset patients with PD, there are increased L-DOPA unresponsive axial motor disabilities that give rise to balance and gait disorders earlier in the course of the disease."

Lewis et al. (2005b) similarly find that Parkinson's is a highly heterogeneous disease. That is, the fundamental biological and chemical mechanisms associated with PD can cause a wide spectrum of symptoms to manifest. The authors evaluated 120 patients in terms of the severity of their symptoms using the Beck depression inventory (BDI) as a basis for measuring altered cognitive status and UPDRS to establish H&Y readings. They concentrated on demographic, motor, mood, and cognitive data based on UPDRS data collected from patients in early-stage PD, or the first 3 stages of the H&Y scale. Lewis et al. found a number of sub-categories of Parkinson's. First, patients with younger onset tended to have significantly slower progression, warranting their own class within PD patients. In addition, the study found several diagnosed tremor-dominant subgroups of PD patients who exhibited significant tremor but not the cognitive characteristics (including depression) associated with PD. A third subgroup consisted of PD patients who didn't suffer significant tremor, but still experienced cognitive impairment and depression. The final group did not experience cognitive impairment, but had the most rapid disease onset of the entire group.

Selikhova et al. (2009) also identified a number of subtypes in PD. Their study involved 242 pathologically verified PD subjects. They separated cases according to their disease onset, whether they were tremor-dominant, and whether the disease progressed with or without dementia:
- early onset: 60 (25%)
- non-tremor dominant: 87 (36%)
- rapid onset/no dementia: 20 (8%)

In particular, they found a strong association between cognitive impairment (depression and dementia) and non-tremor dominant diagnoses of PD. The group with the earliest (youngest) diagnoses tended to live longer over the course of the disease while delaying the onset of obvious PD symptoms, including tremor, falls, and cognitive impairment. Tremor-dominant patients, on the other hand, did not live longer than non-tremor dominant patients, and between them there was little difference in the onset of gait disorders and hallucinations. Rapid progression through the H&Y phases I-III was strongly associated with "older age, early depression and early midline motor symptoms, and in 70% of the cases, tremulous onset." Non-tremor dominant subgroups also showed significant neuropathological differences, such as "higher mean pathological grading of cortical Lewy bodies than all other groupings (P=50.05) and more cortical amyloid-b plaque load and cerebral amyloid angiopathy than early disease onset and tremor dominant groups (P=0.047)."

Diagnosis

Figure 2:
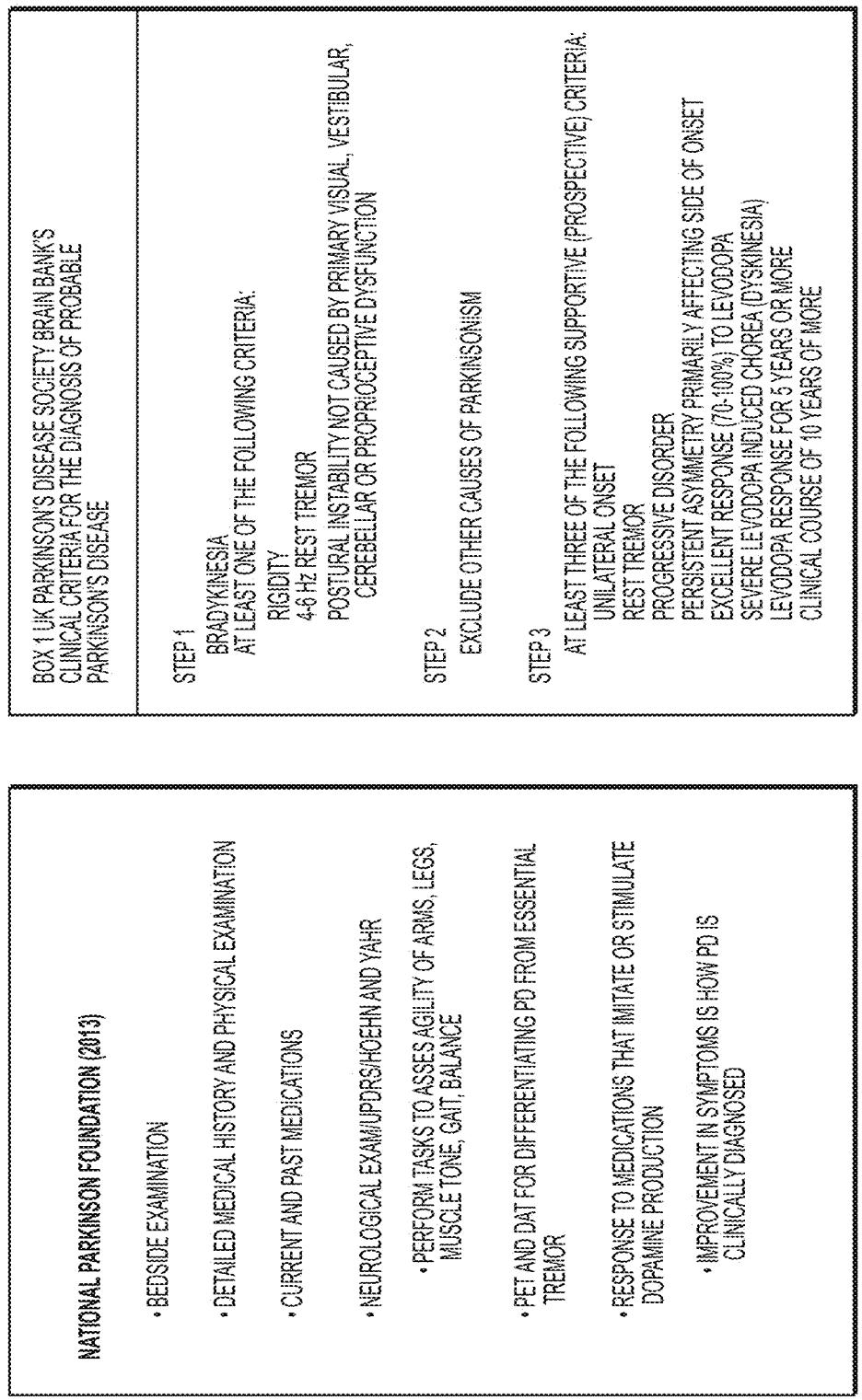
FIG. 2 is an exemplary diagram of two examples of criteria and procedures for clinical diagnosis of PD.

PD is most often diagnosed based on medical history and a neurological exam (Jankovic, 2008). Currently, there is no definitive test to diagnose PD until post mortem examination; instead the disease is diagnosed primarily based on clinical criteria, as illustrated in FIG. 2 (Jankovic, 2008). The cardinal symptoms of PD are abbreviated as TRAP; tremor at rest, rigidity, akinesia or bradykinesia, and impaired postural stability (Jankovic, 2008). Secondary motor features include freezing, hypomimia, dysarthria, dysphagia, and sialorrhoea. Diagnosis possibilities range from genetic tests, sampling cerebrospinal fluid to brain imaging (Barton et al., 2012; Sioka et al., 2010; Wu and Hallett, 2005). Brain scans are often used to rule out disorders that could present similar symptoms (Tolosa et al., 2006; Yekhlef et al., 2003). Physicians may confirm a diagnosis by giving patients L-DOPA and observing relief of motor impairments.

Lewy bodies are currently the gold standard for clinical confirmation of PD, which can only be established post-mortem (Calne et al., 1992; Gibb and Lees, 2008; Jankovic, 2008; Levine et al., 2003a). Lewy bodies are not exclusively associated with Parkinson's disease however, and in fact are related to several other forms of dementia (Hughes et al., 1992). Dementia with Lewy bodies (DLB) is, like PD, a progressive NDD, which fluctuates in severity, and is indicated by psychoses and extrapyramidal features rather than movement impairments. Furthermore, Lewy bodies are not always present in all types of PD. For example, post-encephalitic Parkinsonism is not associated with Lewy bodies, but current opinion suggests that any PD associated with dementia is likely to have Lewy bodies, because virtually all idiopathic PD will progress to dementia given enough time (Hughes et al., 1992).

FIG. 2 illustrates two examples of criteria and procedures for clinical diagnosis of PD. The Left box is from the National Parkinson Foundation; the right box is from Jankovic (2008).

Current Biomarkers

Although there is a wide range of PD detection measures, including blood tests, genetic tests, cerebrospinal fluid, and imaging, none of these are yet established as a Parkinson's disease biomarker (Bogdanov et al., 2008; Riess and Kruger, 1999; Shi et al., 2011; Stern et al., 1989). PD Biomarker studies are a growing area of research that holds promise for future developments of diagnosis, disease tracking, and drug discovery. Molecular, genetic and biochemical biomarkers of PD have been explored for targeted measures of specific substrates involved in the disease process such as cell restructuring, however the search for a validated biomarker continues.

Genetics

A few cases of PD seem to be hereditary and can be linked to genetic mutations, but there is also evidence that PD is more environmental than genetic. In the past few decades, a number of genes have been definitively linked to hereditary PD (Klein et al., 2009; Riess and Kruger, 1999). A minority of PD patients carry a Parkin or Synuclein gene mutation whose study may illuminate the pathophysiology of idiopathic PD. Other genes include SNCA, PRKN, LRRK2, PTEN, PINK', DJ-1, ATP13A2 (Riess and Kruger, 1999).

Klein et al. (2009) provide an algorithm for "PARK" genes for clinicians to better differentiate the range of diagnoses for inherited conditions that may also show signs of parkinsonism or resemble idiopathic PD. Bertoli & Avella et al. (2005) examined genetic biomarkers in patients with Parkin mutations. They identified 15 Parkin mutations in total. These included 10 exon deletion and 5 point mutations, i.e. splicing. Arg402Cys, Cys418Arg, IVS11-3CG, and exon 8-9-10 deletions were four new mutations found to correlate with PD incidence. Mutations with higher correlation spanned both homozygous and heterozygous mutation modes. Ultimately, the study found that patients with Parkin mutations tend to have an earlier onset of PD, as well as longer disease duration. These patients carried point mutations (splicing or missense) that contributed to the neurological disorder; however such patients are extremely rare. Nalls et al. (2011) performed a meta-analysis of genome-wide association studies. They newly identified five risk loci for Parkinson's (ACMSD, STK39, MCCC1/LAMP3, SYT11, and CCDC62/HIP1R).

Imaging

Prior to onset of clinical symptoms of PD, there are significant changes to the dopaminergic neurons of the mid-brain, yet these changes are not detectable with standard MRI; CT and MRI scans usually appear normal in PD patients (Brooks, 2010). Because the changes in the brain that cause Parkinson's take place on a chemical level, they are microscopic and therefore not visible using MRI. Macroscopic changes to the structure of the brain in PD are usually not apparent until later stages of disease progression, if at all. Nevertheless, MRI has shown some success for the differential diagnosis of idiopathic Parkinson's, atypical parkinsonism, multiple system atrophy, supranuclear palsy and other conditions (Stern et al., 1989; Yekhlef et al., 2003).

Fang et al. (2011) used the regional SVM ensemble to construct a predictive model for classifying MRI brain images indicative of PD. Highly discriminative regions in the MRI images they examined showed similar results as previous neuropathologic studies, which suggests significant potential as PD markers. Fang et al. (2011) separated the three-dimensional brain image into smaller regions of 20 cubic voxels, isolating local features in each possible orientation (sagittal, coronal, and axial). Features distinguishing PD patients from healthy controls included elevated ROC scores (area under receiver operating characteristics curve) in limbic areas such as the hippocampus, and was largely consistent with the results of prior detection methodologies.

Neuropathology and Voxel Based MRI Morphometry have been used to examine PD brains, but with contradictory findings. Menke et al. (2013) did not find Voxel-based morphometry and volumetry of subcortical grey matter to yield significant results for group differences. Although, they found that shape analysis was capable of detecting changes in the right pallidum in early PD patients. However, they acknowledge that the changes that take place in the subcortical grey matter outside of the substantia nigra are subtle, and therefore this technique would be difficult to use for early diagnosis. Menke et al. (2009) combined DESPOT1 imaging and Diffusor Tensor Imaging (DTI) to see characteristics of the Substantia nigra of PD patients versus controls. They found that the DESPOT1 method combined with DTI provided a clear visualization of the substantia nigra in PD patients and could potentially serve as a diagnostic tool for PD.

Available Treatments

Figure 4:
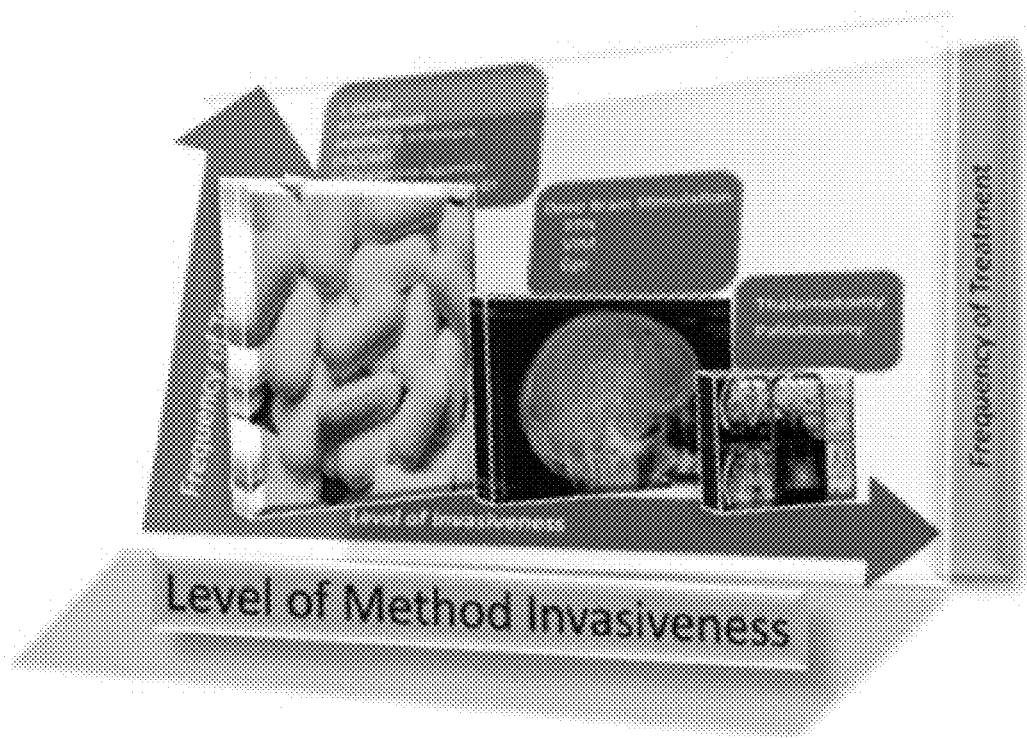
FIG. 4 is an exemplary diagram of a frequency of most common PD treatment and level of invasiveness.

Pharmaceutical intervention, namely Levodopa (L-DOPA) has consistently been the most common treatment of PD for decades (Jankovic and Aguilar, 2008; Levine et al., 2003b; LeWitt, 2008). FIG. 4 illustrates the frequency of the most common PD treatment options and level of invasiveness.

Levodopa (L-DOPA)

For more than 30 years L-DOPA has been the most widely used treatment for Parkinson's patients (Barbeau, 1969; Fehling, 1966; Foster and Hoffer, 2004). L-DOPA passes the blood brain barrier and is converted by surviving dopaminergic neurons and DOPA (decarboxylase) into dopamine needed to control motor movement. Neurons in the substantia nigra pars compacta in the midbrain store large amounts of decarboxylase to convert L-DOPA (Barbeau, 1969; Fehling, 1966). While it is the most effective drug treatment for Parkinson's to date, L-DOPA can have severe side effects, which become more apparent with long-term use, such as dyskinesias and motor fluctuations (Foster and Hoffer, 2004). Dyskinesia side effects include tics, writhing movements and dystonias, as well as occasional periods of time when the medication does not work at all. In addition, a patient's response to the medication may decrease over time, requiring increased dosages (Rascol et al., 2000). With higher doses side effects can worsen. L-DOPA is generally administered at a starting dose of 50 mg taken 3 times daily (LeWitt, 2008). Incremental increases in dosage are required up to a maximum of 1000 mg per day. However, there is significant controversy about how high the dosage should be, and when it should first be administered (Fahn et al., 2004; Foster and Hoffer, 2004). Often L-DOPA is combined with dopa decarboxylase inhibitors, such as Carbidopa, to prolong the effectiveness of treatment (Jankovic and Aguilar, 2008). To manage negative effects of L-DOPA, usually occurring after 5 years of use, a COMT inhibitor, MAO-I inhibitor or a Dopamine agonist inhibitor is added to treatment regimen (Jankovic and Aguilar, 2008). Because the efficacy of L-DOPA diminishes over time and causes motor fluctuations and dyskenias after a period of about 5 years dopamine agonists can be used in early stage as initial treatment until symptoms are severe enough to warrant use of L-DOPA (Caraceni and Musicco, 2001; Jankovic and Aguilar, 2008; Levine et al., 2003a). Dopamine agonists present side effects and benefits over L-DOPA, which still remains open to debate and is administered on a case by case basis (Factor, 2001).

Some research suggests that L-DOPA treatment should begin as soon as symptoms are detected claiming that the earlier the disease can be detected, and L-DOPA therapy is initiated, the more effective the treatment will be (Markham and Diamond, 1986). On the other hand, opponents of early administration of L-DOPA argue that the medication may be neurotoxic. Some studies suggest a dose-dependent decrease in neuronal activity and significant changes in neural morphology, but the mechanisms that cause this toxicity are still unknown (Du et al., 2009; Lipski et al., 2011; Scholz et al., 2008).

Surgery and DBS Treatment

There are three basic categories for surgical interventions in PD: (1) ablative procedures such as pallidotomy and thalamotomy, in which these regions of the brain are destroyed; (2) deep brain stimulation (DBS), in which a surgical device is implanted within the brain and emits electrical impulses at a set rhythm (See FIG. 3); (3) direct tissue transplantation (Arle and Alterman, 1999; Hallett and Litvan, 1999; Starr et al., 1998; Walter and Vitek, 2004).

Figure 3:
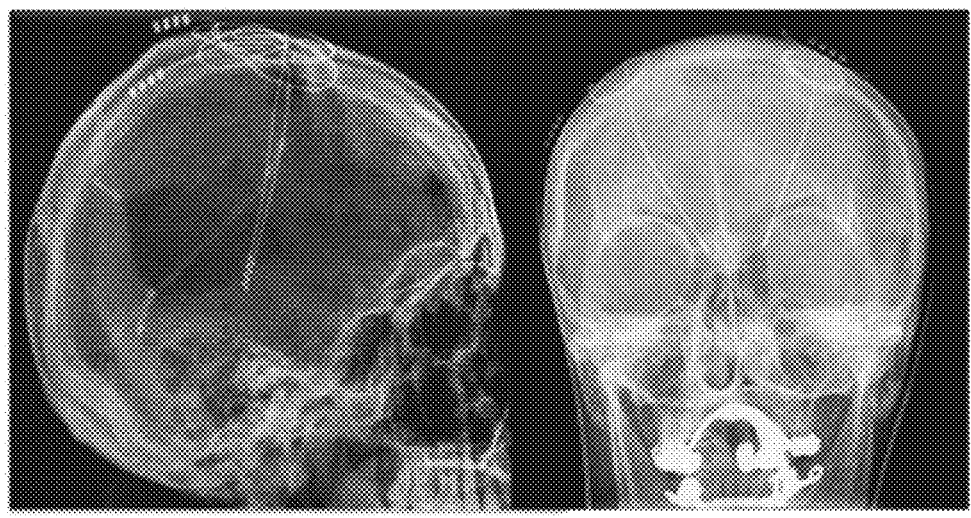
FIG. 3 is an exemplary diagram of a surgical device is implanted within the brain that emits electrical impulse treatment.

FIG. 3 illustrates an example of a surgical device implanted within the brain that emits electrical impulse treatment, which is considered a highly invasive treatment, image from MEMS 2010.

One of the primary objectives of ablative procedures is to reduce tremor and dyskinesia and other medicinal side effects in PD patients who have been treated with L-DOPA (Starr et al., 1998). Patients who undergo DBS surgery, particularly of the subthalamic nucleus (STN), often significantly reduce their L-DOPA doses. In one study, a pre-DBS mean of over 1000 mg of L-DOPA per day decreased to less than 450 mg to achieve the same effect on Parkinsonian tremor (Ardouin et al., 1999; Arle and Alterman, 1999; Hallett and Litvan, 1999; Starr et al., 1998). DBS also provides a means to record local field potentials from implanted electrodes, which may offer biomarkers of PD (Abosch et al., 2012).

During the 1980's, transplantation of neurons from one brain region to another, as well as fetal brain tissue transplants, gained popularity as a method for improving motor skills and gait issues caused by PD. Tissue transplant appears to be most effective in patients under the age of 60, but dyskinesia-related side effects are prominent (Freed et al., 2001). Transplant is now the least popular of the Parkinson's surgical regimes due to the ethical problems of finding suitable tissue and the limited efficacy so far achieved.

FIG. 4 illustrates an example of a frequency of most common PD treatment and level of invasiveness.

Need for Improved Detection

Neurodegenerative disorders are highly complex and usually feature multiple levels of symptoms and signs that are not immediately apparent. Often a combination of factors contributes to diagnosis rather than a single indication. There is a significant amount of evidence arguing that Parkinson's neurodegeneration process begins before motor symptoms manifest (Hawkes et al., 2010; Savica et al., 2010). The exact preclinical timeline remains unknown with findings ranging from 5 years to 20 years (Braak et al., 2004;

Savica et al., 2010). From autopsy examination of Lewy bodies, Fearnley and Lees (1991) suggest that the pre-symptomatic phase of PD is approximately five years. Other studies suggest that non-motor symptoms linked to PD, such as constipation and rapid eye movement sleep behavior disorder may occur up to 12 years prior to the onset of motor symptoms (Abbott et al., 2001; Fearnley and Lees, 1991; Schenck et al., 1996). Other symptoms such as anxiety and anemia may predate motor symptoms by 20 years or more (Bower et al., 2010; Fearnley and Lees, 1991; Shiba et al., 2000). Although these findings require further research to be conclusive, they highlight the possibility of diagnosis prior to the onset of visible, cardinal motor symptoms. Furthermore, these studies support a diagnosis method that accounts for non-motor symptoms. Current diagnosis of PD is clinical (Barton et al., 2012; Fahn, 2003; Jankovic, 2008; Meara et al., 1999; Pahwa and Lyons, 2010; Paulsen et al., 2013). Detection mainly relies on the appearance of outwardly observable motor symptoms, yet according to Braak et al. (2004) observable motor symptoms do not manifest until stages 3 & 4 of disease progression. Often the presence of dopaminergic neuron degeneration and discovery of Lewy bodies upon autopsy examination serve as confirmation that a patient had PD (Gibb and Lees, 2008; Jankovic, 2008). However, Koller's (1992) study found that Lewy bodies occur in 10% of normal, non-PD subjects over age 50, which further complicates PD diagnosis. In a 2003 AHRQ literature review, Levine et al. evaluated 59 studies, comprising 3,369 patients to review results of neuroimaging and other diagnostic tests for determining PD diagnosis. All methods showed inconclusive or insufficient evidence to determine PD diagnosis, except for 3:

Six autopsy studies provided evidence to support its role in confirming clinical diagnosis of PD.

Seven studies of olfactory function provided evidence for the ability to distinguish parkinsonism from healthy controls, but not to distinguish PD from atypical parkinsonism.

Three studies of PD test battery (including tests of motor function, olfaction, and depression) provided preliminary evidence suggesting usefulness in diagnosing PD, but long-term confirmatory studies are needed.

In addition to diagnosis, tracking the progression of PD is challenging. A recent systematic review of over 180 biomarker studies of PD progression concluded that there is "insufficient evidence to recommend the use of any biomarker for disease progression in PD clinical trials, which may simply reflect the poor quality of research in this area" (McGhee et al., 2013).

Many approaches to diagnosis rely on single-method evaluations such as fMRI and EMG (Rissanen et al., 2007). These methods, while somewhat effective on their own, suffer from two primary weaknesses (McGhee et al., 2013). First, each requires an independent analytical methodology. Second, these data are mutually exclusive, meaning that only limited measurements can be taken at a given time.

Undiagnosis and Misdiagnosis

Often PD is misdiagnosed or not diagnosed at all; it is claimed that there are possibly 20 undiagnosed cases of Parkinson's for every diagnosed case (Barton et al., 2012; Caine et al., 1992; Jankovic, 2008; Meara et al., 1999; Tolosa et al., 2006). In a population based study Schrag et al. (2002) found that as many as 15% of PD patients do not fulfill the clinical criteria for diagnosis, and as many as 20% are misdiagnosed or undiagnosed. Even then, diagnosis is highly subjective, mainly relying on clinical judgment of the severity of observable symptoms (Barton et al., 2012; Jankovic, 2008; Meara et al., 1999; Pahwa and Lyons 2010). An alternative approach is needed to measure the same factors observed in clinical based diagnosis, but in a significantly more standardized, accurate manner and earlier in the course of disease progression.

Benefits of Early Intervention

By the time motor symptoms present themselves, it is estimated that at least 60% of the dopamine-producing neurons within the basal ganglia are irrevocably lost (Pagan, 2012). With effective treatments, the potential benefits of early intervention in PD include slowing down progression, delaying and reducing both motor and non-motor symptoms, increasing patient quality of life and economic benefits of avoiding the long-term costs (Murman, 2012). Delayed treatment can lead to worse symptomatic deterioration and diminished quality of life (Fahn et al., 2004; Murman, 2012).

Despite the potential side effects, PD patients who are treated early with L-DOPA or dopamine agonists tend to do better long-term than those who have delayed treatment. Markham and Diamond (1986) followed effects of early L-DOPA administration in a group of 19 PD patients for 12 years. They concluded that symptom severity over time was due to the progression of the disease and not due to the medication. Over the course of the study, 32% of the group that began early L-DOPA treatment within 1-3 years of onset of symptoms died at a mean age of 76, whereas 50% (mean age 74.7) and 57% (mean age 71.5) died in the groups who started delayed treatment 4-6 and 7-9 years, respectively, after onset of symptoms.

It is possible that early treatment may have a neuroprotective or disease modifying effect. Early treatment has been shown to be effective in decreasing and slowing symptom progression. The clinical trial known as ADAGIO conducted a double-blind study to examine disease modifying outcomes of rasagiline (MAO-B inhibitor) in 1,176 early stage PD patients (Olanow et al., 2008). Medication was administered to an "early-start" group for 72 weeks and a "delayed-start group" for 36 weeks subsequent to 36 weeks of placebo. Over the course of the study, the early start group showed a better outcome and experienced fewer symptoms than the delayed start group. The early start group also had a lower rate of worsening UPDRS score (Olanow et al., 2009). Similarly, in a long-term study, Hauser et al. (2009) assessed the effectiveness of early rasagiline treatment in PD patients. Over a period of 6.5 years, the early start group showed improved UPDRS scores (mean 2.5 units) and slower progression of symptoms compared to the delayed start group.

Early intervention can improve the quality of life for PD patients and their caregivers by reducing symptoms and potentially slowing disease progression. Early stage PD patients not receiving treatment report significantly lower quality of life scores compared to patients receiving treatment (Grosset et al., 2007). Although controversial, surgical intervention such as DBS, has been used in early PD stages, as it can help prevent cognitive decline and motor symptoms from worsening (Groiss et al., 2009). It is clear that the earlier diagnosis can be established, the more treatment options there are available; the earlier treatment begins the more effective disease modifying outcomes may be (Fahn et al., 2004; Fehling, 1966; Hauser et al., 2009; Murman, 2012; Olanow et al., 2009).

Foundations of a New Approach

Although there is a wide range of detection possibilities including genetic tests, sampling cerebrospinal fluid, fMRI and medical imaging of the brain, clinical diagnosis remains the gold standard (Sioka et al., 2010; Wu and Hallett, 2005).

However, earlier detection of PD requires a methodology that can match the heterogeneous pathology and symptomology of the disease (Braak et al., 2004; Lewis et al., 2005a). Given the motor and non-motor features of the disease and complex timeline, I propose an approach that collects multiple data measurements during everyday living. My approach focuses on three broad domains: the motor system, cognitive function, and brain activity. Features from each domain can be measured quantitatively to link cognitive and behavioral indicators of disease.

Figure 5:
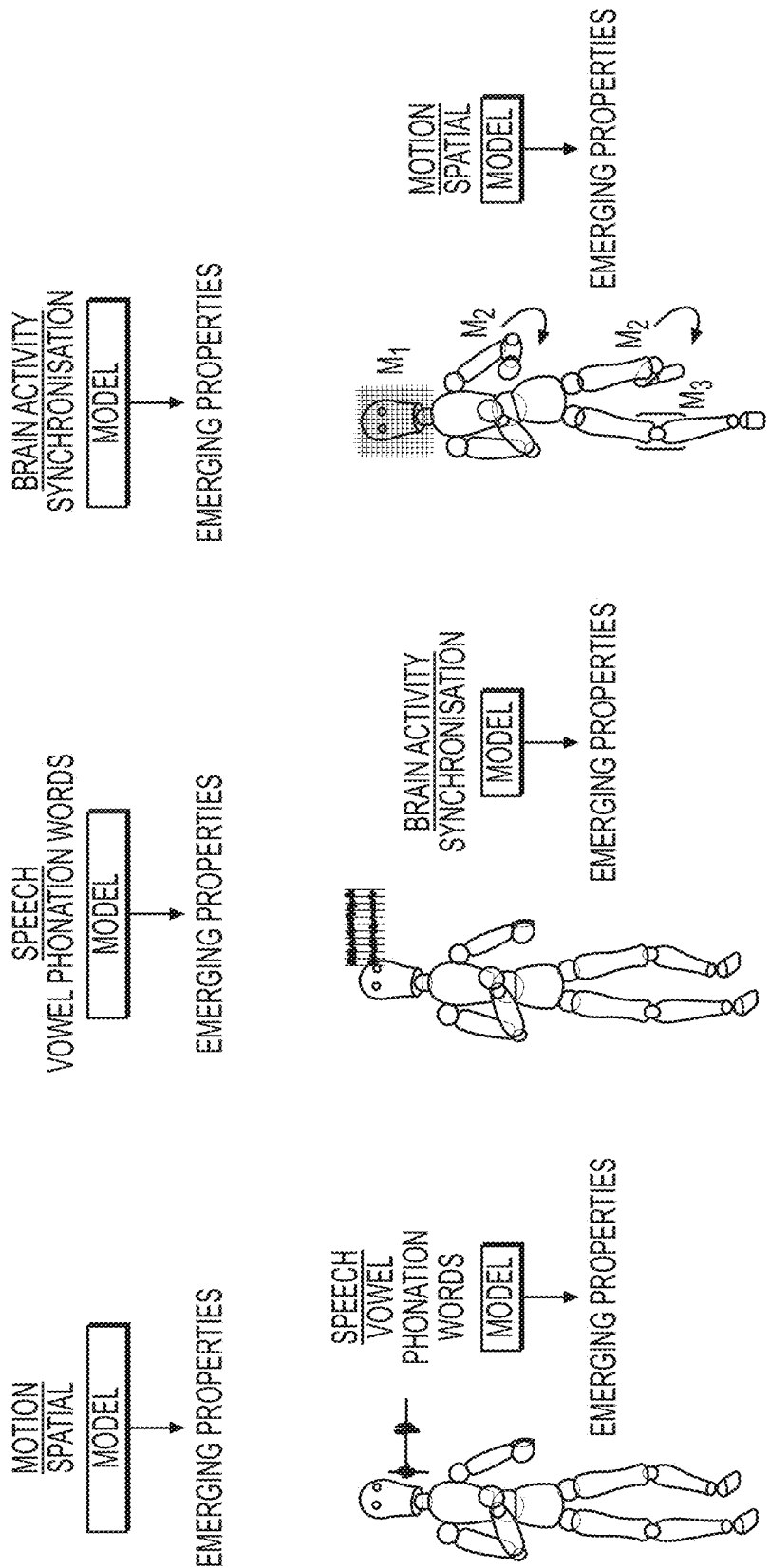
FIG. 5 is an exemplary diagram of an approach to measure emerging properties from parameters of 3 domains.

FIG. 5 illustrates an example of an approach is to measure emerging properties from parameters of 3 domains: the motor system, cognitive function, and brain activity. Measures of interest discussed in this thesis are facial expression ($M_1$) upper and lower limb movement ($M_2$) balance ($M_3$) speech and neural oscillations.

Motor Symptoms

The classic defining features of Parkinson's disease are motor symptoms. Although it is unclear exactly when motor symptoms manifest in relation to substantia nigra degeneration and onset of non-motor symptoms, it is evident that movement impairments are an important aspect of the disease. For example, although essential tremor is regarded as a different (cerebellar) disease it is a risk factor for PD. Likewise, postural tremor, arguably phenomenologically identical to essential tremor, can predate onset of other PD features by years sometimes decades (Shahed and Jankovic, 2007). Thus sensitive measurements of movement, as opposed to observation of outwardly visible motor symptoms, may provide valuable early data for diagnosis, disease progression, and symptom management.

Lower Limb

The locomotor system is inherently a dynamical system; the body has to cope with both external and internal perturbations. The extent to which we can correctly react to these perturbations is influenced by our anatomy, physiology, and motor control. In the case of Parkinson's, this ability can be directly affected by the disease process resulting in joint and skeletal deformities, which are often under-recognized (Ashour and Jankovic, 2006; Gnadingera et al., 2011). Joint and skeletal deformities are associated with severe stages of PD and after L-DOPA treatment (Ashour and Jankovic, 2006). However, joint deformity can be a subtle early sign of PD predating the development of other classical signs (Ashour and Jankovic, 2006).

Blaszczyk and Orawiec (2011) found anteroposterior (AP) and mediolateral (ML) sway ratios were notably increased in PD patients when compared to age-matched controls. Increased sway ratio is attributable to a progressive decline of postural stability control due to pathology of the disease. The cumulative effects of the impairments related to PD can be observed in increased stochastic joint instability attributable to changes in proprioception (Konczak et al., 2009).

Han et al. (2006) provide a number of useful biomarker variables in their study of gait and its relation to PD incidence. Specifically, they provide a rigorous twofold definition of gait, as "a cyclic movement of the feet in which one or the other alternate in contact with the ground, [whose essential measurable features] are equilibrium and locomotion, which are impaired in abnormal gait" (Han et al. 2006). Their study emerges from the spatiotemporal limitations that have arisen in advancing gait measurement technologies from the simple (ruler and stopwatch) to the more complex (video imaging systems for gait monitoring). But video imaging systems limit observation to small areas, and thus the amount of raw data available for analysis is limited.

Using tiny motion sensors allows a similar data resolution and offers a significant leap in quantity, since the sensors can be worn almost anywhere (Han et al. 2006). A number of gait segments were devised to classify quantitative metrics: stopping and moving, stance and swing phase, and positive peaks in acceleration. As a result, the authors devised a "general gait detection algorithm" using 3 dimensional acceleration measurements in the ankles of PD and non-PD patients. From the output of the general gait detection algorithm, "kinetic data" (speed, balance etc.) can later be extracted and analyzed (Ebersbach et al., 1999).

Niazmand et al. (2011) use "freezing of gait" (FOG) as a primary biomarker for PD, and constructed a detection regime based on wearable accelerometer-based sensors. "MiMed-Pants" were tested on 6 patients on two standardized walking courses, and FOG indications by the devices were corroborated by an attending physician. Using this method, the authors were able to attain an 85% accuracy rating compared against the physician's interpretation (Niazmand et al. 2011). Ghilardi et al. (2000) examined the role of visual feedback in reaching movements in PD patients who did not suffer from cognitive impairment. This study was based less on muscle memory than it was on the critical information supplied by the eyes when motor commands are issued. The authors found that while PD patients and controls did not differ significantly in terms of the Mini Mental State Examination (MMSE), grading their cognitive state, there were large variations in visual feedback (0.5 vs. 0.7 cm linear error) suggesting that visual data analysis is another important potential biomarker for PD. The cumulative effects of the impairments related to PD can also be observed in increased stochastic joint instability (Konczak et al. 2009). Obtaining accurate information about the changes in physical and cognitive function may allow for differentiation of PD from other neurodegenerative diseases.

Upper Limb

Previous studies have shown that Parkinson's patients exhibit irregularities in upper limb movement kinematics, such as linear speed and corrective movements (Dounskaia et al., 2009a; Dounskaia et al., 2009b; Isenberg and Conrad, 1994; Konczak et al., 2009; Sande de Souza et al., 2011; Tresilian et al., 1997). Further examination of the trajectories of the upper extremity could be useful not only for potential diagnostic value, but also because underlying brain processes may be influencing these motor function irregularities (Ray et al., 2009).

Twenty years ago Flash et al. (1992) investigated the characteristics of Parkinson's patients' upper arm trajectories. Their experiment consisted of confining the range of motion of the patients, so that shoulder motions took place only in the horizontal plane, and shining a "target LED" light source for the patient to follow with his/her arm. Measuring the acceleration time/deceleration time (DT/AT) ratio allowed the authors to develop velocity profiles for different patients performing different upper arm tasks. They reported a number of factors unique to PD patients. For instance, the velocity profiles of PD patients were "characterized by their lack of smoothness and the presence of multiple corrections" (Flash et al. 1992). Specifically, the mean reaction time for target movement was 346 ms for age-matched controls, but more than twice that (798 ms) for PD patients, who corrected their shoulder motions numerous times during the assigned tasks. Significant variation was also found in movement time, suggesting that patients with PD have a number of specific and unique motor tendencies. What is unclear, however, is the stage at which these aberrations become apparent.

Mittal et al. (2010) used video recording to collect movement data abnormalities from young adults with prodromal PD risk syndrome. A number of other measures were taken, including verbal comprehension, perceptual organization, auditory memory, and IQ, from each patient over the course of the experiment. The authors focused on upper-body movement aberrations, and found that dyskinesia correlated with higher levels of cognitive defects, such as early-stage psychotic disorders. While they gathered a broad spectrum of data, the IQ tests and auditory tests were not administered simultaneously, therefore the assessments were not conducted under consistent conditions. In addition, the study did not examine the potential causal links between each of the effects discussed and the levels of analysis at which they were addressed. This highlights the need for an unobtrusive data collection tool that simultaneously integrates cognitive state evaluation without significantly impeding the experimental progression.

Orofacial

Motor impairments do not only affect the upper and lower limbs. Rigidity (muscle stiffness) can affect the face, neck, trunk and shoulders (Ainhi et al., 2013; Riley et al., 1989). Orofacial motor control deficits can affect lips, jaw and tongue muscles (Abbs et al., 1987). Loss of control of facial expressions, expressionless face (also called stone face or "masked face"), and reduced blink rate are also symptoms of PD (Bologna et al., 2013; Gibb, 1988; Jankovic, 2008). Facial bradykinesia can impair spontaneous, emotional and voluntary facial movements in PD, which suggests basal ganglia dysfunction (Bologna et al., 2013). Rigidity and Bradykinesia can also impair swallowing causing excessive drooling and difficulty speaking (Factor and Weiner, 2002; Jankovic, 2008).

Speech and vocal impairments, such as tremor, jitter and difficulty swallowing are common in Parkinson's patients, more than 90 percent of Parkinson's patients experience speech impairments (Sapir et al., 2008). Speech and voice characteristics associated with PD include, reduced loudness, monoloudness, monopitch, hoarseness, imprecise vowel articulation, vocal tremor and excess jitter (Factor and Weiner, 2002; Sapir et al., 2008; Skodda et al., 2011).

Cognitive Function

Emotional and Psychological Problems

Current methods of PD diagnosis are limited to the observation of motor symptoms, yet it has been acknowledged that nonmotor symptoms commence long before the visibility of motor symptoms (Abbott et al., 2001; Bower et al., 2010; Braak et al., 2004; Fearnley and Lees, 1991; Hawkes et al., 2010; Shiba et al., 2000; Tolosa et al., 2006). Therefore, nonmotor symptoms may offer an opportunity for earlier diagnosis. Although PD is characterized by changes in physical movement, cognitive impairments and neuropsychological problems, such as depression and dementia-like symptoms, are often associated with PD (de la Monte et al., 1989; Jankovic, 2008; Starkstein et al., 1989; Wertman et al., 1993).

Most patients experience trouble with emotional control and dementia in early and later stages of the disease (de la Monte et al., 1989; Jankovic, 2008). A high incidence of feelings of apathy has been observed in early-stages of PD (Savica et al., 2010; Shiba et al., 2000; Walsh and Bennett, 2001). Various depressive states, including "depression, characterized by sadness, remorse, and lack of confidence," are also found to have a higher incidence in Parkinson's patients than in the general population. Hong et al. (2013) found that 30% of patients later diagnosed with Parkinson's exhibited depressive mind states and panic attacks well before motor symptoms began to manifest. Hong also found that the severity of depression did not appear to change or increase as the disease progressed, which suggests that these cognitive states are not a result of the patient's emotional reaction to having the disease, but are rather part of the disease itself Cognitive Decline In addition to depression, dementia symptoms are also common in PD (Aarsland et al., 2007; Barton et al., 2012; Burn et al., 2006). Some studies estimate more than 75% of PD patients have dementia (Aarsland et al., 2003). Symptoms of cognitive decline worsen with disease progression, but can occur in early stages, often prior to motor symptoms, these generally include impairment to sensory functions such as visual and spatial processing, memory, and control of conscious thoughts and emotions (Aarsland et al., 2003; Caballol et al., 2007; Sanchez-Ferro et al., 2012). Aarsland et al. (2004) measured the rate and predictors of change on the Mini-Mental State Examination in patients with PD. These changes were also compared with results from the examination taken by patients with AD and non-demented subjects. Results showed an average annual decline of 1 point for PD patients; in patients with both PD and dementia the average was closer to that of patients with AD who declined 2.3 points on average.

Pillon et al. (1991) compared severity and specificity of cognitive impairments in various neurodegenerative diseases, including Alzheimer's and PD. Their findings suggest that there are specific cognitive impairments distinguish patient groups when matched to specific cognitive deteriorations such as remote memory and linguistic disorders. They conclude that dementia itself is not homogeneous but requires further classification and division of cognitive impairment subtypes. Burn et al. (2006) found that a postural instability gait difficulty (PIGD) motor subtype of PD is associated with an increased rate of cognitive decline compared to tremor dominant (TD) or indeterminate (IND) subtypes of PD. In this subtype of PD, incident dementia occurs more commonly than in other subtypes. Emotions affect cognitive processes such as decision-making and language processing. This is clearly illustrated by the effect of positivity on mood and executive functions (Ashby and Isen, 1999; Mitchell and Phillips, 2007). Cognitive and emotional changes are often reflected in speech and discourse, and there has been a growing interest in the ability to exploit this for detection of various mood states and disorders. For example emotion recognition from acoustic variables and speech discourse (Lee et al., 1999) has been explored as well as detection of depression (Cummins et al., 2011; Low et al., 2011; Ooi et al., 2013a), bipolar disorder (Vanello et al., 2012) Alzheimer's disease (Thomas et al., 2005) and Parkinson's (Tsanas et al., 2012) from speech. By analyzing both speech production (e.g. frequency, tremor) and language content, it may be possible to identify biomarkers associated with different cognitive and neuropsychological functioning to develop models for detecting disease onset and tracking progression.

Cognitive Processing

Movement impairments in Parkinson's disease patients (PD) are worsened under dual-task conditions that require simultaneous performance of cognitive and motor tasks, such as walking, standing and sitting, gait and posture, when compared to healthy controls (Bavelier et al., 2006; Bond and Morris, 2000; Brown and Marsden, 1991; O'Shea et al., 2002; Rochester et al., 2004; Woollacott and Shumway-Cook, 2002). In order to maximize disease-related functional differences, multiple task paradigm activities commonly found activities of daily living (standing, moving, speaking) can be used to observe attentional demands of speaking, joint stability and arm trajectory to potentially quantify motor and cognitive decline.

Brain Activity

Neural Oscillations

Studying neural oscillations can provide a wealth of information about function and dysfunction in the human brain. Neural oscillations are periodic changes in neural activity in both repetitive and rhythmic waveforms. These oscillations play an important part in perception, cognitive function and motor function by allowing neuronal firing to become synchronized either locally or in distributed neural circuits (Llinas et al., 1998). Such rhythmic waveforms have demonstrated a link between neural synchronization and cognitive function (Fell et al., 2004). Changes in the frequency, amplitude, and character of neural activity are associated with performance of normal brain functions, including motor activities, audio and visual processing, and cognitive reasoning (Baker, 2007; Niedermeyer, 1997; Peelle and Davis, 2012). There is also evidence that the frequency of oscillatory wave activity may modulate states of conscious and unconscious brain activity (Madler et al., 1991). Many studies have suggested the potential value of recording neural oscillations to understand neurological disorders (Uhlhaas and Singer, 2010; Ward, 2003).

Studies on PD animal models and humans have found changes in firing rates, increased synchrony and abnormal oscillations in the basal ganglia, particularly the subthalamic nucleus (STN) and the globus pallidus (GPi) (Alonso-Frech et al., 2006; Hammond et al., 2007; Liu et al., 2002; Tachibana et al., 2011a; Tachibana et al., 2011b). Brain activity in PD has been characterized by excessive synchrony of neural oscillations in the beta frequency band (15-30 Hz)(Hirschmann et al., 2013; Moran et al., 2011; Weinberger et al., 2006). Beta oscillatory activity in the subthalamic nucleus (STN) has been found to be significantly increased in PD and linked to motor symptoms (Hirschmann et al., 2013). Dopaminergic treatment and DBS in the STN have been found to decrease beta band activity and alleviate motor symptoms (Weinberger et al., 2006).

The underlying mechanism of abnormal oscillations in PD is not yet fully understood. Silberstein et al. (2005) argue that the role of changes in the cortical synchronization that take place in the progression of PD is unclear. PD pathophysiology has moved away from explanations based on the firing rate of neurons, because it has been shown that more subtle temporal variations in neural activity strongly correlate with Parkinson's. To that end, Silberstein et al. (2005) studied the effects of oscillatory stimulation and pharmaceutical interventions in attenuating PD tremor by recruiting 16 patients. They found a striking similarity between the effects of 10-35 Hz stimulation and pharmaceutical interventions such as L-DOPA. Based on these results, it appears that dopaminergic therapy and STN stimulation both help to restore normal cortico-cortical interactions and to reduce tremor. The potential to reproduce the positive effects of pharmaceutical treatments such as L-DOPA with a stimulus that mimics the normal EEG is particularly promising because many undesirable side effects of drugs might be avoided (Sorensen et al., 2011; Wang et al., 1999). Thus, Silberstein's study is suggestive of a new clinical direction for a PD treatment that relies less on pharmaceuticals.

Research Statement

My research goal is to explore the development of non-invasive medical diagnostic methods with the long-term goal of enabling early detection of PD. Through the application of novel data collection methods and aggregation of multiple streams of simultaneous data, it may be possible to uncover new relationships and correlations between biomarkers, disease onset, and even treatment effectiveness. Such research may ultimately improve the early detection time and rate for PD.

This approach requires the development of tools and methods to collect and integrate multiple data streams from everyday living. The idea is to use computational techniques that can fuse complex behavioral and cognitive data to provide objective signatures, ones that best reflect emergent properties of neuronal systems measured across dimensions and at a high temporal resolution. Future work will combine information across multiple levels with data streams beyond the proposed sensors discussed in this thesis. A single integrated system would provide a tool that can measure across dimensions providing insight into emerging properties of the brain and detect early signs of PD before clinical diagnosis is currently capable of Aims of this Thesis My research focuses on foundations for a new, more general approach towards measuring global cognitive function non-invasively during everyday life. Methods capable of integrating multiple data streams into a single platform to measure brain function are still conceptual models at this stage and will require validation in future work. Instead, this thesis presents the initial development of tools and methods to non-invasively measure features of the motor system, cognitive function, and brain activity during everyday behavior as potential sensitive measurements of global cognitive function. This requires both validation of conceptual hardware and computational approaches.

The thesis describes preliminary validation of a class of tools and methods that build upon the idea of developing a single system that can link everyday behavior with cognitive function. While the full development of an unobtrusive system is a long-term goal, the aim of the current work is to validate body-worn sensor modules that measure movement and stability, with the future addition of audio, video and EEG units (see FIG. 6).

Figure 6:
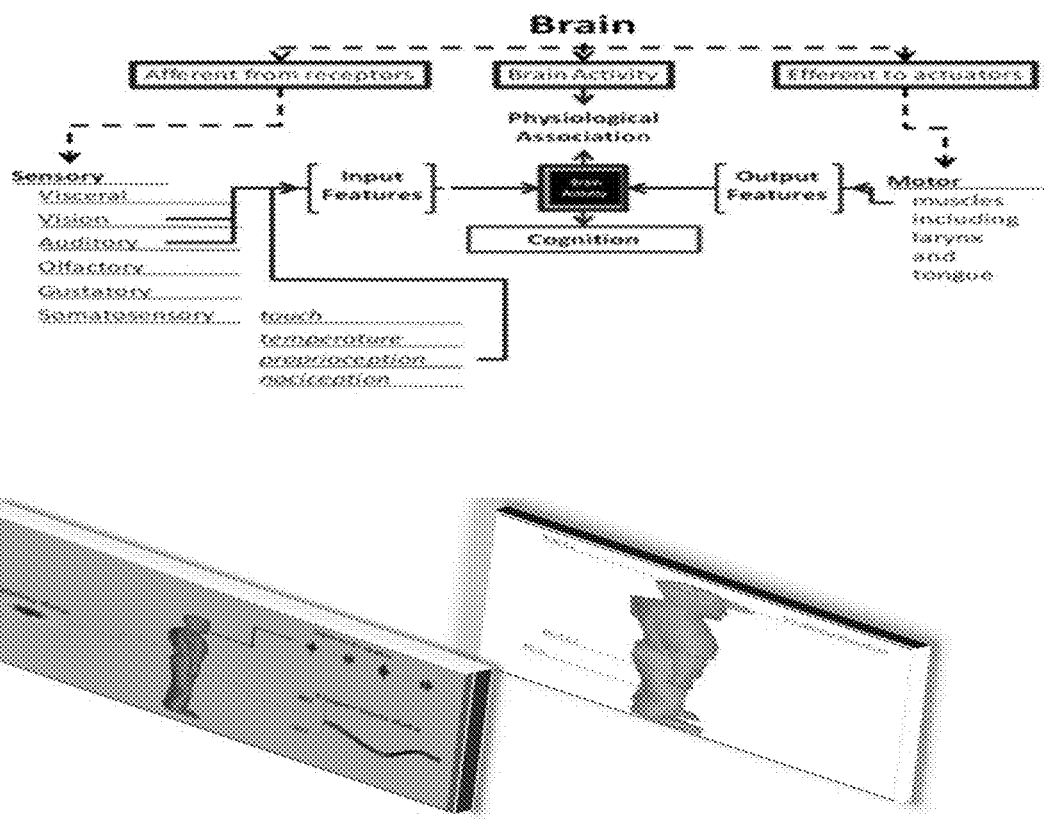
FIG. 6 is an exemplary diagram of IMU and ICS sensors to measure upper limb data and lower limb stability data.

FIG. 6 illustrates examples of IMU and ICS sensors to measure upper limb data and lower limb stability data. Video/Audio to measure speech data and facial expression will be added in future work. EEG is of interest to add in future work but requires further research and hardware development.

The Specific Aims of this Thesis

1. Test the accuracy of measuring upper limb movement with a body sensor network (BSN) against the gold standard optical system
2. Test if BSN system and wavelet analysis can be used to quantify user interactions with everyday objects
3. Test if wavelet analysis can be used to define spatial and temporal changes in shoulder motion between patients and controls
4. Test if BSN can measure acceleration under extreme conditions
5. Test if BSN can measure movement with functional placement
6. Test an Integrated Clothing Sensing System (ICSS) to measure joint stability
7. Explore to what extent combining everyday motion and speech tasks affect cognitive function
8. Explore correlations between speech and movement symptoms 9. Test if a biomarker found with in vivo recording can be detected in EEG recordings using the NOD algorithm; and determine the minimal number of electrodes required.

10. Test emotion classification and facial feature extraction using machine learning algorithms.

Section Two: Approach

Behavioral biomarkers are a broad category of measures that clinicians and researchers can use to detect diseases and disorders. PD exhibits both cognitive and motor symptoms; clinical tools need to address both in order to offer a thorough diagnosis. Behavior is defined as the internal responses (actions or inactions) to internal and/or external stimuli, excluding responses understood as developmental changes (Levitis et al., 2009). With that in mind it is important to take into account a system's synergy. The interaction of multiple elements in a complex biological system requires the measurement of a minimum subset of the elements. The selection of elements to describe behavioral biomarkers comes from the logical reasoning that behavior perceived by humans relies mainly on interpretation of movement and posture (motor system) as well as speech and language. Therefore, these two systems form an important set of modalities of interest in terms of behavioral biomarkers. In addition, it is known that these components arise from neural electrical activity. The approach is therefore based on measuring features from 3 domains: (1) motor system (2) cognitive function and (3) brain activity. This approach aims to provide a better understanding of how global cognitive function and everyday behavior are linked for the purpose of detecting PD. This section describes the overall approach and gives an overview of neural and clinical measures included in the current work and measures of interest for future work. Measures of interest in the motor system domain are upper limb movements, knee joint stability, facial expression, and components of speech production. Measures of interest in the cognitive function domain are language and facial expression. Measures of interest in the brain activity domain are neural oscillations. FIG. 7 illustrates the three domains, within which are the specific measures of interest discussed in this thesis. Measuring non-intrusively and during everyday life are the points of departure for the approach and methods to be developed from.

FIG. 7 illustrates an example of a measure of interest discussed in this section and its associated domain. Notice facial expression is a potential measure of the cognitive function domain, while facial features are a potential measure of the motor system. Speech production is a potential measure of the motor system domain, while language is a potential measure of cognitive function.

Neural and Clinical Measures of Interest

The Motor System

Upper limb trajectories, or arm motions made towards a specific goal such as picking up a stationary object, are of particular interest to PD research (Flash et al., 1992; Ghilardi et al., 2000; Plotnik et al., 1998; Tresilian et al., 1997). Studies have shown that Parkinson's patients exhibit impaired postural coordination and irregularities in upper limb movement kinematics, such as abnormal hand trajectories, decreased linear speed and increased corrective movements when compared to healthy controls (Dounskaia et al., 2009a; Dounskaia et al., 2009b; Isenberg and Conrad, 1994; Konczak et al., 2009; Sande de Souza et al., 2011; Tresilian et al., 1997). Some research suggests the role of the basal ganglia in impaired upper limb kinematics (Berardelli et al., 2001; Moisello et al., 2011) while other findings indicate impaired function of the dorsolateral pre-frontal cortex (Dayan et al., 2012; Ghilardi et al., 2000). Bradykinesia, a general slowness of movement, is a cardinal symptom of PD and a distinctive feature of basal ganglia disorders (Berardelli et al., 2001; Isenberg and Conrad, 1994; Jankovic, 2008). The onset of bradykinesia is usually characterized by slow movement and reaction times, particularly during activities of daily living that require fine motor control (Berardelli et al., 2001; Jankovic, 2008).

Upper limb movement, particularly of the hand and wrist, is involved in everyday tasks requiring fine motor control. The ability to quantify interactions with the environment, especially human-object interactions, would offer a valuable measure of motor control. Slight changes in motor function, such as slowing of movements as in the case of bradykinesia in PD, may go unnoticed at first, but a sensitive measurement device could detect these changes before they are apparent (FIG. 8).

Upper limb movement is not just based on the anatomical properties of the arms; more precise motor control is also necessary. Movements are controlled by the brain and communication deficits between the musculoskeletal and nervous system lead to changes in motor behavior. Even in the earliest stages of life, spontaneous movements differ between premature infants with brain injuries and those without (Ohgi et al., 2008). Motor patterns also change during our life span and changes are likely to relate to the development of neural mechanisms that underlie the control of the arm and hand (Zoia et al., 2006).

Figure 8:
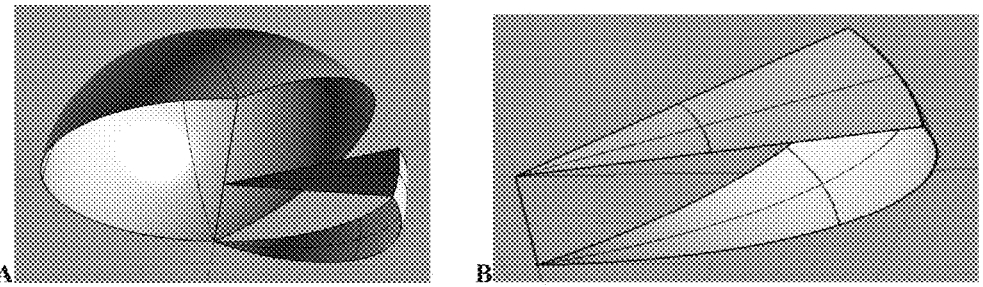
FIG. 8 is an exemplary diagram of an abstraction of 3D movement space.

FIG. 8 illustrates an example of Abstraction of 3D movement space. (A) Example of "normal" movement space of an individual. (B) Example of restricted space due to loss of certain functions.

Further examination of upper limb movement is of great interest for potential detection value, especially because underlying brain processes influence these motor functions and irregularities (Ray et al., 2009). However, deeper analysis of these processes requires a broad collection of unconstrained movement data (Bonato, 2005). Upper limb studies, such as (Dounskaia et al., 2009a), are mainly concerned with two sets of two-dimensional values: the position of the object where the subject was instructed to point, and the position of the patient's finger (i.e., pointing at the object). Many studies only measure the result of movement tasks; instead a method capable of measuring everyday movement trajectories with more fine-grained detail in three spatial dimensions (x,y,z) is needed.

Knee Joint stability

PD patients experience impairments in postural stability, balance, gait, standing, and joint and skeletal deformities (Blaszczyk and Orawiec, 2011; Han et al., 2006; Konczak et al., 2009). Essential to all motor tasks is the ability to maintain and restore postural and joint stability (Mayagoitia et al., 1996). Knee impairments have been observed in PD patients as part of gait impairment, postural stability, and isokinetic knee strength (Nocera et al., 2010; Rosin et al., 1997). Therefore measuring knee-joint stability can indicate impairments in postural stability, balance, and joint and skeletal deformities (Nocera et al., 2010). Postural stability is an essential part of functional mobility necessary for maintaining purposeful activities during everyday living (Bergmann et al., 2012a). The postural system is responsible for relaying information and coordinating activity within the motor system, maintaining balance and keeping the body in a neutral position so that it remains sensitive to future changes in the environment (Adkin et al., 2003; Huxhold et al., 2006). In the case of Parkinson's, along with other neurodegenerative disorders, postural stability can be affected by the disease process, resulting in joint and skeletal deformities, which are often under-recognized (Ashour and Jankovic, 2006; Gnadingera et al., 2011). The presence of joint and skeletal deformities is more often associated with severe PD and the use of L-DOPA therapy (Ashour and Jankovic, 2006). However, joint deformity can be an early sign of PD, predating the development of other symptoms (Ashour and Jankovic, 2006), and therefore may be a valuable measure for early detection. Although postural instability is associated with late and advanced stages, it has been observed in early stage patients (Lee et al., 2012). Currently, tests such as the Pull Test, the Timed Get Up and Go test, the Berg Balance Scale, the Functional Reach Test and self-reports are used to evaluate postural stability, mobility, and balance (Hunt and Sethi, 2006; Lim et al., 2005b). These methods are non-standardized and most often inadequate in assessing postural stability and balance (Munhoz et al., 2004). The UPDRS is the most widely used evaluator of PD. However, its self-reporting/questionnaire based method may be inadequate in measuring motor impairment. Nocera and Hass (2012) compared gait impairment measures from UPDRS scores and optical tracking during 8 meter walking trials. They found only a fair to moderate agreement between the objective and subjective gait measurements. Being able to adequately and objectively measure lower limb movements to assess gait variability and postural stability is important for predicting risk of falling and tracking disease progression. Measuring postural stability may also indicate cognitive decline. Several studies have found that decreased cognitive function plays an important role in gait variability and postural stability (Allali et al., 2010; Mazilu et al., 2013; O'Shea et al., 2002; Sheridan et al., 2003).

Figure 9:
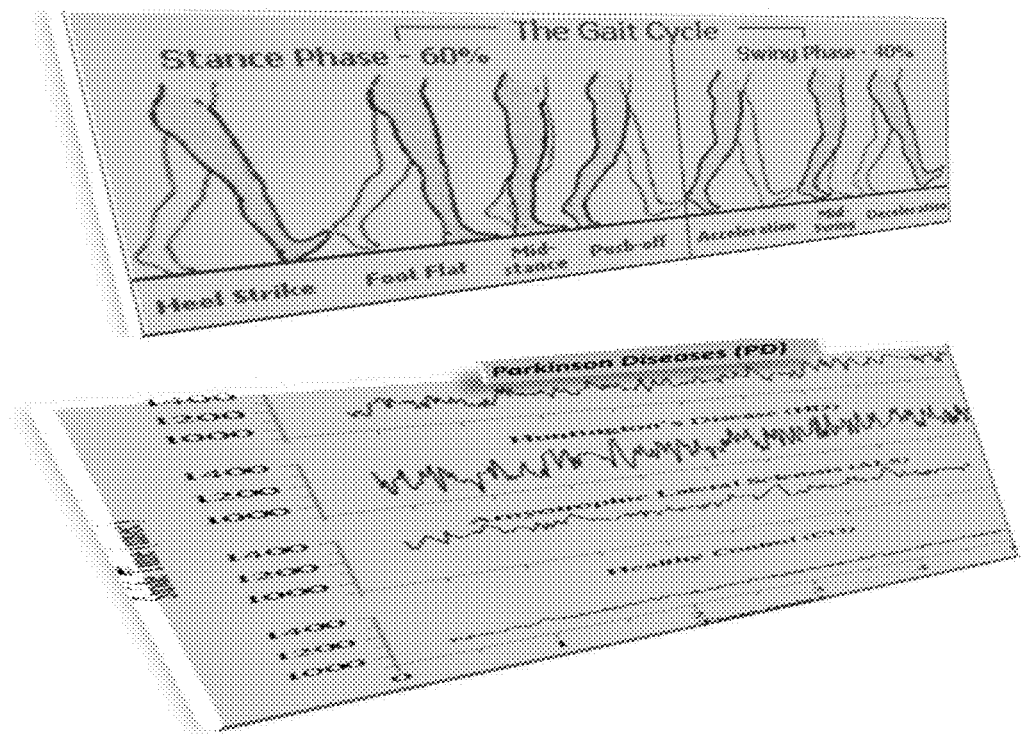
FIG. 9 is an exemplary diagram of the gait cycle.

FIG. 9 illustrates an example of the gait cycle. The graphs show stride time variance in patients with PD (top row), Huntington's Disease (second row), Amyotrophic Lateral Sclerosis (third row) and healthy controls (bottom row) (physionet). The greatest value range was observed in Huntington's patients.

Facial Features

Facial features are affected by spontaneous and voluntary motor impairments. Tremor can affect the head, neck, chin, lip and tongue (Jankovic, 2008). Early signs of PD include "facial masking" or an expressionless face caused by muscle rigidity. Bradykinesia causes a general reduction and slowness of voluntary and involuntary facial movements (Bologna et al., 2013; Bowers et al., 2006). Eye tremors and reduced blink rate are common in PD, possibly the cause of blurred or double vision experienced by many patients of PD. Blink rate in PD patients has been cited as low as 12-14 blinks per minute, compared to a healthy control rate of 24 (Karson et al., 1984). In a recent study, all 112 PD patients tested exhibited small rhythmic movements of the eyes when trying to keep a fixed gaze (Gitchel et al., 2012). Although ocular tremors are too small to be observed clinically video based systems can be used to see them.

It is unclear to what extent these symptoms are spontaneous or voluntarily initiated. Reduced facial expressions may also be affected by emotional problems, since the basal ganglia play an important role in emotional processing. Given the prevalence of facial feature impairments in PD analyzing these may be a valuable data stream to consider for early detection. Facial features can be non-invasively recorded using video and analyzed for measures of blink rate, eye movement, tremor, and expression.

Speech

Most PD patients have speech or vocal impairments such as tremor, jitter, difficulty swallowing, reduced loudness, monoloudness, monopitch, hoarseness, and imprecise vowel articulation (Factor and Weiner, 2002; Sapir et al., 2008; Skodda et al., 2011). Speech deficits can occur in early stages of PD (Skodda et al., 2012) and can affect pronunciation (Neel, 2008; Skodda et al., 2011). Speech and voice impairments such as reduced loudness, monopitch, breathy, hoarse voice, imprecise articulation, vocal folds, and vocal tremor are common features of PD, which are possibly related to disordered respiratory function (Factor and Weiner, 2002). There has been a recent interest in PD detection and monitoring using voice recordings (Afza, 2013; Skodda et al., 2011; Tsanas et al., 2011; Tsanas et al., 2012). Speech/voice impairments have been linked to movement impairments (Goberman, 2005; Tsanas et al., 2010) indicating that speech is an important feature of the motor domain that requires additional research. Speech and vocal measurements may offer useful data streams for detection and monitoring of PD.

Cognitive Function

Dual Tasking/Cognitive Load

Recent studies suggest that cognitive processes can be measured with indicators of motor function (Alfaro-Acha et al., 2007; Huxhold et al., 2006; Mielke et al., 2013; O'Shea et al., 2002; Resch et al., 2011). As cognitive decline progresses, the ability to process multiple tasks at once, such as those found in ADL, is diminished (Rochester et al., 2004). A method of defining how these behavioral streams relate to cognition is to compare between cognitive loaded and unloaded conditions. Cognitive loading can show us what happens if processing cannot attend to multiple tasks at once, such as a motor task and a cognitive task (e.g. following an obstacle course and responding to questions), which to some extent reflects the conditions of everyday life.

Balance was long thought to be unaffected by cognitive loading (Resch et al., 2011), a feature known as the 'posture first' strategy, (i.e. that individuals would always prioritize balance). However, a recent study aimed to mimic real-life scenarios showed that balance was clearly affected by cognitive loading (Liston et al., 2013). Dual-task paradigms and experimental design using cognitive load may offer valuable insights into processing and attentional demands in PD, which may offer a method for measuring cognitive decline (Brown and Marsden, 1991; Kelly et al., 2012; O'Shea et al., 2002).

Natural Language

Analyzing speech may not only detect vocal tremors and speech impairments, which are caused by muscle decontrol, but may also provide information about cognitive and neuropsychological changes. The language chosen can indicate changes in mood (Ooi et al., 2013b; Polzin and Waibel, 1998). Thus cognitive states specific to PD, such as premotor depression, may be detectable from language analysis. Current methods of measuring cognitive function (MMSE etc.) are subjective questionnaire-based reports that must be given repeatedly over a long period of time in order to measure cognitive decline. By decoding and analyzing meta-characteristics of human speech and language, it may be possible to identify biomarkers associated with different levels of cognitive functioning to develop models for predicting disease onset and progression.

Not all speech symptoms respond to L-DOPA treatment; non-speech motor impairments yield significant improvement, but speech and voice impairments tend to be less responsive (Goberman, 2005). This suggests that some speech impairments may be a result of non-dopaminergic mechanisms. Speech is an access point to a multi-level system of linguistic, cognitive, and neurobiological information. Language analysis offers a clinical assessment tool that gives insight into underlying cognitive processes (Baslow, 2009). Language plays an important role in developing long-term neural connections that inform cognition (Elman, 1993). Language is the most direct representation of our thoughts, emotions and perceptions (Chomsky and DiNozzi, 1972). Therefore, spoken and written language can provide direct access to one's thoughts and psyche. The simplification of language into a semantic exchange of words omits the underlying structures wherein physiological and psychological phenomena exist. Psychological processes are involved in perception of the world and personal expression; therefore words can only be analytically intelligible if axiological elements like conception, perception and intention and their production mechanics are taken into consideration. The linguistic foundation humans possess is shared and rooted in the same natural language regardless of the language each of us speaks (Lamb, 1999). Lamb (1999) suggests that many different cognitive processes, including those perceptual and conceptual in nature, share a similar structure. The underlying concept used to construct these networks is what he calls the functional web. When dementia or depression occurs, whether as a result of a neurodegenerative disorder or not, it is a reflection of damaged neural networks in the brain, which will be reflected in language. Therefore, language content may offer a valuable measurement of cognitive decline and emotional state.

Neuropsychological problems, such as depression and anxiety are gaining more and more awareness as common symptoms of PD (de la Monte et al., 1989; Jankovic, 2008; Shiba et al., 2000; Starkstein et al., 1989; Wertman et al., 1993). Methods of language analysis for detecting emotional states could have meaningful applications for the diagnosis and monitoring PD. Several methods have been developed demonstrating high accuracy in detecting emotional states from speech or text (Howard and Guidere, 2011; Howard and Guidere, 2012; Neuman et al., 2012; Ooi et al., 2013b; Roberts and Kassel, 1996). Predictive linguistics deals primarily with the conceptual, perceptual, and intentional factors that are specific to a particular tongue or individual. In this sense, predictive linguistics is proactive instead of simply descriptive. Performing in-depth analysis of language can help to ascertain a state of mind or state of cognition. Because language is the primary outward manifestation of our intentions, analysis of speech and written text may provide unprecedented real-time analysis of patient cognitive states. Changes in a patient's conceptual expressions, both verbal and written, may be used to characterize a cognitive state (Howard, 2011; Howard and Bergmann, 2012; Roberts and Kassel, 1996).

An individual's behavior and the biological mechanisms of their brain are tightly linked and therefore linked in neurological disorders. For example, in some brain disorders, structural abnormalities or specific chemical imbalances are observed. Such abnormalities lead to changes in whole brain function, which in turn affect (or disturb) behavioral functioning such as language, thought, movement, etc. On the other hand, language faculties are likely more dependent on intact cognitive processing (McDonald and Pearce, 1998). This suggests that in a brain disorder patient, language may carry information about the manner in which the brain functions and could point to the structural or chemical changes that cause the diseased state. Specific language features such as metaphors that rely on patient's description of their behavioral state might provide further information about their brain state (Assaf et al., 2013a; Gandy et al., 2013; Kircher et al., 2007; Lakoff and Johnson, 1980; Maasen and Weingart, 1995; Maki et al., 2013; Monetta and Pell, 2007; Neuman et al., 2013; Neuman et al., 2012; Schmidt et al., 2007; Schmidt and Seger, 2009). Metaphors may even serve as "units of translation" of the brain (Maasen et al., 1995; Maasen and Weingart, 1995).

Facial Expression

As previously mentioned, facial feature extraction is of interest to measure motor features such as blinking and rigidity, but also as an emotional classifier. Facial expressions are predicated on both spontaneous and voluntary responses involved the limbic system and frontal cortex, respectively. Some studies suggest that the "masked face" observed in PD only affects spontaneous facial expressions (Bowers et al., 2006), however, lower facial expressiveness has been observed for both voluntary and spontaneous responses (Peron et al., 2012). This implies the role of the basal ganglia not only in motor control but also in cognitive function and emotional processing. In addition to facial rigidity and bradykinesia, PD patients can also have difficulty perceiving negative facial expressions and emotional affect, such as fear and disgust (Jacobs et al., 1995; Peron et al., 2012). In a study involving 14 PD patients and 39 controls matched for age, gender, education and IQ, Suzuki et al. (2006) found that the PD group scored significantly lower on facial recognition of disgust.

Facial expressions not only involve muscle control, but also emotional states (Ekman, 1993). Facial expression is theorized to largely be mediated by personality and psychopathology (Keltner et al., 2003). This has been observed in studies involving emotional responses in psychological disorders. For example people with depression tend to exhibit more facial expressions of negative emotions and although they report similar emotional responses, schizophrenic patients are less facially expressive than control subjects (Berenbaum and Oltmanns, 1992). Thus a real-time system to analyze facial features and expressions would be useful for detecting and monitoring mental states (El Kaliouby and Robinson, 2005).

Brain Activity

Neural Oscillations

It has been suggested that neural oscillations hold potential value for better understanding brain disorders (Başar, 2012; Bosl et al., 2011; Bystritsky et al., 1999; Catarino et al., 2013; Gandhi et al., 2010; Sankari et al., 2012; Smith, 2005; Stikic et al., 2011; Uhlhaas and Singer, 2010; Ward, 2003). Rhythmic activities are not limited to a particular dimension, as they exist at various levels of magnitude (Haken, 2002). At the neuronal level, neurons display oscillatory waveforms that mediate the transfer of information in the brain. Oscillatory activity is visible in sub-threshold membrane potentials, though these may be less important for understanding the neural circuit as a whole (Wang, 2007). Mesoscopic observation also reveals oscillatory waveforms during interneuronal activity. As these waveforms increase in size, the ability to observe their activity also increases. Electroencephalography (EEG), and magnetoencephalography (MEG) can measure these large-scale oscillations from outside the scalp (Nunez, 2006; Winter et al., 2007).

Neural oscillations can be examined by exploring the summation of synchronous activities across many neurons by recording the EEG. The EEG results from the activity of an ensemble of neural oscillators generating rhythmic activity, which is quasi random (Başar, 2012). These generators couple and act together in a coherent way under specific conditions. This could imply that certain disorders show deviations from the norm in terms of rhythmic activity. Useful biomarkers for diagnosis and treatment could be based on these abnormalities if they could be reliably classified using EEG recordings. Detection of PD from EEG relies on external measurements of electrical waves originating in neuronal ion current flows (Sorensen et al., 2011). Although low in spatial imaging resolution compared to magnetic resonance imaging, the millisecond-range temporal resolution of EEG makes it an ideal tool for determining the presence or absence of electrical irregularities that characterize PD, such as tremor and glossokinetic artifacts (Klassen et al., 2011; Soikkeli et al., 1991a).

Studies of the EEG in PD have found distinct abnormalities in PD patients compared to controls and between PD subgroups (Soikkeli et al., 1991b; Tanaka et al., 2000). Many findings indicate a generalized slowing of the EEG in PD patients (Klassen et al., 2011; Pezard et al., 2001; Sarnthein et al., 2006; Soikkeli et al., 1991b; Wang et al., 1999). Handojoseno et al. (2012) recently used EEG recordings and wavelet entropy to detect the onset of Freezing of Gait (FOG) with accuracy around 75%. The EEG has also been used to analyze cognitive decline in PD patients (Schlede et al., 2011; Sinanovic et al., 2005).

While brain region connectivity is generally computed from EEG signals, volume conduction often presents problems when interpreting results (Winter et al., 2007). In one study, Chiang et al. (2009) present a new approach: a source separation technique where EEG signals are used in the representation of a "state-space framework." The model accounts for two primary phenomena: the underlying brain signal sources and the connectivity between those sources, which is represented as a generalized autoregressive (AR) process. Chiang et al.'s model indicated the presence of abnormal beta wave activity in PD patients. In addition, the biological networks shown in the AR process framework were similar to those found in previous studies, suggesting that the model is a valid algorithmic method for interpreting EEG signals.

Although EEG recordings yield low spatial resolution and are unable to identify specific locations of the brain, like PET and MEG, it offers several methodological advantages for early detection of PD during everyday living. Besides the benefit of being non-invasive, recent advances offer the potential opportunity to record EEG using small, portable devices. Low-cost consumer and medical-grade EEG devices have recently become widely available, but require further validation to be used in clinical applications.

Design Approach

Activities of Daily Living (ADL)

Brain function is shaped by our environment (Hari and Kujala, 2009) and, therefore, should be measured in order to gain knowledge of the overall neuronal and cognitive system. The most important activities of daily living are those that involve mobility, such as stair climbing (Valderrama-Gama et al., 2000). In general, ADL are of clinical interest, for they have long been used as predictors of cognitive risk, independent living, admission to a nursing home, use of hospital services and even mortality (Allaire and Willis, 2006; Branch and Jette, 1982; Fried et al., 1998; Ganguli et al., 2002; Jette and Branch, 1981; Manton, 1988). The inability to perform activities of daily living is a significant factor affecting quality of life for PD patients (Scalzo et al., 2012).

Given the spectrum of PD types, heterogeneity of symptoms, varied onset and rate of progression, detection would be most effective with large amounts of data collected often. Restricting diagnosis to physical examinations in a doctor's clinic will not improve chances of earlier detection. Measuring movement and speech features during everyday life may offer a beneficial platform to detect PD earlier than currently possible.

Non-Intrusive

In order to measure movement during activities of daily living, a non-invasive, portable, and robust data collection system will be required. The system should also be user friendly and easy to use during everyday life for optimal data collection (Bergmann et al., 2012a; Bergmann and McGregor, 2011b).

Body Sensor Networks

The concept of using body-worn sensors to gather behavioral information in itself is not new. Applying sensor systems to measure animal behavior has been important for understanding how animals interact with their environment, which is one of the fundamental aims of ecology (Shamoun-Baranes et al., 2012). Moreover, sensors have been used to track human behavior, most often used for monitoring activity and energy expenditure (Dobkin and Dorsch, 2011; Verloigne et al., 2012). BSNs/wearable systems have been developed for stroke rehabilitation (Mountain et al., 2010; Paulis et al., 2011) cardiovascular disease (Lo et al., 2005) Post-operative monitoring (Atallah et al., 2013; Aziz et al., 2007) blood pressure monitoring (Chan et al., 2007; Espina et al., 2006) and management and prevention of asthma (Seto et al., 2009). Therefore, the technology proves its clinical utility for several applications, yet BSN systems have not been validated or adopted by the clinical community for measuring movement or for detection of NDD. But Body Sensor Network (BSN) technology meets the basic criteria to collect measurements in real-world situations; it also provides a cheaper alternative to the laboratory-bound optokinetic systems (Veltink et al., 1996).

Usually, kinematics and biomechanical aspects of movement have been studied with an optical motion analysis system in laboratory settings. Although this research provides valuable information, the results are only valid and applicable in conditions where no reaction to a real-world environment is required (Bergmann et al., 2009a). It is preferable to collect data on location, in real-life situations where individuals express "normal" behavior, as this has a higher degree of ecological validity and is, therefore, more likely to yield results with greater external validity (Locke, 1986). However, this requires a portable sensor system that can collect body segment orientation in any environment under a range of different conditions.

Smartphone Integration

Monitoring devices used to measure ADL should not affect the normal daily behavior (Bergmann and McGregor, 2011b). Clinical technologies can only be sustainable if they adapt to users and interact with them in an intuitive manner. One solution to improve user acceptance is to integrate measurement systems with existing devices used in daily life by a wide range of people.

Recent advances in mobile electronics, most notably smartphones, hold a wealth of potential as a platform for data collection. Intel's Moodphone™, as well as software-based applications such as WellDoc and Tonic-App provide data acquisition and limited analysis interfaces for evaluating user-input health data. Clinical smartphone apps tend to focus on self-reporting or passive reporting, but smartphones themselves can be used as a data collection tool.

Smartphones have the potential to measure behavior continuously, without the need for changing normal daily behavior (Lu et al., 2010).

Clothing Integration

Clothing sensors to accurately measuring human movement is a recent concept. Sensor systems can be integrated into clothing to measure movement in ecological valid environments (Bergmann et al., 2012b). Clothing integrated sensors aim to improve patient quality of life by obtaining rich, real-life datasets valuable for monitoring and detection. Currently, there are various methods used to measure joint motion outside of the laboratory setting, including electrogoniometers, inertial measurement units, and e-textiles. However, the current state of these technologies is limited due to the fact that they are bulky and obtrusive or rely on time-consuming and cumbersome setups (Veltink and De Rossi, 2010). It can nullify the clinical usefulness of any developed system if patients and clinicians are reluctant to use them (Bergmann and McGregor, 2011b).

Conclusion

This research aims to develop, test, and validate the proposed hardware and analysis methods towards early detection of disease. While the majority of current PD diagnosis methods rely on subjective evaluations or single data entities (e.g. one-off imaging procedures) I aim to collect data from 3 domains (motor system, cognitive function, and brain activity) during everyday life and combine their analysis. The overall aim is to be able to measure the earliest neurodegenerative deviations from normal, healthy function. This section discussed the overall approach and domain-specific features of interest to measure emerging symptoms of PD. The next section will discuss methods for data collection and analysis.

Figure 10:
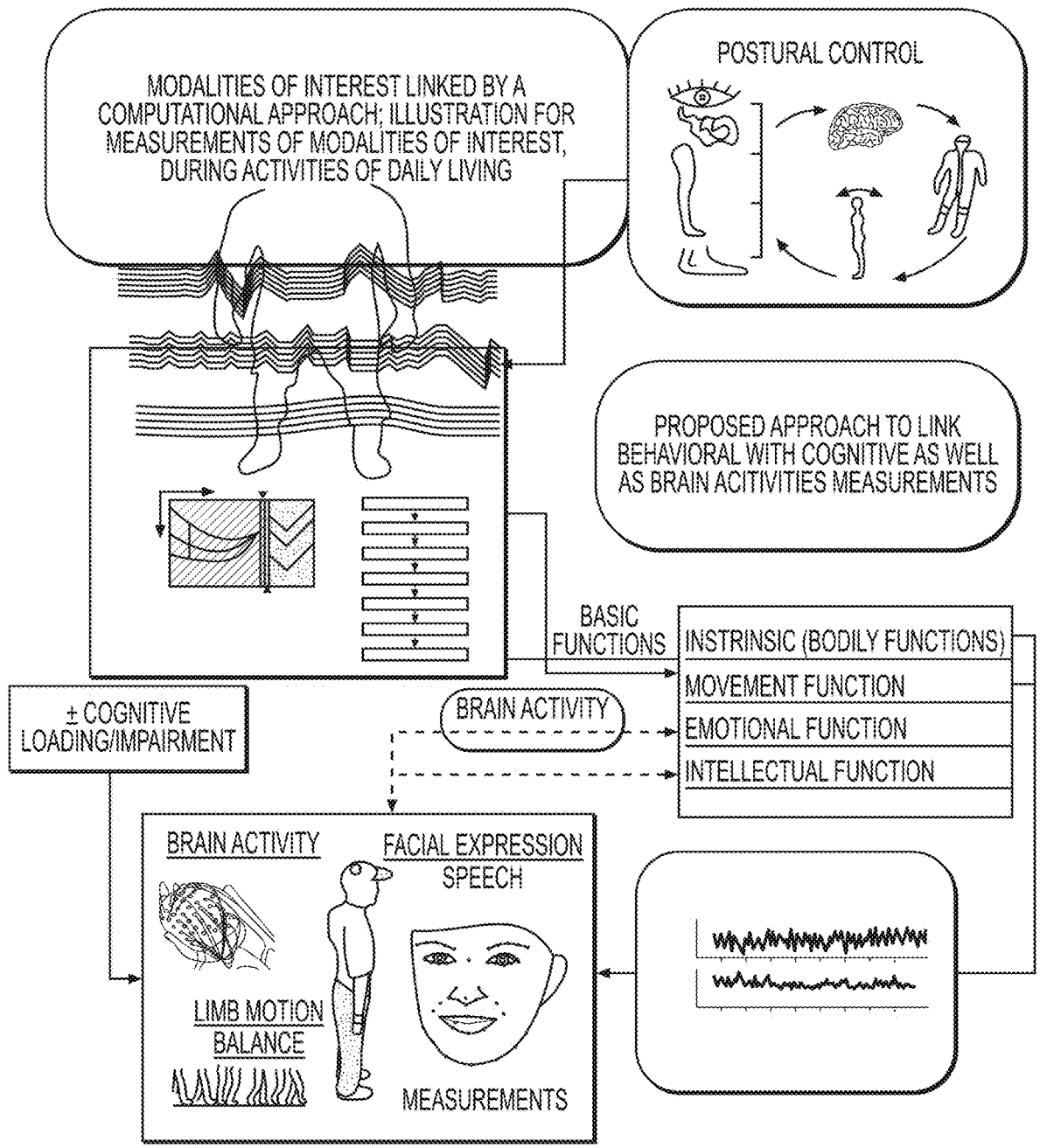
FIG. 10 is an exemplary diagram of an overview of the approach to measure features from motor, cognitive and brain activity domains by taking behavioral and cognitive measurements during ADL.

FIG. 10 illustrates an example of an overview of the approach to measure features from motor, cognitive and brain activity domains by taking behavioral and cognitive measurements during ADL. The image displays measures of interest from upper limb, lower limb, neural oscillations, facial expression, and speech.

Section Three: Methods

Section 1 and 2 discussed the overall approach and measures of interest. This section presents the methods used to develop and validate tools and analysis techniques to quantify the measures of interest. The aim of the methods selected was to allow measurement of speech and movement parameters in order to quantify cognitive and motor decline for the detection and progression tracking of PD.

To measure movement we introduced a non-invasive BSN system that can be used during everyday life. A BSN system for arm movement and postural stability requires unobtrusive sensors that can measure a range of complex motions and functional design criteria for everyday use. To develop this system with sensitivity and accuracy to be used for clinical applications first required validation against current gold standards. The proposed BSN system needed to demonstrate the ability to measure complex movements, interaction with objects, and sensitivity to differentiate between healthy and impaired movement. Data analysis required analytical methods that take into account motion, time, and a changing environment.

Measuring everyday speech required longitudinal datasets. Existing data collected with standard measures of speech was examined first to evaluate data collection needs. Simultaneous speech and movement tasks are often required during ADL; a cognitive load study was initially conducted to test sensors and analysis methods in order to measure cognitive processing during various levels of attentional demand. To validate the NOD algorithm, a biomarker found with in vivo recording was tested against similar EEG recordings. Facial expression classification required a large database to test and train the machine learning algorithms.

My approach attempted to link behavior of the motor system to physiological processes in realistic contexts with functional outcomes. Data analysis methods that fail to take into account physiological parameters will be limited in producing new insights. The same applies to over-fitting physiological parameters into data processing models. Therefore, we developed statistical analyses, continuous wavelet transform (CWT), and machine learning algorithms to analyze data.

Data Collection

Body Sensor Networks

Inertial Measurement Units

Inertial Measurement Units (IMU) allow body motion to be measured unobtrusively in three dimensions (Bergmann et al., 2013c). Inertial Measurement Units (IMUs) have become more and more popular in the human movement and clinical research field, as they combine certain notable benefits: they are small, portable and lightweight (Veltink and De Rossi, 2010). IMUs consisting of a triaxial gyroscopes, magnetometer, and accelerometers provide the most accurate measurements of angular orientation during movement (Luinge and Veltink, 2005) and have demonstrated accurate measurements of estimating arm position (Zhou et al., 2008a).

Triaxial gyroscopes were used to measure the angular orientation of a body segment, by integrating the angular velocity signal. However, a relatively small offset error of the signal can introduce large integration errors. As the majority of normal human movement generates accelerations below the gravitational acceleration of 9.81 m/s2, accelerometers can be used to provide additional inclination information. Because the accelerations that occur are relatively small compared to the gravity vector, the magnitude of the acceleration with respect to gravity can often be neglected, thus providing inclination information that can be used to correct the drifted orientation estimate from the gyroscopes (Roetenberg, 2005). It has been shown that a triaxial accelerometer and gyroscope can be fused together to accurately measure the orientation of human body segments (Luinge and Veltink, 2005). However, this method is less accurate for movements with relatively large accelerations and does not provide information of the rotation component around the vertical axis. Further improvements can be made by adding a triaxial magnetometer to the measurement unit. A magnetometer is sensitive to the earth's magnetic field and gives information about the heading direction. This information was used to correct for drift of the gyroscope about the vertical axis (Roetenberg et al., 2003).

Accelerometry has been used on a small scale to assess balance and attempts have also been made to investigate balance during functional tasks (Mayagoitia et al., 2002a; O'Sullivan et al., 2009; Veltink et al., 1996). Dedicated accelerometers are more commonly worn to monitor activities of daily living and can be used as a measurement of general health (Yang and Hsu, 2010). Usually wireless accelerometers are placed at the level of the center of mass, located on the lower back at the S2 level of the sacrum, as well as on the chest or thigh (Cheung et al., 2011; Winter, 2009; Zijlstra and Hof, 2003). However, these placements are not the most convenient or functional for daily wear and need to be tested with more functional placement. IMUs including triaxial gyroscopes, magnetometers, and accelerometers were validated against gold standard systems for accuracy of measuring complex arm movements.

Optical Tracking

Optical tracking systems were used as the criteria standard to compare the accuracy of BSNs (Bergmann et al., 2009a; Mayagoitia et al., 2002b). Marker based optical tracking systems, such as VICON, are considered the "Gold Standard" for human movement analysis (Godwin et al., 2009; Zhou and Hu, 2008). The state of the art in optical tracking requires a laboratory setting, and attachment of many markers. However, the standard, optical systems present several disadvantages. They require both hardware and software to be used in "line of sight" during data collection making portability and measurement in real-world environments a challenge (Godwin et al., 2009). The use of markers attached to the skin can produce surface movement errors and does not allow for measurement of joint movement (Zhou and Hu, 2008). Minimal detectable differences are hard to establish, because most studies do not focus on real life situations (Lim et al., 2005a; Steffen and Seney, 2008). Data collection and analysis needs to account for these limitations.

Optical motion tracking was performed using an active motion analysis system (Codamotion, Charnwood Dynamics, Leicestershire, UK) to measure the three-dimensional positions of the upper extremity. Markers were placed on the arm, scapula, and thorax. All markers were fixed using double-sided adhesive tape. Segments and joint rotations were calculated using a combination of local coordinate systems constructed from bony landmarks and marker positions. The glenohumeral rotation center was estimated by regression analysis. A functional method was used to define the center of rotation of the glenohumeral joint (rather than geometrical) and thus a range of motion tests was conducted at the start of the protocol. The scapula landmark markers were placed in accordance with the functional method, which can be small rotations at low levels of elevation (to minimize scapula movement) exploring the full range of motion including internal/external rotation. The forearm maintained flexed to 90 degrees. Local coordinate systems, segment and joint rotations were defined following the New Castle Shoulder Model (Murray and Johnson, 2004). Marker placement is detailed in Table 1, which is an example of marker placement used to measure the three-dimensional position of the upper extremity

TABLE 1

| | |
|---|---|
| Ulnar styloid | Radial Styloid |
| Proximal ulna (distal to olecranon) | Origin of brachoradialis |
| Biceps belly | Insertion of deltoid |
| Xiphoid process | Manubrium |
| C7 processus spinosus | T9 rib in line with inferior angle of scapula |
| Right acromion (placed on the acromioclavicular joint) | Left acromion (placed on the acromioclavicular joint) |
| Scapula tracker medium stem | Scapula tracker short stem |
| Scapula tracker long stem | T8 processus spinosus |
| root of scapula spine | Angulus inferior |
| (slightly medial from the) Angulus acromionalis | Epicondyles |

Because dynamic tracking of the scapula is difficult, measurements were performed using a new method that relates scapula motion to a scapular tracker (Karduna et al., 2001a; Karduna et al., 2001b). The method consists of a tracker with a hinge joint at the base that allows it to conform to the subject's scapular spine. The method has been previously validated, but errors due to skin motion are likely to occur. However, it is known that skin artifacts of the lower extremity are reproducible within subjects, but not between subjects (Leardini et al., 2005). Therefore, corrections for skin artifacts were made by conducting individual calibrations. A method proposed by Bourne et al. (2009) showed that multiple digitizations of scapular landmarks can be used to compensate for skin motion artifacts, allowing for non-invasive measurements of scapular kinematics by placing a grid of markers over the scapula. Digitization of the three scapular landmarks (acromial angle, inferior angle, medial root of the scapular spine) was performed during 0, 33, 66, and a 100% of the total movement (both on the ascent and descent) by placing markers on the scapula at these intervals. The digitizations occurred once at zero, once at ⅓, once at ⅔, once at full range, once at ⅔ range, once at ⅓ and once at zero. The digitization was performed for rotation and elevation of the arm in different planes.

Open-Source Data

Open source datasets were used to analyze PD speech and movement data. Longitudinal studies with rich datasets offer a valuable amount of information that can help to better understand speech and movement in PD and shape the development of our approach and methods for future data collection.

The Unified PD Rating Scale (UPDRS) is a commonly used scale to measure symptom severity in PD patients. The UPDRS includes 4 sections: Part I indexes non-motor aspects of the experiences of daily living, Part II, motor aspects of experiences of daily living, Part III, motor examination, Part IV, motor complications. Each UPDRS question is rated on a scale of 0-4, normal to severe. UPDRS is collected by interview, observation or self-reporting (Ramaker et al., 2002). There are several measures in UPDRS that directly relate to speech and motor symptoms in the context of everyday living, such as balance/postural stability and speech, which were used for data analysis.

Data Analysis

Statistical Analysis

For statistical analysis the following checkpoints were taken into consideration:

1. What was the linearity of the relationship between dependent and independent variables? The linearity of the plot of observed versus predicted values, which is generated as part of the analysis was assessed. If there were issues with linearity appropriate transformation (e.g. power, sqrt, etc.) were performed.
2. What was the independence of the errors? Were there serial correlations? An autocorrelation plot of the residuals was calculated. Most of the residual autocorrelations fell within the 95% confidence intervals around zero.
3. What was the homoscedasticity (constant variance) of the errors? Divergence of residuals over time was checked when plotting the residuals against time or other independent variables.
4. What was the normality of the error distribution? The normal probability of the residuals was plotted and checked for normality.
5. Step 5 was needed only if the above failed. Other equally valid tests were examined such as a Generalized Linear Models (GLM). GLMs were preferred as they allow the variance of a parameter as a function of its predicted value to be estimated.

Pearson

The Pearson correlation coefficient (r) is a statistical analysis to measure dependence between two variables. Pearson analysis measures the linear correlation between two variables, often a time-series measurement of some responding scalar variable. Pearson was used to correlate upper limb measurements collected from IMU BSNs and optical tracking using the following formula:

$$r = \frac{\sum XY - \frac{\sum X \sum Y}{N}}{\sqrt{\left(\sum X^2 - \frac{(\sum X)^2}{N}\right)\left(\sum Y^2 - \frac{(\sum Y)^2}{N}\right)}} \quad (1)$$

Linear correlation is particularly useful for minimizing impact of repeated values and outliers. Analysis of UPDRS data using Pearson was initially considered for speech and movement symptoms, but because UPDRS is categorical it was not included.

Spearman

Spearman's rank correlation coefficient, also called Spearman's rho, was introduced as a means of monotonically describing the trajectory of a measured variable over time. Spearman values approaching 1 tend to have constantly increasing, non-repeated values. Spearman's method is less sensitive to sudden changes in data patterns or outliers on either end of a time series. Because UPDRS data is categorical and contains repeated values and outliers, spearman analysis was used. Spearman's correlation coefficient was computed using the following formula:

$$\rho = 1 - \frac{6 \sum d_i^2}{n(n^2 - 1)}. \quad (2)$$

Here, $\rho$ stands for the Spearman coefficient, d is the difference between observations of x and y, and n is the total number of samples.

Kendall

Kendall tau rank correlation coefficient, also called Kendall's tau, is used to measure association between two measures. In addition to Spearman, Kendall was also used to analyze UPDRS data. Both Spearman and Kendall correlation were used on the same UPDRS data to verify and confirm results. Kendall analysis uses the following formula:

$$W = \frac{12S}{m^2(n^3 - n)}. \quad (3)$$

Here, S is the sum of squared deviations, which is calculated as the sum of each value pair's assigned rank minus the mean rank, m is the number of judges, and n is the number of samples, or objects.

Linear Regression

Linear regression is a statistical method to model the relationship between a dependent variable and explanatory variables. Linear regression can be used to perform variable pairing analysis to examine the properties of a dataset composed of values from more than one category symptoms. Linear regression was particularly useful because its incorporation of predictor variables augments the capabilities of the correlation coefficients of Pearson, spearman, and Kendall. In Experiment 8, we performed a number of variable pairing regressions to examine the properties of UPDRS data of values from two (instead of just one) categories of symptoms. Linear Regression was computed for 15 variable pairings; regressions were plotted and checked for normal distribution.

Linear regression is based on the following formula:

$$Y = \beta_0 + \beta_1 X_1 + \beta_2 X_2 + \ldots + \beta_n X_n + \varepsilon$$

where Y is the dependent variable
$\beta_0$ is the intercept term
$\beta_n$ are the n coefficients for independent variables
$\varepsilon$ is the error term.
(4)

Euclidian Norm

The Euclidian norm of the acceleration of a signal can be used as a main feature, as accelerations can be applied to differentiate between different motions (Bergmann, et al. 2013). In experiment 1 and 2 the norm was determined with a as the 3D acceleration vector $[a_x, a_y, a_z]$. The norm was computed for each index point and the signal was then segmented into 1-second windows.

Euclidian norm is based on the following formula:
$\|d\|$ is determined by $$d_i = [X_i Y_i Z_i] \quad (5)$$

$$\|d_i\| = \sqrt{X_i^2 + Y_i^2 + Z_i^2} \quad (6)$$

with $d_i$ representing a vector based on $X_i$, $Y_i$ and $Z_i$ with index point i Wavelet Analysis Wavelet analysis is a relatively recent form of signal processing that has found applications ranging from electrical engineering and imaging analysis to the evaluation of clinical data. Generally speaking, wavelets are approximations of signals received over time that can be expanded both spatially and temporally while maintaining fidelity to the original signal source data, allowing greater extrapolation and close examination than was previously possible with trigonometric analyses such as Fourier transforms.

Wavelets are functions that are localized in both physical space and wave-number space unlike the Fourier transform which is based on functions (sines and cosines) localized in wave-number space, but not in the physical space (Schneider and Vasilyev, 2010). A wavelet is a special case of a vector in a separable Hilbert space that generates a basis under the action of a collection of unitary operators defined in terms of translation and dilation operations (Dai and Larson, 1998; Larson, 2007).

The wavelet function approximation works by splitting existing functions or data streams into separate components based on their frequency. This allows a more discrete analysis. For example, one-dimensional shear operation is applied to a two dimensional image. Each dimension is assigned an eigenvector based on the magnitude and direction of the shear operation, its length and orientation are unchanged, and it is assigned an eigenvalue of 1. In this example, wavelets can be used to isolate the eigenvectors of interest without altering the original image data. This "decomposition" process is thus mathematically reversible due to the preservation of movement data. Wavelet analysis often invites comparison with other frequency domain analysis methods, such as the Fourier transform. This family of functions is unique in that instead of displaying signal data with respect to time, they show the proportions of signals that lie in specific frequency bands.

The Fourier transform lacks the ability to represent signals in the time domain in a way that offers time and frequency localization due to the inherent properties of the trigonometric functions used to approximate the signal function. As a result, the Fourier transform is less effective for focused, localized analysis of signals. Wavelets help to overcome this obstacle through the use of "mother wavelets," which are functions used to generate daughter wavelets, or scaled and translated versions of the mother. Because wavelet function composition contains this inherent relationship between components and because Fourier transforms involve function summation, wavelet transforms offer a better way to examine small components of signals and functions with great precision. Fourier transforms, on the other hand, are better suited to capturing global features, or harmonic components that span the entire signal.

A continuous wavelet transform (CWT) is a multi-resolution transformation that uses a variable window size at each level. This retrieves more information from the signal in the time-frequency (time-scale) domain. The resolution needs to be set to a fixed number of levels based on the maximum possible decomposition that can be performed considering a sampling frequency at a determined Hz (number of levels $\leq \log_2 (X/n)$). Therefore each t sec. window is represented by determined value vectors $\{X_i\}_i^x$, which represent the wavelet coefficients at each of the levels.

Energy: power sum of the coefficients at the i-th level. For a vector Xi of length n, the energy is defined as:

$$E_i = \sum_{k=1}^{n} X_i(k) \quad (7)$$

Average value: represents the mean value of the coefficients power at the i-th level. For a vector Xi of length n, the average energy is defined as:

$$\overline{E_i} = \frac{1}{n}\sum_{k=1}^{n} X_i(k)$$

Variance: represents a dispersion measure from the mean energy at each level. For a vector Xi of length n, the variance of the energy is defined as:

$$\text{Var}(E_i) = \frac{1}{n}\sum_{k=1}^{n}(X_i(k) - \overline{E_i})^2 \quad (8)$$

First derivate: average value of the first derivate of the energy at each level. For a vector Xi of length n, the average value of the first derivate is defined as:

$$\overline{E_i'} = \frac{1}{n-1}\sum_{k=2}^{n}(X_i(k) - X_i(k-1)) \quad (9)$$

Entropy: represents the uncertainty value of the energy at each level. Let $\aleph = \{X, p\}$ a discrete space of probability. That is, $X = \{X_i, \ldots, X_n\}$ is a finite set in which each element has probability p $(X_i)$. Then, the Shannon entropy $\aleph$ is defined as:

$$H(\aleph) = -\sum_{i=1}^{n} p(X_i) \cdot \log_2 p(X_i) \quad (10)$$

Summarizing each window in seconds (for finite samples) is characterized by n values (x levels×X features), which represents reduction of the input space. Mathematically, each sample can be represented by a vector as shown below:

$$[E_1\overline{E_1}\text{Var}(E_1)E_1'H(X_1), \ldots, E_6\overline{E_6}\text{Var}(E_6)E_6'H(X_6)] \quad (11)$$

Everyday living tasks involving interaction with a variety of different objects were performed to test the BSN system. The BSN measured the upper limb movement during several pouring tasks with different containers. This data could have been analyzed using a range of methods; because the signal varies in time, a Fourier analysis, which relies on adding together the appropriate infinite sum of sine waves, could have been used. However, most behavioral signals are finite and require the detection of localized features. So for this type of data the use of wavelets was more appropriate. The wavelet coherence can be interpreted, to some extent, as a measure of local correlation (Vacha and Barunik, 2012). Coherence measures the variability of time differences between two time series in a specific frequency band (Thatcher, 2012). A CWT was applied to divide the signal into wavelets, allowing us to analyze the frequency content over time. This information was then used to compare two signals to find a potential relationship between them. Regions where the signals have equal power or phase behavior indicate an association.

Both speech and voluntary movement can be transformed to wavelets to provide a signal that can resonate (Howard et al., 2013c; Kronland-Martinet et al., 1987). The fundamental frequency of speech is roughly 5-210 Hz (Traunmüller and Eriksson, 1994) and for movement the relevant physiological range is 0.5-10 Hz (Barnes et al., 1978). Signals are normalized against those ranges generating a unitary pseudo frequency. The association between these modalities can be determined based on the coherence between wavelets from normalized signals.

Measuring Object Interaction (Experiment 2) Bergmann, J., Langdon, P., Mayagoita, R. & Howard, N. 2013. Exploring the use of sensors to measure behavioral interactions: An experimental evaluation of using hand trajectories. *PLOS ONE, Forthcoming*.

It can be expected that the variance for a behavioral task is somewhat comparable across repetitions performed by the same subject with the same object, such as pouring water into a cup. Furthermore, changes should be detectable for the same repetitive motor behavior if a change in environment is introduced (Kee et al., 1983), such as pouring with different containers (kettle, jug, teapot). Therefore, the wavelet-coherence was initially computed within repetitions and a subsequent comparison was made based on the summed results for each condition (subject, object). A Morlet waveform was used because it accounts for frequency and location (Howard et al., 2013d). The wavelet coherence of two time series x and y can be described as, $$C = \frac{S(CW_x^*(a,b)CW_y(a,b))}{\sqrt{S|CW_x(a,b)|^2}\sqrt{S|CW_y(a,b)|^2}} \quad (12)$$

where S is the smoothing operator, while $CW_x(a,b)$ and $CW_y(a,b)$ denote the continuous wavelet transforms of the signal x and signal y at the scales a and the positions b (Catarino et al., 2013). The wavelet coherence was used to compare signals between subjects or between objects.

Measuring Subject interaction Healthy and Impaired Movement (Experiment 3) Howard, N., Pollock, R., Prinold, J., Sinha, J., Newham, D. & Bergmann, J. 2013d. Effect of Impairment on Upper Limb Performance in an Ageing Sample Population. In: STEPHANIDIS, C. & ANTONA, M. (eds.) *Universal Access in Human-Computer Interaction. User and Context Diversity.* Springer Berlin Heidelberg.

In order to be developed for PD detection and progression tracking, the BSN system must be able to measure with a high enough level of sensitivity to differentiate between healthy and PD movement. We measured the upper limb performing a task at normal and fast paced speeds in a patient group and a control group to compare differentiation between their movements. Wavelet analysis was used to analyze this data because it can capture frequency, time, and location. Movement data within and between subjects was analyzed using wavelet coherence. This technique was used to assess how the signal differs between the "normal" and "fast" conditions within each group. Signals were aligned at the starting point of movement using a threshold value algorithm that identified the alignment point of the movement, defined by the first crossing of the 10% value of the maximum ROM.

A bi-orthogonal Gaussian waveform was used for the wavelet analysis for fast and slow range of motion. The wavelet coherence of two time series x and y can be described as, $$C = \frac{S(C_x^*(a,b) C_y(a,b))}{\sqrt{S|C_x(a,b)|^2} \sqrt{S|C_y(a,b)|^2}} \quad (13)$$

where S is the smoothing operator, while Cx(a,b) and Cy(a,b) denote the continuous wavelet transforms of the "normal" signal x and the "fast" signal y at the scales a and the positions b.

Measuring Cognitive Load (Experiment 7) Bergmann, J., Fei, J., Green, D. & Howard, N. 2013. Effect of Everyday Living Behavior on Cognitive Processing. *PLOS ONE, In Preparation.* Bergmann, J., Fei, J., Green, D. & Howard, N. 2013a. Effect of Everyday Living Behavior on Cognitive Processing. *PLOS ONE, In Preparation.*

Figure 11:
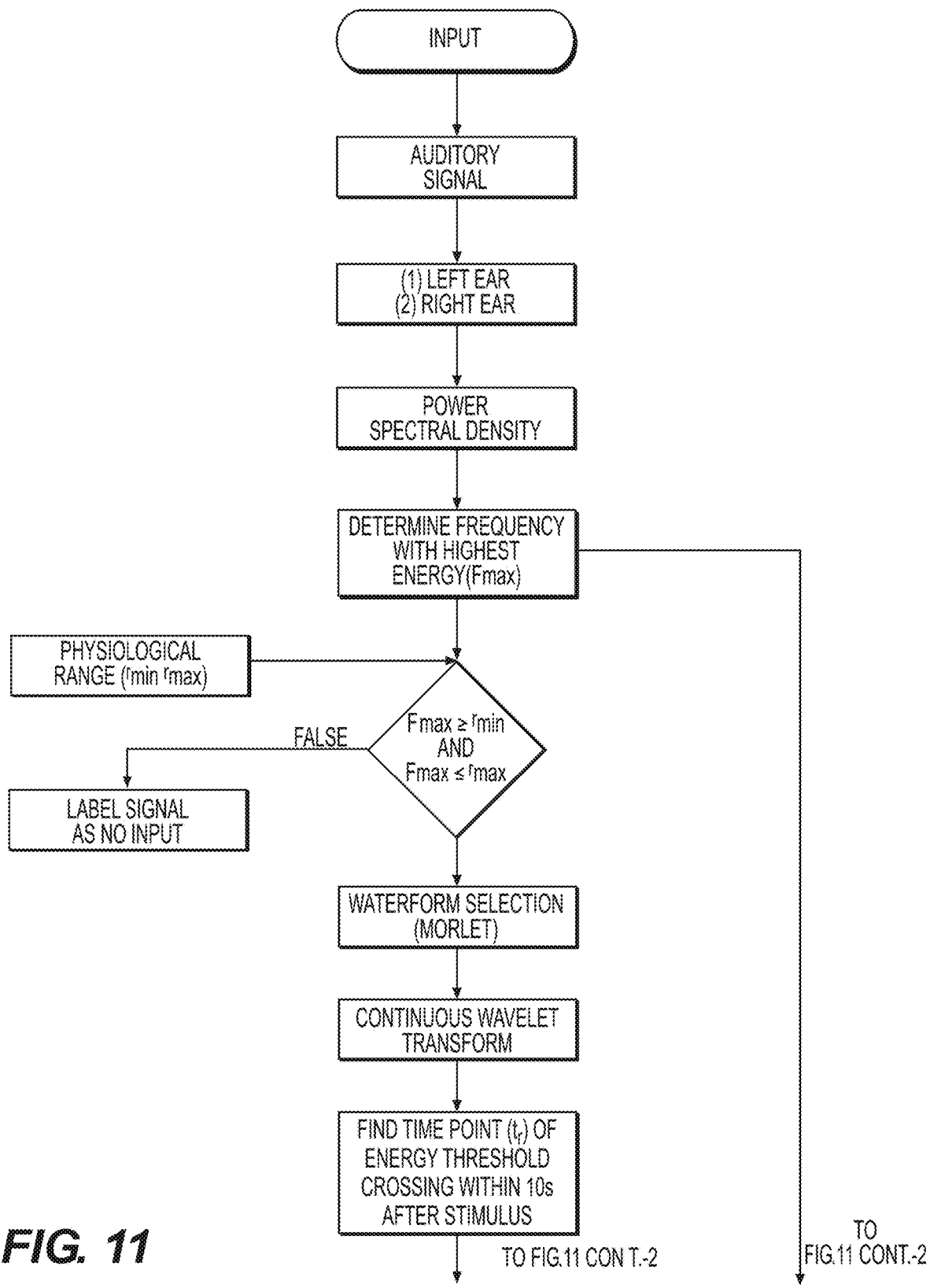

To measure cognitive processing under various loaded conditions, a spatial stroop task was combined with movement and speech tasks simultaneously. The input signal consists of a spatial signal in the left or right ear and a response by shaking the head up and down for "yes" or sideways for "no." Wavelet analysis was used for response detection from pitch and yaw signals obtained from a head-mounted sensor. The flowchart of the cognitive load analysis is depicted in FIG. 11. The aim of the signal processing was to detect changes in the signal, due to a relevant response to the stimulus. However, differences between and within subjects complicate detection based on e.g. simple thresholding techniques or Fourier transform. Unlike Fourier, wavelets have properties that not only characterize the signal within a frequency or scale, but also for location. Therefore, wavelet was an appropriate technique for detecting changes in angular velocity due to movement.

A Morlet wavelet was used to detect responses. This wavelet is the product of a complex exponential wave and a Gaussian envelope. The Morlet wavelet's function $\psi(t)$ is taken from (Lin and Qu, 2000) and can be described by $$\psi(t) = e^{\frac{-\beta^2 t^2}{2}} \cos(\pi t)$$

The following descriptions of the wavelet equations are adapted from (Hartmann, 2013; Strang, 1993). To be able to scale and shift the wavelet, a generic function can be defined as, $$\psi_{n,k}(t) = 2^{\frac{n}{2}} \cdot \psi(2^n t - k) \quad \text{for } n, k \in \mathbb{N}$$

With t denoting the independent variable and n,k integers within the range;

$$n \geq 0$$

$$0 \geq k \leq 2^n$$

The Morlet wavelet can be defined as a "mother" wavelet from which a range of wavelets can be generated by scaling and translating, $$\psi_{a,b}(t) = \frac{1}{\sqrt{a}} \cdot \psi\left(\frac{t-b}{a}\right) \quad \text{for } a > 0, b \in \mathbb{R}$$

a is the scaling parameter and b is the translation parameter. The collection of wavelets that arise from this can be used as an orthonormal basis. The relevant coefficients can be obtained by, $$C_{a,b,f(t),\psi} = \int_{-\infty}^{\infty} f(t) \cdot \psi_{a,b}(t) dt$$

Varying the values of a and b will provide the continuous wavelet transform coefficients $C_{a,b}$ indicating how closely the wavelet is correlated to the original signal. These coefficients are of course dependent on the selected waveform ($\psi$) and function ($f$). A larger value for $C_{a,b}$ shows a greater similarity between $\psi$ and $f$.

A scalogram of wavelet coefficients will be generated. The start of a specific response is defined as the point at which the energy level of the scale related to $f_{max}$ crosses a preset boundary. A limitation with applying a single value crossing is the selection bias. In order to overcome this as much as possible a range of thresholds (T) should be explored with:

$$T_i = \frac{E_{max}}{i} \quad \{i \in \mathbb{N} \mid 1 \leq i \leq 100\} \quad (19)$$

$E_{max}$ being the maximum energy variable.

FIG. 11 illustrates an example of a flowchart algorithm for measuring cognitive processing during cognitive load tasks.

Example of CWT

Examples of simulated outcomes for wavelet coherence are given in FIG. 12. The examples show the wavelet coherence between sine and Haar waves. The first example (A) shows the outcome between two almost identical sine waves. The second example (B) shows a Haar and sine wave with the exact same frequency. In example C there is a factor 2 difference in frequency, between the two waves. It is clear from FIG. 12 that the localized similarities differ depending on the signals that are compared. The level divergence can subsequently be described, as an average wavelet coherence value ($\overline{C}$). This value is simply computed by first averaging across the scales at each time point (columns) and subsequently across the time points themselves, $$\overline{C}_1 = n^{-1} \Sigma_{j=1}^{n} C_{ij} \text{ for } i=1:m \tag{20}$$

$$\overline{C} = m^{-1} \Sigma_{i=1}^{m} \overline{C}_i \tag{21}$$

with C representing the coherence with rows i and columns j for lengths n and m.

FIG. 12 illustrates an example of how the wavelet coherence changes over a range of three sample wave patterns. Zero-mean Gaussian noise is added to all signals. Top plots: (A) the red signals shows a sine wave with a frequency f and the blue trace has a frequency of 1.001f. (B) The red signal depicts a sine with a frequency f and the blue is Haar wave with the same frequency f, (C) The red signal shows a sine wave with a frequency f and the blue trace has a frequency of 2f. The bottom plots show the wavelet coherence for each example. The heat map displayed on the side shows the phase, wherein dark blue represents 0° and dark red represents 180°. The mean wavelet cross spectrum value (C) is displayed in the corner of each wavelet coherence plot.

The high scales are associated with low frequencies, while the low scales portray the high frequencies. The high scales (low frequencies) are of particular interest, as everyday living activities normally take several seconds to complete and even longer when restricted due to impairments (Adams et al., 2003).

Machine Learning

Machine learning is a rapidly growing field and is more frequently being explored as a method for clinical applications, including diagnosis of Alzheimer's disease and Autism (Bosl et al., 2011; Datta et al., 1996; Trambaiolli et al., 2011) and also detection and prediction of freezing of gait in PD (Mazilu et al., 2013). In general terms, machine learning is to construct a system that can learn from data inputs (Mazilu et al., 2013). There exists a variety of machine learning models for different applications. Generally speaking, there are two groups of machine learning algorithms: supervised learning and unsupervised learning. In supervised learning, labels of each observation in the dataset (training data, specifically) are known, and the goal is to construct a function to predict the label of a new observation; in unsupervised learning, the labels of the dataset are not known and the goal is to find the hidden structure of the data.

Naïve Bayes

Naive Bayes is a probabilistic classifier based on Bayes' theorem of independent assumptions, or an independent feature model. The Naïve Bayes classifier assumes that the presence of one attribute of a class is unrelated or independent to the presence of other attributes. Naïve Bayes is surprisingly one of the most effective machine learning algorithms particularly for real world data (Elkan, 1997).

$$P(W \mid L) = \frac{P(L \mid W)P(W)}{P(L)} = \frac{P(L \mid W)P(W)}{P(L \mid W)P(W) + P(L \mid M)P(M)} \tag{22}$$

Support Vector Machine (SVM)

SVM are supervised learning techniques that can be used for classification or regression. SVMs are grounded in statistical learning theory and can learn from small datasets with good generalizability. SVMs non-linearly map input vectors into a high dimensional feature space to an optimal separating hyperplane, where data points are separated linearly (Cortes and Vapnik, 1995).

$$\text{Maximize } W(\alpha) = \sum_{i=1}^{n} \alpha_i - \frac{1}{2} \sum_{i,j=1}^{n} \alpha_i \alpha_j y_i y_j K(x_i, x_j)$$

$$\text{subject to} \begin{cases} \sum_{i=1}^{n} \alpha_i y_i = 0 \\ \alpha_i \in [0, C], \quad i = 1, \ldots, n \end{cases}$$

$$\min_{\theta} \min_{w,b,\xi} \frac{1}{2} \|w\|_2^2 + C \sum_{i=1}^{N} \xi_i$$

subject to: $y_i(w^T \psi(\theta * x_i) + b) \geq 1 - \xi_i \wedge \xi_i \geq 0 \wedge \|\theta\|_1 \leq \theta_0$ Fuzzy C-Means Clustering Clustering is a type of unsupervised machine learning algorithm. The goal of clustering is to group the observations in a dataset in a way that observations in the same group are more similar to each other than to those in different groups. The groups are called clusters. In contrast to hard clustering in which observations are grouped into distinct clusters, in a fuzzy clustering algorithm each observation can belong to more than one cluster. Fuzzy clustering analysis has been applied in the past to a variety of data sets, and can be readily applied to PD detection in a very similar manner. Fuzzy c-means begins with N data points $x_1$, $x_1, \ldots x_N$ which are identified by their coordinates located in a P-dimensional feature space where $x_k = (x_{k1}, x_{k2}, \ldots, x_{kP})$.

The algorithm then constructs a set of c centroids $v_1$, $v_2, \ldots, v_c$, or points that share a common feature space, that represent the c clusters, and a set of cN membership values $\mu_{(ik)}$, $i=1, \ldots, c$; $k=1, \ldots, N$. These membership values are used to determine the "degree of membership" of a point $x_k$ in a class $c_i$, where $0 \leq \mu_{(ik)} \leq 1$, as follows, $$\sum_{i=1}^{c} \mu_{ik} = 1, \quad k = 1, \ldots, N.$$

Finding an ideal arrangement of points by cluster membership and optimal placement of the centroids, it uses a given objective function J, which is minimized when the distribution is optimal: $(\mu((_0, v_0) = \arg \min J (\mu((,v))$, where $\mu=(\mu_{(ik)})$ and v=represent the sets of the variables to be found and $\mu_0, v_0$ are the optimal solutions. An expression often used for J is, $$J_P(\mu, v) = \sum_{i=1}^{c} \sum_{k=1}^{N} \mu_{ik}^p \|x_k - v_i\|^2, \quad \|x - y\|^2 = \sum_{l=1}^{P} (x_l - y_l)^2$$

where the power p>1 is a given parameter that controls the degree of fuzziness of the obtained clusters (we used p=2) (Ibid). The optimal solution of a constraint optimization problem is given by, $$v_i = \frac{\sum_{k=1}^{N} \mu_{ik}^p x_k}{\sum_{k=1}^{N} \mu_{ik}^p}, \quad \mu_{ik} = \frac{1}{\sum_{j=1}^{c} \left(\frac{\|x_k - v_i\|}{\|x_k - v_j\|}\right)^{\frac{2}{p-1}}}$$

Neural Oscillation Detection (Experiment 9) Howard, N., Rao, D., Fahlstrom, R., Bergmann, J. & Stein, J. 2013. The Fundamental Code Unit—Applying Neural Oscillation Detection Across Clinical Conditions. *Frontiers, Commissioned.*

To test the NOD algorithm EEG recordings were used to detect a biomarker previously identified with in vivo recording. A neuropathic pain biomarker observed by Green et al. (2009) was recorded from local field potentials deep within the periaqueductal grey and the sensory thalamus. This biomarker will be referred to as "pain spindles," the term is used in this thesis interchangeably with alpha spectrum Pain evoked an increase in spindle shaped bursts in 8-12 Hz in the PAG and 17-30 Hz in the sensory thalamus. Therefore, the NOD algorithm used the alpha band as input features for machine learning. Raw EEG data was input into the algorithm, which consists of pre-processing, signal processing, and machine learning. The algorithm flowchart is shown in FIG. 13.

Figure 13:
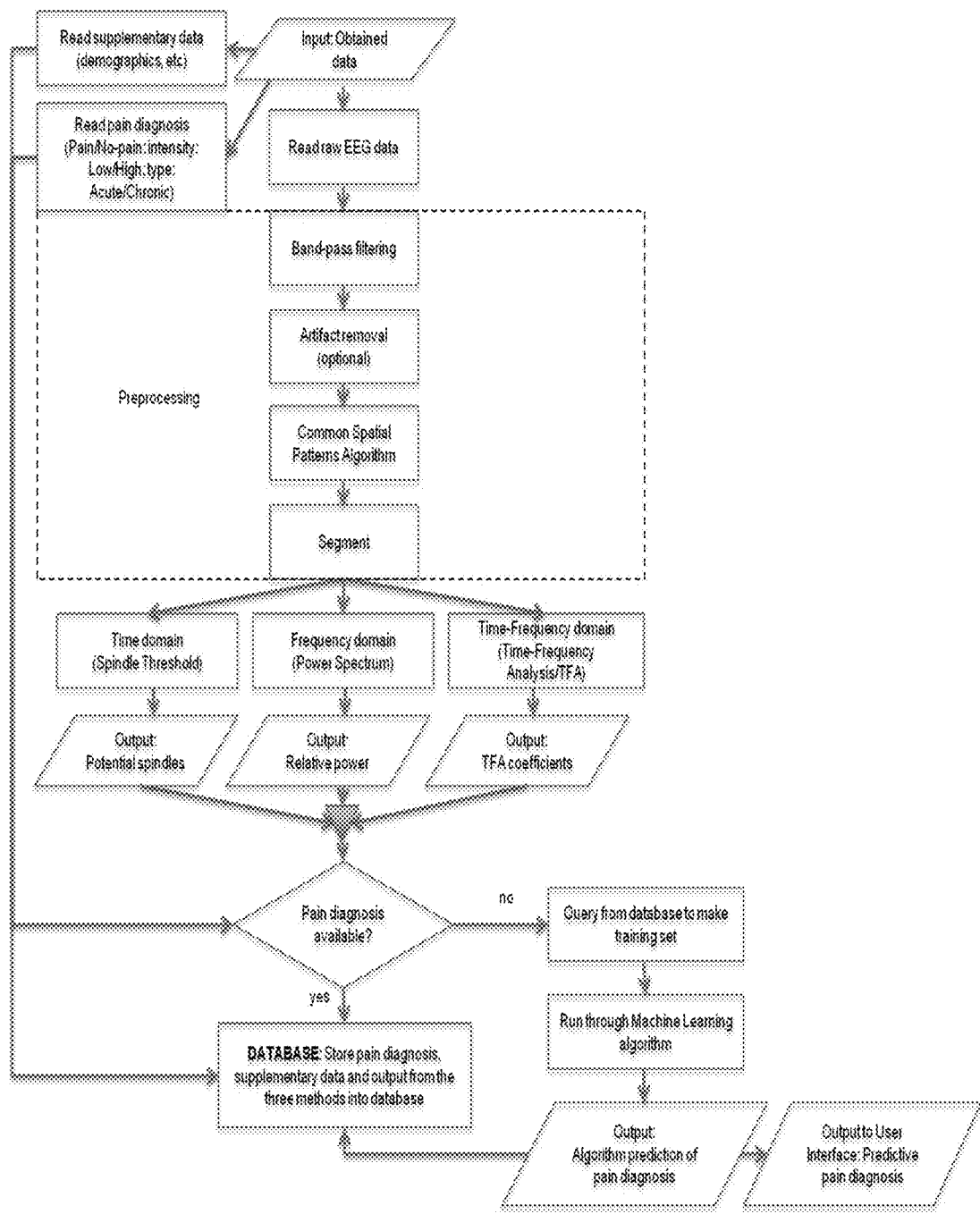
FIG. 13 is an exemplary flow diagram of a detection algorithm including three stages: pre-processing, signal-processing, and machine learning.

FIG. 13 illustrates an example of a detection algorithm flowchart consisting of three stages pre-processing, signal-processing and machine learning.

(1) Stage One: Pre-Processing

The pre-processing stage filtered the data at 4-45 Hz for the complete spectrum (Hipp et al., 2012) and 8-12 Hz for the broad alpha range (Green et al 2009). After filtering the data, artifact removal was performed. Corrupted electrodes were detected using a weighted average of their three nearest electrode neighbors, where the weights were inversely proportional to the Euclidian distance between the electrodes. Next the common spatial pattern algorithm (CSP) was performed for electrode selection (Higashi and Tanaka, 2011), in order to optimize the data analysis by preselecting the EEG electrodes that showed the highest variance in their signal, presumed to reflect the pain biomarker. This approach minimizes the computational requirements during further processing, as only the highest-ranking electrodes were used for further analysis.

After CSP, segmentation of the data was performed. Segmentation of EEGs was done to obey the "stationary assumption", which is the assumption that the EEG is composed of periodic waves of several frequencies and none of the waves change in amplitude or frequency.

Common Spatial Patterns (CSP)

The CSP algorithm was used to determine the most appropriate electrode(s) for further analysis based on extracting discriminative spatial filters for the classification of EEG (Wang et al., 2006).

$$w = \mathrm{argmax}_w \frac{\|wX_1\|^2}{\|wX_2\|^2} \quad (27)$$

Figure 14:
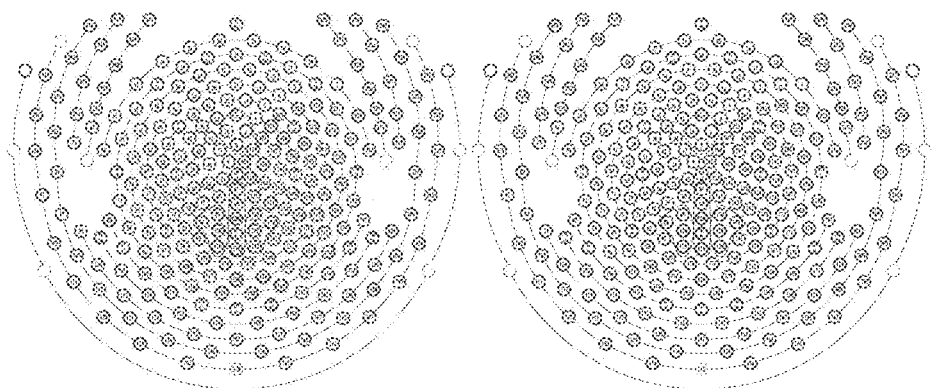
FIG. 14 is an exemplary diagram of a sensor layout for 256-channel Hydrocele Geodesic Sensor Net.

X1 (n,t1) and X2 (n,t2) are two windows of a multivariate signal, n is the number of signals and t1 and t2 are the respective number of samples The CSP algorithm was performed for the full electrode set and the physiologically relevant electrode set. Physiological sensor selection was based on evidence of the spatial locations of pain biomarkers (Green et al 2009, Chen et al 1994 and 1998, Chang et al 2002). FIG. 14 shows a representation of a physiologically relevant electrode and the full electrode sets. Physiological sensor selection can be biased due to the fact that propagation of electrical activity along physiological pathways or through volume conduction in extracellular spaces can give a misleading impression of the location of the source of the electrical activity (Smith, 2005). Furthermore, the relative locations of the electrodes, in regards to specific brain structures of an individual, can only be rough estimates.

FIG. 14 illustrates an example of sensor layout for 256-channel Hydrocele Geodesic Sensor Net (nose at the top of the figure). These figures are modified from (Luu et al 2011). A: represents the pain selection of physiologically relevant electrodes (n=85) given in red. B: shows blank template, which includes all electrodes channels (256).

(2) Stage Two: Signal Processing

After the pre-processing stage EEGs were analyzed using three methods: spindle threshold analysis (time domain), power spectrum analysis (frequency domain), and wavelet analysis (time-frequency domain). Each method was applied to the complete frequency spectrum and alpha frequency spectrum (based on the pain biomarker).

Spindle threshold analysis was used to identify pain spindle activity (Green et al., 2009). The maximum amplitude in the recording was determined by using thresholds starting at the maximum value and reducing by 10% of the maximum amplitude until a threshold of 0 µV was reached. Spindles were declared when a region of 0.5 seconds of the recording exceeded the threshold.

Power spectrum analysis was performed in order to determine the power of each frequency that was contained in the recording. The Fast Fourier Transforms was used to decompose the recording into component frequencies. Next, the relative power of the frequencies in the recording was calculated.

Time-frequency analysis will demonstrate the changes in pain-related dominant frequencies that might contain spindle activity over time based on Green et al. (2009). Time-frequency analysis can be executed using either short-time Fourier transform or wavelet transform. Time is mapped into frequency and phase by the Fourier transform and time is mapped into scale and time for the wavelet transform. When using the Fourier transform, there is a tradeoff between frequency resolution and time resolution. The wavelet transform is a more sophisticated method for analyzing non-stationary signals, which does not have a tradeoff between time and frequency resolution. It was most appropriate to use Morlet wavelet, which is commonly used in EEG time-frequency decomposition. Because Morlet wavelets have a sinusoid shape weighted by a Gaussian kernel it can capture local oscillatory components in a time-series.

(3) Stage Three: Machine Learning

The goal of the machine learning stage was to correctly classify with highest accuracy possible, the sensitivity and specificity of pain vs. no-pain and high vs. low pain intensity in order to objectively provide a pain diagnosis. Features for the machine learning algorithms were obtained from each of the three analysis methods performed in signal processing. Results were presented as the complete spectrum or alpha spectrum and full electrode set or physiologically relevant electrode set. Machine learning algorithms tested were Naïve Bayes, 1 and 2 Nearest Neighbors and SVM. Results were compared from these algorithms to select the best performing classifiers across groups.

Validation Technique

A cross validation technique was used to evaluate the performance of the classification. A 10-fold cross validation approach was applied to the dataset and sensitivity to determine specificity and accuracy.

The sensitivity of a clinical test refers to the ability of the test to correctly identify patients with a condition (Lalkhen and McCluskey, 2008).

$$\text{Sensitivity} = \frac{\text{True positives}}{\text{True positives} + \text{False negatives}}$$

A test with 100% sensitivity correctly identifies all patients with the pain signature.

The specificity of a clinical test refers to the ability of the test to correctly identify those patients without the condition (Lalkhen and McCluskey, 2008).

$$\text{Specificty} = \frac{\text{True negatives}}{\text{True negatives} + \text{False positives}}$$

A test with 100% specificity correctly identifies all patients without the pain signature.

The accuracy is computed by $$\text{Accuracy} = \frac{(\text{True positives} + \text{True negatives})}{(\text{True positives} + \text{True negatives} + \text{False positives} + \text{False negatives})}$$

The accuracy provides a selection criterion upon which the optimal number of electrodes and best performing algorithm could be determined. It also allows for comparison between the complete spectrum and alpha band regarding the obtained outcomes for each.

Overview of Experiments

Table 2 gives a detailed overview of the methods, measures of interest, purpose and relevance to PD for each of the experiments reported in this thesis. To summarize briefly, experiments 1-3 (Section 4) focus on validation of BSNs to measure: upper limb movements, interactions with objects, and between patients and healthy subjects. Experiments 4-6 (Section 5) explore engineering and design criteria suitable for real world conditions. Experiment 7 (Section 6) tests sensors and wavelet analysis to measure cognitive load during everyday tasks. Experiment 8 (Section 7) explores associations between speech and movement symptoms and reviews types of speech. Experiment 9 (Section 8) tests the NOD algorithm to detect a pain signature found with deep brain electrodes. Experiment 10 (Section 9) tests machine learning to classify facial expressions and facial features.

Table 2. presents the method, measure of interest, purpose, and relevance to PD for each experiment:

TABLE 2

| Experiment | Method | Measure of Interest | Purpose | Relevance to PD |
|---|---|---|---|---|
| (1.) Testing BSN to measure upper limb movements | Body Sensor Network- Inertial measurement units (IMU) & Statistical Analysis | Upper limb (Motor System) | Validate BSN for measuring upper limb movement | Abnormal hand trajectories in PD patients (Flash et al 1992) PD patients exhibit decreased linear speed and more corrective hand movements (Dounskaia et al., 2009a; Dounskaia et al., 2009b; Isenberg and Conrad, 1994; Konczak et al., 2009; Sande de Souza et al., 2011; Tresilian et al., 1997) Upper limb kinematics in PD suggests role of basal ganglia (Moisello et al., 2011) |
| (2.) BSN to measure an everyday task using continuous wavelet transforms | Body Sensor Network- Inertial measurement units (IMU) & Wavelet Analysis | Upper limb, hand (Motor System) | Test BSN and wavelet analysis techniques for measuring everyday interaction with objects | Measure movement during activities of daily living Living routine previously identified in the Motor Activity Log (MAL) for the upper extremity |
| (3.) Measuring impaired upper limb movements using wavelet analysis | Motion tracker & Wavelet Analysis | Upper limb, shoulder (Motor System) | Test wavelet technique for differentiating patients and healthy controls | In addition to other upper limb impairments, PD patients exhibit frozen shoulder and other shoulder disturbances (Riley et al., 1989) |
| (4.) Testing a sensor network to measure | Traxial accelerometer & | Engineering and hardware design | Explore the ability of sensors to measure in | Design considerations for BSN- e.g. plane, |

TABLE 2-continued

| Experiment | Method | Measure of Interest | Purpose | Relevance to PD |
| --- | --- | --- | --- | --- |
| acceleration during water-ski jumping | Statistical Analysis | | harsh and extreme conditions | train, or equivalent acceleration conditions (Guidelines for Occupational Therapy in PD Rehabilitation, 2011) |
| (5.) Comparison of median frequency between traditional and functional sensor placements during activity monitoring | Triaxial accelerometer & Statistical Analysis | Engineering and Hardware design | Test if BSN sensor can measure movement from pocket placement | Design consideration: BSN must be unobtrusive for ADL Design considerations for iPhone and tablet integration |
| (6.) Testing an integrated clothing sensing system for measuring joint stability | ICSS & Statistical Analysis | Engineering and Hardware design & Knee Joint Stability (Motor System) | Test fully unobtrusive BSN to measure knee joint stability | Design consideration: BSN must be unobtrusive for ADL Knee impairments have been observed in PD patients as part of gait impairment, postural stability, and isokinetic knee strength (Nocera et al., 2010; Rosin et al., 1997). |
| (7.) Effect of everyday living behavior on cognitive processing | Xsens sensor & Wavelet Analysis | Processing, attentional demands (Cognitive function) | Test to what extent combining everyday motion and speech tasks affect cognitive processing | Impairments in PD patients are worsened under dual-task conditions requiring simultaneous performance of cognitive and/or motor tasks when compared to healthy controls (Kelly et al. 2012; Rochester et al. 2004; O'Shea et al 2002; Woollacott & Shumway-Cook 2002; Bond& Morris 2000; Brown & Marsden 1991). |
| (8.) Everyday Speech and Motor Symptoms | Statistical analysis | Speech (Cognitive function) & Walking, Swallowing, Salivating, Freezing, Tremor (Motor System) | Identify correlations between speech and motor symptoms | Speech impairments have been identified as possible markers for PD detection and progression (Tsanas et al. 2011; Skodda, Gronheit, & Schlegel, 2012). Imprecise vowel articulation has been observed even in mild stages of PD and commonly contributes to reduced speech intelligibility (Neel, 2008; Skodda, et al., 2011). |
| (9.) Neural oscillation detection | EEG & Wavelet Analysis & Machine Learning | Neural Oscillation (Brain Activity) EEG Engineering and Hardware design | Test if EEG and NOD algorithm can detect a neuropathic pain biomarker found using deep brain electrodes Determine minimum number of electrodes necessary to detect it | Excessive beta band oscillations found in PD (Brown et al. 2001) LFN in the Subthalamic nucleus of PD patients shows high-frequency oscillations (15-30 Hz) (Levy et al. 2002) Engineering design considerations: portable EEG? |

TABLE 2-continued

| Experiment | Method | Measure of Interest | Purpose | Relevance to PD |
|---|---|---|---|---|
| (10.) Sentiment Classification and Facial Feature Extraction- a 2 part Data Analysis | Machine learning | Facial features (Motor system) Emotion from facial expression (cognitive function) | Test ability of machine-learning algorithm to classify emotion from facial expression in a large dataset. To identify facial features in PD patient. | Blink rate, facial rigidity, bradykinesia and masked face (Abbs et al., 1987; Bologna et al., 2013) Emotional problems, such as depression and anxiety, common in PD (Shiba et al., 2000; Walsh and Bennett, 2001) |

Figure 15:
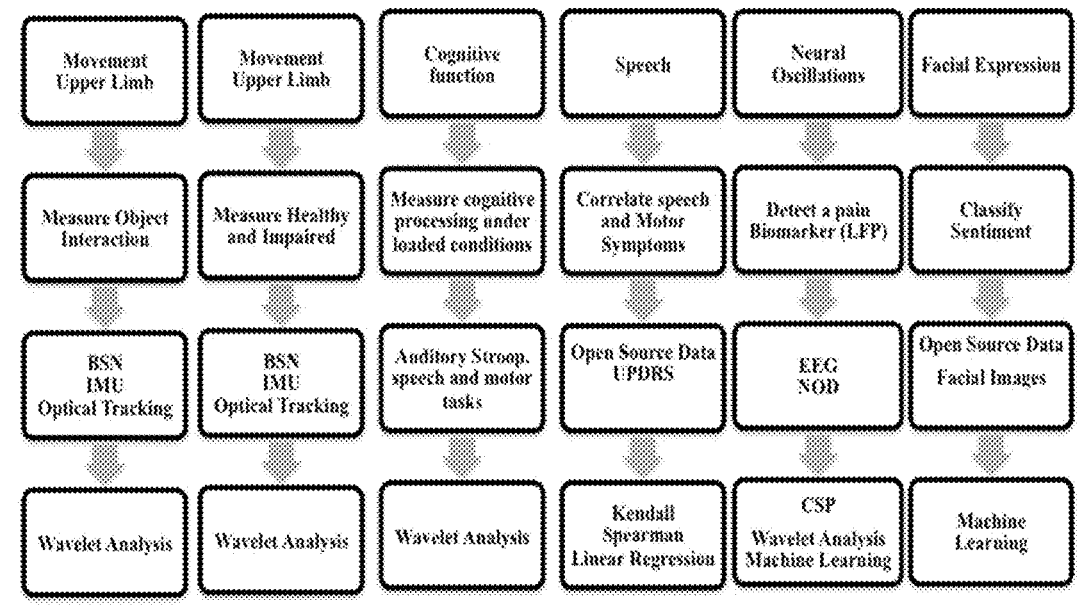
FIG. 15 is an exemplary diagram of an overview of a measure of interest, specific feature to be measured, data collection method, and analysis method.

FIG. 15 illustrates an example of an overview of measure of interest (first row), specific feature to be measured (second row) data collection method (third row) and analysis method (fourth row).

This section discussed the methods, data collection and analysis used for the initial development and validation of a more general approach to early detection of PD. The potential measures of interest, (discussed in Section 2) are broad, for they spread across three foundational domains: the motor system, cognitive function and brain activity. The approach is predicated on multi-modal data analysis across three domains to capture the heterogeneity of the PD spectrum. Analysis methods therefore needed to account for time, location, physiology, and changing environment in order to develop a system that measures during everyday living. The above methods will be summarized in the write-up for each experiment with focus on its specific application and procedures.

Section Four: Measuring Upper Limb Movement

Introduction

The 3 experiments presented in this section discuss validation and testing of body sensor measurements and analysis methods towards the goal of developing an unobtrusive system with sufficient sensitivity to detect movement deviations during everyday tasks. The first experiment validates a BSN against optical tracking for its ability to measure complex upper limb movements. The second experiment develops the model further to test if BSN can measure the interaction with an object during an everyday task. The third experiment tests BSN's ability to differentiate between healthy and impaired movement.

BSNs have been used in other research fields, but have not yet been established for clinical use in PD (Moore et al., 2007). BSNs have been used for upper arm rehabilitation in stroke patients (Mountain et al., 2010; Paulis et al., 2011) and monitoring in cardiovascular disease (Lo et al., 2005). BSN has also been explored for post-operative monitoring (Atallah et al., 2013; Aziz et al., 2007) blood-pressure monitoring (Chan et al., 2007; Espina et al., 2006) and prevention and management of asthma (Seto et al., 2009). Body sensors have more recently been developed for physiological measuring of joint angles, stair climbing, arm trajectory, and knee joint angles (Bergmann et al., 2013c; Bergmann et al., 2009a; Bergmann et al., 2010; Bergmann et al., 2012c; Favre et al., 2009). Because BSNs are not validated for clinical applications, the use of a gold standard measurement is needed to verify the accuracy of the proposed device.

Gold Standard

In experiment 1, 2 and 6 marker based optical tracking systems are used as the criteria standard to validate the accuracy of BSNs (Bergmann et al., 2009a; Godwin et al., 2009; Mayagoitia et al., 2002b; Zhou and Hu, 2008). The external validity of measuring movement (within a certain level of SNR and sensitivity) depends on the device and its application. Ideally, the BSN system should translate to a clinical detectable difference. In other words, what level of sensitivity is needed to detect clinically relevant changes? In order to answer this question, free-living data from real world environments needs to be established with the modalities of interest, hence the need to develop new measurement systems.

Experiment 1

Testing a Body Sensor System to Measure Upper Limb Movements. Bergmann, J, Langdon, P., Mayagoita, R. & Howard, N. 2013c. Exploring the use of sensors to measure behavioral interactions: An experimental evaluation of using hand trajectories. PLOS ONE, Forthcoming.

Background

Quantifying arm movements made towards a specific goal, such as picking up an object, are of interest to PD research (Tresilian et al. 1997; Plotnik, Flash, Inzelberg, Schechtman et al. 1998; Flash et al. 1992; Ghilardi et al. 2000). Upper limb movement irregularities, such as linear speed and corrective movements have been exhibited in PD patients and could potentially be used as a measure of early detection (Dounskaia et al., 2009a; Dounskaia et al., 2009b; Isenberg and Conrad, 1994; Konczak et al., 2009; Sande de Souza et al., 2011; Tresilian et al., 1997).

Performance is not only based on the anatomical properties of the limb, since motor control defines the level of efficiency at which the movements are executed. Movements are precisely controlled by the brain and communication deficits between the musculoskeletal and nervous system lead to direct changes in (motor) behavior. Research of upper limb movements could potentially be valuable for diagnosis markers, and to gain a better understanding of underlying brain processes influencing motor function impairments (Ghilardi et al., 2000; Ray et al., 2009). However, a sensitive, non-obtrusive tool is needed to measure complex upper limb movement.

Aim: The purpose of this study was to test the accuracy of a wearable sensor system to measure the distal position of the arm (a solid hand and wrist complex) compared with gold standard data acquired with optical tracking during a series of arm movements.

Methods

Study Design

The method computed hand positions using a wearable sensor system and validated it against a gold standard reference measurement (optical tracking device). The experiment used IMUs to measure arm movements of one human subject. The validity of the sensor device is examined by determining how closely the distal position of the arm (a solid hand and wrist complex) relates to the measurements acquired by an optical tracking device, during a series of predefined arm movements.

Data Collection

Figure 17:
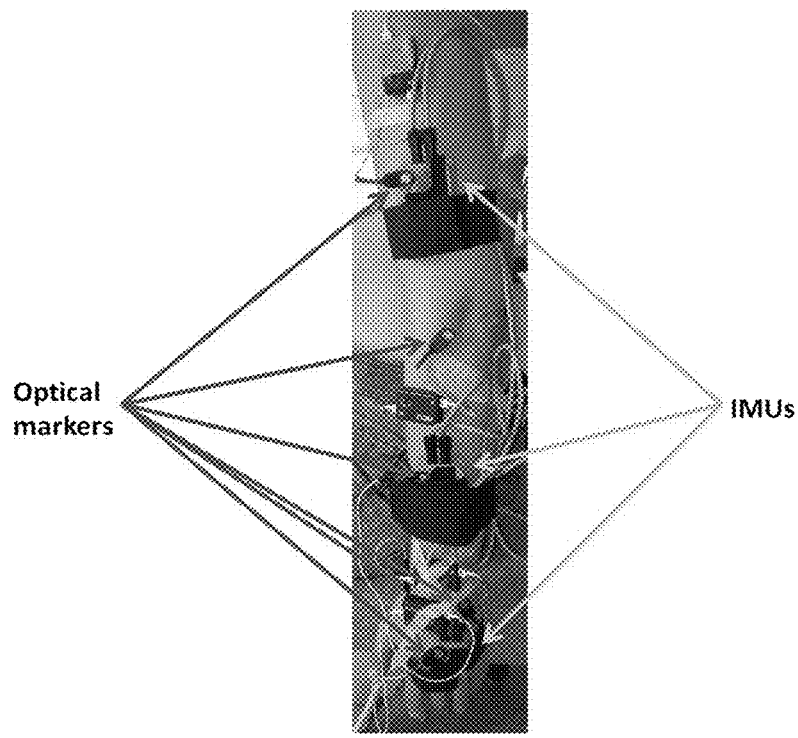
FIG. 17 is an exemplary diagram of Optical tracking markers and Inertia Measurement Units (IMUs).

One 37-year-old healthy female subject (height 171 cm, weight 61 kg) participated in this study. Three IMUs (MTx, Xsens Technologies B. V., Enschede, Netherlands) were placed on the subject at three different points along the left arm; one on the upper arm above the elbow, another just below the elbow, and a third sensor near the wrist (FIG. 17).

The participant sat on a chair with the arm rested at the side of the trunk. The subject was asked to perform three different sequences each consisting of three different positions (FIG. 16) and each held for roughly 10 seconds. The first sequence started with the arm fully extended, hanging by the side, in the start position, followed by flexing the elbow to 90° and keeping the forearm in neutral, after which the participant was asked to move to 90° of shoulder anteflexion, with the arm fully straight and pointing forward (sequence A). In the second sequence, the participant began in the same starting position as the first sequence and was then instructed to move to 90° of shoulder abduction with the elbow fully extended, from this position the elbow was flexed to 90° and an internal rotation was performed (sequence B). The last sequence also had the same starting position as the previous two, from which the participant moved her arm to 90° of shoulder abduction and 90° elbow flexion with an external rotation; this was followed by moving to 45° retroflexion in the shoulder and 120° of flexion in the elbow (sequence C).

Figure 16:
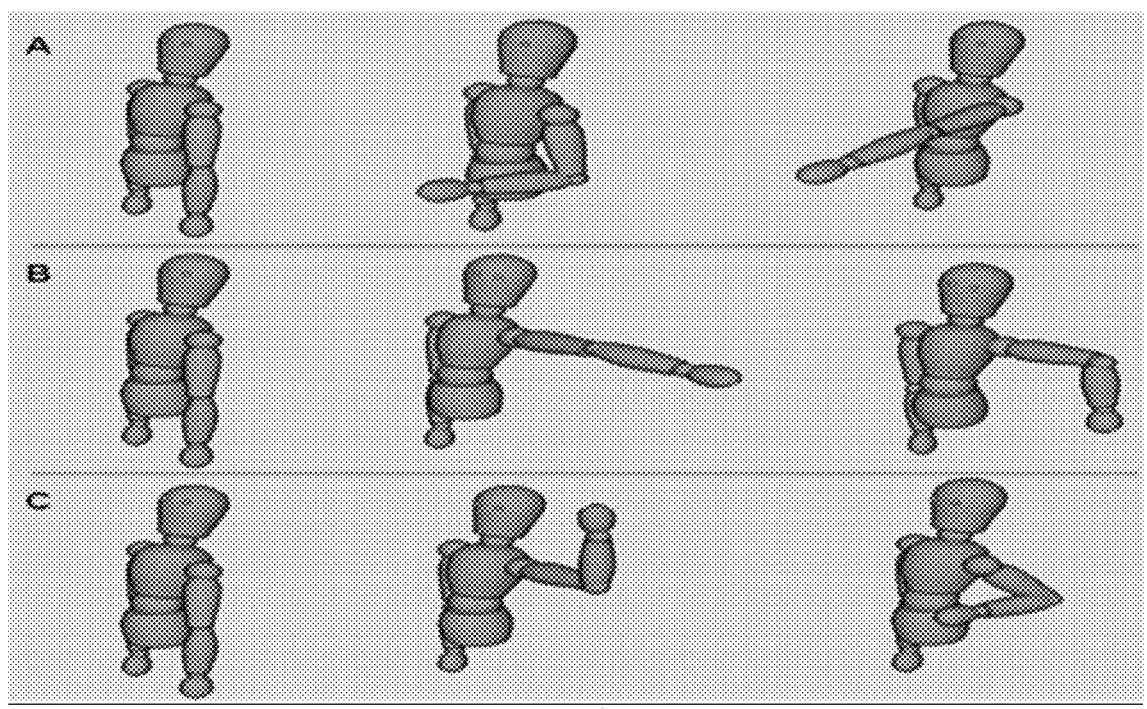
FIG. 16 is an exemplary diagram of sequences A, B, and C each with three arm positions.

FIG. 16 illustrates an example of sequences A, B and C each with three arm positions.

Equipment

FIG. 17 illustrates an example of optical tracking markers and Inertia Measurement Units (IMUs) attached to 3 points on the left arm.

The sensors were securely attached to each body segment in order to ensure that the orientation of the sensor with respect to the body segment did not change. Straps were used to provide a preloading force in order to minimize measurement errors (Bergmann et al., 2009b; Forner-Cordero et al., 2008).

The placement of the sensors determined the relationship of the sensor's axis to the anatomical coordinate system, as the sensor coordinate system was fixed to the device. The Z-axis of each IMU coordinate system was physically placed to run perpendicular, as close as possible, to the sagittal plane, while at the same time minimizing relative motion between sensors and underlying bones. As the participant sat as still as possible with the left arm hanging at the side of the body, further analytical correction was applied by using software (MT Software V2.8.1, Xsens Technologies B. V., Enschede, Netherlands). The alignment program placed the Z-axis of each IMU in line with gravity (vertical plane) with the new X-axis of all the sensors perpendicular to the Z-axis and along the line of the original global X-axis, while the Y-axis was chosen to obtain a right handed coordinate frame. The non-orthogonality between the axes of the body-fixed coordinate system was less than 0.1°.

Active Codamotion (Codamotion, Charnwood Dynamics, Leicestershire, UK) markers were placed using double-sided adhesive tapes, on the radial styloid process, ulnar styloid process, lateral epicondyle, medial epicondyle, acromion, spinous processes of the seventh cervical vertebra and the IMUs. A standard system configuration was used for data acquisition by the Codamotion and Motion Tracker software. The cameras of the optical tracking device were positioned in such a way that the position data of the right side could always be obtained during movement. The three dimensional (3D) position of these markers can be determined with an accuracy of ±1 mm (Lichtwark and Wilson, 2006).

Data for both the Codamotion and the IMUs was acquired at 100 Hz, and an electronic pulse was used to synchronize the two measurement systems. All further data analysis was done using Matlab (MathWorks, Inc., Natick, Mass., USA) (Bergmann et al., 2009c).

Data Processing and Analysis

Biomechanical Model

Figure 18:
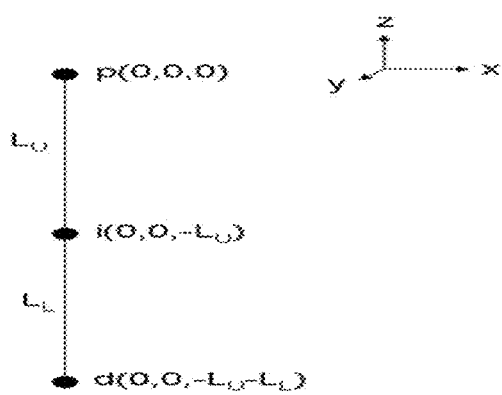
FIG. 18 is an exemplary diagram of an initial condition of the two-link model.

The upper extremity can be approximated as a multi-link chain, with each body part as a rigid segment and its movement represented by one IMU (Winter, 2009). A simplified two-segment 3D model was used that consisted of two (upper and lower arm) rigid segments (FIG. 18). The shoulder blade (scapula) movement was not taken into account. In addition, the hand and wrist were considered a single rigid segment for ease of application of the model. It has been suggested that functional changes of the hand-wrist complex directly affect movement patterns at the shoulder (May-Lisowski and King, 2008). To keep the model as simple as possible only the signals from the sensors that were absolutely vital to reproduce the general movement pattern were selected. Body segment lengths were calculated from anthropometric data (Winter, 2009) as a percentage of the body height of the participant.

Analysis

The 3D representations of the distal point of the left arm (Point [d] in FIG. 18) obtained using the two measurement devices were compared by calculating a two-tailed Pearson product-moment correlation coefficient (r) and by calculating the root mean square error (RMSE) between the two signals (Bergmann et al., 2009a; O'Donovan et al., 2007; Thies et al., 2007). The dynamic range, defined as the largest possible signal (full range of motion) divided by the smallest possible signal (maximum error) (Halamek et al., 2001), was calculated for the IMU based model. Independent analysis of each direction of movement, referred to as X, Y and Z, was performed. The Euclidean norm was also calculated for each sequence.

FIG. 18 illustrates an example of an initial condition of the two-link model. Segment lengths were taken from anthropometric data (Winter, 1990). The proximal point (p) represents the shoulder; the intermediate point (i) is the elbow and the distal point (d) the hand. All positions are given in (X,Y,Z). ($L_U$) length of the upper arm; ($L_L$) length of the lower arm and hand.

Results

Figure 19:
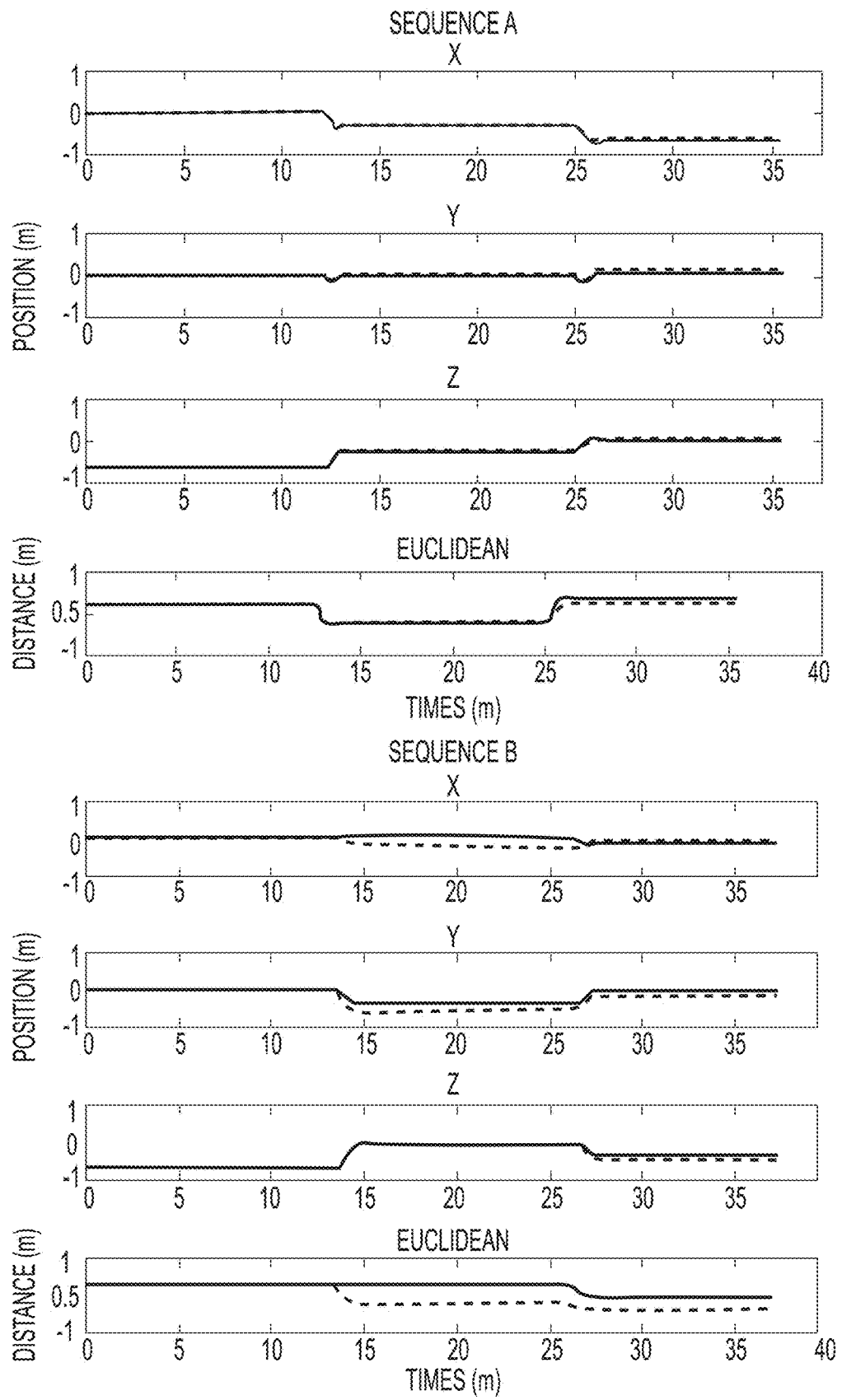
Figure 19:
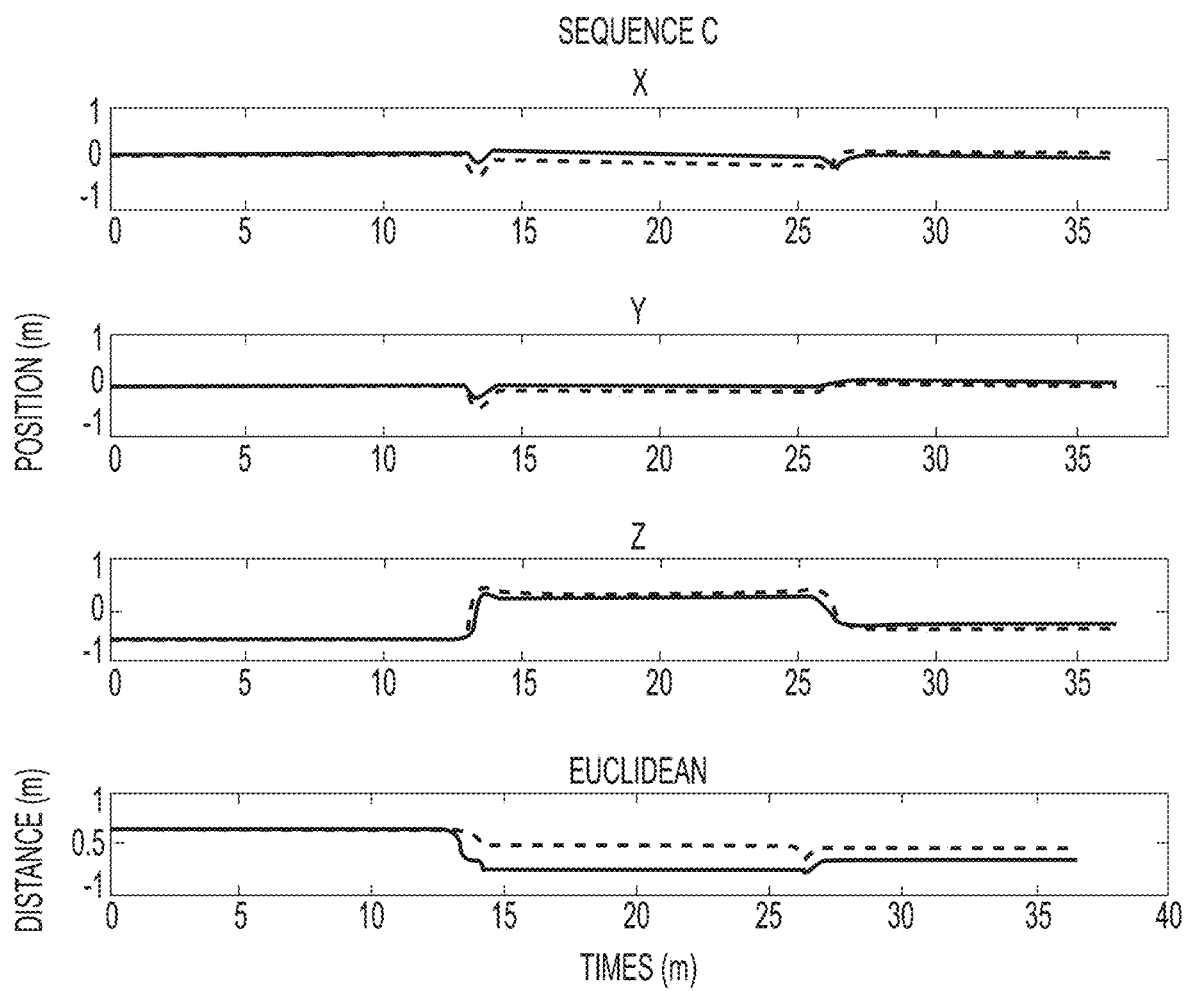

The shape of the curve describing the movement was on the whole, highly comparable between the two measurement methods (FIG. 19). High Pearson Correlation Coefficients (PCC) were found in both the Y and Z direction for all 3 movement sequences (Table 3). After an initial high correlation in the X direction for sequence A (0.99), there was a significant drop in correlation for the subsequent sequence. The movement of the hand in the X direction was poorly correlated in sequence B (−0.11). However, the RMSE calculated in the X direction for sequence B was not higher than those found for sequence A and C. The best accuracy was found for sequence A, with RMSE ranging from 0.02 to 0.05 meters. Sequence B not only had the poorest correlation between the methods; it also suffered from the highest RMSE (Euclidean norm). The Euclidean norm showed a lower correlation for sequence B, but had very strong correlations for both A and C. The highest dynamic range was found for sequence B in direction X. In general, the Z direction performed the best in terms of highest correlations and lowest RMSEs. It also had relative high dynamic ranges across all sequences.

FIG. 19 illustrates an example of positions of the hand in each direction (X, Y and Z) and Euclidean norm for every sequence (A, B and C). Dashed blue lines are the positions obtained from the optical tracking device and the solid red lines correspond to hand positions calculated by the sensor and biomechanical model. Table 3 shows Pearson correlation coefficients, Root Mean Square Errors and dynamic range between the positions obtained by both methods. S stands for motion sequence. X, Y and Z represent the directions of movement for the upper limb point. $\|d\|$ is the Euclidean norm.

TABLE 3

| | Pearson correlation coefficient ($p < 0.01$) | | | Root Mean Square Error (meters) | | | Dynamic Range | | |
|---|---|---|---|---|---|---|---|---|---|
| S | A | B | C | A | B | C | A | B | C |
| X | 0.99 | −0.11 | 0.60 | 0.04 | 0.14 | 0.13 | 50.46 | 0.95 | 0.97 |
| Y | 0.95 | 0.97 | 0.93 | 0.05 | 0.15 | 0.08 | 3.46 | 2.38 | 2.10 |
| Z | 0.99 | 0.98 | 0.99 | 0.02 | 0.07 | 0.10 | 44.76 | 7.35 | 9.48 |
| $\|d\|$ | 0.98 | 0.73 | 0.95 | 0.03 | 0.17 | 0.15 | 7.0 | 2.07 | 1.3 |

Discussion

Correlations between the IMU body sensors and the optical tracking device ranged from 0.99 to −0.11 (with a calculated average of 0.81) and root mean squares ranged from 0.02 to 0.15 meters. The results demonstrated that the proposed system allows for accurate tracking of general movement patterns. Single plane movements (sequence A) seemed to provide the best correlations between the 2 measuring methods. However, even in more complicated movement patterns (such as sequence B and C) motion of the distal part of the upper limb model relates well to the motion of the optical tracking marker in both the Y and Z direction. The one low negative correlation found in sequence B does not affect the overall movement pattern significantly, as the position changed more for the Y and Z direction ($\Delta Y=0.39$ and $\Delta Z=0.68$ m) than for the X direction ($\Delta X=0.25$ m).

The Euclidian norm provides a method for dimensionality reduction and the results indicate it performed relatively well across the explored sequences. On the whole, the principal movement patterns can be picked up by the proposed method based on body-worn sensors, but do not provide absolute accuracy of the position of endpoints. The dynamic range showed that information could be extracted from the dominant planes of motion. Yet, smaller deviations, particularly in the X direction, did (almost) not register beyond the noise level. The proposed method can, therefore, best be applied to movement patterns, with large changes of positions. This illustrates the need of this model to focus on motor behavior that involves large ranges of motion at the shoulder complex.

Although motion artifacts do have an effect on the outcome, the largest source of accuracy errors is most likely due to the fact that the biomechanical arm model was based on only two segments. Bergmann et al. (2012) found that, contrary to popular belief, motion artifacts are not always the primary source of accuracy errors in measuring human motion. In their initial sequence of experiments, in which only two segments were used for motion analysis, Bergmann et al. (2012) determined that accuracy errors from measuring motion and position was more due to the analytical model used. By increasing the number of sensors attached to each extremity the sensors will generate redundancy in the data, which can be used to minimize error. It is thus possible to negate or at least minimize the effect of motion artifacts on data acquisition.

It has been shown that IMUs can obtain accurate estimations of arm position when applied during movement patterns that require a very limited range of motion (Zhou et al., 2008b). The sequences in this study were selected in order to obtain insight into the accuracy of the proposed model over the full range of arm movements. In addition, the difference found between the two methods could be contributed to inaccuracies associated with the relative movement of the sensors or markers compared to the underlying bones. Due to this relative movement between the optical tracking marker and the underlying bony landmark, artifacts in position data can occur (Cappozzo et al., 1996). Displacements of more than 20 mm between skin and underlying bone have been reported for optical tracking systems (Garling et al., 2007).

Validation outcomes relate to the agreement of the two systems within the presented study. These results do not reflect the validation of this system for out of sample populations and are meant to provide the required internal validation that is needed for further exploration of the method within this study.

Experiment 2

Testing BSN to Measure an Everyday Task Using Continuous Wavelet Transforms. Bergmann, J., Langdon, P., Mayagoita, R. & Howard, N. 2013c. Exploring the use of sensors to measure behavioral interactions: An experimental evaluation of using hand trajectories. *PLOS ONE, Forthcoming*.

Background

Given the results of the BSN's ability to measure arm movement in Experiment 1, the sensors and upper limb model were further tested by measuring changes in motor behavior during object interaction in a changing environment. The purpose of these measurements was to show the utility of the sensing system to determine the coherence in motor behavior related to the individual or object used in the everyday task. The validity of the sensing device is examined by determining how closely the distal position of the arm (a solid hand and wrist complex) relates to the position acquired by an optical tracking device.

Aim: To test the utility of the BSN system and wavelet analysis to identify behavioral changes with small alterations in the environment during everyday interaction with objects.

Methods

Study Design

An IMU/BSN experiment using three human subjects who performed an everyday task. Data was analyzed using CWT. Object interaction was measured by comparing movement patterns from three slightly different object constraints.

Data Collection

Three healthy subjects (2 males and 1 female, aged between 27 and 42 years) repeated a pouring task five times, using three different liquid container designs (pitcher, teapot and kettle). From the initial starting position (hands placed along their side), participants were asked to pick up the container with liquid and pour a little bit into a cup without spilling. Both the container and cup were placed in a preset location to ensure agreement between subjects and tasks. Apart from these basic constraints, participants were free to choose their own preferred movement path and speed. Subjects performed the tasks for data collection after practicing the pouring task eight times during two previous trials. The start and end position consisted of the arm resting on the side of the body. Measurements were taken in the kitchen where the subjects would normally prepare their drinks.

Equipment

3 IMU sensors were securely attached to the right arm on each body segment. Straps were used to provide a preloading force in order to minimize measurement errors (Forner-Cordero et al., 2008). The placement of the sensors determined the relationship of the sensor's axis to the anatomical coordinate system, as the sensor coordinate system was fixed to the device. IMUs data was acquired at 100 Hz.

Data Processing and Analysis

Data analysis was done using Matlab (MathWorks, Inc., Natick, Mass., USA). Hand traces were computed using a two-linked segment model. Observation of the initial results shows that the difference is more profound, between subjects than within subjects.

FIG. 20 illustrates an example of traces of the hand computed using a two-linked segmental model. All figures starting with A compare the patterns between three subjects (blue, red and green) interacting with a pitcher (A.1), teapot (A.2) and kettle (A.3). The figures labeled with a B show the traces for each subject (B.1, B.2 and B.3) using pitcher (blue), teapot (red) and kettle (green). All plots show a 2D projection of the data for each plane.

CWT was used to analyze the frequency content over time. The calculation was then used to compare the signals and find differences between them. CWT was first computed within the repetitions and then a comparison was made based on the summed results for each condition (subject, object). A Morlet waveform was used.

Because the subjects repeated each condition (container) several times, the mean wavelet coherence was calculated for all possible pairwise comparisons across the repetitions performed. Based on the outcomes between and within subjects, C was computed by taking the average either for all subjects or objects. This provided a measure of consistency in motor behavior. All analysis was performed for the Euclidean norm.

Results

The average duration of the pouring tasks was 10.6±2.1 seconds (±standard deviation) with a range of 7.3 to 16.8 seconds. The coherence results are provided in FIG. 21. Inspection of the wavelet coherence plots shows that subject 1 has a distinctively different outcome compared to subject 2 and 3. Subject 1 also showed the highest overall phase difference (0.73) with respect to time and scale. Overall the pitcher yielded the highest $\bar{C}$ across subjects (0.82), while the kettle had the lowest (0.77). This example shows the ability of the analysis method to differentiate between movement patterns. The difference in localized features indicates how much and when motor behavior differs within subjects and between objects.

FIG. 21 illustrates an example of wavelet coherence plots of the Euclidean norm. The mean phase difference across 8 movement repetitions is displayed for each subject utilizing one of three containers. At the end of the rows, all coherences per subject are averaged (Within). At the bottom of each column, all subjects are averaged for each container (Between). The warmer the color of a region, the lower the relative phase difference between the two signals. The full wavelet coherence is subsequently averaged to generate a single value ($\bar{C}$) displayed in the top corner of each plot.

Discussion

This preliminary dataset demonstrates the possible utility of the simplified upper limb model in a real-life setting, by combining concepts such as wavelets and unitary math. The results showed that wavelet analysis could be applied to compare everyday movement tasks, such as pouring. The wavelet coherence estimates the association between two signals of two processes with respect to both time and scale. The outcomes obtained in the wavelet coherence focused on how consistent motor behavior was within and between subjects. It became clear that subject 1 was the least consistent in motor behavior, which potentially relates to the selection of an alternative motion path compared to subjects 2 and 3. The pitcher also seemed to possibly yield a condition in which each subject was able to display more consistent behavior. The example explored in this study has limited generalizability, due to the small sample size. However, it aims to show that behavioral consistency in activities of daily living can be explored in more detail using the suggested approach. The importance of situations for determining behavior is known and cross-situational consistency of behavior has already been associated with the amount of similarity between situations (Furr and Funder, 2004). A higher measurement resolution could provide a richer understanding of these behaviors. It even allows for possible detection of small changes, such as a slightly different interaction object, that are now often are overlooked.

Defining behavior within the field of behavioral science has led to many different interpretations and opinions (Levitis et al., 2009). A recent study generated an evidence based definition that defines behavior as the internally coordinated responses of whole living organisms to internal and/or external stimuli, excluding responses more easily understood as developmental changes (Levitis et al., 2009). The majority of these responses reflect coordinated actions of the human musculoskeletal system. Despite the fact that these actions are emerging properties of multiple attributes. The focus on repeatability of motor behavior comes from one of the most cited articles in cross-species behavior (Bell et al., 2009). The authors found that the repeatability estimates were higher in the field compared to the laboratory and repeatability was higher when the interval between observations was short. Although, humans are likely to differ from other species these findings offer an interesting standpoint. In addition, there is evidence that repeatability increase with human ageing and this has been linked to the process of consolidated identity or reputation (Dail et al., 2004; Roberts and DelVecchio, 2000).

Experiment 3

Measuring Impaired Upper Limb Movements Using Wavelet Analysis. Howard, N., Pollock, R., Prinold, J., Sinha, J., Newham, D. & Bergmann, J. 2013d. Effect of Impairment on Upper Limb Performance in an Ageing Sample Population. In: STEPHANIDIS, C. & ANTONA, M. (eds.) *Universal Access in Human-Computer Interaction. User and Context Diversity*. Springer Berlin Heidelberg.

Background

Range of motion and speed of movement can both be affected by a number of different age-related diseases and other impairments. Performance parameters, such as movement velocity can be used to better differentiate between young and older subjects. However, normal processes of ageing can be further complicated by disease. For these reasons, high-sensitivity data collection and analysis are crucial for the detection of and distinction between abnormal patterns. This provides insight into a new method that aims to quantify and compare changes in motor behavior with greater detail.

The purpose of this study was to determine how movement differed between healthy controls and injured patients and if that difference can be quantified using wavelet analysis. The aim is to define the difference between clinically relevant groups and the potential application of a new analysis method. Motion tracking is used to measure shoulder movement during several range of motion tasks. In future work, the method can easily be validated using Body sensor networks in place of optical tracking.

The patient group consists of subjects with rotator cuff injury, as rotator cuff tears are among the most common conditions affecting the ageing shoulder (Williams Jr et al., 2004). The rotator cuff consists of four muscle-tendon units that move the shoulder joint. They are particularly important for achieving maximum shoulder rotations and damage can subsequently minimize the volume of space through which the arm can travel. The large range of motion that is available for the shoulder complex requires a multitude of different joints to be coordinated in a stable manner. The trade-off between operational volume and stability puts an enormous strain on the rotator cuff. Current functional shoulder measurements used clinically often test an average level of system performance at a single comfortable speed. Increasing the speed during shoulder activities can disperse groups that initially seemed similar. How specific gestures change across speeds remains unclear.

Aim: To measure spatial and temporal changes in shoulder motion between rotator cuff patients and healthy controls using wavelet analysis.

Methods

Study Design

A patient group and a control group performed range of motion tasks at different speeds. Wavelet analysis method is used to differentiate the patient data from the control data.

Data Collection

Seven healthy controls and eight pre-operative patients participated in the study. Demographic data for each group can be found below in the Table 3-2 shows the mean (±standard deviation) values for the demographics of all subjects. No significant differences were present between groups as tested with an independent t-test.

TABLE 3-2

|  | Age (yrs) | Height (m) | Mass (kg) |
|---|---|---|---|
| Controls | 41 ± 18 | 1.75 ± 0.04 | 82 ± 11 |
| Patients | 53 ± 10 | 1.74 ± 0.03 | 81 ± 10 |

Figure 22:
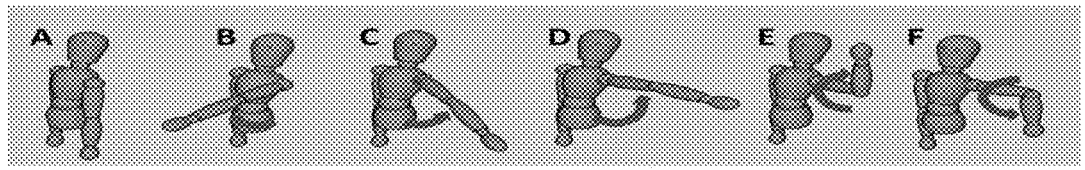
FIG. 22 is an exemplary diagram of movements performed by participants.

Participants were asked to perform five range-of-motion (ROM) tasks (FIG. 22) at "normal" and "fast" speeds. The normal speed was performed at a self-selected pace and maximum speed was the maximum pace each subject was capable of performing. Prior to taking measurements, the patients were allowed to practice the movements to ensure they understood the patterns that needed to be performed. The ROM tasks consisted of elevation in the sagittal (forward flexion), scapular and frontal (abduction) plane (FIG. 22). Participants were also asked to perform axial rotation consisting of external and internal rotation of the arm during 90 degrees of abduction. From the initial starting point with the arm relaxed by the side, subjects were instructed to reach a maximal joint angle for each ROM task, then participants were asked to repeat each task three times.

FIG. 22 illustrates an example of movements performed by participants (A) Starting position for each movement (B) sagittal (forward flexion) plane rotation (C) scapular plane rotation (D) frontal (abduction) plane rotation (E) external rotation and (F) internal rotation.

Equipment

Figure 23:
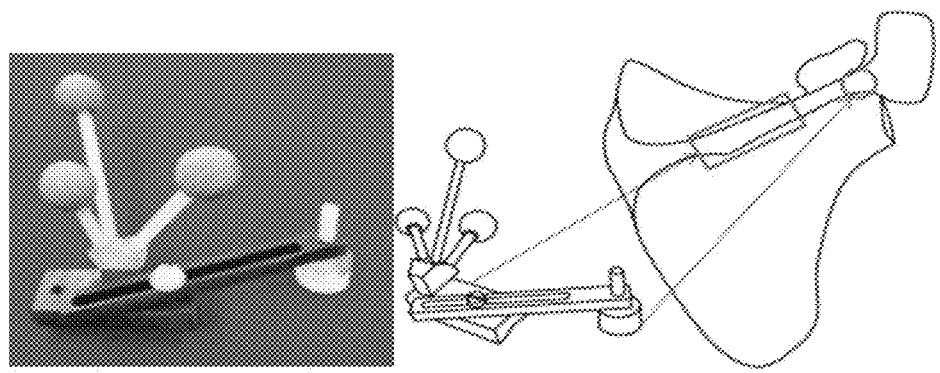
FIG. 23 is an exemplary diagram of a scapular tracking device used for measuring scapula (shoulder blade) movement.

To accurately measure three-dimensional positions of the upper extremity, an active motion analysis system (Codamotion, Charnwoord Dynamics, Leicestershire, UK) was used to perform motion tracking. Markers were placed on the thorax, humerus, and scapula. For the digitization of the shoulder, markers were placed on the origin of brachoradialis, biceps, belly, insertion of deltoid, acromion (marker placed on the acromioclavicular joint) and the short, medium and long stem of a scapula tracker (FIG. 23). Markers were attached to the skin using double sided adhesive tapes. Local coordinate systems and segments were established using bony landmarks and marker positions as defined by the New Castle Shoulder Model (Murray and Johnson, 2004). A functional, rather than geometrical, method relying on linear regression was used to define the center of rotation for the glenohumeral joint (Gamage and Lasenby, 2002). This method required subjects to perform a series of small rotations at low levels of elevation in order to minimize shoulder blade movement. The movement performed explored the 3D space and included internal and external rotations. The forearm was kept flexed at 90° throughout this functional assessment. Joint angles were defined using the International Society of Biomechanics standardization proposal of the international shoulder Group (Wu et al., 2005). Dynamic tracking of the shoulder blade can be difficult due to its movement under the skin; therefore measurements were obtained using a new procedure that associates scapula motion to a skin-fixed scapula tracker (Karduna et al., 2001a). The scapula tracker consists of a tracker with a hinge joint and the base that allows it to conform to the subject's scapular spine and an adjustable 'foot' that is positioned over and attached to the posterior-medial aspect of the acromion process (FIG. 23). This technique has been validated, but errors due to skin motions are still possible with measurement errors of less than 5° (Prinold et al., 2011). The selected joint angles were obtained between the humerus and scapula segments.

FIG. 23 illustrates an example of a scapular tracking device used for measuring scapula (shoulder blade) movement.

Data Processing and Analysis

All data analysis, subsequent to data collection, was done in Matlab (Mathworks, Inc., Natick, Mass., USA).

Statistical Analysis

Range of motion and mean angular velocities were compared between groups (controls and patients) and between conditions ("normal" and "fast" speeds of movement). A one-way ANOVA with a Bonferroni multiple comparison correction was used for statistical analysis, as normality was assumed based on obtained histograms. Movement data within subjects was also analyzed using wavelet coherence. This technique can be used to assess how the signal differs between the "normal" and "fast" conditions within a group. Signals were aligned at the starting point of movement using a threshold value algorithm that identified the alignment point of the movement, as defined by the first crossing of the 10% value of the maximum ROM.

Wavelet Analysis

CWT was performed to divide the signal into wavelets and analyze the frequency content over time. Data was analyzed using the wavelet toolbox in Matlab (MathWorks, Inc., Natick, Mass., USA). A bi-orthogonal Gaussian waveform was selected for the wavelet analysis, as it was expected to show the best match with the performed activities. Regions of interest were from 2 seconds onward (signal embedded from that point on). The first two seconds were a period of no activity to make sure there was similarity across all comparisons and to take into account edge effects due to finite length time series (Torrence and Compo, 1998).

Two examples of simulated outcomes for wavelet coherence are given in FIG. 24. These examples show the wavelet coherence of two generated sine waves, which mimic the "fast" and "normal" condition. In example (A.1) there is a factor 2 difference in movement frequency between the conditions, while the second example (A.2) shows a very small offset from the baseline frequency. It is clear from FIG. 24 that there are more localized similarities in B.2 compared to B.1.

FIG. 24 illustrates an example of wavelet coherence based on two waves with different frequencies. A.1 The red signal shows a sine wave with a frequency f, while the blue trace has a frequency of 2f. Zero-mean Gaussian noise is added to both signals. A.2 The red signal shows a sine wave with a frequency f and the blue trace has a frequency of 1.001f. Zero-mean Gaussian noise is added to both signals. B.1/B.2 The heat map shows the modulus, wherein dark red represents 1 and dark blue 0. Small arrows are used to represent the relative phase between the two signals.

A visual representation of localized similarities between the "fast" and "slow" conditions within a group can be obtained by superimposing all wavelet coherence graphs. This procedure will be performed for the frontal plane, as this plane is essential in both 2D and 3D gesture recognition. All data was normalized for each subject to both maximum amplitude and duration. This normalization allowed for the comparison of the relative similarities in patterns for the "normal" and "fast" conditions.

Results

ANOVA F values and degrees of freedom for ROM and Angular Velocity are given in Table 4. Three subjects were not taken into account for the Internal/External task, due to missing data (obstruction of markers). There are no interactions, as it is one dependent variable with 4 levels (groups), so only main effect outcomes are given. Table 4 shows ANOVA F values and degrees of freedom for ROM and Angular Velocity.

TABLE 4

| Task | Range of Motion | Angular Velocity |
| --- | --- | --- |
| (B) Sagittal elevation | $F(3, 26) = 10.14$, $p < 0.05$ | $F(3, 26) = 40.00$, $p < 0.05$ |

TABLE 4-continued

| Task | Range of Motion | Angular Velocity |
| --- | --- | --- |
| (D) Frontal elevation | $F(3, 26) = 5.60$, $p < 0.05$ | $F(3, 26) = 32.24$, $p < 0.05$ |
| (C) Scapular elevation | $F(3, 26) = 7.91$, $p < 0.05$ | $F(3, 26) = 31.66$, $p < 0.05$ |
| (E, F) External/Internal Rotation | $F(3, 23) = 0.63$, $p > 0.05$ (ns) | $F(3, 23) = 6.32$, $p < 0.05$ |

Range of Motion

The glenohumeral shoulder joint range of motion (ROM) showed significant differences between control subjects and patients across all elevations at "normal" speed (FIG. 25). The greatest difference between groups was found for the sagittal elevation, with a mean difference of 40° (p<0.01). By increasing the speed of movement, this difference was brought back to 33° (p<0.05). Frontal elevation range of motion showed a decrease between groups when motion was voluntarily speeded up (37° [p<0.05] for "normal" vs. 33° for "fast"). However, the increasing rate of motion only further increased differences in the scapular plane. Scapular elevation difference changed from 30° (p<0.05) during the "normal" speed to 35° (p<0.01) for the fast condition. No significant difference was found in axial rotation between groups. No significant within group differences were found across all tasks.

FIG. 25 illustrates an example of a maximum range of glenohumeral motion (A) and mean angular velocity (B) at the shoulder joint. Control group data is shown as blue circles and patient data is represented by red squares. Filled circles or squares give data at "normal" speeds, while open circles and squares relate to the "fast" speeds. Cont=controls, pre=pre-operative patients, normal=normal movement speed, fast=fast movement speed. Asterisks indicate significant differences between groups or conditions. *=p<0.05, =p<0.01 and *=p<0.001.

Angular Velocity

Higher angular velocities (p<0.05) were found for controls compared to patients across all elevations. This difference between groups became greater when participants were asked to increase the movement speed. The most significant difference between groups was found for scapular elevation during the "fast" movements, with a difference of 24°/s. No significant difference between groups was found for the internal/external rotation activity.

Angular velocity data showed that both subject groups speed up their movements during the "fast" condition when compared to the "normal" condition. However, the controls significantly increased velocity across all tasks when asked to go "fast," while significant differences in angular velocity in patients were present for the sagittal and scapular elevation, but not for the frontal elevation and axial rotation.

Wavelet Coherence

Figure 26:
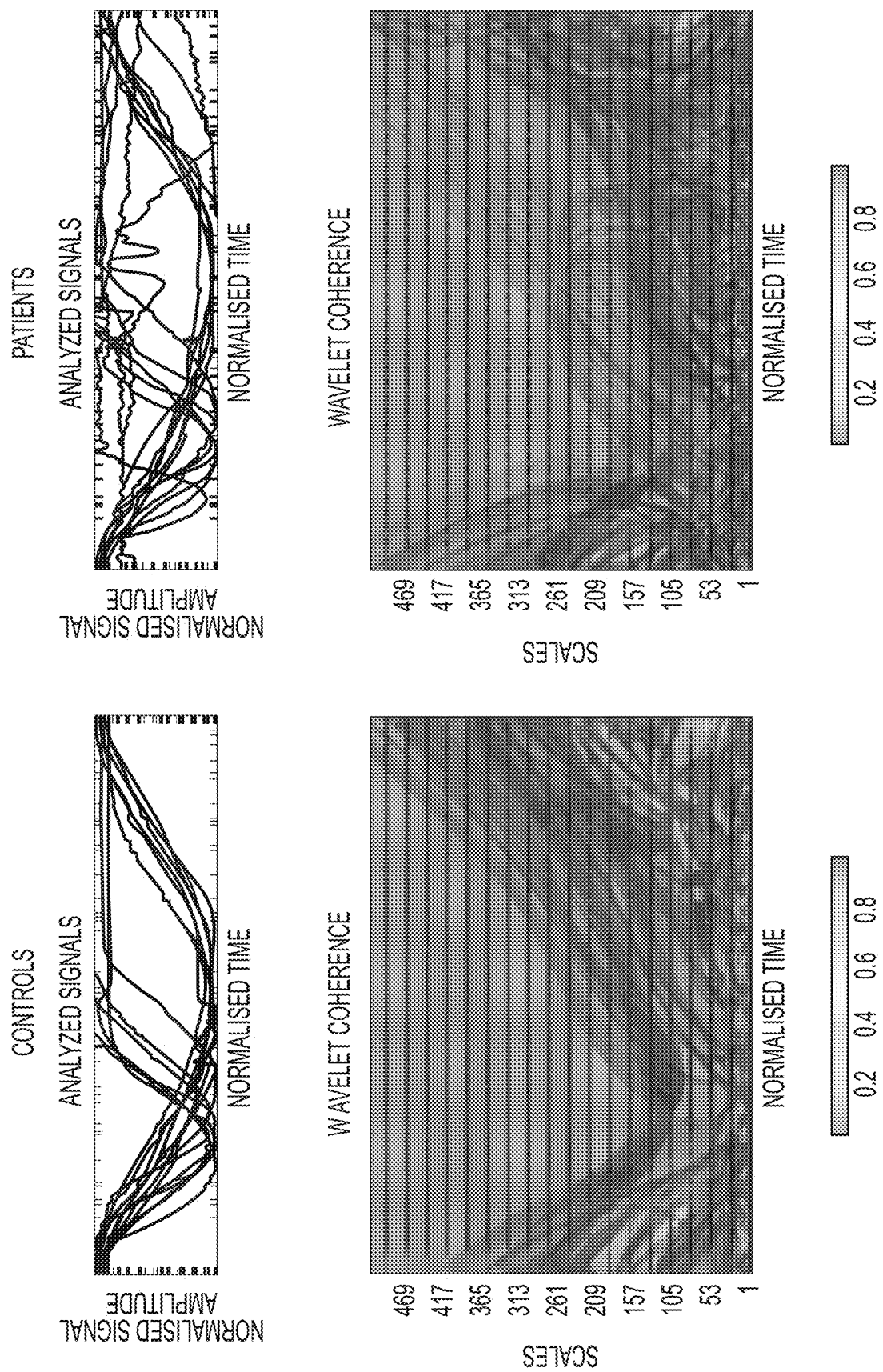
FIG. 26 is an exemplary diagram of wavelet coherence of all subjects during elevation in the frontal plane.

Determining the wavelet coherence and superimposing the phase of the smoothed wavelet cross spectrum shows that data from the two conditions often exhibited coherence near 1 for the majority of the signal in the frontal plane, as well as showing an approximately constant relative phase at the scales of interest (FIG. 26). There is a relative phase shift across the scales when the modulus becomes zero. These shifts are mainly seen at the lower normalized scales (higher frequencies). The lower normalized frequencies of (<3 Hz) start at scale 93 and is represented by the top 82% of the wavelet coherence plot. Several variations in the relative phase shift within the lower frequencies can be observed between participants of both groups. However, the wavelet coherence patterns from the control group provide a more ordered arrangement than that of the patient group.

FIG. 26 illustrates an example of wavelet coherence of all subjects during elevation in the frontal plane. Top two plots show all the traces for the "fast" (blue) and "normal" (red) condition for both groups. Time was normalized to the start of the "normal" movement till the end of the motion pattern. Signals were normalized to maximum amplitude measured within a subject. Bottom two plots show the overlap of modulus and relative phase changes. The non-linear patterns indicate the occurrence of large relative phase shifts.

Discussion

The aim of this study was to explore the ability of wavelet analysis to differentiate between rotator cuff patients and age matched controls using shoulder motion data for different speeds of movement. The wavelet analysis showed significant differences between healthy and patient groups.

The results show that the ROM is not affected by the velocity at which a particular task is performed. Instead, the ROM is affected by musculoskeletal damage. A decrease of up to 40 degrees was found in the elevation tasks when control subjects were compared to patients. The findings of this study between patients and controls are similar to results found in the literature (Bergmann et al., 2008). The peak rotations related to the available volume in which gestures can be performed. The diminished ability to lift or rotate the arm will significantly compress the gesture workspace. Peak rotations were related to the allowable volume in which movements can be performed.

In addition to a change in movement range, differences in angular velocity were also found. As anticipated, the angular velocities were greater in the "fast" speed versus the "normal" speed. Control subjects showed a greater rotation velocity during "normal" speed, and also showed a greater increase when switching to the "fast" speed compared to patients. The difference in angular velocities also increased between the two groups when subjects were instructed to move faster. On average, the control subjects were able to perform the elevation tasks at a greater speed than those individuals in the patient group. Although no notable difference was found for the internal/external rotation activity, there was a trend towards a greater group differentiation at the faster condition. The wavelet coherence analysis showed that patients have a greater variance in localized features compared to controls. The power of the wavelet coherence analysis is the ability to detect short episodes of coherence within single measurements, which would not be possible using classic Fourier-based coherence (Lachaux et al., 2002). Some patients compensate well for the musculoskeletal damage, while the compensation abilities of others are diminished; this indicates that there are subgroups within the patient population.

The normalization technique produces relative patterns that can be compared between subjects, indicating that the divergence between these patterns relate to relative differences in amplitudes and times. On average, the patient group showed a greater coupling of the "fast" and "slow" speeds, in addition to a higher overall variance, this indicates more inconsistency for the estimators of movements. Therefore, differentiation between movements is harder to accomplish for the patient group independent of the ROM reached or the angular velocity at which the movement is performed. This finding indicates a more fundamental generational gesture difference between healthy and impaired individuals that exceeds the level of range of speed. Gesture recognition requires a consistent difference between two or more movements, but increasing the range of motion and angular velocity of the patients does not automatically bring the patient group closer to the controls.

The analysis methods discussed in this experiment can be transferred to a flexible data acquisition system, such as BSN. In future work, the method will be validated using BSN in place of optical tracking. We are confident that the BSN will perform with a sensitivity level close to the level of the optical tracking system given the results in Experiments 1 and 2, which demonstrated the ability of the BSN to measure complex movements. BSN may even provide a more accurate measure of shoulder movement because it does not present the issue of marker obstruction like optical tracking. Optical tracking uses markers attached to the skin, which can produce surface movement errors, therefore a BSN may be able to measure joint movement with less error (Zhou and Hu, 2008).

The experiment presented here was conducted within a laboratory setting. It is known that differences in ecological validity exist between lab-based results and those obtained during real-world interaction. Laboratory testing can be somewhat artificial and divorced from real-world interaction (Zajicek, 2006). Future work will also focus on testing the analysis method during ADL.

Conclusion

The development of the BSN tool focuses on measuring aspects of arm movement, which represents only a small part of overall human behavior. Recently, patients with and without the behavioral variant of frontotemporal dementia have been identified as similar in a caregiver-based assessment of activities of daily living, whereas a clear distinction was identified on a performance based measurement (Mioshi et al., 2009). This example highlights the need to quantify (motor) behavior beyond the level that is currently available. Small changes in our environment are not often taken into account, while they do often influence our behavior. For instance, it is known that changing colors and shapes directly alter behavior (Bellizzi et al., 1983; Flanagan and Beltzner, 2000). We propose here that wearable sensor systems can be utilized to measure small changes in real-life environments. This approach combined with well-developed research protocols could help us better quantify our everyday behavior. A system to measure movement during everyday living could help to improve PD detection and symptom tracking. Quantified measures of PD motor symptoms, such as bradykinesia or tremor, collected during ADL would offer a more objective assessment than current measures, such as UPDRS, which are largely subjective and observational.

Experiment 1 demonstrated that the BSN system measures movement with similar accuracy to gold standard optical tracking. Average correlation between the two systems was 0.81, with root mean squares ranging from 0.02 to 0.15 meters. In Experiment 2 IMU sensors and wavelet analysis were used to test if behavioral changes were detectable from small changes in the environment during an everyday task using different objects. Results showed that the behavioral adjustments to a variable environment could be identified with wavelet cross-spectrum techniques. There were clear differences in movement patterns for each container (Bergmann et al., 2013c). The mean phase difference for all 3 objects within subjects ranged from 0.73 to 0.84. Experiment 3 demonstrated that wavelet analysis could differentiate between healthy and impaired movement. Healthy subjects and rotator cuff patients showed mean differences ranging from 30° ($p<0.05$) for scapular elevation to 40° ($p<0.01$) for sagittal elevation. The experiment used optical markers to collect ROM data to validate wavelet analysis, but the method will easily be transferable to a BSN system.

In general, the minimum clinical difference ranges from 11°-16° for a single evaluator and 14°-24° for two evaluators (Muir et al., 2010). Our system falls well within this range in terms of rotational error (Bergmann et al., 2009a). The method introduced in this study can take on other variables as well. The Euclidean norm was used for data analysis, as it represents a simple magnitude value, but caution needs to be taken when only applying the norm as the parameter, as there may be dimensional reduction and consequent loss of information.

The small subject sample of each study minimizes generalizability of the presented results. Small sample sizes have been used to pilot applications for body-worn sensors (Loseu et al., 2012), but it comes with a limitation that further research needs to be done in order to establish the external validity of the proposed system and analysis method. Even though, the coherence approach should provide relevant outcomes with only a few trials (Bigot et al., 2011), it is recommended not to extrapolate these results beyond the explorative nature of this study. A larger study is required to determine if the system can be used to determine how consistency in everyday living behavior depends on personal factors. Small alterations (e.g. different container) in the surroundings in which a person operates could directly affect motor behavior and consistency. Comparing the obtained outcomes to a large reference database would provide a method to track changes of the patterns over time. The methodology can potentially be developed into a long-term tracking system that identifies how people interact in everyday life, thus providing a continued data stream for investigating the behavior of an individual during ever changing natural environment. With additional validation of the device and testing on PD patients at various stages, and patient groups of different NDD (See 2014 Pilot Study—An exploratory study of the utility of a Body Sensor Network in the clinical detection of Parkinson's disease), this approach can be further developed for early detection and monitoring disease progression. Future work will focus on an even less intrusive version of this device, as it has been shown that utility might be affected by the measurement tool itself if it is not fully unobtrusive (Bergmann and McGregor, 2011a).

Section Five: BSN Engineering and Design

Introduction

The 3 experiments presented in this section explore engineering and design concepts of the body sensor device towards the goal of developing an unobtrusive measurement system for ADL. In experiments 4, 5, and 6 sensor design is tested for durability, unobtrusiveness and functional integration with everyday objects.

Experiments 1, 2 and 3 demonstrated that BSNs are capable of measuring upper limb movement during every-day tasks and that wavelet analysis can differentiate between patients and healthy controls. The system requires additional validation and refinement in order to be suitable for proposed clinical use of detecting or monitoring PD. To effectively measure movement during ADL the sensors need to be fully unobtrusive and ideally fully integrated into daily life using familiar objects.

Experiment 4 evaluates BSN in an extreme setting to assess hardware criteria needed for everyday life conditions. In experiment 5, we perform a first level feasibility test for future smartphone integration. In experiment 6, we test a clothing integrated sensor system to measure knee joint stability.

Experiment 4

Testing a Sensor Network to Measure Acceleration During Water-Ski Jumping. Bergmann, J. & Howard, N. 2013. Design considerations for a wearable sensor network that measures accelerations during water-ski jumping. IEEE Body Sensor Network Conference. Cambridge, Mass.

Background

The previous experiments demonstrated that the BSN systems could be used for measuring everyday interaction. This experiment aims to test the robustness of a BSN system in a real world-harsh environment. In order for a wearable system to collect data during everyday living, it must be able to accommodate a wide range of activities and environments including vehicles, planes, trains and other conditions of acceleration (Bergmann et al., 2012a; IHWM et al., 2008). The purpose of this study is to test a BSN in an extreme environment. Water-skiing is a high-impact sport; upon landing, there are vertical forces imposed upon the body caused by the large amount of deceleration at the moment the skier hits the water. Forces in water-ski jumping are estimated at 5-9 G (Roberts and Roberts, 1996). Therefore, we found water-skiing to be an ideal environment to test the robustness of the wearable body sensor system.

Aim: To test ability of the Body Sensor Network to measure acceleration in a harsh environment.

Methods

Study Design

A Body Sensor Network experiment using wearable body sensors compared to optical tracking to measure acceleration of 4 human subjects during water ski jumping.

Data Collection

Seven juvenile water-ski jumpers participated in the study. Subject group had a mean age: 14±2 years standard deviation (see Table 5). Each of the 4 subjects performed 2 jumps for a total of 8 jumps. Each participant was instructed to perform a correct landing, using natural landing style. Table 5 shows demographics of the water-skiers.

TABLE 5

| | Characteristics | | | |
|---|---|---|---|---|
| Subjects | Age (yr) | Height (m) | Weight [a] (kg) | Area (m$^2$) |
| Mean | 15 | 1.66 | 69 | .73 |
| (Range) | (11-17) | (1.48-1.89) | (56-92) | (66-.82) |

[a] Weight measured in full water-logged gear

Equipment

Accelerometer

Figure 27:
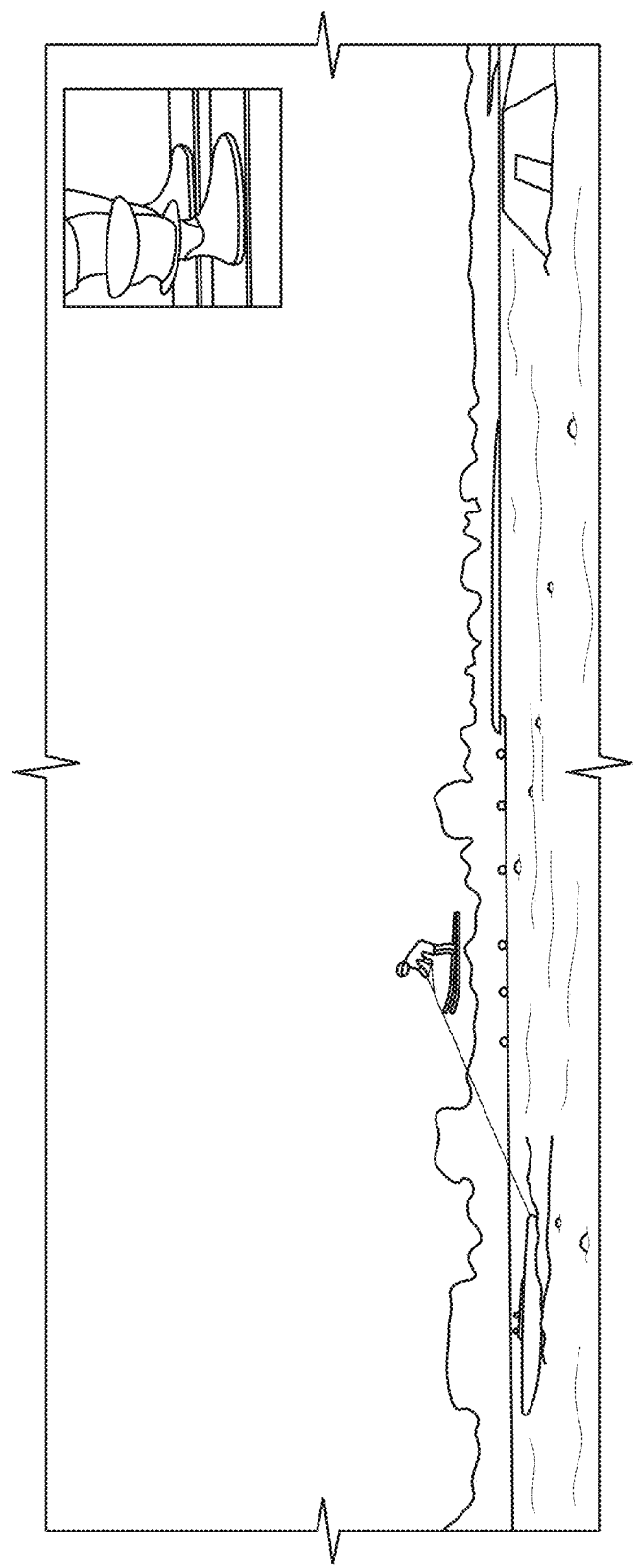
FIG. 27 is an exemplary diagram of a water-ski jump performed by a participant.

A ±5 g triaxial accelerometer (3D-TBA, Vernier Labpro, Oreg., US) was securely placed either on the lumbar spine or the lower leg. The accelerometer has an accuracy of ±0.05 g and was powered by 30 mA direct current at 5V. Data was stored at 25 Hz using a datalogger (LabPro, Vernier Labpro, Oreg., US) comprised of a microprocessor, ROM, and flash RAM. The system was attached with water resistant Velcro straps (FIG. 27). A ruggedized waterproof sealing bag was used to safeguard the system under the jump conditions. Placement was checked before and after jumping to verify that the orientation and placement was maintained. FIG. 27 illustrates an example of a water-ski jump performed by participant. Inset picture shows the placement of the water-proofed accelerometer and datalogger.

High Frequency Camera

A high frequency camera setup was used to estimate the deceleration of the ski (at the binding site), knee joint and estimated Centre of Mass (CoM). Video data was collected with a high-frequency camera (Kodak Motion Corder Analyzer, SR series with Digital images storages in Dynamic Random Access Memory (DRAM), resolution: 256×240 pixels, frequency 1000 Hz) and a low-frequency videocamera (Sony DCR-HC17E PAL, resolution: 500×800, frequency 25 Hz) placed on tripods with spirit levels. Camera systems were placed perpendicular to the landing location. The low-frequency camera was used as a virtual lab book for the study to identify skiers and applied setup for each individual. Markers were attached on the skiers' knee joint on the right above the iliac crista, representing (COM). A calibration frame at the site of interest was used to calibrate the video data during data analysis for the high frequency camera. The markers were reflective, round and had a diameter of 0.06 m. No marker was attached to the ski binding, because it would not be visible during the landing due to the water spray that occurs. A line-line intersection procedure was used based on extrapolating the visible parts of the ski and lower leg. Participants' weight was measured using a mechanically working weight scale with a 1 kilogram weight graduation.

Pinnacle Studio (Version 8.8.15.0) was used to digitalize the video data. The position data of the water-skier were determined, using WINanalyze (Version 1.4 3D). The maximum position error, as defined as the greatest linear distance between pixels within an area that could be labeled as marker, was on average 0.024 m for the high frequency camera. A low-pass fourth-order Butterworth filter at a cutoff frequency of 50 Hz was used for kinematic data before further processing (Ford et al., 2007).

Vertical velocity of the different body segments of the skier was calculated from the position f for frames l=1: n $$\frac{df}{dt}(i) = \begin{cases} \frac{\left(\begin{array}{c}2f(i+2)+f(i+1)-\\f(i-1)-2f(i-2)\end{array}\right)}{10dt} & \text{if } 2 > i < n-2 \\ \frac{(f(i+1)-f(i-1))}{2dt} & \text{if } i = 2 \vee i = n-1 \\ \frac{(f(i+1)-f(i))}{dt} & \text{if } i = 1 \\ \frac{(f(i)-f(i-1))}{dt} & \text{if } i = n \end{cases} \quad (1)$$

n denotes the maximum number of frames within a movie and dt is the timestamp. The same numerical differential equation was used to determine vertical acceleration, but now with vertical velocity as input. Subsequently, the peak velocity and acceleration at impact were determined for each body location.

Data Processing and Analysis

FIG. 28 illustrates an example of the video analysis. The top row consists of the frames from the high frequency camera showing the landing of a skier entering from the right side of the frame. The subsequent plots show the position f of the ski binding and the two derivatives with m representing meters and s denoting seconds. The red line shows the data low-pass filtered at 50 Hz, while blue lines show "non-filtered" data. Peak acceleration occurs during the initial landing period highlighted by the filled blue box.

Limitations of the High Frequency Camera

A measurement error (ME) arises during digitizing of each frame of the film and it will increase with greater sample frequencies. As film speed increases, the distance moved per frame decreases, so the digitizing error becomes a greater proportion of the measured distance (Harper and Blake, 1989). The measurement error for the acceleration-time data can be derived by using the equation given by Harper & Blake (1989)

$$\varepsilon_{\ddot{f}} = \varepsilon_f \left(\frac{1}{dt}\right)^2 \quad (2)$$

In which $\varepsilon \ddot{f}$ denotes the measurement error of the double derivative of f, $\varepsilon f$ denotes the digitization error of position f and DT represents the timestamp. The position data was lowpass filtered at 50 Hz. We therefore inputted the following value for equation (2), $$\left(\frac{1}{dt}\right) = 50 \quad (3)$$

Entering the previously determined measurement error for $\ddot{f}$ yields a $\varepsilon \ddot{f}$ of 60 m/s². However, it should be mentioned that the high frequency camera is normally used in a controlled setting and that using this method in a practical outdoor setting is unique and prone to greater measurement errors. It might be that the found error is several factors greater, due to issues concerning alignment of the camera and jumper, as well as the obstruction of the marker on the ski binding. A model for determining the impact of an object on a liquid was, therefore, applied in order to further establish the specifications of body sensor network that can be used to measure juvenile ski jumpers.

Modeling Impact of an Object on Liquid

Figure 29:
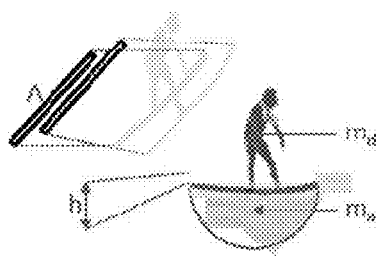
FIG. 29 is an exemplary diagram of an impact of the water-skier on water.

A model is presented for the impact of a water-skier as an additional estimator of the expected decelerations during landing. We define a model for the impact of a water-skier on the water surface after the launch from a ramp. FIG. 29 illustrates an example of impact of a water-skier on water. Mad denotes the total mass of the Skier, ma is mass of water that is being displaced, h is defined as the depth of the ski at the moment of cavity closure and A is the area of both skies.

We assume the ski to approximate a horizontal orientation during the landing. This specific orientation of the skies has been observed during the jump of the juvenile water-skiers (FIG. 27). It has been suggested that snow skiers with severe injuries often hit the ground with high perpendicular velocity components showing the importance of velocity changes across the vertical motion axis (Hubbard, 2009). The proposed model therefore focuses on the deceleration component that is orthogonal to the water surface. The deceleration can be found by applying the equation characterized by (Glasheen and McMahon, 1996)

$$(m_a + m_d)\ddot{h} = m_d g - \rho AC(\tfrac{1}{2}\dot{h}^2 + gh) \quad (4)$$

In which $m_a$ denotes the mass of half a cylinder of water, $m_d$ represent the full weight of the water-skier, h gives the deceleration upon landing, g denotes gravity (9.81 m/s²), ρ is the mass density of water, A is the area of both skies, C is a coefficient that takes drag and the hydrostatic pressure into account and has the value 0.7 (Glasheen and McMahon, 1996), h is the velocity at impact and h denotes displacement. Displacement was taken from the time-point the ski-binding hits the water until the most submerged position is reached. The velocity at impact was calculated by taking the maximum velocity given by equation (1), while displacement is estimated from the difference in position at peak velocity and zero velocity. The virtual water mass $m_a$, which was originally defined as a sphere for a disk that enters the water, is now assumed to be half a cylinder and is computed by $$m_a = \frac{1}{2}\pi w r^2 \quad (5)$$

In which the width of two skis is given by w and r denotes half the length of one ski. This adaptation reflects the difference in dimensions between the ski and a disk.

Computed impact of water-skier during landing

The average acceleration computed by the model is 260±126 m/s². The maximum value found by applying equation (5) is 539 m/s². The impact model normally relies on data inputted under controlled lab conditions. As mentioned before, the data entered from the high frequency camera is likely to be affected by conducting the optical tracking directly in the field. However, the jumpers were also measured with a calibrated low-frequency video-camera (Sony DCR-HC17E PAL). The low-frequency video data can be utilized as an additional confirmation of inputted parameters. A similar digitization process was performed as previously described for the high frequency camera. An approximate average jump height of 2.45 m was established, providing the means to compute a rough indication of the impact velocity. Applying the kinematic free fall equations gave a value 7 m/s, which is in line with the velocity values that were inputted into the model. Nonetheless, the model still showed on average a factor 4 difference with the findings from the high frequency camera. This is not very surprising as results from this model has been identified as consistently lower compared to experiments (Glasheen and McMahon, 1996). Despite the fact that both procedures suffer from measurement errors and rely on approximations, both methods did show that greater impacts arise compared to those suggested in the only available reference study (Roberts and Roberts, 1996).

Results

The decelerations encountered could not be measured by the accelerometer. The peak deceleration was out of range for all subjects, despite the low sample frequency used. Therefore, the high frequency camera data was used to estimate the deceleration at the ski-binding site, knee joint and estimated COM.

Results from high frequency camera

Peak velocities and accelerations are given in Table 6. The average peak velocity during landing remains relatively stable across the different body locations. No significant changes were seen when data was analyzed using a repeated measures analysis of variance (rmANOVA). Table 6 shows Peak Velocities and Accelerations"

TABLE 6

| Body Location | Ski | Knee | CoM |
|---|---|---|---|
| Peak $\frac{df}{dt}\left(\frac{m}{s}\right)$ | −8.6 ± 1.8 | −7.0 ± 1.7 | −7.3 ± 1.2 |
| Peak $\frac{d2f}{dt2}\left(\frac{m}{s^2}\right)$ | 1038 ± 344 | 661 ± 524 | 425 ± 124 |

The peak accelerations during landing showed significant differences (p<0.01) between the body locations when an rmANOVA was applied. To further investigate main effects, post-hoc analyses were done using two tailed paired t-tests and a modified Bonferroni correction (Rom, 1990). A significant difference (p<0.01) was found between acceleration computed at the ski and the CoM. The initial landing phase, defined as the time from water impact up to the velocity becoming positive again, lasted 35±17 milliseconds.

Discussion

Very high accelerations were found for water-ski jumping that exceed previously reported values. A ±5 g triaxial accelerometer was not able to measure peak deceleration, so a high-speed camera and a model were used to calculate the required sensor specifications for measuring deceleration. It was established that a 100 g triaxial accelerometer would be able to measure the deceleration of water-ski jumping.

Depending on the analysis method used, average accelerations of 26-104 g were observed during landing. Accelerations at the CoM were less, but still considerably higher than previously reported. Our analysis suggests that a 100 g accelerometer BSN would be capable of measuring acceleration during water-ski jumping. For a BSN system to be used during water-ski jumping, we propose a wireless sensor node that consists of two 100 g triaxial accelerometers (Triaxial Accelerometer Cube, MicroStrain Inc. Williston, Vt.). The speed of data acquisition would be set to 1,000 Hz, as the initial landing phase can be completed within milliseconds. The micro-controller would be programmed to only store maximum accelerations for every 1000 ms time window to minimize battery life. One sensor would be placed on the ski binding to measure impact at the water level and one would be placed on the lower back at the S2 level of the Sacrum.

This study was valuable for engineering and design considerations for BSN hardware development. This study determined the design criteria for a minimally obtrusive BSN system to measure acceleration during water-ski jumping. The study demonstrates the capability of BSNs to measure in a harsh-environment and therefore suggests adequacy to measure activities of everyday living, which do not present conditions as extreme as water-ski jumping, but nonetheless require measures of a similar demand such as traveling on a plane, train etc. (IHWM et al., 2008). A BSN system for clinical use measuring movement in daily life, will not need to be able to measure acceleration as high as water-ski jumping, but it does need to be accounted for. Less obtrusive wearable sensors are necessary to easily integrate these systems into daily life. The experiment also shows the need for a priori knowledge of the working environment in order to ensure the sensor specifications are correct.

Experiment 5

Comparison of Median Frequency Between Traditional and Functional Sensor Placements During Activity Monitoring. Bergmann, J., Graham, S, Howard, N. & Mcgregor, A. 2013b. Comparison of median frequency between traditional and functional sensor placements during activity monitoring. Measurement, 46, 2193-2200.

Background

The quality and quantity of data collection would significantly benefit from an unobtrusive system integrated into objects already used on an everyday basis (Bergmann et al., 2012a; Bergmann et al., 2012b; Bergmann and McGregor, 2011b). Compliance issues arise when people integrate sensors into their daily lives (Bergmann et al., 2012a; Bergmann and McGregor, 2011b). Most sensor systems interfere with everyday life and prevent normal activities from being carried out (Bergmann et al., 2012a; Bergmann and McGregor, 2011b). Mobile devices provide an opportunity for clinicians and researchers to measure behavior outside the laboratory and enhance ecological validity (Bergmann et al., 2010). This is particularly relevant for observing changes in ADL, which are an essential part of clinical frameworks. Many studies still place wireless accelerometers approximately at the level of the center of mass, located on the lower back at the S2 level of the Sacrum, as well as at the chest or thigh (Cheung et al., 2011; Winter, 2009; Zijlstra and Hof, 2003). However, these placements do not coincide with where one's mobile phone is usually kept. Information about how a more functional sensor placement relates to conventional placement is needed. With this in mind, we begin to explore mobile phone integration by testing a sensor's functional placement in a pocket.

Accelerometers can be used to provide information about activities of daily living. The median frequency ($f_m$) of acceleration has recently been suggested as a powerful parameter for activity recognition (Bergmann et al., 2013b; Cheung et al., 2011). More functional placement may provide higher levels of conformity, but may also affect the quality and generalizability of the signals. How $f_m$ changes as a result of more functional sensor placement is unknown. This study investigates the agreement in $f_m$ between conventional placement of a sensor on the back and functional placement in the pocket across a range of daily activities. In this study the translational and gravitational accelerations are also examined to determine if the accelerometer should be fused with additional sensors to improve agreement.

The hypothesis is that the direction of change in the median frequency of the accelerometer is independent of sensor placement. Subsequently, the question arises if the accelerometer should be the only sensor integrated into the system. There is an option to fuse together additional sensor modalities, such as gyroscopes and magnetometers (Roetenberg et al., 2003). An accelerometer will record translational and rotational inertial accelerations, as well as gravitational acceleration, as long as parts of these acceleration vectors are in line with the accelerometer's axis of sensitivity (Elble, 2005). The accelerometer will only provide the sum of these components making it hard to determine if the translational components should be obtained separate from the rotational components. A further partition between rotational and translation components can be performed by fusing several sensors together (Roetenberg et al., 2003).

Aim:

To compare the median frequency between traditional sensor placement and more functional placement in the pocket across various kinds of movement.

Methods

Study Design

A Body Sensor Network experiment using human subjects to investigate the median frequency of two sensor placements, traditional and functional.

Data Collection

Twelve healthy adult subjects participated in this study. The participants consisted of seven men and five women, with the mean age of 24 years, a mean height of 172 cm and a mean weight of 70 kg.

Subjects were asked to stand still for 30 s, walk for 4 m and climb 3 steps. The stairs had a rise of 17 m and a length of 20 cm from step to step, with a width of 60 cm. After standing for 30 seconds, subjects were asked to walk, ascend and descend the stairs at a self-selected speed. Only the standing activity was timed; walking and climbing tasks were measured for the duration of time it took to complete the activity. Each activity was measured 3 times per subject to obtain a robust linear calibration equation.

Equipment

A wired triaxial accelerometer (Vernier Labpro, Oreg., US) was placed either on the back or on the pocket during the standing, walking, and climbing activities. The type of accelerometer used in this study is a piezoelectric accelerometer with a similar frequency response and resolution to the LIS302DL MEMS iPhone accelerometer (Chan et al., 2011). Each sensitive axis of the accelerometer was calibrated prior to data collection using the rotational calibration method described by Krohn et al. (2005). Instead of orienting each axis to the earth's center of gravity, several different orientations were explored and all measurements were repeated four times to obtain a more robust linear calibration equation.

Figure 30:
FIG. 30 is an exemplary diagram of marker cluster placed on the wired accelerometer.
Figure 31:
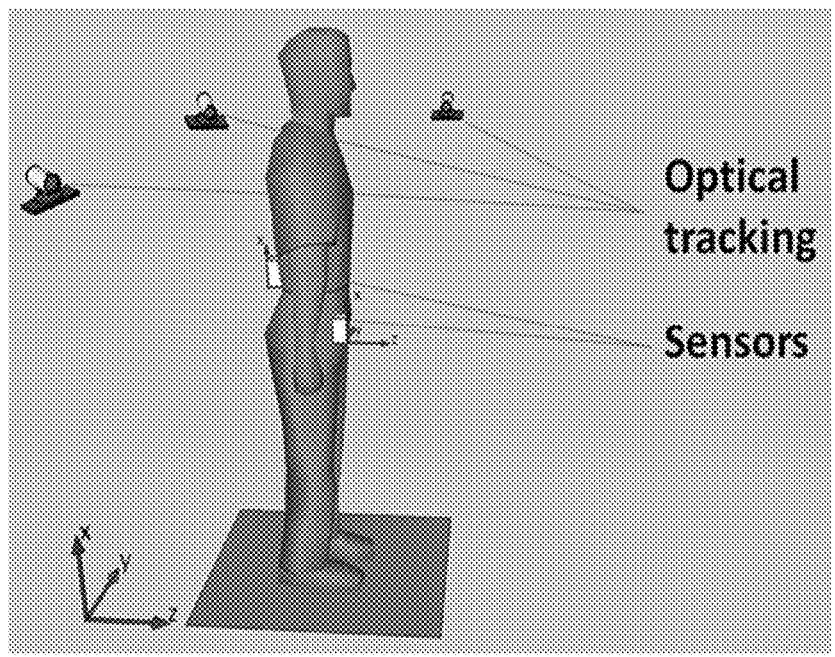
FIG. 31 is an exemplary diagram of an experimental setup used including local (sensor based) and global coordinate frames. 106

In addition to the wired sensor, a passive optical tracking system (Vikon, Oxford, UK) was used to explore possible changes in median frequency for each acceleration component separately. A custom made coordinate frame consisting of four optical tracking markers was physically aligned with the accelerometer (FIG. 30). The marker cluster and sensor were placed directly on the back and the outside of the pocket; they could not be placed inside the pocket, because the markers needed to be visible to the cameras. To mimic a smartphone device, a stiff polymer case was placed inside the pocket. Displacement between the polymer case on the inside of the pocket and the sensor on the outside of the pocket was checked before and after each trial. FIG. 30 illustrates an example of a Marker cluster placed on the wired accelerometer. The markers were used for the construction of a local coordinate frame Initially, each axis was represented by a 3D unit vector derived from a pair of markers. Data was collected at 100 Hz for both the wired system and the optical system. The 2 devices were synchronized through a block pulse generated by the MX module (Vicon). The local coordinate frames were developed in Matlab (Mathworks, Inc., Natick, Mass., USA). The axes were redefined to align the coordinate system of the back sensor with the pocket sensor (FIG. 31). The signs of the acceleration signal from the z and y-axis on the accelerometer were inverted in order to align al local coordinate frames. FIG. 31 illustrates an example of an Experimental setup used including local (sensor based) and global coordinate frames.

Although, the marker frame was constructed with the subjects' arms perpendicular, small alignment errors can be expected. To increase the accuracy of the representation of the local coordinate frame further computations were performed. Firstly, the dot product of each plane, that consisting of two vectors was calculated. The plane that yielded a dot product closest to zero was selected and the vector that was not part this plane was virtually reestablished by calculating the cross product of the two remaining axes. The plane with the second lowest dot product outcome, which would include the previous computed axis, was identified and another new vector was calculated based on the two vectors that defined that plane. Finally, the two newly calculated vectors were used to determine the last vector by means of cross product computation. This method provided us with a coordinate frame that was truly perpendicular.

Data Processing and Analysis

Gravitational acceleration, translational inertial acceleration, and the total acceleration were calculated. The gravitational and translational accelerations were added for each sensitive axis to get a total acceleration measurement that could be compared to the values obtained by the accelerometer. The root mean square error (RMSE) between systems was calculated for each trial (Bergmann et al., 2010).

Gravitational Acceleration

A vector was generated that represented the gravity vector. It started at the origin of the local coordinate frame, while running parallel to the vertical axis of the global reference frame. Subsequently, the amount of gravity measured by each sensitive axis was defined by the in plane angle between the gravity vector and each of the sensitive axes separately. A simple verification was performed by checking that the summed accelerations of the axis produced a constant outcome of 9.81 m/s².

Translational Inertial Acceleration

Translational accelerations were computed by a double differentiation of the origin of the local coordinate frame, within the global coordinate frame. Marker position data was low-pass filtered with a 4th order Butterworth (Thies et al., 2007) using a cut-off frequency of 10 Hz, before calculating the derivative. The same filtering was applied for the obtained velocity data before differentiation was performed. The mount of translational acceleration that ended up at each sensitive axis was established in utilizing the same method described for the gravitational acceleration. The rotational acceleration was not modeled because preliminary data showed it to be very low for the range of tasks that were explored in this study.

Total Acceleration

The gravitational and translational acceleration were added for each sensitive axis to obtain a total acceleration measure that could be compared to the values obtained by the accelerometer. A root mean square error (RMSE) between systems was calculated (Bergmann et al., 2010) for each trial. FIG. 32 illustrates an example of data illustrating the acceleration trajectories obtained from the two measurement systems. Data were collected at the pocket during a walking trial. The total accelerations obtained from the sensor (Accel Tot Sensor) and optical tracking systems (Accel Tot Optical), as well as computed translational accelerations (Accel Trans) are shown for each axis (x, y and z).

Median Frequency

The median frequency ($f_m$) was calculated using a moving window method. The windows encompassed 3 s and at each iteration were shifted by one data point, over the full length of the signal. A duration of 3 s was selected to allow this technique to be applied in future free-living studies. It also covered a time period appropriate for patients or age group whose pace might be lower than those of a healthy or younger aged group. All signals were offset against the mean of the first 50 data points, i.e. the time when the subjects were standing still. Apart from a short time interval (–1 s) at the beginning and the end of the signal, the majority of the signal related to the task that was performed.

Features in the frequency domain were examined using the power spectral density derived from the periodogram function in Matlab (Chung et al., 2008). The periodogram was chosen because it is a computationally economical way of estimating the power spectrum. A one-sided (in frequency) power spectral density was calculated in units of power per radians per sample. The ƒm was computed by first dividing the summed power of the windowed signal by two and then determining the frequency at which the cumulative power exceeded the previous determined threshold value. The median value over all windows was obtained per trial to ensure frequencies relating to the waiting element at the start and the end of each measurement did not affect the final result. The average value over all three trials was calculated, and the concluding value obtained was used for further analysis.

Statistical Analysis

Agreement of fin between the sensor locations was evaluated using Intraclass Correlation Coefficients (ICC) (Portney and Watkins, 2000) and Bland and Altman analyses (Bland and Altman, 1986). The ICCs were computed for the gravitational, translational and total acceleration. Bland and Altman plots were constructed to examine the difference between the two placements against the average value. The 95% limits of agreement were calculated and plotted using GraphPad Prism 5.0 (GraphPad Software, San Diego, Calif., USA). Indications of agreement, such as poor or moderate, were taken from (Portney and Watkins, 2000).

Results

Figure 33:
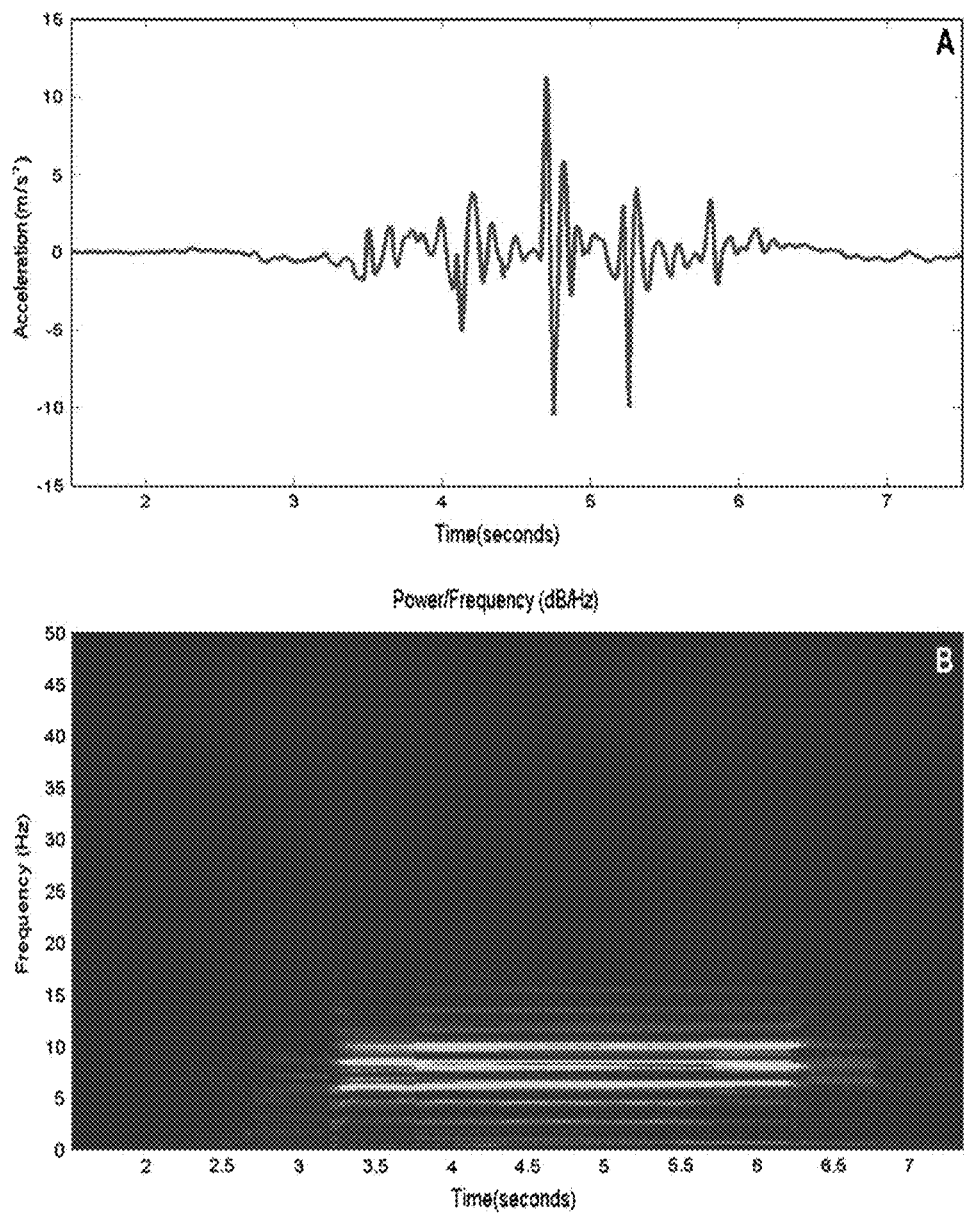
FIG. 33 is an exemplary diagram of acceleration recorded from a sensor placed on the back.

Accelerations between the two placements showed good correspondence (FIG. 32), as was expected based on other studies using similar techniques to determine accelerations from optical tracking data (Thies et al., 2007). An example of a walking trial and associated power/frequency using a moving window is given in FIG. 33. It shows the identification of the walking activity in the time-frequency plot devised using the previously described analysis method. The frequencies are rounded to the nearest discrete Fourier transform bin that matched the resolution of the signal. In FIG. 33, the median frequency was 6.45 Hz over the whole duration.

FIG. 33 illustrates an example of acceleration recorded from a sensor placed on the back. Data are shown for the x-axis only during a single walking trial. Graph B is the related power/frequency plot using a 3-second moving window.

Figure 34:
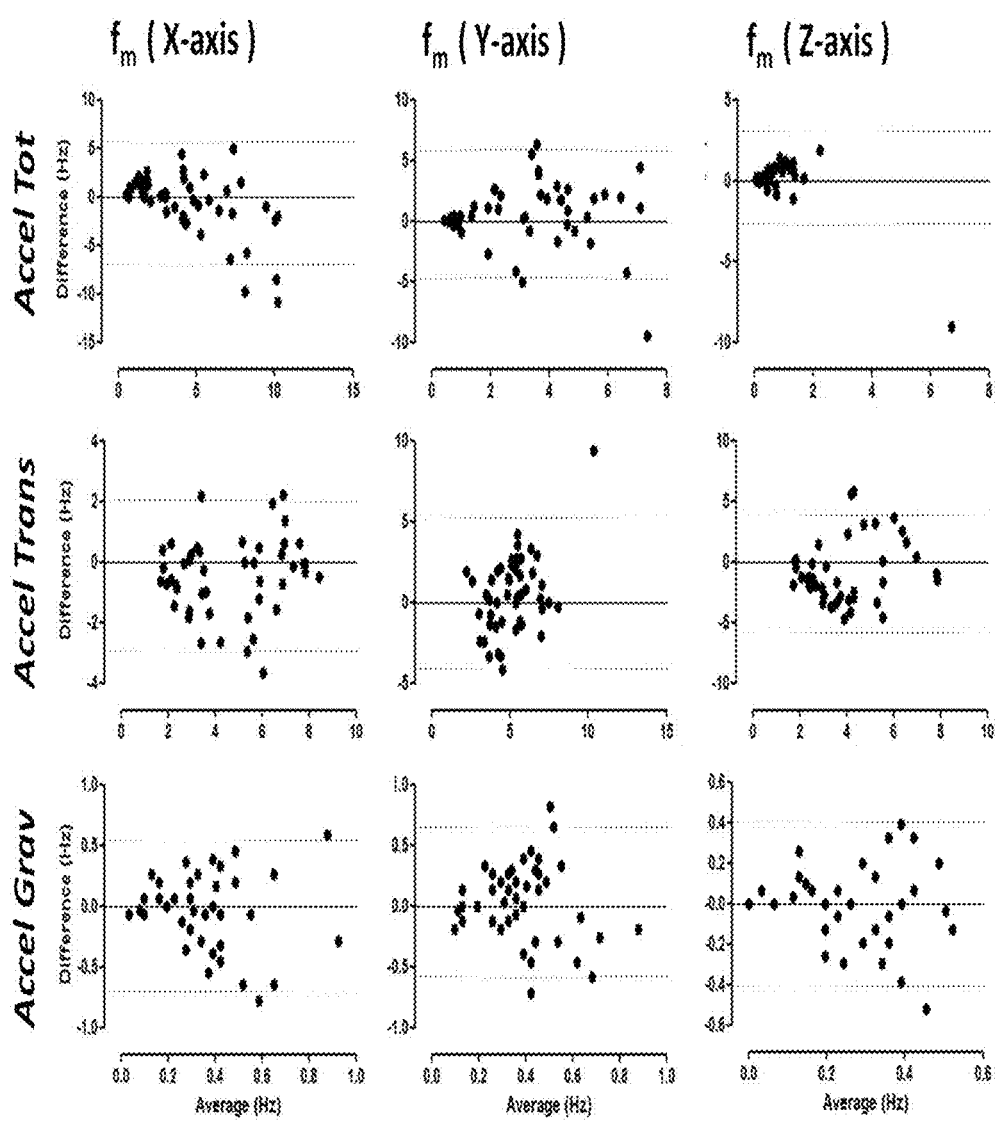
FIG. 34 is an exemplary diagram of Bland and Altman plots given for the total acceleration (Accel Tot), translational (Accel Trans) and gravitational (Accel Gray) acceleration per sensitive axis.

Total acceleration had a moderate agreement between sensor placements for the x-axis (FIG. 34). The y- and z-axis had a fair and poor agreement across the activities. A nearly perfect agreement was found for the translational acceleration in x direction, but became only fair after correction for outliers. The y and z directions only yielded a poor correlation for this component. The gravitational component yielded a poor relationship across all axes.

The Bland and Altman plots (FIG. 34) visualize the difference between the two systems. It gives an overview of how the difference related to the magnitude of the signal (propagation across magnitude) and outliers. The plots in FIG. 34 show that for the total acceleration output, the variation of the sensor location is dependent on the magnitude of the measurement. Meaning, that the "greater" the signal, the "higher" the variation. This was found across all axes. An outlier, as defined by (Grubbs, 1969) was identified for the z direction. Another outlier was observed for the y-axis of translational acceleration. No other systematic differences were observed across either the translational or gravitational accelerations.

FIG. 34 illustrates an example of Bland and Altman plots given for the total acceleration (Accel Tot), translational (Accel Trans) and gravitational (Accel Gray) acceleration per sensitive axis.

FIG. 35 illustrates an example of a median frequency (±standard deviation) over all subjects given for each sensitive axis and activity.

Discussion

The aim of this study was to compare the ƒm of the traditional placement on the back versus a more functional placement, in the pocket. After corrections for outliers, the ICC showed a moderate agreement for acceleration in the x-axis. Assessing these values on an ordinal scale showed that the median frequency between the two locations remained similar. This indicates that the direction that the median frequency shifts is independent of placement and strengthened the possibility of using more functional placements for activity monitoring or functional mobility tests. Partitioning the signal into separate components reduced the overall agreement, indicating that applying sensor fusion (Roetenberg et al., 2003) to assess specific orientations and translations minimizes the generalizability of the values across sensor locations. Applying multiple sensors will provide a richer dataset, but also allows for greater divergence between sensor locations. The overall recognition rate for activity monitoring is likely to increase by combining several sensors, but a fixed sensor placement might be needed to ensure this level accuracy. A single sensor system seems to provide a more robust method if locations are variable during activity monitoring. A single sensor device has the additional benefit that it will speed up data mining, decrease storage requirements and minimizes cost.

The results of this study confirm those of other studies; Chung et al. (2008) found an $fm$ of 3.107 Hz (±0.534) during walking, which is similar to the findings for some of our participants (e.g. one subject produced an $fm$ of 3.22 Hz (±1.03). Despite the similar findings between our study and Chung et al. (2008) it should be noted that $fm$ differences between the optical tracking and accelerometer are probable. The optical tracking data has been filtered in order to obtain the acceleration signal, while the accelerometer signal has been kept original. This difference is likely to affect the $fm$ outcome, especially in the case of the standing still task. Further deviations can be expected between the two systems, due to the motion artifacts of the optical tracking system that were not filtered out. Despite these limitations, the gathered data still classified well on an ordinal scale. Also, the type of accelerometer affects outcomes, as it has been suggested that frequency responses depend on sensor type (Meydan, 1997).

The placement of the sensor on top of the pocket may have produced slightly altered outcomes compared to a sensor placed inside the pocket. However, displacement between the polymer case and the outside sensor was very low. This was particularly true for garments that were more fitted to the leg. Low displacement suggests that the sensor closely mimicked the movements of the case (representing a phone) inside the pocket. The pocket placement was chosen because it is a common location to place an everyday object. Studies show that the pocket location has a greater step count validity for a range of body types compared to placement on a belt or around the neck (Silcott et al., 2011).

The development of long-term monitoring techniques that use familiar, everyday objects of interest. Patients and clinicians agree that unobtrusiveness is the most essential feature for user-acceptance of sensors (Bergmann and McGregor, 2011b). Patients may prefer having a sensor device in their pocket, as it is convenient and less visible. The added benefit of sensor integration with a mobile phone is that it is more discrete than a dedicated monitoring device, which is also an important feature for user acceptance (Sposaro and Tyson, 2009). Smartphones have the potential to be a platform for clinical tools for monitoring and detection. It can even allow for GPS tracking to determine subsets of activities, such as driving. This study also demonstrates the need for a more evidence-based approach for selecting sensor placement.

Experiment 6

Testing an Integrated Clothing Sensing System for Measuring Joint Stability. Bergmann, J. H. M., Goodier, H., Howard, N. & Mcgreggor, A. 2013 An Integrated Clothing Sensing System for Measuring Knee Joint Stability. In Preparation.

Background

Shape is essentially what is left when the differences, which can be attributed to translations, rotations, and dilatations have been filtered out (Kendall, 1984). If the human form is taken as one entity, the changes in shape mainly relate to movement of the musculoskeletal system. This indicates the potential use of flexible sensors to measure deformity due to human movement. The goal of this study is to test a patient centered, clinically driven design for an integrated clothing sensor system (ICSS) that can be used to measure knee joint stability. Pilot data will be presented to determine the relationship between the sensor system and the gold standard apparatus (Cybex/CSMI Humac Norm dynamometer, USA).

Aim: The purpose of this study was to determine how well knee joint stability could be measured using an Integrated Clothing Sensing System (ICSS) in relation to the gold standard measurement system.

Methods

Study Design

A Body Sensor validation experiment using an Integrated Clothing Sensing System (ICSS) worn by human subjects during various activities to measure knee joint stability. The study was designed as a randomized, controlled, crossover allowing a comparison of a stable and unstable task between participants, by both systems, optical tracking and the ICSS. It also presented insight into the variability amongst participants during the tasks.

Data Collection

Figure 36:
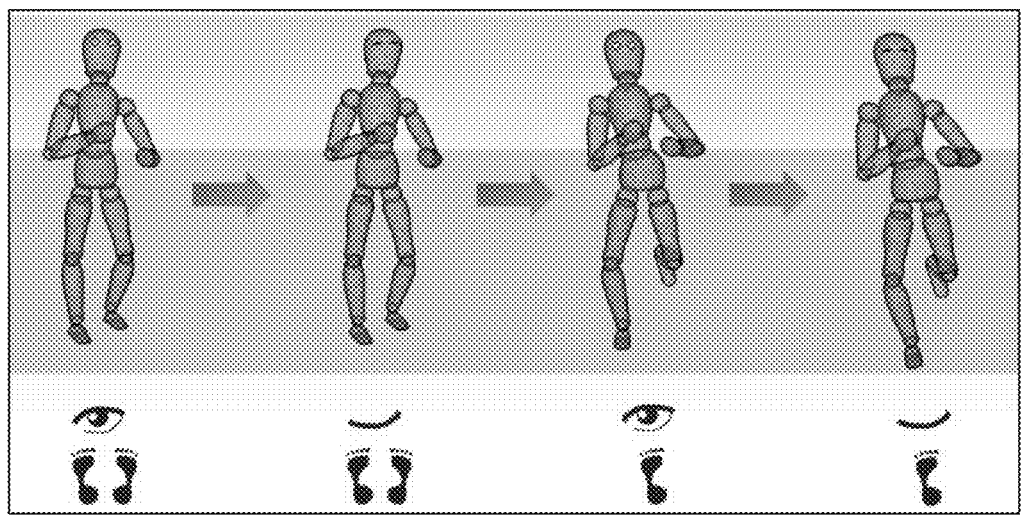
FIG. 36 is an exemplary diagram of the four tasks performed by the participants.
Figure 37:
FIG. 37 is an exemplary diagram of subject wearing the ICSS garment and optical tracking markers.

Ten healthy subjects participated in the study, 7 male, 3 female, with a mean age of 22.5 years (range 19-26), mean height 180.35 cm (range 158-193 cm), and mean weight 77.95 kg (range 49-95 kg). None of the subjects had any major injuries or history of such and no known neurological, rheumatic or orthopedic disease and none were pregnant. All of the participants wore the ICSS garment and had optical tracking markers placed on the lower extremity (FIG. 37). The 10 subjects were asked to perform four activities requiring different levels of knee joint stability while the ICSS measured in 30-second time intervals. Participants were asked to do the following four tasks in a randomized order. FIG. 36 illustrates an example of a depiction of the four tasks performed by the participants. Shown left to right: stand on two legs with eyes open (2LO), stand on two legs eyes closed (2LC), stand only on measured leg eyes open (1LO), stand only on measured leg eyes closed (1LC).

(1) Stand on two legs with eyes open (2LO)
(2) Stand on two legs eyes closed (2LC)
(3) Stand only on measured leg eyes open (1LO)
(4) Stand only on measured leg eyes closed (1LC)

During the procedure, a member of the study team was standing near the participant in case they became unsteady. Each task was held for thirty second and repeated five times.

Equipment

The ICSS sensor consisted of a cost-effective composite material comprising 20% carbon black and 80% polymer polyurethane Texin985 (Bayer Material Science, Leverkusen, Germany). A sensor was constructed from this base material and attached to a garment. The sensor was then connected to a Wheatstone bridge configuration and data was collected by an A/D converter (USB 6211 DAQ, National Instruments, USA). Angles were obtained from a calibrated accelerometer that was attached to the dynamometer. This information was gathered using the same A/D converter in order to ensure absolute synchronization between the different measurements.

A passive optical tracking system (Vicon Oxford, UK) was used as a reference system to validate results from the ICSS during the four tasks. Nine reflective markers were placed on key anatomical locations (See Table 7). The reflective markers needed to be visible to the cameras throughout recording. The markers were assimilated into a 3D construct using Vicon Nexus from which data was then exported to Matlab. Table 7 shows Reflective marker locations for Vicon

TABLE 7

Vicon Reflective Marker Locations

Greater trochanter of the hip
Lateral epicondyle of the knee
Medial epicondyle of the knee
Lateral epicondyle of the ankle
Medial epicondyle of the ankle
First metatarsal joint of the foot
Fifth metatarsal joint of the foot
Talus bone (heel)
Patella Data was collected from both systems at 100 Hz. A synchronization pulse was sent from Vicon to ICSS to signal when data acquisition had been initiated. This allowed the data from the two systems to be synchronized during post-processing. The Matlab data acquisition was run for 35 seconds, and the marker trajectories were collected for 30 seconds within that period. Marker position data was low-pass filtered with a $4^{th}$ order Butterworth using a cut-off frequency of 10 Hz, before calculating the derivative. The same filter was applied to the data produced by the ICSS.

FIG. 37 illustrates an example of a subject wearing the ICSS garment and optical tracking markers.

Data Processing and Analysis

Stability for both the ICSS and the optical tracking system was obtained by computing the maximum value of a root mean square moving window technique on each signal. Because the data was not normally distributed a spearman correlation was performed.

Results

Figure 38:
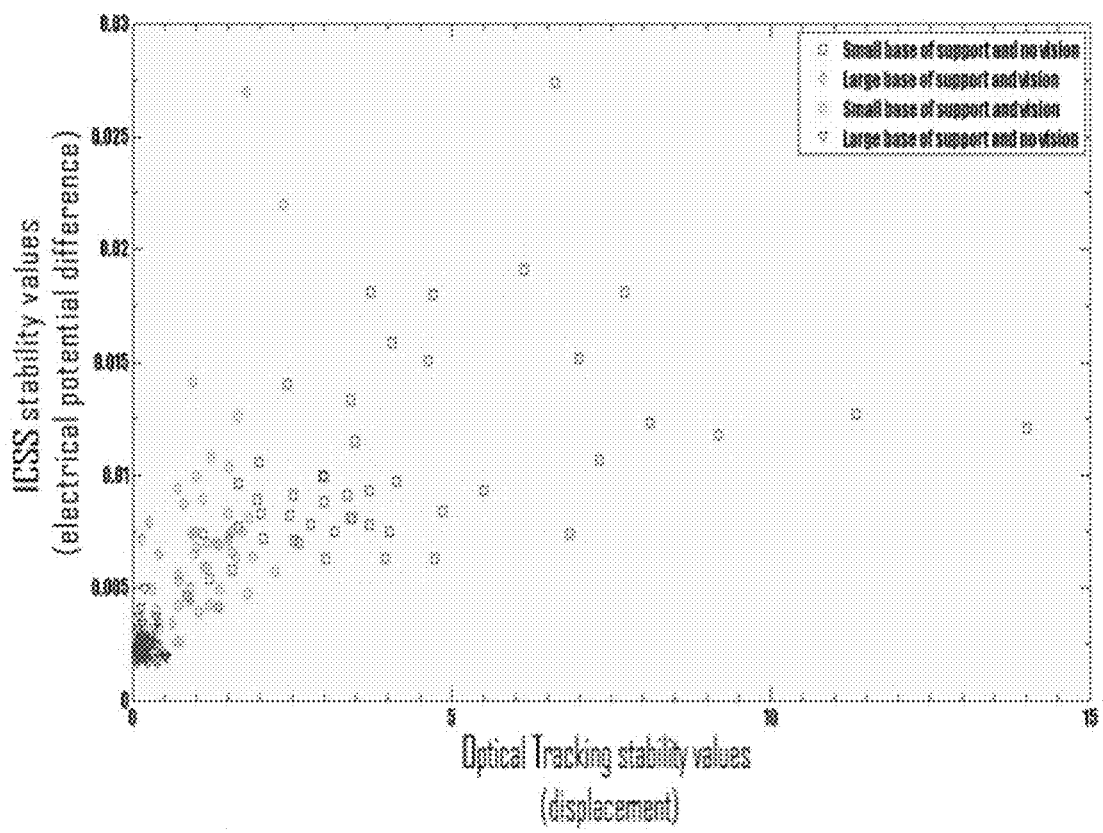
FIG. 38 is an exemplary diagram of stability values for the ICSS and optical tracking during 4 different activities.

A Spearman correlation coefficient of 0.81 (p<0.001) was calculated, indicating a strong association between the ICSS and the optical tracking system across the 4 activities. FIG. 38 illustrates an example of the stability values for the ICSS and optical tracking during the 4 different activities. Stability values for the ICSS and optical tracking during 4 different activities. Red square refers to standing only on measured leg with eyes closed (1LC), pink diamond refers to standing on two legs with eyes open (2LO), green circle refers to standing only on measured leg with eyes open (1LO), and purple triangle refers to standing on two legs with eyes closed (2LC).

User Feedback

Participants were asked to fill out an informal questionnaire after completing the study. A summary of the responses are given in Table 8. Participants were given a short questionnaire to fill out; answers were on a scale of 1-10, 10 being the highest.

TABLE 8

| Question | Average Rating | Range of Responses |
|---|---|---|
| Ease of putting on the device? | 9 | 6-10 |
| How comfortable was it to wear? | 9 | 7-10 |
| Ease of taking off the device? | 9 | 6-10 |

Discussion

A static trial was performed before participants undertook the functional tasks, consisting of sitting still with the leg in rest. During all sitting trials Vicon measured a mean RMSE of 0.26 mm, with a standard deviation of 0.14 mm. Vicon typically produces up to 1 mm of error for static trials and a RMSE of less the 0.5, which suggests that the Vicon operated well within its expected error value (Richards, 1999). The polymer system produced a mean signal of 2.4 mV, and a standard deviation of 0.4 mV. Table 9 shows RMSE values for static trial:

TABLE 9

| Vicon RMSxyz | .26 (±.14) mm |
|---|---|
| Vicon accuracy | .62 mm |
| ICSS RMS | 2.4(±.4)*10-3 V |
| ICSS accuracy | 4[0-2]*10-3 V |

The ICSS showed a good differentiation between the highest and lowest levels of stability. The ICSS demonstrated that it is capable of measuring different levels of joint stability with a strong association to optical tracking. Generalizability is limited, but user feedback was positive, indicating that the ICSS is comfortable and easy to use.

Conclusion

Experiments 4, 5 and 6 discussed engineering and design principles for development of a BSN system for early detection of PD. It has been shown that utility of a measurement system can be affected by the device itself if it is not fully unobtrusive (Bergmann and McGregor, 2011a). Integrating the sensor system into a garment or smartphone is a potential adaptation that would make the system less noticeable, subsequently providing data sets that even more closely represent real-life behavior.

Experiment 4 tested the BSN in an extreme condition to assess the hardware needs of measuring acceleration. Experiment 5 indicated that the functional sensor placement could yield acceptable agreement levels with traditional sensor placement. This suggests that everyday objects, such as smartphones, could be used to measure clinically relevant movement data. Experiment 6 demonstrated the utility of an integrated clothing sensor system to measure knee joint stability with similar accuracy to marker based optical tracking. A BSN system integrated into a garment would offer a non-obtrusive way to measure movement during everyday life.

This section demonstrates the initial development and design of a non-invasive BSN system for everyday life. The system will require further hardware testing in order to be used for clinical application. Future work will include testing the sensor system in real-life settings outside of lab environments.

Section Six: Speech and Movement—Measuring Cognitive Load

Experiment 7

Effect of Everyday Living Behavior on Cognitive Processing. Bergmann, J., Fei, J., Green, D. & Howard, N.

2013. Effect of Everyday Living Behavior on Cognitive Processing. *PLOS ONE, In Preparation*.

Background

Not only is cognitive function affected by behavior, but also the opposite is equally true. Behavioral aspects themselves have an effect on cognitive function and processing. For example, impairments in PD patients are exacerbated under dual-task conditions that require the simultaneous performance of cognitive or motor tasks such as gait and posture, when compared to healthy controls (Bond and Morris, 2000; Brown and Marsden, 1991; Kelly et al., 2012; O'Shea et al., 2002; Rochester et al., 2004; Woollacott and Shumway-Cook, 2002).

This study aimed to explore to what extent combining everyday motion and speech tasks affect cognitive processing. We often combine these functions during normal living, but it remains unclear if the interaction between them directly affects our cognitive functioning (Bergmann et al., 2013a). The goal is to understand how the brain copes when multiple processing is required during normal everyday tasks. Measuring performance and quantifying the potential decrease in performance can indicate how much the brain is affected by having to cope with multiple real-life tasks. This knowledge is essential before we attempt to fuse multiple data streams, such as speech and movement to measure cognitive decline. Current cognitive identification algorithms focus on single modalities; yet, cognition is affected across several dimensions of human functioning and thus requires attention sharing across these functions.

This study explores how everyday motion and speech tasks can affect cognitive processing measured by performance on a cognitive stroop task. The overall aim of this early detection research was to explore non-invasive methods to measure everyday behavior as potential indices of global cognitive function. The goal was to expand current detection models to include multiple information streams for identification. The purpose of this pilot study was to explore to what extent combining everyday motion and speech tasks affect cognitive function.

Aim: To test to what extent combining everyday motion and speech tasks affect cognitive processing.

Methods

Study Design

A pilot study using human subjects and cognitive loading conditions consisting of movement and auditory-stroop tasks. Cognitive function was tested using movement and auditory-stroop tasks and cognitive processing was analyzed using a wavelet method. The movement task consisted of an everyday living routine identified in the Motor Activity Log (MAL) for the upper extremity (Uswatte et al., 2005).

Data Collection

Eleven healthy subjects underwent a stroop task during performing a free speaking task or preparing a sandwich or both.

Stroop Task

Figure 39:
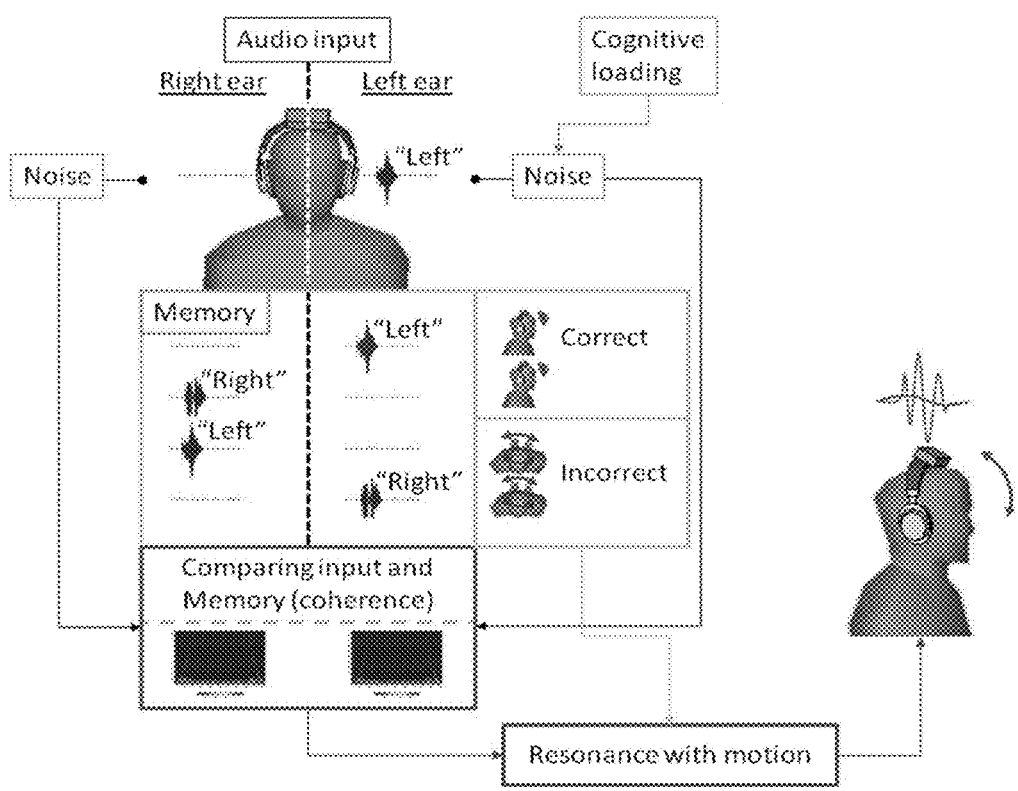
FIG. 39 is an exemplary diagram of auditory stroop task design.

The cognitive loading task consisted of a specific audio-spatial assignment. The auditory spatial task utilized a spatial stroop design and was presented through wireless stereo headphones (FIG. 6-1). The subject was requested to respond to unilateral aural stimuli (Barra et al., 2006). The stimulus consisted of the words "Left" and "Right" delivered through either the left or right headphone speaker. If the word matched the side it was presented to (i.e. "Left" in the left ear) the result was congruous and therefore the appropriate response was to tell the researcher it was correct by shaking the head up and down, as is accustomed in the study population. If incongruous, the subject was asked to state it was incorrect by shaking sideways. FIG. 39 illustrates an example of an auditory stroop task design. Stimulus is given over wireless headset into the left or right ear. If stimulus matches side it was delivered to ("left" delivered in left ear), the subject responds by shaking head up and down. If the stimulus does not match the side it was delivered to, the subject responds by shaking the head sideways.

A sensor (Xsens Technologies Ltd., The Netherlands) attached to the back of the head was used to obtain this information. Drift corrected angular velocity was used as the conditions were pseudo-randomized in order to eliminate sequence effects in the outcomes. The single task conditions consisted of 6 stimuli per subject and the dual task condition had 9 stimuli. The lower number of stimuli in the single task condition was due to the simpler nature of the task.

Equipment

A sensor (Xsens Technologies Ltd., The Netherlands) attached to the back of the head was used to obtain the nodding up and down and nodding sideways responses to the stroop task. Auditory stimuli were delivered through wireless stereo headphones.

Data Processing and Analysis

Response Detection Using Wavelets

Angular velocity was used to detect changes that reflected nodding up and down ("stating it was correct") or sideways ("stating it was incorrect"). These pitch and yaw signals were directly obtained from the head-mounted sensor, as a segment fixed coordinate frame is appropriate to detect these responses to the stimulus. Angular velocity data from the head mounted sensor was taken and the power spectral density was estimated using Welch's method (Welch, 1967). This method has the benefit of noise reduction in the power spectra. The frequency at which the power spectral density reaches its maximum ($f_{max}$) is taken as a dynamic base value. Subsequently, the frequency at which the energy is the highest is referenced against a relevant physiological range of 0.5-10 Hz (Benson and Barnes, 1978). Frequencies outside this range are assumed as unlikely to be physiological responses and data is then labeled as "no response" given. There are cases where the power spectral density shows a double peak at the lower frequencies, often with the initial peak (<1 Hz) containing more energy than the subsequent peak (>1 Hz). All signals were checked for this subsequent peak if they fell initially outside the physiological range in order to prevent an incorrect dismissal of the data. The continuous wavelet transform was computed for signals that indicate response(s) were given. The identified responses (and non-responses) were placed in a truth matrix that provided information regarding the correctness of a given response and the reaction time.

Figure 40:
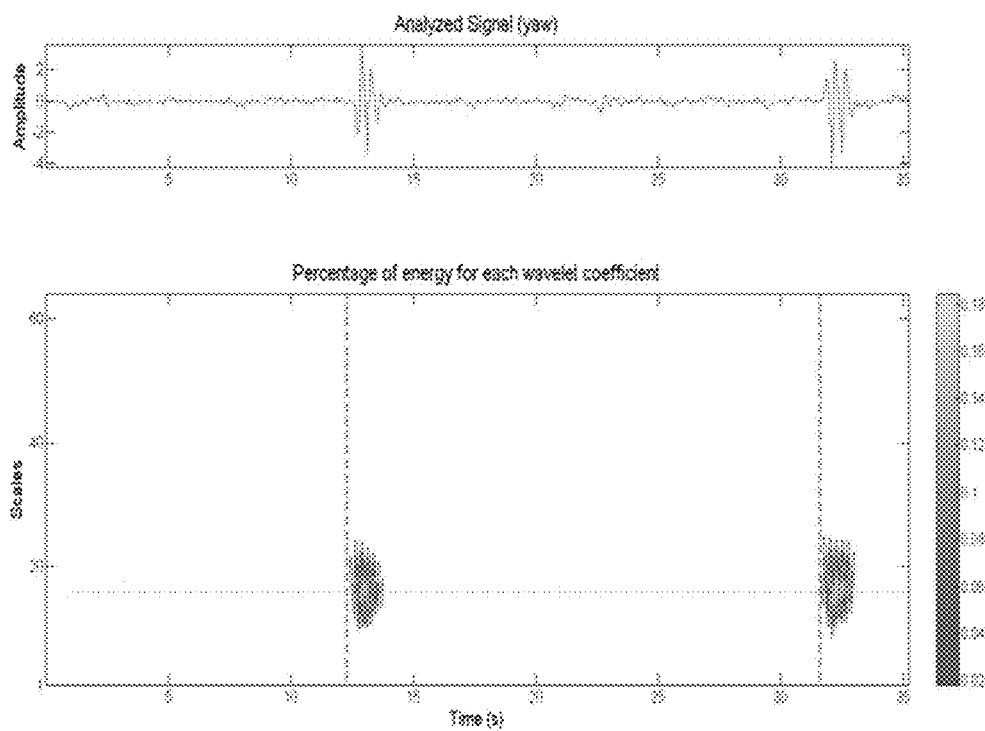
FIG. 40 is an exemplary diagram of a scalogram of wavelet coefficients.

The same initial approach applied for response detection can be used for detecting the auditory signals. According to the National Center for Voice and Speech (USA), baby cries have an average fundamental frequency of 500 Hz, while child speech ranges from 250-400 Hz, adult females tend to speak at around 200 Hz and adult males around 125 Hz. The fundamental frequency of speech ranges roughly 5-210 Hz in adults (Hartmut Traunmüller 1994). This frequency range was, therefore, used to obtain the initial threshold value for detection of speech The Morlet wavelet was an appropriate waveform for speech detection (Tan et al., 1996). Yet, the range of human hearing is far higher, from 20 Hz to 20 kHz, and it has been shown that speech carries information beyond the fundamental frequency (Smith, 1998). The range can, therefore, be extended to at least 1 kHz. In this study, the auditory cue was given and it was therefore known what the person was processing. However, for completeness the audio task was modeled as initial input into the analysis. This showed good identification of responses, as shown by FIG. 40, which illustrates an example of a scalogram of wavelet coefficients. The plot at the top shows the original yaw signal obtained from subject 1 during a cognitive loaded task. The bottom plot provides the percentage of energy for each coefficient depicted by a heat map that is shown on the side. Dotted green lines show identified crossings of the set threshold.

The time at which the auditory stimulus was given was subtracted from the time determined for the response. This value represented the response time of the subject. The response was labeled "incorrect" if no response was given or if an incorrect response was given within 10 seconds after the stimulus was presented. A comparison was made with the expected response if the response was given within the set response interval. If the response was expected to occur within that specific direction (yaw or pitch) the response was labeled "correct." Otherwise, the response was deemed incorrect. The identified responses (and non-responses) were placed in a truth matrix that provided information regarding the correctness of a given response and the reaction time.

Truth Matrix

The truth matrix consists of four columns. The first column reflects the correctness (0=incorrect, 1=correct) of the answer given in the yaw direction, the second column contains information for pitch direction (0=incorrect, 1=correct), the subsequent column holds the reaction time for yaw and the last column is reaction time for pitch. Reaction times will be assigned the value 0 if no reaction is expected or observed. Both yaw and pitch need to be correct before any reaction time value becomes valid. If the expected response to a stimulus was "nodding" the audio cue was correct then the pitch direction should contain a nodding signal and the yaw direction should be empty. This would translate to the sequence [1 1] for the first two columns. Only when this sequence is presented do the subsequent two columns become relevant and reaction time can be determined. This reaction time can e.g. be 0.34 so column three and four should show the following sequence [0 0.34]. Each row relates to a specific stimulus-response pair, in which the first row is the first represent the stimulus-response pair. However, it could be that there is a response signal present on both yaw and pitch. In this case, it needs to be determined if a corrective action (yaw and pitch are separated in time) has taken place or if it is crosstalk of the channels due to, for example, rigorous shaking. Crosstalk is defined as one signal overlapping the other in the time domain as:

$$t_{yaw(i)} < t_{pitch(n)} \wedge t_{pitch(1)} < t_{yaw(n)}$$

In which $t_{yaw(0)}$ and $t_{pitch(0)}$ are the time points at the start of the response and $t_{yaw(n)}$ and $t_{pitch(n)}$ are indicating the end of the response. If an overlap is detected, the signal with the highest mean energy is identified as the leading signal (1 is assigned) and the other signal is seen as the crosstalk signal (0.5). If both signals are equal in terms of average energy, they are both assigned a value of 0.5 and it can be stated that it is inconclusive which response the subject wanted to give. In this case there is no crosstalk because the original values are maintained in the truth matrix and the response times can be used if a correct response was incorrectly corrected or the other way around. However, for consistency a double response is labeled as incorrect. In terms of the truth matrix the data is easily dichotomized into correct or incorrect. The first two cells of each row can be summed and if this value is greater than 1 it can be labeled as correct. This easy computation provides a quick top-level view of provided responses. The summed outcome is labeled as extracted response $(r_e)$.

Six experimental test sets were generated, during which three were fully correctly answered and three incorrectly. Each test set consisted of three stimulus and three responses given in accordance with these stimulus. The extracted responses $(r_e)$ from the truth matrix were compared to the expected outcomes $(r_{exp})$. The results show that, across the test datasets, no incorrect classification was made regarding the responses detected and those expected. FIG. 41 illustrates an example of results of classification algorithm between extracted $(r_e)$ and expected $(r_{exp})$ outcomes. For the yaw and pitch signals a correct response is labeled 1, an incorrect response is labeled 0 and cross talk has a 0.5 value. The variables $t_{yaw(1)}$ and $t_{pitch(1)}$ represent the reaction time for a given response. Those that represent the reaction time of a correct response are given in bold. Dataset 1-3 contains only correct responses and 4-6 only incorrect.

Statistics

Missing data points were given as a percentage of the total data set. Frequencies for correctly given responses were determined within groups for the data from which the missing points were removed. Reaction times of correct responses were analyzed by applying a Repeated Measures Analysis of Variance (rANOVA) with a Bonferroni correction for multiple comparisons. Significance level was set at 0.05.

Results

The single loaded tasks consisted either of speaking (speech) or preparing the meal (motion), while the dual task required both. The results are given in Table 10. The F values and degrees of freedom were F(2,220)=1.879, p>0.05 (ns). There were no interactions just main effects. Table 10 shows performance outcomes across the different tasks.

TABLE 10

|  | Speech (n = 66) | Motion (n = 66) | Speech + motion (n = 99) |
| --- | --- | --- | --- |
| Missing data (%) | 5 | 6 | 1 |
| Correct responses (%) | 88 | 94 | 77 |
| Reaction time (s) Mean ± standard deviation | 2.15 ± .75 | 1.80 ± .47 | 2.11 ± 1.53 |

Discussion

It appears that subjects were able to maintain a stable reaction time across the three conditions. However, the percentage of correct responses to the stroop task decreased when individuals spoke freely compared to making a sandwich. The combination of both tasks showed a further decrease in correct responses. This suggests that combining multiple everyday tasks decreases cognitive processing.

The approach for detecting response of the stroop task was previously tested in a small subset demonstrating near perfect accuracy. However, in future work we will use a camera (60 Hz, 1080p, built in G-sensor) for monitoring head movement instead of exterior sensor detection. Although wavelet analysis was not necessary for detecting responses to the stroop task, we wanted to test its ability to differentiate nodding and shaking of the head for the purpose of measuring more complex movements in the future.

Cognitive decline is a common symptom of PD. An estimated 40% of patients with PD exhibit cognitive impairment or dementia symptoms prior to motor impairments. These include impairment to sensory functions such as visual and spatial processing, memory. PD patients are likely to have more difficulty sharing neural processing to multiple cognitive and motor demands compared to healthy controls. An objective measure of cognitive decline would be a valuable tool for detection and monitoring progression of PD. Future work will focus on how motion and speech are affected by cognitive loading in PD patients versus healthy controls.

Section Seven: Everyday Speech and Motor Symptoms. Howard, N., Stein, J. & Aziz, T. 2013 g. Early Detection of Parkinson's Disease from Speech and Movement Recordings. Oxford Parkinson's Disease Center Research Day 2013. Howard, N., Bergmann, J. & Howard, R. 2013a. Exploring the Relationship Between Everyday Speech and Motor Symptoms of Parkinson's Disease as Prerequisite Analysis for Tool Development. *Lecture Notes in Computer Science*, MICAI 2013.

Introduction

It is unclear exactly when speech impairments occur in the progression of PD, but symptoms, such as vowel articulation, have been observed even in early stages of PD (Skodda, Visser, & Schlegel, 2011). There has been a growing interest in analyzing PD speech and voice data for detection and progression tracking (Afza, 2013; Guo et al., 2010; Little et al., 2009; Tsanas et al., 2010; Tsanas et al., 2011; Tsanas et al., 2012). For example, Guo et al. (2010) use genetic algorithms and machine learning algorithms to analyze voice features to classify healthy subjects from PD subjects. Tsanas et al. (2012) use speech signal processing algorithms to classify healthy controls from PD patients and were able to achieve 99% accuracy using 10 dysphonia features. Goberman (2005) tested acoustic measures and UPDRS motor scores and found the most significant correlation between acoustic articulation and postural tremor. Tsanas et al. (2010) map dysphonia features to UPDRS scores to test the predictability of speech tests as an indicator of overall disease severity. Their method extracts dysphonia features using speech signal processing algorithms and correlates them to UPDRS scores using regression techniques. They are able to replicate clinician UPDRS scores within 7.5 points of accuracy. They find strong correlations between speech and motor function and between speech and overall health decline, including mood. They suggest that dysphonia features alone may be able to indicate overall PD symptom severity. My approach builds on these studies and seeks to relate multiple data streams for both speech and movement. Whereas other studies have examined voice or phonation, my general approach to PD detection aims to combine speech from everyday living and movement symptom data. Detection of PD may benefit from combining voice and movement data for several reasons. First, there are several motor impairments that affect vocalization in PD patients. For instance, many patients that have trouble swallowing also have problems with saliva retention and facial rigidity (Bologna et al., 2013; Jacobs et al., 1995; Jankovic, 2008). These symptoms themselves are contributing factors to speech impairments. The presence of multiple speech and speech motor symptoms may possibly indicate a higher probability of PD, whereas the presence of just vocalization issues may indicate another disorder altogether. In addition, the use of multiple separate data streams increases the diversity of tests available to medical practitioners. Movement and vocalization data can be tested independently, or they can be tested simultaneously and used to uncover new biomarker patterns (Guo et al., 2010; Howard et al., 2013b; Howard et al., 2013 g; Tsanas et al., 2010; Tsanas et al., 2011; Tsanas et al., 2012).

This section describes a data analysis study that uses speech and motor data to explore PD symptom correlations. The data analysis uses statistical tests to correlate UPDRS scores to examine relationships between speech and selected movement symptoms. The purpose of the study is to explore correlations between motor and speech symptoms in diagnosed PD patients. Before we can collect and combine speech and movement data from PD patients during everyday living we first need to establish if there is a simple linear relationship between them. As a follow-up to the data analysis, this section also includes a review of current literature on PD speech analysis and a discussion of the most relevant modes of speech for future data collection.

A 2-year longitudinal clinical dataset was selected to examine symptom correlations. The UPDRS dataset was sourced from the archives of the Parkinson's Progression Markers Initiative (PPMI). The dataset consists of scores from the UPDRS, which assesses the severity of PD symptoms on a 0-4 scale; consequently, the data had a relatively low resolution and did not categorize different types of PD or PD stages.

The UPDRS is widely used to quantify symptom severity in PD patients. The UPDRS includes 4 sections: Part I non-motor aspects of experiences of daily living (13 questions), Part II motor aspects of experiences of daily living (13 questions), Part III motor examination (18 questions), and Part IV motor complications (6 questions). The UPDRS uses a rating scale of 0-4, representing normal to severe. Symptoms are rated by interview, clinical observation, and patient or caregiver questionnaire (Ramaker et al., 2002). Although UPDRS includes 4 sections, we limited our analysis to data from Part II because we wanted data that most closely reflected "everyday living" variables such as difficulties with walking, swallowing, and tremor experienced on a daily basis. Additionally, we excluded data from Part III "motor examination" because it involved assessment of patients after administration of L-DOPA medication. Part IV also evaluates patients on the basis of their therapy regimens and other interventions that are outside the scope of the current research question, but will be visited in future work.

Given the limitations of the data, we focused our aims towards a better understanding of known signs and symptoms as a means to develop tools and methods for physiological and behavioral biomarker metrics. The analysis is limited to 6 variables of interest taken from Part II, which consist of speech and motor symptoms during everyday living that reflect measures of interest discussed in Section 2. UPDRS "everyday living" variables for walking and balance, tremor, and freezing were selected because a BSN system has been preliminarily tested to measure knee joint stability, an indicator of balance, and future work aims to further develop sensors to measure gait and tremor. The UPDRS "everyday living" measures for difficulty with speech, swallowing, and salivation were selected because our future work intends to combine data from speech production and speech content.

Experiment 8

Examining Everyday Speech and Movement Symptoms
Background

This study uses symptom severity ratings from the UPDRS to examine correlations between speech and movement measures. Most PD research, such as Nandhagopal et al.'s (2011) longitudinal study and Ravina et al.'s (2005) study using radiotracer imaging, has been primarily concerned with the evolution of individual symptoms or indicators over time, however, our study seeks to determine how multiple symptoms relate to one another within a 2 year timeframe. I aimed to identify potential correlations between selected speech and movement measures from UPDRS data collected over 2 years. Statistical analysis was used to correlate severity of symptoms. The study is broken down into 3 analyses. The analyses only includes selected UPDRS measures from Part II in order to narrow down the UPDRS data to everyday measures of clinical interest that could potentially be measured in future work, such as measuring walking and balance with a BSN system. The analysis focuses on how several movement symptoms correlate with the speech metric, which asks the patient or patient's caregiver if their speech is intelligible during daily living. Speech is particularly suited to multivariate analysis because it can be tied to other speech-affecting factors, such as salivation, to create a vocalization-based data stream. This data stream can then be used to analyze the relationship between speech and movement symptoms over time at a higher level of precision.

Aim: This data analysis aims to determine if there is a correlation between speech and 5 other motor symptoms of everyday living and to determine if there is a correlation between all possible pair combinations of speech and movement symptoms.

Methods

Study Design

A data analysis study using statistical analysis techniques on UPDRS data to find correlations between speech and movement symptoms. Three different statistical analyses were performed on the data.

Data

Data was gathered from the PPMI open source archives. Data was organized in excel and analyzed in matlab and R. The UPDRS dataset included 1,120 subjects with 1 to 10 evaluation visits per patient over an observation period of about two years. UPDRS data is based on a 5 point-scale each answer ranging from 0-4 (normal to severe). There were a total of 2,363 independent evaluations of these patients. Our analyses only used 6 variables from the dataset from section II: speech, salivation, swallowing, walking, tremor, and freezing. While we used data from each of the 2,363 evaluations, we only used the scores of 6 variables. See Table 11 for a detailed description of the 6 variables. Table 11 shows UPDRS Part II variables used in analysis (table taken in part from the Movement Disorder Society)

TABLE 11

| | | |
|---|---|---|
| NP2SPCH | Speech: over the Past week have you had problems with your speech? | 0-normal: not at all, no problems<br>1-slight: my speech is soft, slurred or uneven, but it does not cause others to ask me to repeat myself<br>2-mild: my speech causes people to ask me to occasionally repeat myself, but not everyday<br>3-moderate: my speech is unclear enough that others ask me to repeat myself everyday even though most of my speech is understood<br>4-severe: most or all of my speech cannot be understood |
| NP2SALV | Saliva & Drooling: Over the past week, have you usually had too much saliva during when you are awake or when you sleep? | 0-normal: not at all, no problems<br>1-slight: I have too much saliva, but do not drool<br>2-mild: I have some drooling during sleep, but none when I am awake<br>3-moderate: I have some drooling when I am awake, but I usually do not need tissues or a handkerchief<br>4-severe: I have so much drooling that I regularly use tissues or a handkerchief to protect my clothes |
| NP2SWAL | Chewing & Swallowing: Over the past week, have you usually had problems swallowing pills or eating meals? Do you need your pills cut or crushed or your meals to be made soft, chopped or blended to avoid choking? | 0-normal: no problems<br>1-slight: I am aware of slowness in my chewing or increased effort at swallowing, but I do not choke or need to have myfood specially prepared.<br>2-mild: I need to have my pills cut or myfood specially prepared because of chewing or swallowing problems, but I have not choked over the past week.<br>3-moderate: I choked at least once in the past week.<br>4-severe: Because of chewing and swallowing problems, I need a feeding tube. |
| NP2TRMR | Tremor: Over the past week, have you usually had shaking or tremor? | 0-normal: not at all, I have no shaking or tremor<br>1-slight: shaking or tremor occurs but does not cause problems with any activities.<br>2-mild: Shaking or tremor causes problems with only a few activities3-moderate: I choked at least once in the past week.<br>3-moderate: shaking or tremor causes problems with many of my daily activities.<br>4-severe: shaking or tremor causes problems with most or all activities. |
| NP2WALK | Walking & Balance: Over the past week, have you usually had problems with balance and walking? | 0-normal: not at all, no problems<br>1-slight: I am slightly slow or may drag a leg. I never use a walking aid.<br>2-mild: I occasionally use a walking aid, but I do not need any help from another person.<br>3-moderate: I usually use a walking aid (cane, walker) to walk safely without falling. However, I do not usually need the support of another person.<br>4-severe: I usually use the support of another person to walk safely without falling. |
| NP2FREZ | Freezing: Over the past week, on your usual day when walking, do you suddenly stop or freeze as if your feet are stuck to the floor? | 0- normal: not at all (no problems).<br>1-slight: I briefly freeze but I can easily start walking again. I do not need help from someone else or a walking aid (cane or walker) because of freezing.<br>2-mild: I freeze and have trouble starting to walk again, but I do not need someone's help or a walking aid (cane or walker) because of freezing.<br>3-moderate: When I freeze I have a lot of trouble starting to walk again and, because of freezing, I sometimes need to use a walking |

TABLE 11-continued aid or need someone else's help. 4-severe: Because of freezing, most or all of the time, I need to use a walking aid or someone's help.

Data Analysis

Analysis 1 Spearman and Kendall Correlation As explained above, we only used data from 6 variables: NP2SPCH, NP2SALV, NP2SWAL, NP2TRMR, NP2WALK, NP2FREZ (see Table 11). Spearman's Rank-Order Correlation and Kendall Rank Correlation Coefficient were calculated to measure the association between NP2SPCH and the each of the 5 other variables and a composite sum of all 6 variables.

Analysis 2: Variable Pairing Correlation Analysis Again for analysis 2, only data from the 6 selected variables were included (NP2SPCH, NP2SALV, NP2SWAL, NP2TRMR, NP2WALK, NP2FREZ). Instead of testing for correlation to NP2SPCH as in analysis 1, the variables were analyzed as pairs (15 total). Spearman's correlation coefficient was calculated for each pair of symptoms, 15 total.

Analysis 3: Linear Regression

In analysis 3, Linear Regression was computed for the same 15 variable pairings as in analysis 2. Regression values were plotted and checked for normal distribution.

Results (See UPDRS for patient plots, regression graphs and additional analyses not included in this section) Table 12 shows a summary of results of the three statistical analyses:

TABLE 12

| Analysis | Most Significant Correlation | Result |
|---|---|---|
| Spearman & Kendall | Speech/ Salivation (0.43) (0.39) | The high correlation between speech and salivation is not unexpected. These two factors interact directly, because difficulty controlling salivation will affect the patient's ability to speak and enunciate. |
| Pair Correlation | Speech/ Salivation (0.43) | Similarly, pair correlation found that the highest correlation occurred in the speech/salivation pair. However, the coefficient result for speech/walk (0.31) suggests a relationship between two symptoms that aren't necessarily expected to be highly correlated. |
| Linear Regression | Salivation/ Freeze (0.82) | The high correlation between salivation and freezing suggests the degradation of disparate motor skills at a similar rate. |

Analysis 1 Spearman and Kendall Correlation

Kendall and Spearman found similar correlations between speech and each of the 5 variables. The highest correlation was found between speech and salivation, the lowest correlation was found between speech and freeze (see Table 13). The p-values for all of the correlations were significant ($p<0.001$) (see Table 14). Table 13 shows Spearman and Kendall correlation coefficients for Speech and 5 variables and the composite sum of all variables:

TABLE 13

| Spearman Analysis Results | | Kendall Analysis Results | |
|---|---|---|---|
| NP2SALV | 0.43 | NP2SALV | 0.40 |
| NP2SWAL | 0.32 | NP2SWAL | 0.30 |

TABLE 13-continued

| Spearman Analysis Results | | Kendall Analysis Results | |
|---|---|---|---|
| NP2WALK | 0.31 | NP2WALK | 0.30 |
| NP2TRMR | 0.20 | NP2TRMR | 0.18 |
| NP2FREZ | 0.19 | NP2FREZ | 0.18 |
| COMPOSITE | 0.68 | COMPOSITE | 0.59 |

Table 14 shows Spearman Rank-Order Correlation Coefficient with corresponding p-values measuring the correlation between speech and 5 motor variables

TABLE 14

| Motor Variable | Spearman Correlation Coefficient | P-value |
|---|---|---|
| Salivation | 0.43 | 1.283e−107 |
| Swallowing | 0.32 | 2.882e−56 |
| Walk | 0.31 | 7.363e−54 |
| Tremor | 0.20 | 1.437e−23 |
| Freeze | 0.19 | 2.355e−21 |

Analysis 2 Pair Correlation Analysis

The highest correlation was found for the speech/salivation pairing ($r=0.438$), speech/swallow had the second highest correlation ($r=0.317$). Correlation was lowest for the swallow/tremor pairing ($r=0.105$) (See Appendix B). The p-values were normally distributed with a mean of 0.383 and a standard deviation of 0.193 (FIG. 7-2). A statistically portion of the pairings' correlation coefficients fell in the lower half of the distribution curve. Pair correlation was lowest overall for swallow/tremor (0.105), and highest for speech/salivation (0.438). Meaning that severity scores were most correlated for speech/salivation symptoms. Speech/swallow had the second highest correlation (0.317). Correlation coefficients had a mean of 0.383 and a standard deviation of 0.193. A statistically significant portion of the pairings' correlation coefficients fell in the lower half of the distribution curve.

Analysis 3 Linear Regression

Linear Regression was highest for salivation/freeze (0.8278) and lowest for swallow/tremor (0.0638) (See Appendix B). Speech/salivation pairing was second highest. Linear Regression values were normally distributed (See Appendix B).

Discussion

The results of the Spearman and Kendall in Analysis 1 suggest that speech and the 5 motor symptoms are highly correlated. It was expected that related symptoms, such as speech, salivation, and swallow were likely to correlate with each other given that speech impairments are observed in more than 90 percent of PD patients (Sapir et al., 2008). Speech and salivation had predictably high correlation coefficients for both spearman correlation in analysis 1 and spearman pairing in analysis 2, but was in the middle of the linear regression values in analysis 3. We expected to see higher correlations between the 3 pairs for tremor, walk and freeze in the spearman and linear regression analysis. Walk/freeze was the most correlated out of those 3 pairings, but was lower than speech/walk in analysis 2 and was almost the same as speech/freeze in analysis 3. Salivation/freeze was most correlated in linear regression analysis, yet was in the bottom half of the spearman correlation pairings with a coefficient of 0.1936. Overall we found the 3 analyses to be somewhat inconclusive in determining what speech and movement symptoms are most correlated. Analysis 1 and 2 found the highest correlation for speech/salivation, but linear regression results were contradictory.

The correlations for walk/tremor/freeze symptoms were overall lower than speech/salivation/swallow symptoms. This is an interesting finding given that tremor and postural stability (balance) are the cardinal symptoms of PD (NP2WALK refers to walking and balance see Table 12). This indicates the importance of measuring speech impairments with higher-resolution data from everyday living. While most correlation coefficients were high, the lowest correlations may show different results if measured at a higher resolution. It is important to note that there were inconsistencies in the dataset, such as frequency of visit, which may have affected results. UPDRS data is based on clinician observation or self-questionnaire. Although UPDRS is a standardized rating scale, subjective evaluation presents unavoidable bias and margin of error. Symptom tracking and disease progression would benefit from more objective evaluations, such as body sensor networks to measure motor symptoms such as walking and balance, tremor and freeze. Using body sensor networks to measure motor features instead of subjective ratings may provide more objective, quantitative data. Speech and motor data measured during everyday living, as opposed to a doctor's office or lab would also yield more valuable data about PD symptoms. We recommend that higher-resolution, quantitative, speech and motor data is needed in order to determine symptom correlations. Being able to map speech and movement symptoms that correlate or progress at the same rate could be useful for managing disease progression. Symptom tracking could help to identify disease progression biomarkers and possibly even PD detection. Correlating multiple data streams over time could be used to develop symptom trajectories and recommend treatment therapies.

Future research should continue mapping speech and movement symptoms that appear to progress at the same rate to see if these mutually reinforcing features can be used to develop new biomarkers. (See 2014 Pilot Study—An exploratory study of the utility of a Body Sensor Network in the clinical detection of Parkinson's disease). Additionally, this approach may help to track symptom progression. For example, will a patient with a level 1 speech score and a level 1 utensil handling score eventually progress to level 3 for both, or do the two impairments develop at different rates? Applied over many patients, this technique may help identify not only whether an individual is at risk for PD, but also the subtype of PD based on the early symptoms they manifest. This approach could also be used to develop symptom trajectories for individual patients to recommend treatment modalities based on the particular conditions unique to their disease.

Review of Everyday Speech

The findings of experiment 8 instigated additional research questions about speech symptoms in PD:

1. Can speech be collected non-intrusively during everyday life with audio quality sufficient for processing?
2. What is the best method for collecting running speech during everyday life?
3. What features are most significant? Measures of speech production, such as dysphonic features or language content?

A review of current literature on PD speech analysis was conducted together with partial replication of an analysis by (Tsanas et al. 2010).

Dysphonia Features

There has been a growing interest in analyzing speech and voice for detection and progression tracking (Afza, 2013; Guo et al., 2010; Tsanas et al., 2010; Tsanas et al., 2011; Tsanas et al., 2012). Tsanas et al. (2010) use sustained vowel phonations to estimate overall symptom severity by mapping dysphonia features to UPDRS scores. They are able to predict total motor UPDRS scores within 6 points of accuracy and total UPDRS scores within 7.5 points of accuracy. Their analysis provides additional evidence for correlation between speech and motor symptoms as well as speech and general health.

The dataset used by Tsanas et al. (2010) included 42 PD patients diagnosed within the previous 5 years and unmedicated for the duration of the study. Speech and UPDRS scores were collected over a period of 6 months. 5,923 30-second vowel phonations of the vowel "aaahhh . . . " were collected. Speech processing algorithms (Little et al., 2009) were used to extract 16 dysphonia features (described in Table 15). Measures include variation of fundamental frequency (jitter), several measures in amplitude (shimmer), noise to harmonics ratio (NHR), harmonics to noise the ratio (HNR), detrended fluctuation analysis (DFA), and pitch period entropy (PPE). The data also included total motor UPDRS scores (section 3, total of measures 18-44) and the total UPDRS scores (all 3 sections, total of 44 measures). However, because UPDRS ratings were not collected on a weekly basis, UPDRS values were linearly interpolated. The dataset was collected from Intel's at home telemonitoring system (AHTD) and recently used in several studies (Tsanas et al. (2011), Tsanas et al. (2010), Little et al. (2009) and Goetz et al. (2009). The dataset was made available by the University of California Irvine's repository of machine learning database.

I replicated the correlation analysis using the same dataset as Tsanas et al. 2010, which included UPDRS motor and total scores and dysphonia features. Spearman Correlation was used to calculate the association between the 16 dysphonia features and the total motor UPDRS scores. Analysis was done using matlab. Table 15 shows 16 dysphonia features from voice recordings:

TABLE 15

| | Variable name | Description |
|---|---|---|
| 1 | Jitter (relative) | If we picture human voice patterns as a |
| 2 | Jitter (absolute) | waveform with respect to time, then high |
| 3 | Jitter: RAP | variation in jitter, or fundamental frequency, |
| 4 | Jitter: PPQ5 | means that the lowest frequency per unit time |
| 5 | Jitter: DDP | is in flux, suggesting a change in tone of voice, or inability to control voice tone |
| 6 | Shimmer | High indicates lack of normal voice modulation |
| 7 | Shimmer (dB) | |
| 8 | Shimmer: APQ3 | |
| 9 | Shimmer: APQ5 | |
| 10 | Shimmer: APQ11 | |
| 11 | Shimmer: DDA | |
| 12 | NHR | NHR and HNR measure the ratio of noise to |
| 13 | HNR | tonal components. |
| 14 | RPDE | DFA is a Signal fractal scaling exponent (DFA) |
| 15 | DFA | PPE is a nonlinear measure of fundamental |
| 16 | PPE | frequency variation, similar to jitter. |

Spearman analysis (Tables 7-6) showed a positive correlation between the total motor score and 14 of the 16 voice measures. Two of the voice measures, HNR and DFA, had a negative correlation. The negative correlation with HNR in particular suggests that background vocalizations within existing amplitude and fundamental frequency limits are not strongly related to PD. However, aberrations significant enough to affect either of these metrics were also more significant in their relationship with UPDRS results consistent with PD. Future studies should further investigate if the negative correlation between UPDRS motor scores and both HNR, a ratio of harmonics to noise, and detrended fluctuation analysis (DFA), a signaling fractal-scaling exponent is verifiable and important. There is a strong enough relationship in the data to warrant further investigation with additional data acquisition methods. The relatively small sample size of 42 suggests that, while initial correlation coefficients were low, they may simply warrant a higher-resolution investigation of the signs in question, such as speech aberration. We propose that future work should include running speech in addition to vowel phonations.

Spontaneous Speech

Different modes of speaking, such as conversational and mimicked speech, involve different levels of cognitive and motor function. Spontaneous speech requires an internal motor plan, followed by execution and monitoring, whereas mimicked speech provides a template. Van Lancker Sidtis et al. (2010) argue that subcortical functionality has different effects on speech performance in different speaking modes. They find that dysfluencies are most prevalent in conversational speech (with and without DBS treatment) and HNR improves in mimicked speech when treated with DBS.

A number of speech and language impairments are overlooked when limited to phonemes or mimicked speech tasks. Language processing problems such as "tip of the tongue phenomenon" (Jankovic, 2008) and action-verb impairment (Boulenger et al., 2008; Cardona et al., 2013) could be better understood by analyzing spontaneous speech from everyday life. In a study of spontaneous speech in PD Illes et al. (1988) found several important linguistic features differentiating PD patients from control subjects:

> "an increase in the number of silent hesitations per minute, abnormally long silent hesitations, words per silent hesitation, open class phrases, and optional open phrases per speech sample, and a decrease in the number of modalizations and interjections. An increase in the number of filled hesitations occurring per minute, as well as a decrease in syntactic complexity separated moderate from mild Parkinson's patients."

Specific language features such as metaphors that rely on patient's description of their behavioral state may provide further information about their brain state. Although very little is known about this neural phenomenon, we know that metaphors associated with specific concept types (i.e., predicate metaphors) involve increasingly abstract processing along the lateral temporal cortex and can be analyzed accordingly (Chen et al., 2008). Monetta and Pell (2007) studied metaphor comprehension in PD patients and found that metaphor interpretation is highly dependent on intact fronto-striatal brain regions, which are compromised, in early PD patients. This suggests that PD patients are less efficient in processing metaphors. Maki et al. (2013) studied metaphor comprehension in patients with mild cognitive decline and Alzheimer's disease patients and found that metaphor comprehension deteriorated with disease progression. Kircher et al. (2007) studied metaphoric sentence processing in patients with schizophrenia and controls using functional magnetic resonance imaging (fMRI). They suggest that the inability to utilize the brain regions crucial for context processing, which are the left inferior frontal and right lateral temporal cortex, may underlie schizophrenic concretism.

In order to detect metaphors to diagnose neurological disorders, one has to understand the underlying mechanisms that bring about the disordered state. Pragmatic communication, which includes interpretation of metaphors, relies on higher brain regions as well as an intact language system. Analyzing metaphors in various brain disorder patient cohorts at various stages of disease development might aid in developing a neurodiagnostic strategy to detect the correlates PD early. Neuman et al. (2013) developed a set of algorithms capable of detecting conceptual metaphors from text. The algorithms are the state-of-the-art automated metaphor detection tool with 71% precision and 27% averaged improvement in prediction (Assaf et al., 2013a; Assaf et al., 2013b; Gandy et al., 2013; Neuman et al., 2013).

Collecting spontaneous speech from everyday living would allow analysis of both speech production and linguistic features to potentially measure motor and cognitive changes. Advances in language analysis may be valuable for determining mind states or changes in cognitive states in patients with PD (Bergmann and Howard, 2012; Howard, 2013a; Howard and Guidere, 2011; Howard and Guidere, 2012; Howard et al., 2013 g). The Language/Axiology Input and Output algorithm (LXIO) presents a method for determining and predicting patients' cognitive states from speech or written text. Essentially, this means linking mind axiology, or conceptual beliefs common to particular cognitive conditions, to behavioral trends (Howard and Guidere, 2012; Roberts and Kassel, 1996). This provides a cumulative "value," or cognitive state, based on vocal input from the subject. Using a Mind Default Axiology (MDA) database to associate specific concepts and mental values with the concepts vocalized by the subject to calculate the cognitive state given time frame constraints, which aims to incorporate functionality into a neural ontology (Howard and Guidere, 2011; Roberts and Kassel, 1996).

Conclusion

The results from experiment 8 and the review of dysphonia features suggest that speech and vocal impairments are significant symptoms of PD, in some cases more prominent than motor symptoms. Also, these analyses indicate that there is a relationship between speech and motor symptoms, and to the severity of the overall disease. To determine exactly what that relationship is, and the trajectory over time, requires additional, non-categorical data and research.

In experiment 8, we expected high correlation coefficients for intuitively related symptoms, such as walk/freeze and salivation/speech. For example, speech is affected by the inability to properly control salivation, and difficulty with walking and balance may be related to freezing. While these correlations are valuable, they are not surprising. On the other hand, results also showed unexpected correlations between symptoms such as speech and walking that do not appear to influence one another directly.

This chapter offers support for additional data collection and analysis of both speech and motor symptoms. The findings from experiment 8 are consistent with other studies suggesting correlations between speech and non-speech motor symptoms (Goberman, 2005; Tsanas et al., 2010). However the use of UPDRS data instead of recorded speech is a limitation of our study. Furthermore, we argue that spontaneous/conversational speech from everyday living will be required in order to comprehensively analyze speech and vocal symptoms due to motor and non-motor impairments.

In the review of prior work of Tsanas et al. 2010, dysphonia features were significantly correlated to UPDRS motor scores, but the voice recordings were extracted from sustained vowel phonations ("aaahh . . . ") limited in range and applicability to other analysis methods. We argue that collecting free running speech from everyday living, although criticized for presenting processing complications, would complement dysphonia data and provide a more valuable analysis of PD speech symptoms. Human speech production far exceeds the features of a single vowel and should be analyzed for both speech production and language content.

Despite the low resolution of the data, statistically significant correlations between speech and motor symptoms were indicated, which suggests possible implications for the neurological progression of the disease that can be better understood with a similar analysis based on higher resolution, qualitative datasets. Future work will focus on developing tools and methods to measure the same speech and motor symptoms, but with higher resolution data collected during everyday living.

Limitations of the Study

Open source data was used and although not ideal for the analysis it showed evidence that speech symptoms are significant to the overall disease and possibly correlated with certain motor symptoms. While the UPDRS dataset was collected over 2 years the examination per patient ranged from 1-10. The inconsistency in the frequency of examination across patients most likely affected the results of our analysis. For section II of the UPDRS exam, PD patients (or their caregivers) are asked about symptom severity based on the past week, which only gives a subjective assessment based on memory. Although the scale itself is standardized and widely used, it is fundamentally subjective and often bias evaluation (Shulman et al., 2006). The most limiting aspect of UPDRS and other current methods for measuring PD features, is the lack of data collected during everyday living, which is the environment where symptoms are most authentically represented.

The time period and frequency of collection in the UPDRS dataset may not be adequate to show symptom correlations over time, given the amount of examinations per subject. Instead, we propose a longitudinal dataset with daily measures of speech and motor features. This kind of data collection would be difficult to collect in a lab or clinician's office and would be better obtained during ADL using non-obtrusive methods (Bergmann et al., 2012a; Bergmann and McGregor, 2011b).

Future Work

Using open source UPDRS data was a necessary step in order to provide a basis for development of future work, which will focus on collecting running speech and motor data measured with BSNs from PD patients at different stages of disease progression. Future investigation and data collection of movement and speech aims to validate the utility of these metrics for PD detection and progression tracking.

Beginning in 2014(See 2014 Pilot Study—An exploratory study of the utility of a Body Sensor Network in the clinical detection of Parkinson's disease), a year-long pilot study will collect spontaneous speech and movement measured with BSNs from 60 participants: 20 with AD, 20 with PD, and 20 age matched controls. A data montage such as this currently does not exist and will be valuable to test data fusion of speech and movement. We hope that this future work will be a step towards non-invasive early detection of PD and symptom progression tracking. Being able to isolate symptoms that correlate and measures of symptom severity would provide valuable data for progression tracking and detection.

Chapter Eight: Brain Activity

Introduction

Neural oscillations throughout the brain carry a wealth of information about cognition and brain function. Neural oscillations have long been correlated to a variety of normal brain functions, ranging from motor control, learning and memory, consciousness to sleep (Peelle and Davis, 2012; Ward, 2003). Neural oscillations are composed of several frequency bands: delta (1-4 Hz), theta (4-8 Hz), alpha (8-12 Hz), beta (13-30 Hz) and gamma (30-70 Hz). Normally, neural oscillations establish great precision in temporal correlations of neural networks and therefore disruptions and impairments in these temporal correlations are candidate mechanisms of several neurological disorders.

Disturbance in neural oscillations have been implicated in many neurological disorders (Moran et al., 2011; Uhlhaas and Singer, 2010). For example, neuropsychological disorders are often correlated with altered levels of alpha activity (Sponheim et al., 1994). Bystritsky et al. (1999) found that patients with traditional panic disorder displayed on average lower alpha activity in the right temporal lobe. Hayashi et al. (2010) note that the co-morbidity of panic disorder, epilepsy, and various other neuropsychological dysfunctions quantifies the true value of alpha oscillations. Koenig et al. (2005) also noted a decrease in global EEG synchronization among alpha-bands in Alzheimer's disease. Manu et al. (1994) note a total increase in alpha-delta sleep patterns in patients with chronic fatigue.

Changed oscillations have also been identified in PD. Advances in functional neurosurgery brought the opportunity to record rhythmic activity directly from the basal ganglia field potentials. The STN and GPi have been recognized as two important substrates of synchronized oscillation in PD. Studies have found excessive synchrony of neural oscillations in the beta frequency range, most likely due to dopamine depletion (Abosch et al., 2012; Moran et al., 2011; Weinberger et al., 2006). These excessive oscillations are thought to be caused by altered local neural connectivity (Moran et al., 2011). Tan et al. (2013) show the significance of detecting and coding neural oscillations from different oscillatory activities in the subthalamic nucleus during performance of motor tasks. Their findings indicate a changed relationship between beta and gamma band activities in the sub thalamic nucleus during motor efforts. Hence, exploring neural oscillations using machine learning algorithms could help to determine if analysis of neural oscillations can provide signatures to detect PD and track progression (Howard et al., 20130.

Studies looking at neural oscillations in PD have produced interesting yet inconclusive results, and require further research to determine whether they can be used for early PD detection. Several frequency bands have been suggested. For example, Han et al. (2013) applied wavelet packet entropy to EEG and found that there was an increase in delta and theta power and a decrease in alpha and gamma power in early stage PD patients. Klassen et al. (2011) investigated neural oscillations in PD patients and found background rhythm frequency and relative power correlation with dementia incidence. Beta waves appear to be contingent on dopaminergic function; the reduction of which causes instability and generalized wave synchrony (Brown et al., 2001). The loss of dopamine results in changes in neural firing rates and patterns. Therefore altering oscillatory activity between the subthalamic nucleus and pallidum.

In this chapter, we describe a study that tests the ability of a Neural Oscillation Detection (NOD) algorithm to classify pain patients based on EEG data. The NOD algorithm uses signal processing and machine learning-algorithms to detect oscillation biomarkers of pain from a minimal number of electrodes. The NOD algorithm can potentially be used to detect neural oscillation patterns of other brain disorders, including PD. The purpose of this study is to validate the algorithm using pain patients and EEG recordings.

Currently, the most valuable and accurate brain activity data comes from in vivo recordings, such as local field potentials, which require invasive methods to collect the data. The purpose of our pain study is to determine whether it is possible to use non-invasive methods to analyze neural oscillations at the same level of accuracy as using deep brain electrodes. Our study builds on the work of Green et al. (2009) who identified a neuropathic pain biomarker using local field potentials deep within the periaqueductal grey and sensory thalamus. We tested if it is possible to use EEG data and machine learning algorithms to detect the same neuropathic pain biomarker that was found from the deep brain electrodes.

Furthermore, this study aims to determine the minimum number of electrodes necessary to detect pain at a high accuracy using the NOD algorithm. The approach presented focuses on developing modalities to collect data unobtrusively during everyday life, such as wearable body sensors and voice recording. Recent advances in EEG hardware have allowed the EEG to be measured accurately using portable devices. Mainstream market products such as Neurosky, Emotiv, and AvatarEEG offer portable EEG headsets with up to 14 channels. However, this technology has not yet reached maturation and has not been widely used outside select consumer industries. Nonetheless, this emerging technology could potentially be repurposed and developed for clinical use. By determining the minimum number of electrodes necessary to detect pain, we can work towards developing wearable, portable sensors that can be used to collect EEG data on a daily basis.

Experiment 9

Neural Oscillation Detection. Howard, N., Rao, D., Fahlstrom, R., Bergmann, J. & Stein, J. 2013e. The Fundamental Code Unit—Applying Neural Oscillation Detection Across Clinical Conditions. *Frontiers, Commissioned, In Preparation*.

Background

Although there is an abundance of evidence that abnormal oscillations are associated with brain dysfunction, there is a limited quantification of oscillatory biomarkers (Yener and Basar, 2013). EEG recordings offer a non-invasive method for identifying neural oscillation biomarkers. In this study, we test the accuracy of the NOD algorithm to detect a pain biomarker using EEG data.

It is believed that the neural substrate for pain perception arises from the integration of the pattern of activity in the "central pain matrix," shown by functional imaging studies (reviewed in Iannetti et al. (2005). The amount of activity in these areas has been correlated with the intensity of perceived pain (Ianetti et al 2005). Several researchers have investigated whether neural oscillations measured using EEG can be used to assess the activity in the pain regions of the brain and quantify pain perception. Direct objective neural correlates are yet to be defined. However, neural oscillations could thus be used as a predictor of pain to improve diagnosis, monitoring, and targeting pain management.

One theory for the neural correlate of pain involves changes in synchrony of oscillations. Local field potentials provide information about ensemble neural activity from the brain. The amplitude of oscillations provides information about the level of synchrony of the ensemble activity. It is believed that thalamocortical loops contribute to pain related synchrony, which can be recorded by EEG or MEGs. While in some patients with neuropathic pain, decreased EEG power has been observed, other pain patients show increased EEG power (Sarnthein et al., 2006). The amplitude of gamma EEG has been previously found to correlate with subjective pain intensity (Gross et al., 2007). Zhang et al. (2012) also found that gamma oscillations recorded over the primary somatosensory cortex correlate with pain perception. However, these studies elicited pain using transient and intense nociceptive stimuli. So the changes in EEG may instead have correlated with non-pain specific changes related to attention and arousal (Iannetti and Mouraux, 2010). One drawback of these studies is the use of healthy human subjects and nociceptive stimuli evoking pain, as opposed to recording objective neural correlates from humans experiencing physiological chronic or acute pain.

In order to understand the neural correlates of pain, the most revealing studies would involve in vivo recordings using, for example, local field potentials recorded from the central pain matrix. An interesting discovery from Green et al. (2009) reveals a neuropathic pain biomarker recorded from local field potentials deep within the periaqueductal grey and the sensory thalamus. The neuropathic pain patients consisted of phantom limb, post-stroke, facial pain and brachial plexus injury. Using deep brain electrodes in patients requiring DBS treatment, Green et al found that pain evoked an increase in spindle shaped bursts at 8-12 Hz in the PAG and 17-30 Hz in the sensory thalamus. This demonstrates a possible physiological pain biomarker directly from the brain regions implicated in pain and the target sites for pain management. Given the surgical techniques used to measure pain in this study, we hypothesized that the scalp correlate of the pain biomarker might be detected using EEG. The pain biomarker we studied was the 8-12 Hz alpha range and spindle activity represented in EEG data. In our study we used EEGs from chronic pain patients and using the NOD algorithm that utilized the alpha band as input features for machine learning, we demonstrated that EEGs can be used to detect a physiological pain biomarker as observed by Green et al.

Though current methods of neural oscillation detection offer valuable diagnostic information, organizing the available data into an objective framework is necessary for improved treatment and to provide insight into various neurological disorders that have neural oscillation abnormalities. The past several years have seen pattern recognition and computational intelligence approaches such as machine learning to analyze and detect patterns of activity in the brain (Bosl et al., 2011; Gandhi et al., 2010; Shahaf et al., 2012). Many of these algorithms have suffered from low specificity and accuracy.

In this study, we present the Neural Oscillation Detection (NOD) algorithm. The NOD combines signal processing of EEG data and uses advanced machine-learning tools to classify patients based on the pain biomarker in the alpha range with spindle activity (Green et al 2009). The NOD can be used to organize and analyze neural oscillation data related to any brain disorder and any oscillation biomarker. Here we demonstrate the NOD on high density EEG data from chronic pain (both high and low intensity) and healthy patients.

Aim:

To test if EEG and the NOD algorithm can detect the neuropathic pain biomarker found using deep brain electrodes and to determine the minimum number of electrodes necessary to detect it.

Methods

Study Design

EEG data was collected from chronic pain patients and control subjects. The EEG data was processed and analyzed using signal processing and machine learning methods to train and test the NOD algorithm.

The NOD algorithm was developed on a single platform using Python (Version 2.7.3). EEG data were collected using 256-electrodes. Pre-processing and signal processing extracted relevant data and machine learning was tested to detect the pain.

Data

EEG recordings were obtained from the University of Nebraska, Lincoln from 18 subjects (both male and female), including six healthy controls and twelve chronic pain patients. The patient group consisted of six patients who subjectively reported low intensity pain and six who reported high intensity pain: no-pain healthy controls (n=6), chronic pain (low pain intensity, n=6; high pain intensity, n=6). EEG data were from awake subjects using a 256-electrode system with a sampling frequency of 250 Hz. Durations of the recording varied; on average they were 8±2 (mean±standard deviation) minutes long. The EEG data were continuous recordings and no pain or noxious stimulus was presented during the recording. The original data for each subject was in a sample by channel matrix format.

Data Processing and Analysis

The NOD algorithm was developed on a single platform using Python (Version 2.7.3). The algorithm was bench tested and it was confirmed that the algorithm executes correctly. Data was inputted into the algorithm as text files and raw EEG data was read. NOD consists of three parts: pre-processing, signal processing and machine learning.

Pre-processing

Pre-processing consisted of filtering the data at 4-45 Hz for the complete spectrum (Hipp et al., 2012) and 8-12 Hz for the broad alpha range (Green et al 2009) artifact removal and common spatial pattern algorithm (CSP) for electrode selection (Higashi and Tanaka, 2011). Physiological sensor selection was based on literature evidence suggesting the spatial locations of pain signatures (Chang et al., 2002; Chen and Rappelsberger, 1994; Green et al., 2009).

The CSP algorithm was performed for the following:
Full electrode set
Physiologically relevant electrode set.
After CSP, segmentation was performed.

Signal Processing

Signal processing consists of three methods in the different EEG domains: spindle threshold analysis (time domain), power spectrum analysis (frequency domain), and wavelet analysis (time-frequency domain). The only threshold that identified spindle activity lasting at least 0.5 seconds was 10% of the maximum amplitude value. Power spectrum analysis was performed in order to determine the power of each frequency that is contained in the recording. Time-frequency analysis demonstrates the changes in pain-related dominant frequencies that might contain spindle activity over time based on results of green et al. We selected the Morlet wavelet, which is commonly used in EEG time-frequency decomposition series.

These methods were implemented in the following manner:
Complete frequency spectrum
Alpha frequency spectrum (based on the pain signature)
For each of these spectrums, features for the machine learning algorithms were obtained from each of the three analysis methods. Our goal is to validate the pain signature in the alpha frequency spectrum with spindle activity. Therefore, the results should yield similar or better classification results than the complete frequency spectrum.

Machine Learning

Features selected were spindles, relative power, and wavelet coefficients. Results are presented as complete spectrum or alpha spectrum and full electrode set or physiologically relevant electrode set. The machine learning algorithms tested were Naïve Bayes, 1 and 2 Nearest Neighbors and Support Vector Machine (SVM). We compared results from these algorithms to select the best consistently performing classifiers across groups.

Validation Technique

A cross validation technique was used to evaluate the performance of the classification. A 10-fold cross validation approach was applied to the dataset to determine the sensitivity, specificity, and accuracy.

Results

In order to detect the pain signature of patients, we used a top-down approach to analyze the complete frequency spectrum, to ensure that frequencies other than the original alpha band were not altered due to pain. We present below the results of the complete spectrum first and then focus in on the alpha band. In order to analyze EEG pain data, we first investigated the data obtained from all 256 electrodes (called "Full electrode set"). Then we studied the physiologically relevant electrodes to pain as described in the previous section (referred to as the "Physiologically relevant electrode set"). This approach was intended to reveal whether there is a reduced set of electrodes that are sufficient to detect the pain signature.

Complete Frequency Spectrum (4-45 Hz)

Physiologically Relevant Electrodes

The physiologically relevant electrodes were further reduced by CSP and classification was run with incrementing electrodes until accuracy reached 100% or when addition of electrodes decreased, instead of increasing accuracy (Table 16). Table 16 shows incremental electrode selection with accuracy levels (physiologically relevant electrode set)

TABLE 16

| | 1 Number of Electrodes Used for Classification | |
|---|---|---|
| | 2  1 | 3  2 |
| 4 Pain (pain vs. no pain) | 5  70.0% | 6  100.0% |
| 7 Intensity (high vs. low) | 8  90.0% | 9  100.0% |

The highest-ranking electrodes in CSP for detection of pain vs. no pain were electrode numbers 138 and 150 and for intensity they were 198 and 186. These electrode channels were used for further feature extraction in the spindle threshold, power spectrum and time-frequency analysis methods. Specific features were inputted in four classifiers: Naïve Bayes, 1 Nearest Neighbor and Support Vector Machines (SVM). The performance outcomes for pain detection are given in Table 17. The performance outcomes for classifying intensity across features and machine learning approaches are given in Table 18.

Table 17 shows performance across features and machine learning algorithms for pain vs. no pain with the two highest-ranking CSP electrodes (physiologically relevant electrode set):

TABLE 17

| Features | Algorithm | Correct | Incorrect | Sensitivity | Specificity | Accuracy |
|---|---|---|---|---|---|---|
| Power Spectrum | Naïve Bayes | 89.0% | 11.0% | 91.7% | 83.3% | 88.9% |
| | 1 Nearest Neighbors | 98.0% | 2.0% | 100.0% | 94.4% | 98.1% |
| | 2 Nearest Neighbors | 98.0% | 2.0% | 100.0% | 94.4% | 98.1% |
| | SVM | 87.3% | 12.7% | 97.2% | 66.7% | 87.0% |
| Wavelet Analysis | Naïve Bayes | 33.3% | 66.7% | 0.0% | 100.0% | 33.3% |
| | 1 Nearest Neighbors | 98.0% | 2.0% | 97.2% | 100.0% | 98.1% |
| | 2 Nearest Neighbors | 98.0% | 2.0% | 97.2% | 100.0% | 98.1% |
| | SVM | 86.7% | 13.3% | 97.2% | 66.7% | 87.0% |
| Spindle Threshold | Naïve Bayes | 33.3% | 66.7% | 0.0% | 100.0% | 33.3% |
| | 1 Nearest Neighbors | 100.0% | 0.0% | 100.0% | 100.0% | 100.0% |
| | 2 Nearest Neighbors | 100.0% | 0.0% | 100.0% | 100.0% | 100.0% |
| | SVM | 96.3% | 3.7% | 97.2% | 94.4% | 96.3% |

Table 17. Performance across features and machine learning algorithms for high vs. low pain with the two highest-ranking CSP electrodes (physiologically relevant electrode set)

TABLE 18

| Features | Algorithm | Correct | Incorrect | Sensitivity | Specificity | Accuracy |
|---|---|---|---|---|---|---|
| Power Spectrum | Naïve Bayes | 53.3% | 46.7% | 50.0% | 50.0% | 50.0% |
| | 1 Nearest Neighbors | 53.3% | 46.7% | 41.7% | 66.7% | 54.2% |
| | 2 Nearest Neighbors | 53.3% | 46.7% | 41.7% | 66.7% | 54.2% |
| | SVM | 76.0% | 24% | 75.0% | 75.0% | 75.0% |
| Wavelet Analysis | Naïve Bayes | 56.7% | 43.3% | 83.3% | 33.3% | 58.3% |
| | 1 Nearest Neighbors | 61.7% | 38.3% | 58.3% | 66.7% | 62.5% |
| | 2 Nearest Neighbors | 61.7% | 38.3% | 58.3% | 66.7% | 62.5% |
| | SVM | 38.3% | 61.7% | 50.0% | 25.0% | 37.5% |
| Spindle Threshold | Naïve Bayes | 56.7% | 43.3% | 83.3% | 33.3% | 58.3% |
| | 1 Nearest Neighbors | 100.0% | 0.0% | 100.0% | 100.0% | 100.0% |
| | 2 Nearest Neighbors | 100.0% | 0.0% | 100.0% | 100.0% | 100.0% |
| | SVM | 78.3% | 21.7% | 75.0% | 83.3% | 79.2% |

Full Electrode Set

The full electrode set was also reduced by CSP and classification was run with incrementing electrodes until accuracy reached 100% or when addition of electrodes decreased accuracy (Table 19). Table 19 shows incremental electrode selection with accuracy levels (full electrode set):

TABLE 19

| | Number of Electrodes Used for Classification | | |
|---|---|---|---|
| | 1 | 2 | 3 |
| Pain (Pain vs. No Pain) | 70.0% | 93.0% | 100.0% |
| Intensity (High vs. Low) | 90.0% | 100.0% | |

The highest-ranking electrodes in CSP for detection of pain vs. no pain were electrode numbers 31, 32 and 25 for intensity they were 31 and 1. All features and machine learning techniques were compared for each optimal set of electrode channels. The performance outcomes for pain detection are given in Table 20. The performance outcomes for classifying intensity across features and machine learning approaches are given in Table 21. Table 20 shows performance across features and machine learning algorithms for pain vs. no pain with the two highest-ranking CSP electrodes (full electrode set)

TABLE 20

| Features | Algorithm | Correct | Incorrect | Sensitivity | Specificity | Accuracy |
|---|---|---|---|---|---|---|
| Power Spectrum | Naïve Bayes | 89.0% | 11.0% | 91.7% | 83.3% | 88.9% |
| | 1 Nearest Neighbors | 98.0% | 2.0% | 100.0% | 94.4% | 98.1% |
| | 2 Nearest Neighbors | 98.0% | 2.0% | 100.0% | 94.4% | 98.1% |
| | SVM | 87.3% | 12.7% | 97.2% | 66.7% | 87.0% |
| Wavelet Analysis | Naïve Bayes | 33.3% | 66.7% | 0.0% | 100.0% | 33.3% |
| | 1 Nearest Neighbors | 98.0% | 2.0% | 97.2% | 100.0% | 98.1% |
| | 2 Nearest Neighbors | 98.0% | 2.0% | 97.2% | 100.0% | 98.1% |
| | SVM | 86.7% | 13.3% | 97.2% | 66.7% | 87.0% |
| Spindle Threshold | Naïve Bayes | 33.3% | 66.7% | 0.0% | 100.0% | 33.3% |
| | 1 Nearest Neighbors | 100.0% | 0.0% | 100.0% | 100.0% | 100.0% |
| | 2 Nearest Neighbors | 100.0% | 0.0% | 100.0% | 100.0% | 100.0% |
| | SVM | 96.3% | 3.7% | 97.2% | 94.4% | 96.3% |

Table 21. Performance across features and machine learning algorithms for high vs. low pain with the two highest-ranking CSP electrodes (full electrode set):

TABLE 21

| Features | Algorithm | Correct | Incorrect | Sensitivity | Specificity | Accuracy |
|---|---|---|---|---|---|---|
| Power Spectrum | Naïve Bayes | 53.3% | 46.7% | 50.0% | 50.0% | 50.0% |
| | 1 Nearest Neighbors | 53.3% | 46.7% | 41.7% | 66.7% | 54.2% |
| | 2 Nearest Neighbors | 53.3% | 46.7% | 41.7% | 66.7% | 54.2% |
| | SVM | 76.0% | 24% | 75.0% | 75.0% | 75.0% |
| Wavelet Analysis | Naïve Bayes | 56.7% | 43.3% | 83.3% | 33.3% | 58.3% |
| | 1 Nearest Neighbors | 61.7% | 38.3% | 58.3% | 66.7% | 62.5% |
| | 2 Nearest Neighbors | 61.7% | 38.3% | 58.3% | 66.7% | 62.5% |
| | SVM | 38.3% | 61.7% | 50.0% | 25.0% | 37.5% |
| Spindle Threshold | Naïve Bayes | 56.7% | 43.3% | 83.3% | 33.3% | 58.3% |
| | 1 Nearest Neighbors | 100.0% | 0.0% | 100.0% | 100.0% | 100.0% |
| | 2 Nearest Neighbors | 100.0% | 0.0% | 100.0% | 100.0% | 100.0% |
| | SVM | 78.3% | 21.7% | 75.0% | 83.3% | 79.2% |

Alpha Frequency Spectrum (8-12 Hz)

As mentioned earlier, investigating how pain affects the complete spectrum is important to compare to the effects on alpha spectrum. Based on the original pain signature (Green et al 2009), our hypothesis was that the pain signature would be in the alpha frequency spectrum with the presence of spindles correlating with pain intensity. Therefore, in this section we focus on the alpha band and compare the results of the alpha band to the complete frequency spectrum. Both the physiologically reduced set of electrodes, as well as the full set were assessed in terms of performance on the broad alpha frequency spectrum.

Physiologically Relevant Electrodes

The physiological relevant electrodes were further reduced by CSP and classification was run with incrementing electrodes until accuracy reached a 100% or when addition of electrodes decreased accuracy (Table 22). Table 22 shows incremental electrode selection with accuracy levels (physiologically relevant electrode set):

TABLE 22

| | Number of Electrodes Used for Classification | | | |
|---|---|---|---|---|
| | 1 | 2 | 3 | 4 |
| Pain (pain vs. no pain) | 70.0% | 91.7% | 96.7% | 95.9% |
| Intensity (high vs. low) | 90.0% | 100.0% | 97.5% | |

The highest-ranking electrodes in CSP for detection of pain vs. no pain were electrode numbers 193, 194 and 181 and for intensity they were 170 and 171. The performance outcomes for pain detection are given in Table 23. The performance outcomes for classifying intensity across features and machine learning approaches are given in Table 24.

Table 23. Performance across features and machine learning algorithms for pain vs. no pain with the two highest-ranking CSP electrodes (physiologically relevant electrode set)

TABLE 23

| Features | Algorithm | Correct | Incorrect | Sensitivity | Specificity | Accuracy |
|---|---|---|---|---|---|---|
| Power Spectrum | Naïve Bayes | 75.7% | 24.3% | 80.6% | 66.7% | 75.9% |
| | 1 Nearest Neighbor | 87.0% | 13.0% | 91.7% | 77.8% | 87.0% |
| | 2 Nearest Neighbors | 87.0% | 13.0% | 91.7% | 77.8% | 87.0% |
| | SVM | 77.7% | 22.3% | 86.1% | 61.1% | 77.8% |
| Wavelet Analysis | Naïve Bayes | 33.3% | 66.7% | 0.0% | 100.0% | 33.3% |
| | 1 Nearest Neighbor | 94.3% | 5.7% | 94.4% | 94.4% | 94.4% |
| | 2 Nearest Neighbors | 94.3% | 5.7% | 94.4% | 94.4% | 94.4% |
| | SVM | 88.7% | 11.3% | 100.0% | 66.7% | 88.9% |
| Spindle Threshold | Naïve Bayes | 33.3% | 66.7% | 0.0% | 100.0% | 33.3% |
| | 1 Nearest Neighbor | 96.7% | 3.3% | 94.4% | 100.0% | 96.3% |
| | 2 Nearest Neighbors | 96.7% | 3.3% | 94.4% | 100.0% | 96.3% |
| | SVM | 94.7% | 5.3% | 97.2% | 88.9% | 94.4% |

Table 24. Performance across features and machine learning algorithms for high vs. low pain with the two highest-ranking CSP electrodes (physiologically relevant electrode set)

TABLE 24

| Features | Algorithm | Correct | Incorrect | Sensitivity | Specificity | Accuracy |
|---|---|---|---|---|---|---|
| Power Spectrum | Naïve Bayes | 90.0% | 10.0% | 91.7% | 91.7% | 91.7% |
| | 1 Nearest Neighbor | 100.0% | 0.0% | 100.0% | 100.0% | 100.0% |
| | 2 Nearest Neighbors | 100.0% | 0.0% | 100.0% | 100.0% | 100.0% |
| | SVM | 80.0% | 20.0% | 75.0% | 83.3% | 79.2% |
| Wavelet Analysis | Naïve Bayes | 56.7% | 47.3% | 83.3% | 33.3% | 58.3% |
| | 1 Nearest Neighbor | 100.0% | 0.0% | 100.0% | 100.0% | 100.0% |
| | 2 Nearest Neighbors | 100.0% | 0.0% | 100.0% | 100.0% | 100.0% |
| | SVM | 53.3% | 46.7% | 50.0% | 58.3% | 54.2% |
| Spindle Threshold | Naïve Bayes | 56.7% | 44.3% | 83.3% | 33.3% | 58.3% |
| | 1 Nearest Neighbor | 100.0% | 0.0% | 100.0% | 100.0% | 100.0% |
| | 2 Nearest Neighbors | 100.0% | 0.0% | 100.0% | 100.0% | 100.0% |
| | SVM | 100.0% | 0.0% | 100.0% | 100.0% | 100.0% |

Full Electrode Set

The full electrode set was also reduced by CSP and classification was run with incrementing electrodes until accuracy reached a 100% or when addition of electrodes decreased accuracy (Table 25).

Table 25. Incremental electrode selection with accuracy levels (full electrode set)

TABLE 25

| | Number of Electrodes Used for Classification | | | |
|---|---|---|---|---|
| | 1 | 2 | 3 | 4 |
| Pain (Pain vs. No Pain) | 70.0% | 93.3% | 87.6% | |
| Intensity (High vs. Low) | 90.0% | 90.0% | 94.2% | 93.5% |

The highest-ranking electrodes in CSP for detection of pain vs. no pain were electrode numbers 31 and 25; for intensity they were 220, 211 and 203. All features and machine learning techniques were compared for each optimal set of electrode channels. The performance outcomes for pain detection are given in Table 25. The performance outcomes for classifying intensity across features and machine learning approaches are given in Table 26.

Table 26. Performance across features and machine learning algorithms for pain vs. no pain with the two-highest ranking CSP electrodes (full electrode set)

TABLE 26

| Features | Algorithm | Correct | Incorrect | Sensitivity | Specificity | Accuracy |
|---|---|---|---|---|---|---|
| Power Spectrum | Naïve Bayes | 72.5% | 27.5% | 83.3% | 50.0% | 72.2% |
|  | 1 Nearest Neighbors | 90.0% | 10.0% | 87.5% | 100.0% | 91.7% |
|  | 2 Nearest Neighbors | 90.0% | 10.0% | 87.5% | 100.0% | 91.7% |
|  | SVM | 63.3% | 36.7% | 91.7% | 8.3% | 63.9% |
| Wavelet Analysis | Naïve Bayes | 33.3% | 66.7% | 0.0% | 100.0% | 33.3% |
|  | 1 Nearest Neighbors | 93.3% | 6.7% | 91.7% | 100.0% | 94.4% |
|  | 2 Nearest Neighbors | 93.3% | 6.7% | 91.7% | 100.0% | 94.4% |
|  | SVM | 69.2% | 30.8% | 95.8% | 16.6% | 69.4% |
| Spindle Threshold | Naïve Bayes | 33.3% | 66.7% | 0.0% | 100.0% | 33.3% |
|  | 1 Nearest Neighbors | 93.3% | 6.7% | 91.7% | 100.0% | 94.4% |
|  | 2 Nearest Neighbors | 93.3% | 6.7% | 91.7% | 100.0% | 94.4% |
|  | SVM | 80.8% | 19.2% | 95.8% | 50.0% | 80.6% |

Table 27. Performance across features and machine learning algorithms for high vs. low pain with the two highest-ranking CSP electrodes (full electrode set)

TABLE 27

| Features | Algorithm | Correct | Incorrect | Sensitivity | Specificity | Accuracy |
|---|---|---|---|---|---|---|
| Power Spectrum | Naïve Bayes | 80.8% | 19.2% | 72.2% | 88.9% | 80.6% |
|  | 1 Nearest Neighbors | 91.7% | 8.3% | 94.4% | 88.9% | 91.7% |
|  | 2 Nearest Neighbors | 91.7% | 8.3% | 94.4% | 88.9% | 91.7% |
|  | SVM | 84.2% | 15.8% | 77.8% | 88.9% | 83.3% |
| Wavelet Analysis | Naïve Bayes | 56.7% | 43.3% | 88.9% | 22.2% | 55.6% |
|  | 1 Nearest Neighbors | 89.2% | 10.8% | 94.4% | 83.3% | 88.9% |
|  | 2 Nearest Neighbors | 89.2% | 10.8% | 94.4% | 83.3% | 88.9% |
|  | SVM | 92.5% | 7.5% | 100.0% | 83.3% | 91.7% |
| Spindle Threshold | Naïve Bayes | 56.7% | 43.3% | 88.9% | 22.2% | 55.6% |
|  | 1 Nearest Neighbors | 94.2% | 5.8% | 88.9% | 100.0% | 94.4% |
|  | 2 Nearest Neighbors | 94.2% | 5.8% | 88.9% | 100.0% | 94.4% |
|  | SVM | 94.2% | 5.8% | 88.9% | 100.0% | 94.4% |

Neural Oscillation Detection Optimization

Figure 42:
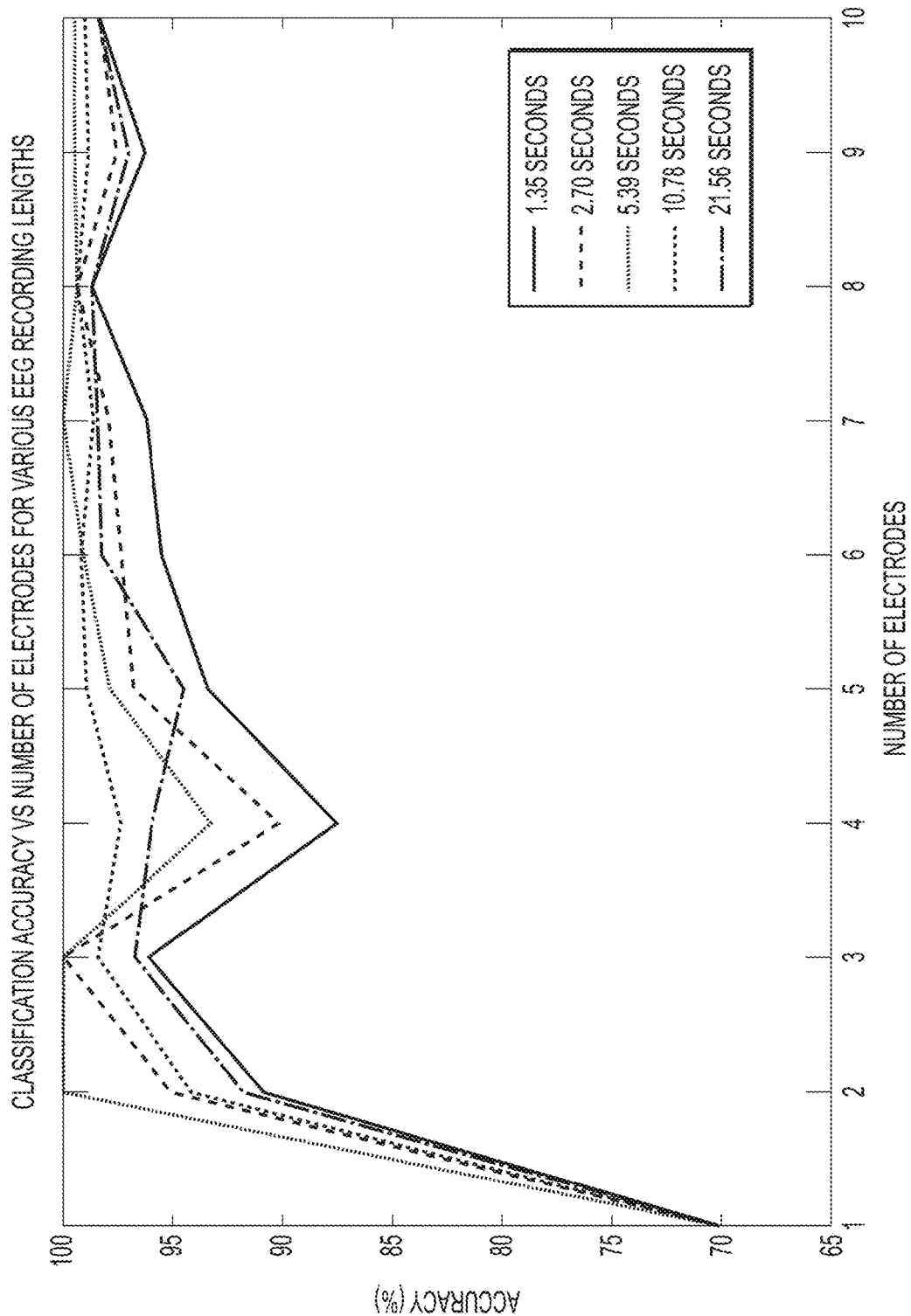
FIG. 42 is an exemplary diagram of classification accuracy with varying number of EEG electrodes and varying EEG recording durations.

In order to determine the scope of data requirement and minimum collection electrodes required to detect pain the electrodes and durations were compared. The pain detection algorithm was implemented with incrementing electrodes until the classification accuracy reached 100% or when the addition of electrodes decreased the accuracy. Executing the algorithm on EEG recordings of various lengths, from 1.35 to 21.56 seconds, showed an inverse relationship between number of electrodes and length of EEG recording. As the length of the EEG recording decreases, more electrodes are required to achieve high classification accuracy, as evident in FIG. 42. FIG. 42 illustrates an example of classification accuracy with varying number of EEG electrodes and varying EEG recording durations.

Discussion

Our results showed that the NOD algorithm was able to distinguish EEGs from chronic pain patients from those of healthy controls and also to discriminate high intensity from low intensity pain with accuracy rates reaching 100%.

We used a top-down approach to investigate pain related changes in the complete frequency spectrum as well as in the chosen alpha frequency spectrum. The results suggest that our spindle threshold analysis detection method provides the most robust classification when combined with a nearest neighbors machine learning technique. Classification in the alpha range yielded results similar to those obtained from the full frequency spectrum. This implies that the alpha range contains the necessary "important" information required for accurate detection of pain, suggesting a pain signature is actually present in this frequency band. These results support our hypothesis that the pain signature exists as spindles in the alpha spectrum, which can be detected in EEG recordings.

The NOD consisted of three different signal-processing methods (Spindle Threshold, Power Spectrum, Wavelet analysis) and four different types of machine learning classifiers (Naïve Bayes, 1 and 2 Nearest Neighbors, Support Vector Machine). After running all relevant combinations of signal processing and machine learning for pain detection, the results showed that the alpha frequency spectrum and pain spindles could robustly classify the presence of pain, as well as pain intensity. The best performing combination of signal processing and machine learning was Spindle Threshold analysis when used as input into the Nearest Neighbors machine learning algorithm. With larger datasets, other signal processing methods and machine learning combinations might work better; this will require further testing. EEG data were collected using a 256-electrode system.

Using our top-down approach, we investigated the pain detection with the full electrode set as well as a physiologically relevant set based on pain literature. Our results showed that the algorithm required only a few electrodes for accurate detection. So we could classify pain with a significantly reduced electrode set.

NOD in the Complete Frequency Spectrum (4-45 Hz)

The complete frequency spectrum results indicate that pain can be correctly classified using the whole EEG frequency spectrum, but does not reveal which specific frequencies or patterns the machine learning classifiers were utilizing to classify. Further, the Power Spectrum and Wavelet Analysis methods performed well in classifying pain groups. Based on the results for the complete frequency spectrum, the "Spindle Threshold" analysis method with "1 or 2 nearest neighbors" machine learning algorithm was the most consistent performing combination for both pain detection and intensity detection. The physiologically relevant electrode selection set performs as well as the full electrode set, indicating that reducing the number of electrodes does not affect classification accuracy.

NOD in the Alpha Frequency Spectrum (8-12 Hz)

The alpha frequency spectrum classification accuracy was as high as the complete frequency spectrum results. This suggests that the machine learning classifiers would have likely picked out the alpha band that was altered by pain. This result would require further investigation to confirm. Based on the results for the alpha frequency spectrum the "Spindle Threshold" with "1 or 2 nearest neighbors" is again the most consistent performing combination for both pain detection and intensity. The physiologically relevant electrode selection set performs almost as well as the full electrode set, indicating that reduction could take place without almost any loss in classification.

However, we can only be cautiously optimistic about the 100% classification accuracy. Such high accuracy suggests the possibility of over-fitting, which is a common problem in machine learning. To address this potential issue, the features entered have been selected to only represent spindle related activity, which we would limit the probability of over-fitting caused by introducing too many features.

The biomarker validation was investigated in continuous EEGs and not event related potentials. Typically in the EEG field, EEG data recorded is either in response to noxious pain stimuli or as continuous EEGs during a subjective pain episode. Pain time durations are typically in the order of milliseconds, inducing pain responses in the brain, but this is not ideal for simulating clinical chronic pain.

The pain signature features we used for the machine learning were recorded in neuropathic pain patients. However, each type of pain is thought to be produced by a different mechanism so it is likely that the various types of pain could each have specific abnormalities in neural oscillations, but could be detected as signatures by the NOD.

The optimization of the pain detection showed that, with decreasing duration of EEG recordings, the NOD requires data from more electrodes to achieve high classification accuracy. These preliminary results suggest that a subset of 5 EEG electrodes (95% accuracy levels) could be fitted for further testing using a portable, wearable headset.

Conclusion

This study tested the NOD algorithm to detect neural oscillation signatures in pain patients originally identified from invasive deep brain field potential recordings. This study demonstrated that the NOD algorithm can detect neural oscillations and distinguish chronic pain patients from healthy controls in EEG recordings and also distinguish high intensity from low intensity pain with accuracy rates reaching 100%. Given the positive results in pain data, the algorithm will be applied to PD in future work. Future studies will investigate PD neural oscillation signatures and build a large EEG database including different PD types and stages. Specific neural oscillation signatures from PD will be used as features for machine learning classification using NOD and will be developed for PD diagnosis or symptom tracking in combination with movement and speech data.

By establishing the minimum number of electrodes required to detect pain, we can begin to consider design criteria for a portable, inexpensive EEG system to measure brain activity during everyday life. The results of the experiment suggest that a subset of 5 EEG electrodes (95% accuracy levels) was adequate for pain detection. Feasibility of a portable EEG headset to detect neural oscillation signatures will require development and testing of hardware. The detection approach described in this thesis advocates a multi-modal system that combines measures from 3 domains: the motor system, cognitive function, and brain activity. Developing an EEG machine that is portable, wearable, and easy to use during everyday life would provide a valuable measure of brain activity. FIG. 8-2 shows a high-level diagram of the development of a portable EEG and NOD based system that could potentially replace current 256e EEG.

Figure 43:
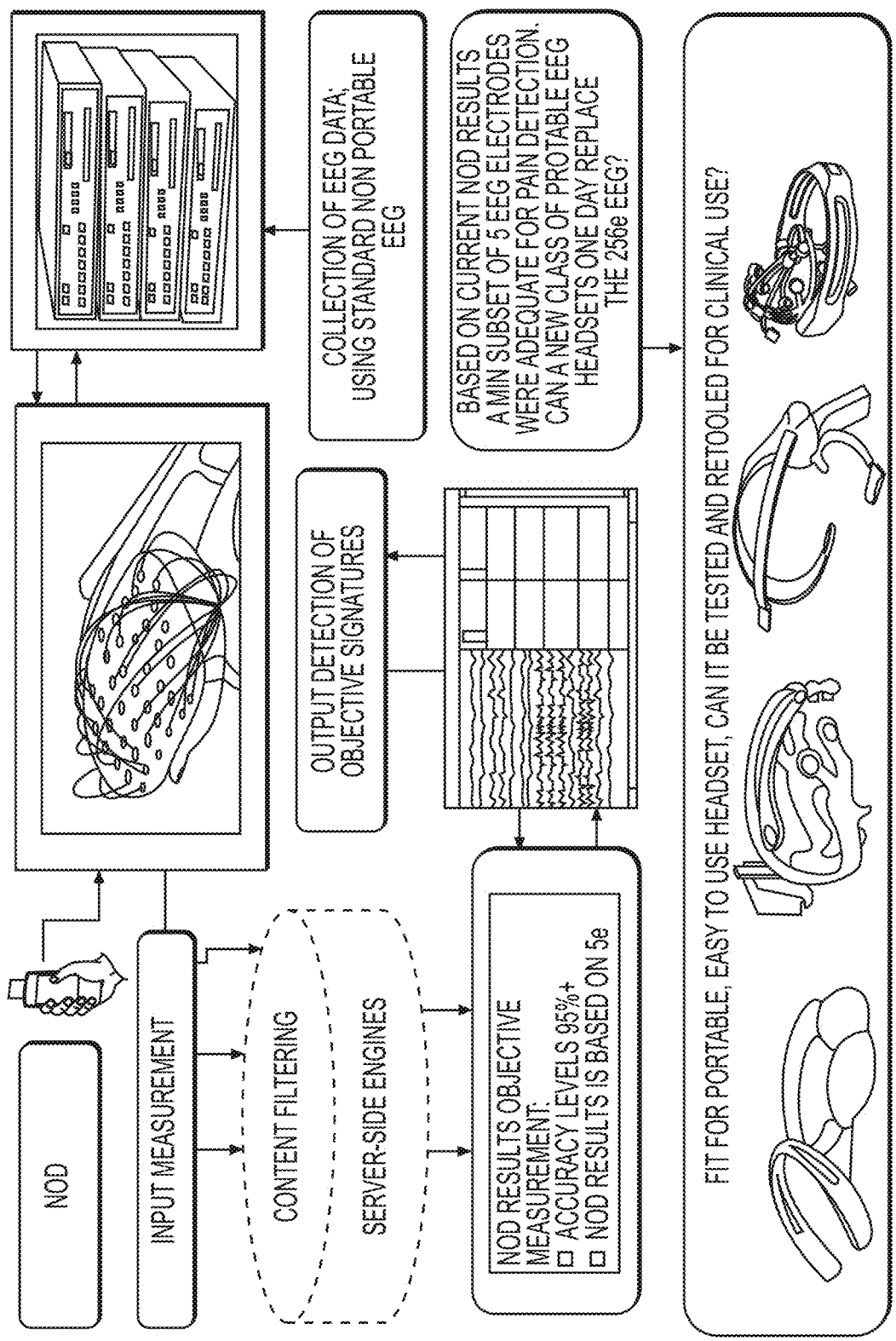
FIG. 43 is an exemplary diagram of NOD and portable EEG development.

Combined analysis of movement, speech, and neural oscillation data could provide objective measures of PD diagnosis and progression. It will require methods for fusing different data formats into a single toolkit. It will also focus on analysis of existing PD DBS and LFP data and collecting EEG data from PD patients at different stages of disease progression to further test the utility of the NOD algorithm. FIG. 43 illustrates an example of NOD and portable EEG development.

Chapter Nine: Facial Feature Extraction: An Example of Machine Learning

Introduction

Extracting facial features offers clinical measures of interest within 2 domains: the motor system and cognitive function. Facial feature extraction is of interest as a measure of motor impairments such as blink rate, facial rigidity, bradykinesia and masked face (Abbs et al., 1987; Bologna et al., 2013). Studies have indicated that measuring blink rate (Karson et al., 1984) eye movement (Gitchel et al., 2012; Hikosaka, 2009) and facial expression could be potential biomarkers for detecting PD (Bowers et al., 2006).

Facial expressions can also be used as an emotional classifier. Several fields of research show that facial expressions can be useful in detecting emotional and cognitive states (Bowers et al., 2006; Dethier et al., 2013; Ekman, 1993; Ekman and Rosenberg, 1997; El Kaliouby and Robinson, 2005; Katsikitis and Pilowsky, 1988; Keltner et al., 2003). Emotions expressed through facial movements play a crucial role in our daily lives. Facial expressions, both spontaneous and voluntary, communicate our feelings to others. Emotional problems, such as depression and anxiety, are also common in PD often before movement impairment (Shiba et al., 2000; Walsh and Bennett, 2001) and may be detectable through facial expression analysis. Facial expression can easily be recorded non-invasively using video and may offer an additional data stream to movement and speech for detecting early indicators of PD.

Facial expression analysis requires further testing and validation to determine its value as a tool for detection of PD. This study explores a sentiment classifier using machine-learning algorithms and tests feature extraction software on a PD patient.

Experiment 10

Sentiment Classification and Facial Feature Extraction—a 2 part Data Analysis

Background

To better understand facial features as they relate to both motor control (i.e. tremor or blinking) and expressions (of emotion and cognitive states) this 2-part data analysis tests machine learning algorithms for classifying sentiment from images and tests feature characteristic points (FCPs) analysis on a PD patient. A CK++ dataset was used to build the training model and an Enterface dataset was used to test the facial expression analyzer. We used facial recognition software to analyze FCPs of a PD patient against a database.

Aim:

To test the ability of machine-learning algorithm to classify emotion from facial expression in a large dataset. To identify facial features in PD patient.

Methods

Study Design

Using open source data, we trained a machine algorithm to classify emotion from facial expression. By annotating a large dataset of images and processing video into images, we tested a two-step classifier.

Then we used open source data and feature extraction software to explore feature characteristic points from two-dimensional images of control data and images of a PD patient processed from video.

A facial expression code written in python was used to build the emotion classifier. CK++ dataset was used to build the training model and an Enterface dataset was used to test the facial expression analyzer. Enterface video was converted into images using matlab.

Luxland FSDK 1.7 was used to extract FCPs in PD and non-PD images. A PD video was processed in matlab. ANOVA tool was used to calculate blink rate.

Data

The CK++ open-source dataset consists of 593 facial image sequences from 210 adults. The image sequences were recorded using two hardware synchronized Panasonic AG-7500 cameras. Participants were 18 to 50 years of age, 69% female, 81%, Euro-American, 13% Afro-American, and 6% other groups. The experimenter asked the participants to perform a series of behaviors, which include single action units or a combination of action units. The image sequences are frontal views and 30 degree views digitized into 640×490 or 640×480 pixel arrays with 8 bit gray scale or 24 bit color values.

The Enterface dataset includes 42 subjects from 14 nationalities who were recorded using a min-DIV digital video camera. They were asked to listen to "six successive short stories, each of them eliciting a particular emotion." Later, they were instructed by the experimenter to give reactions to each of the stories. Sentiment experts manually annotated the subjects during data collection. Annotations were based on Ekman's six basic emotions. Videos from Enterface dataset were converted into image frames using a matlab code.

An interview with a PD patient from an open source database was downloaded and processed into images using matlab.

Data Processing and Analysis

Part 1—Emotion Classifier

A facial expression code previously written in Python was used. We classified the image sequences from the CK++ dataset using matlab according to the annotations based on Ekman's six emotion categories (fear, sadness, joy, disgust, surprise, and anger) plus an extra category 'neutral,' i.e. showing null/void emotion (Ekman, 1992; Ekman and Rosenberg, 1997). The facial expression analyzer was used to automatically classify facial expressions at time T to a definite and discrete emotion category (Pantic and Rothkrantz, 2000).

Starting from time T0 to time Tn, there were n facial images for each subject. Suppose, at time T0 the subject started to express emotions in front of the camera until time Tn; within the period Tn-T0, there is a set of facial images that forms a sequence. Here, Ti denotes a time unit, and for each time unit Ti, there is a corresponding facial image of the subject. In the CK++ dataset, we found that at time T0 (sometimes at T0, T1, T2) the subject expressed a void/null emotion, but at time Tk given that Tk≤T n, Tk>0 the subject expressed an emotion e for the first time, which continued until the end of the time frame. Therefore, there is a transition of emotion (from void emotion to emotion e) between time Tl to time T (l+1). This feature of the dataset motivated us to clean the facial image sequences in order to obtain an optimal set of facial images of that subject expressing a particular emotion. We manually cleaned the facial image sequence into two categories: images expressing void/null emotion and images expressing a clear emotion (e). We classified a few initial image frames to null/void emotion, and the rest of the images in the sequence were classified to an emotion e according to the annotation in the CK++ dataset for that sequence. As an example of the cleaning process, suppose a sequence had 14 facial image frames among which the first two image frames expressed neutral emotion and the remaining 12 image frames expressed a surprise emotion. We included the two 'neutral emotion' images as null/void and the remaining 12 images were included as 'surprise emotion.' Consequently, we formed a large dataset of 5877 facial images.

We used the final dataset to perform 10-fold cross validation using different supervised classifiers. We found SVM outperformed all other classifiers. To classify the facial images we used a 2 step classifier—in the very first step, our classifier determines whether the image illustrated a null/void emotion or one of Ekman's six emotion categories. If the result is not classified as null/void, a 6-way classification is carried out on the image to identify the emotion category of the image otherwise it is declared that the image carries void/null emotion.

We tested the two step classifier on the Enterface dataset. Videos in the Enterface dataset were first converted into the image frames using a matlab code. The videos of Enterface dataset are manually annotated, so we used this dataset as the gold standard dataset i.e. testing and evaluation were carried out on the Enterface dataset. We utilized our 2 stage classifier on the images from the sequences of the video.

Part 2—Feature Extraction in PD Patient

Figure 44:
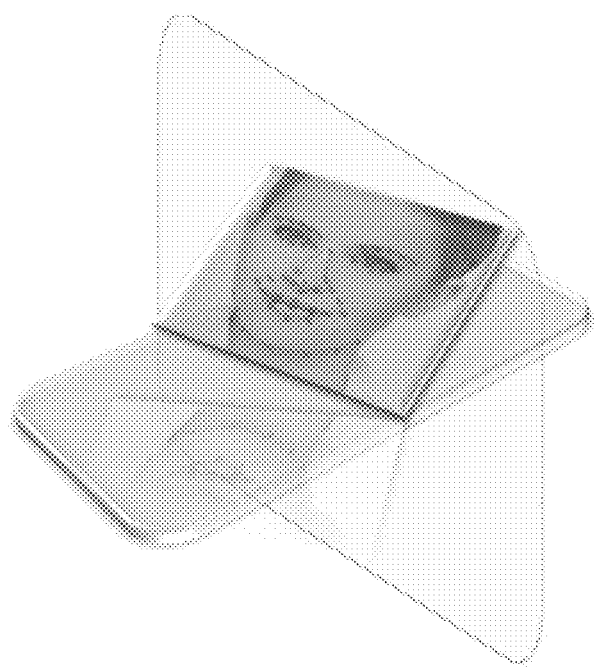
FIG. 44 is an exemplary diagram of 62 Feature Characteristic Points.

A video downloaded from an open source database was processed into image frames. To extract facial feature characteristic points (FCPs) we used a face recognition software called Luxland FSDK 1.7. Luxland extracts 62 facial characteristic points from an image of a face and compares it to a master database (FIG. 9-1). We extracted facial features based on FCPs by measuring the distances between FCPs of interest. We examined several distance-based features between the FCPs. As Kulkarni et al. (2009), Lyons et al. (1998), and Soyel and Demirel (2007) demonstrate, distance-based measures are useful for facial expression analysis. We analyzed the distance between the right eye and the left eye (D(0,1)), the distance between the upper and lower lines of the left and right eyes (D(35,38), D(40,41)), and the distance between the inner and outer corners of the left and right eyebrows (D(12,13), D(14,15)). FIG. 44 illustrates an example of 62 Feature Characteristic Points We also measured blink rate. Using the statistical analysis tool ANOVA, blink rate was measured by the number of times the irises cannot be identified using the facial expression recognition program in 10-second intervals. We also measured eye tremor based on the movements of the facial points of the eyes. The frequency and amplitude of eye tremor were measured in each image by measured eye movement direction as a binary feature, using the FCPs around both eyes.

Results

Part 1 Emotion Classifier

Out of the 593 facial images in the CK++ dataset, only 327 were classified with an emotion. The results of the annotated CK++ dataset are described in Table 27:

TABLE 27

| Expression | # of Samples |
| --- | --- |
| Neutral | 233 |
| Anger | 1022 |
| Joy | 1331 |
| Disgust | 868 |
| Surprise | 1329 |
| Fear | 546 |
| Sadness | 548 |

Our two-stage classification obtained 97.25% accuracy on the Enterface dataset. The two-step classifier enhanced the system's accuracy, for only 86.60% accuracy was obtained using 1 stage 7-way classification, while 95.14% accuracy was obtained using 2 stage 7-way classification. These results show that the classifier is neither biased towards a particular dataset nor over-fitted, but can be scalable.

Part 2 Feature Extraction in PD patient

Feature extraction analysis found significant differences between the PD patient and control group for distance between right eye and left eye (D(0,1)), distance between the upper and lower line of the left and right eye (D(35,38), D(40,41)) and distance between the left, right eyebrow inner and outer corner (D(12,13), D(14,15)). Table 28 lists the FCPs found to have the most difference from the control database. Table 29 describes the facial points and their corresponding measurements.

We found that the blink rate was much lower in PD versus controls. Based on the movements of the facial points on the eyes we found the average eye tremor frequency of the PD data was between 4-6 Hz. Table 28 shows the Most Significant FCPs

TABLE 28

| Facial Point | Description |
| --- | --- |
| 0 | Left Eye |
| 1 | Right Eye |
| 24 | Left Eye Inner Corner |
| 23 | Left Eye Outer Corner |
| 38 | Left Eye Lower Line |
| 35 | Left Eye Upper Line |

TABLE 28-continued

| Facial Point | Description |
| --- | --- |
| 29 | Left Eye Left Irish Corner |
| 30 | Left Eye Right Irish Corner |
| 25 | Right Eye Inner Corner |
| 26 | Right Eye Outer Corner |
| 41 | Right Eye Lower Line |
| 40 | Right Eye Upper Line |
| 33 | Right Eye Left Irish Corner |
| 34 | Right Eye Right Irish Corner |
| 13 | Left Eyebrow Inner Corner |
| 16 | Left Eyebrow Middle |
| 12 | Left Eyebrow Outer Corner |
| 14 | Right Eyebrow Inner Corner |
| 17 | Right Eyebrow Middle |
| 54 | Mouth Top |
| 55 | Mouth Bottom |

Table 29 shows facial points and corresponding measures

TABLE 29

| Features | Distance Measure |
| --- | --- |
| Distance between right eye and left eye | D(0, 1) |
| Distance between the inner and outer corners of the left eye | D(23, 24) |
| Distance between the upper and lower lines of the left eye | D(35, 38) |
| Distance between the left Irish corner and the right Irish corner of the left eye | D(29, 30) |
| Distance between the inner and outer corners of the right eye | D(25, 26) |
| Distance between the upper and lower lines of the right eye | D(40, 41) |
| Distance between the left Irish corner and the right Irish corner of the right eye | D(33, 34) |
| Distance between the left eyebrow inner and outer corner | D(12, 13) |
| Distance between the right eyebrow inner and outer corner | D(14, 15) |
| Distance between top of the mouth and bottom of the mouth | D(54, 55) |

Discussion

Part 1

The supervised classifier demonstrated ability to classify sentiment from images with 97.25% accuracy. The system requires additional training and testing to improve accuracy with a larger and more varied dataset. Additional emotions beyond Ekman's 6 categories should also be explored. Future work will train and test classification of PD and non-PD facial images.

Part 2

Preliminary results demonstrate that facial feature extraction may be a valuable for tool for PD detection. Measures such as low blink rate and rigidity could potentially be detected by video and machine learning algorithms. Our analysis found that the patient with PD had a lower blink rate compared to the control database. Also, distance between right eye and left eye (D(0,1)), distance between the upper and lower line of the left and right eye (D(35,38), D(40,41)) and distance between the left, right eyebrow inner and outer corner (D(12,13), D(14,15)) in the PD patient showed differences from the control database. These differences could be indicators of hypomimia.

Limitations of the Study

The PD video data was only from one patient. Comparing one PD patient against a set of controls is not the best method, the comparison should have an equal number of age matched patients and controls. We cannot be sure that all the subjects in the control group were, in fact, healthy. Additional analysis needs to be performed with more data from PD patients at different stages and age matched controls.

Conclusion

This chapter explored the ability of machine learning algorithms to classify sentiment and analyze facial feature characteristics from images. Analyzing facial expression could be a potentially valuable method for PD detection because it evaluates both motor impairment and emotional states (Bowers et al., 2006; Ekman, 1993; Jacobs et al., 1995; Katsikitis and Pilowsky, 1988; Keltner et al., 2003). Analysis of both spontaneous and voluntary facial expressions, as well as facial features such as rigidity, could lead to new PD biomarkers. Part one of the data analysis demonstrated the potential accuracy of a supervised classifier to detect sentiment from images. Future work will further test the sentiment classifier on larger datasets, which will include both healthy controls and PD patients. The second part of the data analysis showed that there may be value in analyzing facial features for PD detection purposes. There were significant differences in several feature characteristic points of the PD patient compared to a universal database. Although there were limitations of this study, the preliminary findings suggest that there may potentially be PD facial biomarkers. The results of this initial 2-part data analysis provide a feasibility basis for future work, which will require larger databases and testing of additional facial features to match classifiers with the symptoms most common in early PD, such as masked face. Noninvasive facial expression and facial feature analysis may offer an additional data stream to be combined with movement and speech for detecting early indicators of PD. Facial expression and facial feature analysis could potentially be achievable on a daily basis with video recording in the home or on a smartphone platform.

Chapter Ten: Summary and Conclusions

This chapter provides an overview of the thesis, a review of the research contributions and discusses directions for future work.

PD is characterized by a triad of movement symptoms: tremor at rest, muscle rigidity, and bradykinesia (Barton et al., 2012; Calne et al., 1992; Fahn, 2003; Jankovic, 2008; Levine et al., 2003b; Meara et al., 1999; Tolosa et al., 2006). In addition to the three classic symptoms, there are a host of movement impairments, such as gait (Ebersbach et al., 1999; Han et al., 2006; Niazmand et al., 2011; Rosin et al., 1997), postural stability (Adkin et al., 2003; Blaszczyk and Orawiec, 2011; Horak et al., 1992; Mitchell et al., 1995), and upper limb kinematics (Bond and Morris, 2000; Dounskaia et al., 2009a; Dounskaia et al., 2009b; Flash et al., 1992; Isenberg and Conrad, 1994; Konczak et al., 2009; Sande de Souza et al., 2011; Tresilian et al., 1997), that have been observed in PD. In PD the loss of motor control is progressive and irreversible, a manifestation of an overall trajectory of neural deterioration. Impairments of motor control are linked with factors related to the severity of the neurodegenerative disease; it represents a valuable domain space to track neural deterioration over time. Motor impairments typically follow the observable deterioration of global cognitive functioning. Measurements of the motor system in PD patients therefore represent potentially powerful indicators of disease onset and neurodegeneration.

Movement is not only derived from anatomical properties of the limb; brain motor control processing makes it smooth and efficient. The brain controls movements and communication deficits between the musculoskeletal and nervous system can lead to direct changes in (motor) behavior. Motor patterns alter during our lifetime and changes are likely to alter the development of neural mechanisms that underlie the control of the arm and hand (Zoia, Pezzetta et al. 2006). Measurements of arm movement may inform us about neurological functioning throughout normal and impaired development.

However, motor impairment is only one of many possible indicators of PD disease. Cognitive impairments and neuropsychological problems, such as depression and dementia-like symptoms, are associated with PD (de la Monte 1989; Jankovic 2008; Starkstein et al. 1989; Wertman et al. 1993). Studies suggest that neuropsychological changes, such as depression, anxiety, and panic attacks, can predate motor symptoms by years (Aarsland et al., 2007; Bottini Bonfanti, 2013; Bower et al., 2010; Caballol et al., 2007; Shiba et al., 2000; Starkstein et al., 1989; Walsh and Bennett, 2001). Thus, cognitive function is another domain space in which features can be measured for detection and symptom tracking. Changes in cognitive function can potentially be detected from language, and facial expression (Bowers et al., 2006; Cardona et al., 2013; Jacobs et al., 1995; Katsikitis and Pilowsky, 1988; Monetta and Pell, 2007; Ooi et al., 2013b; Roberts and Kassel, 1996). Abnormal oscillations have been indicated in PD, but mostly as it relates to motor impairments and tremor (Brown et al., 2001; Liu et al., 2002; Moran et al., 2011; Tachibana et al., 2011b) and most often found using in vivo recording.

Speech motor impairments have also been suggested as possible markers of onset and progression of PD (Afza, 2013; Howard et al., 2013 g; Illes et al., 1988; Little et al., 2009; Skodda et al., 2012; Tsanas et al., 2011; Tsanas et al., 2012) (Skodda, Gronheit, & Schlegel 2011; Tsanas et al., 2011). Like motor symptoms, speech impairments may not be immediately observable in PD. However, when combined, speech and movement data may offer an earlier picture of neurological health and decline. Measures of speech production relate to the motor system domain, whereas analyzing language content pertains to measures of cognitive function.

Unfortunately, early detection of neurodegenerative disorders remains more an art than a science, dependent largely on the intuition and experience of individual clinicians. Notably, there is a lack of objective, clinically applicable tools and techniques for measuring global cognitive function during everyday life. The approach presented in this thesis seeks to fill this gap by developing non-invasive detection methods that measure features of clinical interest during everyday life. By coding and analyzing meta-characteristics of speech and movement it may be possible to identify patterns associated with varying levels of cognitive function and dysfunction. This work builds on recent studies of behavioral, linguistic, and cognitive signatures for neurodegenerative diseases. For example, researchers Ghilardi et al. (2000) and Mittal et al. (2010) have found that movement impairments and cognitive deficits provide external markers of underlying neural processes associated with the onset of PD.

This work aims to develop tools and methods that can objectively measure features of the motor system, cognitive function, and brain activity to detect PD before symptoms are apparent. To detect the earliest deviations from normal neurocognitive functioning, multiple data streams from everyday living can be combined. The work described in this thesis represents initial development and validation of methods and tools towards achieving the approach. The upper limb movement, knee joint stability, speech, neural oscillation, and facial expression are the initial measures of interest discussed in this thesis.

This thesis had ten specific aims:
1. Test the accuracy of measuring upper limb movement with a body sensor network against the gold standard optical system.
2. Test if BSN system and wavelet analysis can be used to quantify user interactions with everyday objects.
3. Test if wavelet analysis can be used to define spatial and temporal changes in shoulder motion between patients and "healthy" controls.
4. Test if BSN can measure acceleration under extreme conditions
5. Test if BSN can measure movement with functional placement
6. Test an Integrated Clothing Sensing System (ICSS) to measure joint stability
7. Explore to what extent combining everyday motion and speech tasks affect cognitive function.
8. Explore correlations between speech and movement symptoms
9. Test if EEG can detect a biomarker found with DBS and the minimal number of electrodes required.
10. Test emotion classification and facial feature extraction using machine learning algorithms I hope these results and findings considered in a broader context, will have significant implications for early detection, treatment, and management of PD for patients, practitioners, and researchers alike.

Empirical Findings

The findings to date represent small steps towards development of a non-intrusive system to measure speech and movement during everyday life with potential future addition of video and EEG measurements to measure facial expression and brain activity This work demonstrated that sensor networks and wavelet analysis can be used to accurately measure and differentiate complex movement in real-life situations. Data collection from complex arm movements and joint stability showed that the BSN sensors can measure activities of daily living with similar accuracy to gold standard optical tracking (Bergmann et al., 2012b; Bergmann et al., 2013b). Recent motion studies have primarily been concerned with two sets of two-dimensional values: the position of the object where the patient was instructed to point, and the position of the patient's finger (i.e., pointing at the object or not). BSN methods instead allow all three spatial dimensions to be used, and thus provide a potentially more comprehensive analysis of movement. Most studies measure only the result of movement; instead, I aim to measure the process of movement in a more fine-grained manner, which lends itself to analysis that is more complex.

My research has emphasized data-heavy early detection algorithms because the most feasible way to overcome the signal-noise ratio problem when searching for subtle variations in upper limb, balance, speech or cognitive states is to analyze high volumes of high-resolution data. Data capture for these algorithms depends largely on the establishment of cognitive and physiological baselines, or significant samples of "normal" behavior, so that detection of the earliest changes is possible What follows is a summary of my work in terms of the specific aims.

Specific Aim 1: Test the Accuracy of Measuring Upper Limb Movement with a Body Sensor Network Against the Gold Standard Optical System.

Experiment 1 tested BSN system to measure of the distal point of the left arm (hand plus wrist) during elbow movements. Complex arm movements were measured for three different activities: 90-degree elbow flexing from an upright sitting position, 90° shoulder abduction with the elbow fully extended, and 90° shoulder abduction and 90° elbow flexion with an internal rotation, followed by moving to 45° shoulder retroflexion and 120° elbow flexion.

This data was obtained using two measurement devices (optical and inertial), and the resulting data streams were compared by calculating a two-tailed Pearson product-moment correlation coefficient (r). The root mean square error (RMSE) was then calculated for each of the two signals. Independent analysis of each direction of movement, referred to as X, Y and Z, was also performed. We found that the BSN performed comparably to its optical counterpart, with correlations in the X, Y, and Z dimensions reaching 0.99, 0.95, and 0.99 respectively.

Specific Aim 2: Explore if the Body Sensor Network can be Used to Quantify User Interactions with Everyday Living Objects.

The use of this system was further validated by measuring differences in motor behavior, in response to a changing environment. In Experiment 2, three subjects were asked to perform a water-pouring task with three slightly different containers. Wavelet analysis was used to measure behavioral changes within each subject and between all three subjects. There were significant differences in movement with each container. Results showed that body sensors and wavelet analysis can quantify subtle behavioral adjustments due to environmental changes. This preliminary validation shows the potential utility of a BSN system to measure during ADL, which involves a range of object interaction.

Specific Aim 3: Test if Wavelet Analysis can be Used to Define Spatial and Temporal Changes in Shoulder Motion Between Patients and "Healthy" Controls.

Experiment 3 demonstrated that wavelet analysis can differentiate between patients and "healthy" controls (Howard, Pollock et al. 2013). Seven healthy participants and eight rotator cuff patients performed five range-of-motion tasks under different speed conditions. The results showed differences in range of motion and speed of movement between the patient and healthy groups. Rotator cuff patients exhibited ROM limitations compared to control subjects with significant differences across all elevations at "normal" speed.

Specific Aim 4: Test if BSN can Measure Acceleration Under Extreme Conditions

After testing accuracy of the BSN to measure movement, we considered engineering and design criteria for use in real world environments. In Experiment 4, the BSN was tested for robustness in an extreme environment. Accelerometer data was collected from a wearable sensor and high frequency camera. Pilot testing showed that decelerations during water-ski jumping were out of the measurement range using a 5 g accelerometer system. Our analysis computed two 100 g accelerometers would be required to measure decelerations during water-ski jumping. The sensor, circuitry and interface remained working under these extreme conditions. Findings suggest that BSNs are capable of measuring in harsh-environments and would be adequate to measure ADL, which do not present conditions as extreme as water-ski jumping. Design criteria will need to consider acceleration demands such as traveling on a plane, train etc.

Specific Aim 5: Test if BSN can Measure Movement with Functional Placement

Most sensor systems interfere with everyday life and prevent normal activities from being carried out. Better functional placement should provide higher levels of conformity. For this reason, a truly unobtrusive system, integrated into objects that are already used on an everyday basis, would be beneficial for the quality and quantity of data collection. With this in mind, we began to assess the potential for sensor integration into smart phones by testing the BSN's adaptability to functional placement in a pocket. Experiment 5 was conducted to compare traditional and functional body sensor placement. The goal of this analysis was to show the viability of inertia-based activity recognition sensors to determine what types of behaviors a subject is engaging in. Results suggest that the directional shifts of median frequency are independent of the placement, meaning there is a greater possibility of using more functional placement and there is potential to use the BSN in a pocket.

Specific Aim 6: Test an Integrated Clothing Sensing System to Measure Joint Stability By testing the body sensor networks in a harsh environment such as water-skiing, we validated that the current sensors can be used in real world situations. However, less obtrusive methods are necessary to integrate these systems into activities of daily life. More functional placements of the sensors should provide higher levels of conformity, but may affect the quality and generalizability of the signals. Differentiation of the signal into a translational and gravitational component decreased the level of agreement further, suggesting that combined information streams are more robust to changing locations then a single data stream. Integrating multiple sensor modalities to obtain specific components is not likely to improve agreement across sensor locations. This study confirmed the potential to measure signals with more user-friendly sensor configurations that will lead to a greater clinical acceptance of body-worn sensor systems.

In Experiment 6, knee joint stability was measured using an Integrated Clothing Sensing System (ICSS) and compared to the gold standard measurement system (Vicon). Results found that the ICSS is capable of measuring different levels of joint stability. An overall correlation coefficient of 0.81 ($p<0.001$) was calculated, meaning there was a strong association between the ICSS and the optical tracking system during different levels of stability.

Specific Aim 7: Explore to What Extent Combining Everyday Motion and Speech Tasks Reveals Cognitive Function.

We often perform speech and movement tasks simultaneously, but it remains unclear how cognitive processing is effected by multiple demands. Cognition is affected across several dimensions of functioning and requires attention sharing across these functions. Experiment 7 explored whether attentional demands could be assessed using a cognitive load experiment requiring speech, movement, and an auditory Stroop task simultaneously. It focused on everyday living routines previously identified in the Motor Activity Log (MAL) for the upper extremity (Uswatte et al., 2005). This work explored how everyday motion and speech tasks can affect cognitive processing measured by performance on a Stroop task. The single loaded tasks consisted either of speaking or making a sandwich, while the dual task required both. Results indicated that cognitive function is affected by loaded conditions. Correct responses were lowest under dual task conditions.

Specific Aim 8: Explore Correlations Between Speech and Movement Symptoms

Experiment 8 explored correlations between speech and movement symptoms in a 2-year UPDRS dataset. Measures for speech, walk and balance, tremor, freeze, salivation, and swallow were analyzed using statistical methods. Results were somewhat unclear given the resolution of the data, but indicated symptom correlations that should be explored further. Speech and salivation showed the highest correlation, which was expected. Walk/freeze and salivation/freeze also showed a significant correlation. Findings support the need for further analysis of speech, walk, balance, and tremor, which can be quantitatively measured with BSN and voice recording. We propose that spontaneous/conversational speech should be collected as opposed to phonations.

Specific Aim 9: Test if a Biomarker Found with In Vivo Recording can be Detected in EEG Recordings Using NOD Algorithm and the Minimal Number of Electrodes Required Studies on neural oscillations in PD have produced interesting yet inconclusive findings, but require additional research. In Experiment 9, we wanted to test whether the NOD algorithm could identify a biomarker, originally detected in LFPs, using EEG recordings. A signature for neuropathic pain identified in deep brain electrodes LFPs was used to test the NOD algorithm with raw EEG collected from chronic pain patients. The NOD algorithm was able to detect the signature and distinguish pain and control subjects from EEG recordings. The validation of the NOD algorithm with pain data suggests that it may also be useful for PD. In future work, EEG may become a means to link motor and cognitive function, but for now it is being explored as a reference measurement.

Specific Aim 10: Test Emotion Classification and Facial Feature Extraction Using Machine Learning Algorithms To better understand facial expressions as they relate to both motor control and emotions Experiment 10 conducted a 2 part data analysis to test a sentiment classifier and analyze facial feature points of a PD patient compared to a universal database. The emotion classifier algorithm was trained and tested using control data and demonstrated 97.25% accuracy. Given this level of accuracy, future work will develop a PD classifier and database. Luxland analysis of one PD patient indicated several differences between the FCP's of the PD face compared to "normal" averages of a universal database. Significant measures included lower blink rate, distance between right eye and left eye, distance between the upper and lower line of the left and right eye, distance between the left, right eyebrow inner and outer corner. In addition, 4-6 Hz rate of random eye movement was found in the PD patient. Although there were several limitations in the study, the preliminary findings encourage further research on facial features to measure motor impairment and facial expression to detect emotional states.

Future Work

The findings have demonstrated that the BSN performs at a sensitivity level adequate for further development of the detection system (Bergmann et al. 2012; Bergmann et al., forthcoming).

An Exploratory Pilot Study of the Utility of a BSN in the Clinical Detection of PD The ultimate aim of this case-control study will be to develop a simple, pragmatic tool that can be used clinically for the early diagnosis of PD. The specific aim of this preliminary study is to:

(1) Determine which data streams are most sensitive and specific to changes occurring in early PD within the context of the mind state algorithm.

The approach will utilize a BSN. The body sensor system consists of several inertia measurement units (IMUs). A separate microphone will be used to record spontaneous speech production. In this study, we will collect speech and movement data streams simultaneously using the BSN system. These information streams will be analyzed using a linguistic computational algorithm, the Mind State Indicator (MSI) algorithm that will be adapted to include posture and arm movement.

The primary objective will be to determine whether the BSN is able to distinguish early PD from normal healthy age-matched controls, the secondary objective is to determine whether the BSN is able to distinguish early PD from mild Alzheimer's disease. Sixty subjects will be involved in the study: 20 PD patients within 5 years of diagnosis, 20 age-matched control subjects, and 20 subjects with mild AD (MMSE 21-26). Assessments for PD severity, cognition, and depression will be given, including UPDRS, MMSE, and Becks Depression Inventory. While wearing the BSN system, each subject will perform three different activities of daily living: preparing a meal, putting on a cardigan, and opening and closing a lock. During the three daily living tasks, the subjects will be asked to continuously talk to the researcher what they are doing and how comfortable or uncomfortable they find the BSN. Synchronized video collection will be conducted to relate obtained signals to specific activities and for quality assurance purposes. Each task will be repeated three times.

Joint stability and arm movement will be measured using the BSN (Xsens) measurement tool.

The 'Mind state indicator' algorithm will be computed based on joint stability and arm movement trajectory related variables (including position, velocity and acceleration) and linguistic parameters. Speech parameters are dependent on LXIO configuration (Howard & Guidere, 2011), but can also include the following: latency between prompt and spoken answer, the number of speech errors or involuntary tics per minute, and the time taken to pronounce individual syllables; each experimental evolution may involve a separate speech parameter. data will be analyzed across groups, within groups, and for each individual subject for each of the three tasks. Based on initial data analysis, we will further breakdown data for specified movements and for specific time segments and areas of interest. We will use a continuous wavelet transform (CWT) to divide the signal into wavelets, allowing us to analyze the frequency content over time. At successful completion of this study we will have determined whether the 'mind state indicator' derived from the BSN is able to reliably differentiate patients with PD from healthy age-matched controls and from patients with AD.

Development of a General Method to Study the Brain

A method needs to be developed to provide an abstract technique to encode and integrate many different kinds of data. More knowledge could be gained if it was possible integrate neural information with cognitive and behavioral outputs. A model is proposed as a computational method is proposed to combine behavioral and cognitive data. The "brain code" is a model to reflect the emergent properties of the brain neuronal system (Howard, 2012a; Howard, 2012b; Howard, 2013b; Howard, 2013c; Howard and Stein, 2013c). Future work will focus on developing the Brain Code and Fundamental Code Unit framework to integrate and analyze different measurements within the same coordinate system, setting a potential testable multi model collection of data and fusion of heterogeneous data sets and classes (Ioannides et al., 2012). By combining EEG, measures of movement, and speech data into one multimodal signature, a valuable temporal tool can be developed for early detection.

Discussion

I offer this thesis as a step towards the development of novel clinical methodologies to improve detection and diagnosis of neurological disorders. The goal of this research was to develop and validate tools and methods to lay the foundation for a non-invasive detection system using BSN and data analysis techniques. The vision is that one day a noninvasive routine test wearing a sensor system at home, akin to an arm band or knee brace, will be able to detect neurodegenerative disease years before the onset of clinical symptoms. If PD or AD has been diagnosed, a smartphone will automatically collect speech and movement data on a daily basis to monitor your progression and communicate with your doctor, perhaps by that time also we will be able to treat brain disorders by controlling or directing stimulation of appropriate specific neurons, by either electrical, ultrasound, light or chemical interventions. This technology may one day be possible and could save lives, improve quality of living, and reduce the cost of neurodegenerative disease currently burdening healthcare systems.

In addition to the methods outlined in this thesis, a key component of the detection approach will be tracing the relationships between data streams. This occurs at two levels. The first level will be empirical; that is, we will measure the correlation between aberrations in data stream pairs such as speech and movement to determine which are most closely related. To that end, we will use specifically designed hardware to extract properly formatted and temporally congruent speech and movement data. The second and subtler linkage between these data streams occurs within the brain. Many studies have explored the link between thought patterns and brain region activation; the proposed approach will combine the various media used for assessing brain function into a unified method that compensates for each of the weaknesses associated with each individually.

Because none of these measures can provide a complete diagnosis by itself, it will be important to develop a method that integrates all of them, allowing each to compensate for the others' shortcomings. For instance, EEG monitoring alone cannot reveal the precise neural webs being activated during exposure to a stimulus. However, as the amount of data increases, pattern analysis based on a combination of electroencephalographic monitoring, linguistic assessment and behavioral tracking should be able to identify those concepts from a cognitive perspective, as well as the neurological phenomena related to them. Detection may be achievable by analyzing each of these data streams, performing interdependent time series analysis on each, and linking them, ultimately to yield a deeper insight into PD and other NDD. Ultimately, these tools, methods, and techniques will need to facilitate integrated analysis of both high-level behavioral and low-level neuronal data, accounting for shared dimensions, such as time.

The research described here was conducted with the deepest of convictions and admiration for the value we gain as scientists from interdisciplinary research collaborations. I quote the greatest mind of our time who stated that, "after a certain high level of technical skill is achieved, science and art tend to coalesce in esthetics, plasticity, and form. The greatest scientists are always artists as well" (Albert Einstein). I learned through this medical journey that when one becomes aware of inner hidden human capacities; they are as much of a mystery as a thrill, likened to climbing a high mountain for the first time.

Figure 47:
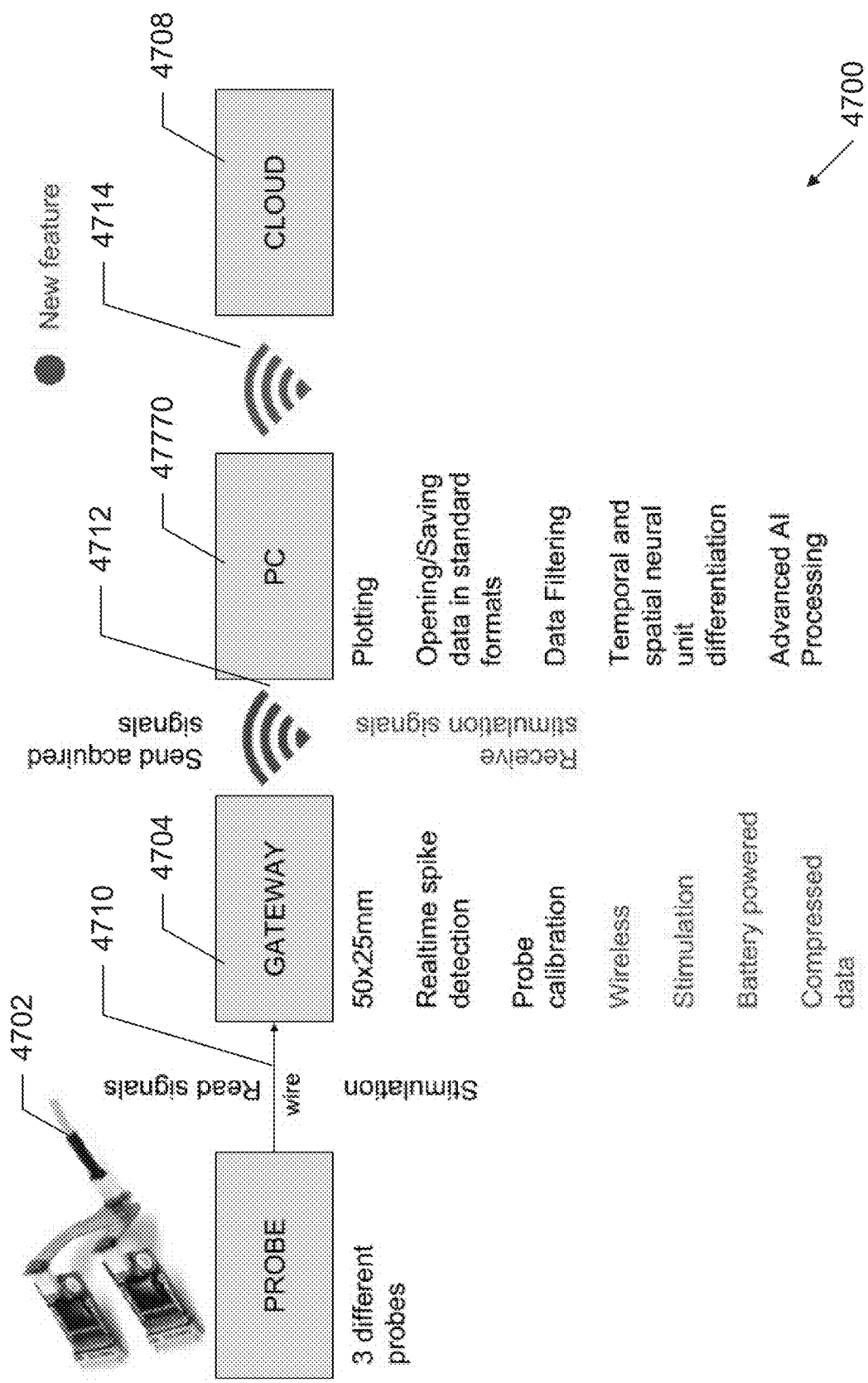
FIG. 47 is an exemplary block diagram of an embodiment of a neural monitoring and stimulation system.

In embodiments, neuronal signals may be monitored or affected using, for example, an implantable (for example, smaller than a pea), miniaturized, low-power, wireless probe with induction charge, such as is shown in FIG. 47. Such neuronal signals may be analyzed similarly to EEG signals and may be gathered in addition to, or instead of, EEG signals. Such a probe may be used for treating neurodegenerative diseases like Parkinson's and Alzheimer through continual neuromodulation and/or as a Brain Machine Interface to monitor neural signal, prevent other medical conditions, such as migraines, and perform cognitive functions augmentation.

For example, such a probe may be used to detect and treat conditions, such as Alzheimer's, of which there are over 6 million total Alzheimer patient growing at 22% of entire population by 2050, according to Alzheimer's Association 2018 Report. For example, such a probe may be used to detect and treat conditions, such as Parkinson's, of which nearly 1 million will be living with Parkinson's disease in the U.S. by 2020, based on Parkinson's Foundation statistics.

In embodiments, a probe may be wireless and implantable, with battery charging provided by an induction charge. In embodiments, carbon nanotubes (CNTs) and/or single-walled carbon nanotubes (SWCNTs) may be used to facilitate a scaffolding for neurons growth and regeneration. In embodiments, an overall system may include artificial intelligence (AI) Analytics. In embodiments, an overall system may include a mobile device that supports and communicates with probes to reduce costs and power and provide AI analytics.

In embodiments, a system may include one or more wireless implantable CNT probes, one or more Gateways, and one or more computing devices.

In embodiments, analog or digital radio may be used for bidirectional Probe-Gateway communication. In embodiments, the probes and/or gateways may be implemented as a system-on-chip (SoC), whether custom, semi-custom, or standard ASIC, based on power, size, partner flexibility, etc. In embodiments, due to analog design, cost, and noise limitations, the selected node may be 130 nm or 180 nm.

In embodiments, the probes may provide the capability for light modulation.

In embodiments, probes may use CNTs and may provide neural activity localization by simulating neural activity models and providing spatial & temporal characterization.

Figure 45:
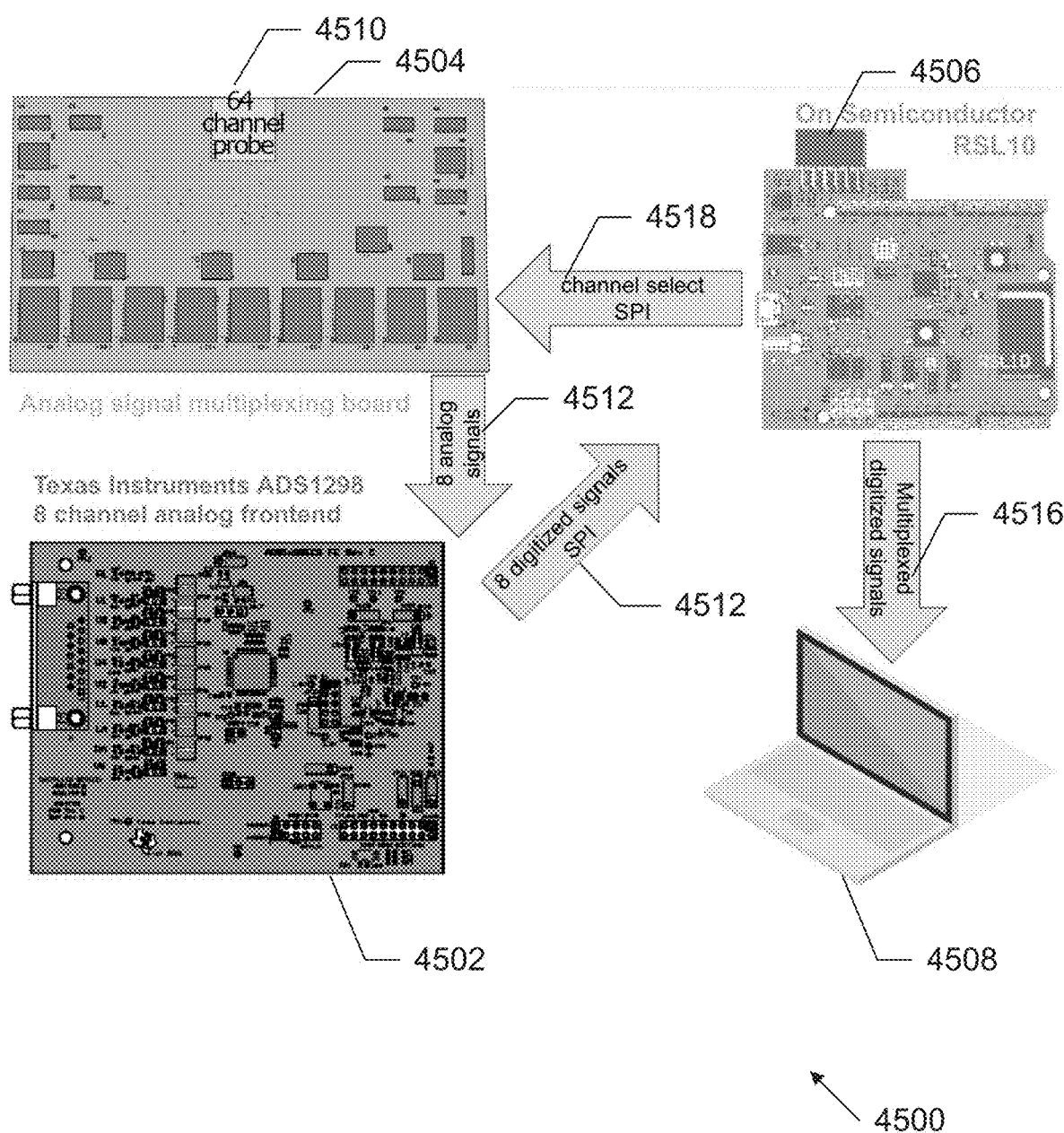
FIG. 45 is an exemplary block diagram of an embodiment of a neural monitoring and stimulation system.

An exemplary embodiment of a neural monitoring and stimulation system 4500 is shown in FIG. 45. In this example, system 4500 may include an analog front end 4502, analog signal multiplexer 4504, controller/communications 4506, and computer system 4508. For example, analog front end 4502 may be implemented as a Texas Instruments ADS1298 8-channel analog front end board. The Texas Instruments ADS1298 is one of a family of multichannel, simultaneous sampling, 24-bit, delta-sigma ($\Delta\Sigma$) analog-to-digital converters (ADCs) with built-in programmable gain amplifiers (PGAs), internal reference, and an onboard oscillator. The boards incorporate features that are commonly required in medical electrocardiogram (ECG) and electroencephalogram (EEG) applications.

For example, analog signal multiplexer 4504 may be interface with 64 channels of probe signals 4510, whether provided by one probe or multiple probes. Analog signal multiplexer 4504 may multiplex the 64 channels of probe signals 4510 to form, for example, eight multiplexed analog signals 4512 that are input to analog front end 4502. Analog front end 4502 may process and digitize the analog signals to form, for example, eight digitized signals 4514, which may be proved to controller/communications 4506, using, for example, the Simple Peripheral Interface (SPI). Controller/communications 4506 may generate and provide channel select signals 4518 to analog signal multiplexer 4504, using, for example, SPI.

Controller/communications 4506 may process and multiplex the digitized signals and communicate the signals 4516 with computer system 4508. Computer system 4508 may be any type of computing device or computer system, including, but not limited to, a smartphone, a personal computer, a workstation, a server, cloud computing, etc.

Functions provided by system 4500 may include power estimates, spike detection algorithms, low-level drivers, etc.

Figure 46:
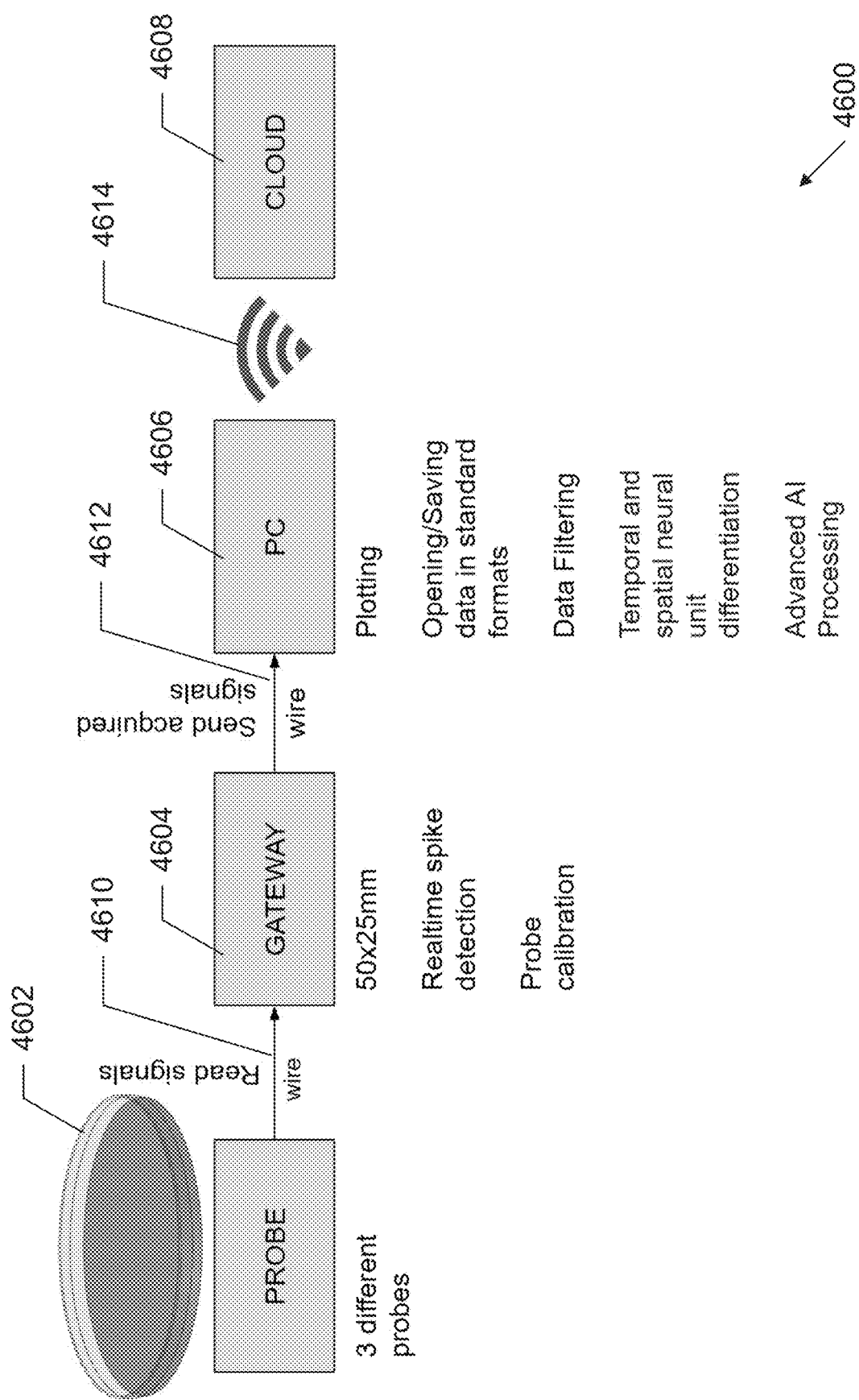
FIG. 46 is an exemplary block diagram of an embodiment of a neural monitoring and stimulation system.

An exemplary embodiment of a neural monitoring and stimulation system 4600 is shown in FIG. 46. The system shown in this example may be used for, for example, in-vitro development and testing. In this example, system 4600 may include one or more probes 4602, gateway 4604, computer system 4606, and cloud 4608. For example, probes 4602 may include one or more different types of probes, as described below. Read signals 4610 may be transmitted from probes 4602 to gateway 4604 over, for example, one or more wires. In embodiments, gateway 4604 may acquire, digitize, and process read signals 4610 and send the acquired signals 4612 to computer system 4606. In embodiments, gateway 4604 may provide realtime spike signal detection and probe calibration.

In embodiments, computer system 4606 may receive acquired signals 4612 and may perform processing on acquired signals 4612, including, for example, plotting the signal data, saving and retrieving the signal data in, for example, standard formats, filtering the signal data, processing the signal data using temporal and spatial neural unit differentiation, and processing the signal data using advanced AI processing. Computer system 4606 may communicate any or all of the acquired, processed, and stored data with cloud 4608, over any communication networks, for example, wirelessly and over the Internet. Cloud 4608 may provide advanced processing of the signal data, as well as aggregate processing of data from a plurality of installed systems including probes 4601, gateways 4604, and computer systems 4606.

In embodiments, gateway 4604 may be a mobile gateway, for example, ranging in size from the size of a nickel (size limited by the battery) to 50×25 mm. In embodiments, gateway 4604 may be based on commonly used frontend analog interfaces and may be implemented as an SoC that includes an ARM Cortex M3 processor, Bluetooth 5 Low Energy communication, for Wireless PC communication, and a DSP core for spike detection acceleration. Embodiments may provide functions such as 32 channel read capability, support for a number of types of commercially available probes, wireless data transfer, several days battery stand-by before recharging, and 8 hours in record mode wired charging for gateway 4604 using a miniature power connector, etc.

In embodiments, computer system 4606 and cloud 4608 may support popular analytics platforms, may perform AI based signal analysis, AI analytics software trained on ICM datasets, and may provide models of disease diagnostics.

An exemplary embodiment of a neural monitoring and stimulation system 4700 is shown in FIG. 47. The system shown in this example may be used for, for example, in-vivo small animal testing. In this example, system 4700 may include one or more probes 4702, gateway 4704, computer system 4706, and cloud 4708. For example, probes 4702 may include one or more different types of probes, as described below. Read and stimulation signals 4710 may be communicated between probes 4702 and gateway 4704 over, for example, one or more wires. In embodiments, gateway 4704 may acquire, digitize, and process read signals 4710 and send the acquired signals 4712 to computer system 4706, as well as receive stimulation signal commands from computer system 4706, generate stimulation signals based on the commands, and transmit the stimulation signals to probes 4702. In embodiments, gateway 4704 may provide realtime spike signal detection, probe calibration, wireless communication 4712 with computer system 4706, data compression, and may be battery powered.

In embodiments, computer system 4706 may receive acquired signals 4712 and may perform processing on acquired signals 4712, including, for example, plotting the signal data, saving and retrieving the signal data in, for example, standard formats, filtering the signal data, processing the signal data using temporal and spatial neural unit differentiation, and processing the signal data using advanced AI processing. In embodiments, computer system 4706 may generate stimulation signal commands and transmit the commands to gateway 4704. Computer system 4706 may communicate any or all of the acquired, processed, and stored data with cloud 4708, over any communication networks, for example, wirelessly and over the Internet. Cloud 4708 may provide advanced processing of the signal data, as well as aggregate processing of data from a plurality of installed systems including probes 4701, gateways 4704, and computer systems 4706.

In embodiments, gateway 4704 may be a mobile gateway, for example, ranging in size from the size of a nickel (size limited by the battery) to 50×25 mm. In embodiments, gateway 4704 may be based on commonly used frontend analog interfaces and may be implemented as an SoC that includes an ARM Cortex M3 processor, Bluetooth 5 Low Energy communication, for Wireless PC communication, and a DSP core for spike detection acceleration. Embodiments may provide functions such as neural writing capabilities with AI controlled modulation, wireless and USB charging, reading & writing on 32/64 channels, additional hardware and software power optimization, and connectors and adapters based on ICM feedback.

In embodiments, computer system 4706 and cloud 4708 may support popular analytics platforms, may perform AI based signal analysis, AI analytics software trained on ICM datasets, AI analytics updates, and may provide models of disease diagnostics.

Figure 48:
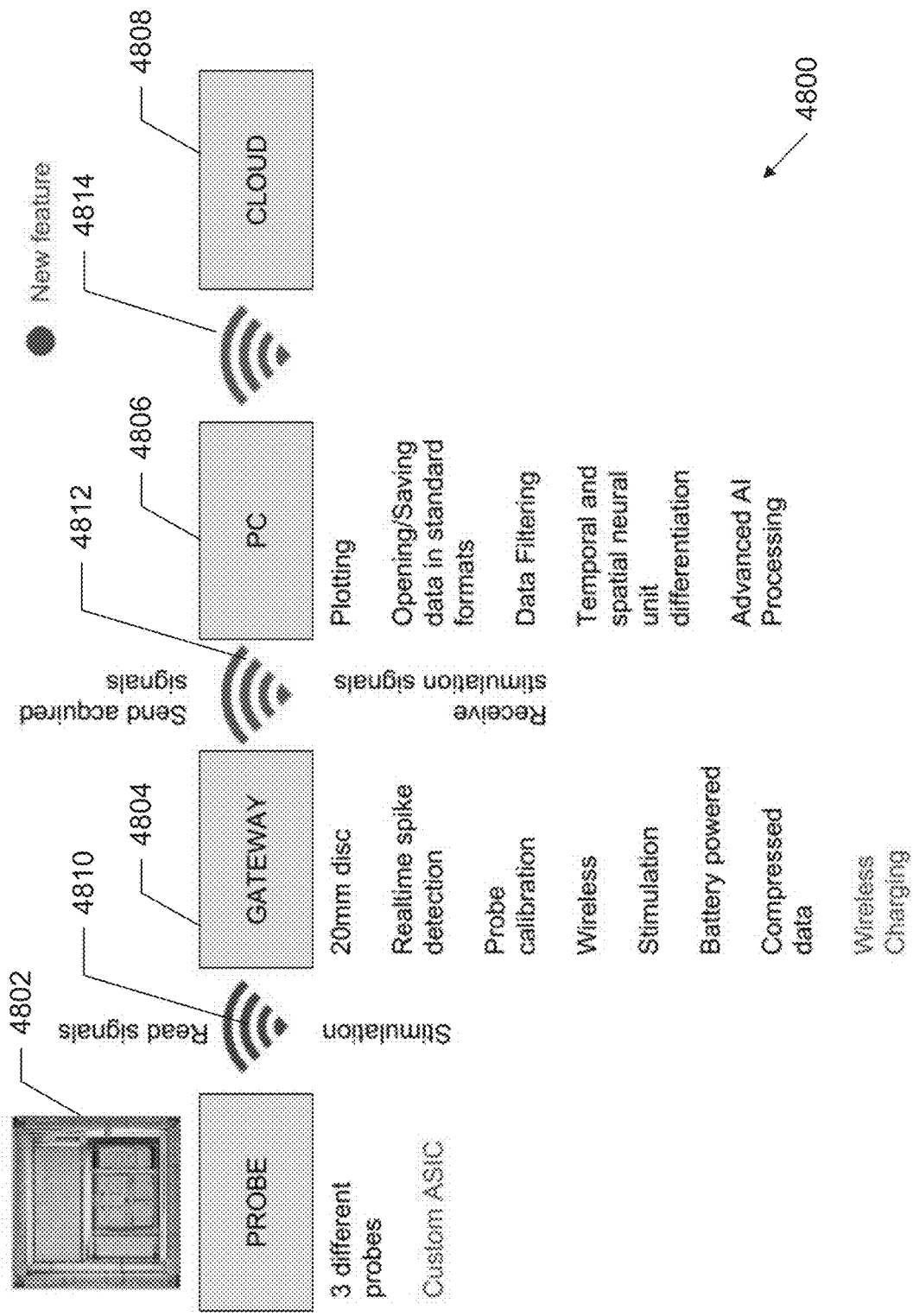
FIG. 48 is an exemplary block diagram of an embodiment of a neural monitoring and stimulation system.

An exemplary embodiment of a neural monitoring and stimulation system 4800 is shown in FIG. 48. The system shown in this example may be used for, for example, in-vivo large animal testing or in-vivo human testing and deployment. In this example, system 4800 may include one or more probes 4802, gateway 4804, computer system 4806, and cloud 4808. For example, probes 4802 may include one or more different types of probes, as described below. In embodiments, probes 4802 may be implemented as custom ASICs. Read and stimulation signals 4810 may be communicated between probes 4802 and gateway 4804 over, for example, one or more wires. In embodiments, gateway 4804 may acquire, digitize, and process read signals 4810 and send the acquired signals 4812 to computer system 4806, as well as receive stimulation signal commands from computer system 4806, generate stimulation signals based on the commands, and transmit the stimulation signals to probes 4802. In embodiments, gateway 4804 may provide realtime spike signal detection, probe calibration, wireless communication 4812 with computer system 4806, data compression, and may be battery powered with wireless charging.

In embodiments, computer system 4806 may receive acquired signals 4812 and may perform processing on acquired signals 4812, including, for example, plotting the signal data, saving and retrieving the signal data in, for example, standard formats, filtering the signal data, processing the signal data using temporal and spatial neural unit differentiation, and processing the signal data using advanced AI processing. In embodiments, computer system 4806 may generate stimulation signal commands and transmit the commands to gateway 4804. Computer system 4806 may communicate any or all of the acquired, processed, and stored data with cloud 4808, over any communication networks, for example, wirelessly and over the Internet. Cloud 4808 may provide advanced processing of the signal data, as well as aggregate processing of data from a plurality of installed systems including probes 4801, gateways 4804, and computer systems 4806.

In embodiments, gateway 4804 may be a mobile gateway, for example, ranging in size from the size of a nickel (size limited by the battery) to 50×25 mm. In embodiments, gateway 4804 may be based on commonly used frontend analog interfaces and may be implemented as an SoC that includes an ARM Cortex M3 processor, Bluetooth 5 Low Energy communication, for Wireless PC communication, and a DSP core for spike detection acceleration. Embodiments may provide functions such as neural writing capabilities with AI controlled modulation, wireless and USB charging, reading & writing on 32/64 channels, additional hardware and software power optimization, and connectors and adapters based on ICM feedback.

In embodiments, computer system 4806 and cloud 4808 may support popular analytics platforms, may perform AI based signal analysis, AI analytics software trained on ICM datasets, AI analytics updates, and may provide models of disease diagnostics.

Figure 49:
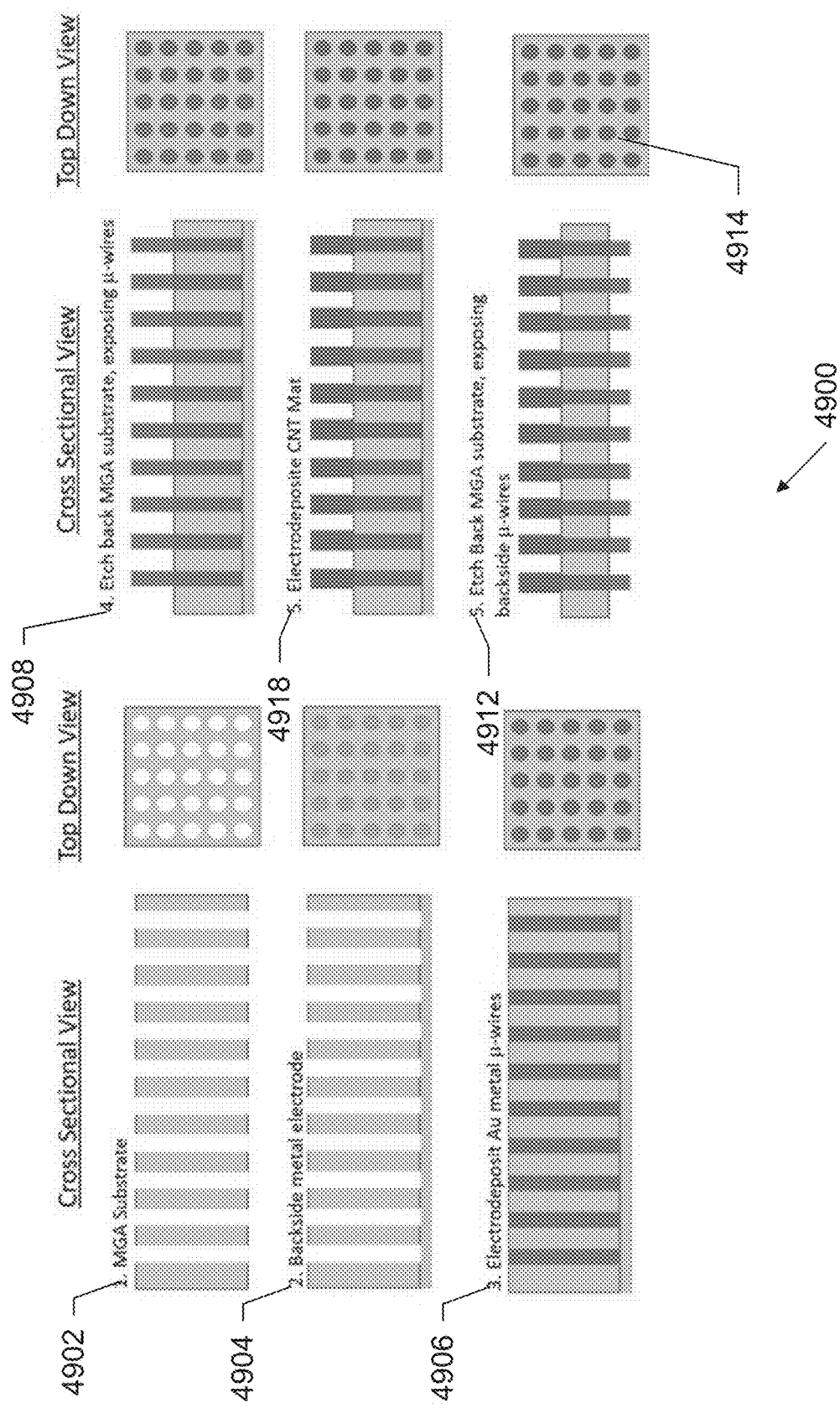
FIG. 49 is an exemplary process diagram of an embodiment of a process of fabrication of CNT implant devices.

An example of a process 4900, which is of a portion of a process of fabrication of CNT implant devices, such as a probe 4802, is shown in FIG. 49. In this example, a microelectrode array of carbon nanotube connections between electronic circuitry and in-vivo human neural tissue may be fabricated.

Probe 4702 may include SWCNTs and CNT Coated Optrodes. For example, a CNT array implant 4914 may include of a minimum of ten (10) CNT wires with fan out electrical leads using pre-existing NRL materials. In embodiments, a new technology may be used to form a microelectrode array of connections between electronic readouts and in-vivo human neural tissue using electroplating as a deposition technique to form a CNT-based microelectrode array through a 1-mm thick microchannel glass array (MGA) substrate. CNT array implant 4914 may include the CNT-based microelectrode on one side of the MGA and metal contacts on the backside of the MGA.

An example of a process 4900, which is of a portion of a process of fabrication of CNT implant devices, is shown in FIG. 49. In this example, a microelectrode array of connections between electronic readouts and in-vivo human neural tissue may be fabricated. Using electroplating as a deposition technique, a CNT-based microelectrode array may be formed through a 1-mm thick micro-channel glass array (MGA) substrate. In an embodiment, the electrode arrays may have CNT contacts on the front side, and metal contacts on the back. In an embodiment the electrode arrays may have metal contacts on both sides.

Process 4900 may begin with 4902, in which an MGA substrate may be formed. At 4904, metal electrodes may be formed on the backside of the MGA substrate. At 4906, gold micro wires may be electrodeposited on the metal electrodes in the micro channels of the MGA substrate. At 4908, the topside of the MGA substrate may be etched to expose the gold micro wires. At 4910, the CNT material may be electrodeposited onto the exposed gold micro wires. At 4912, the backside of the MGA substrate may be etched to expose the backside gold micro wires.

Figure 50:
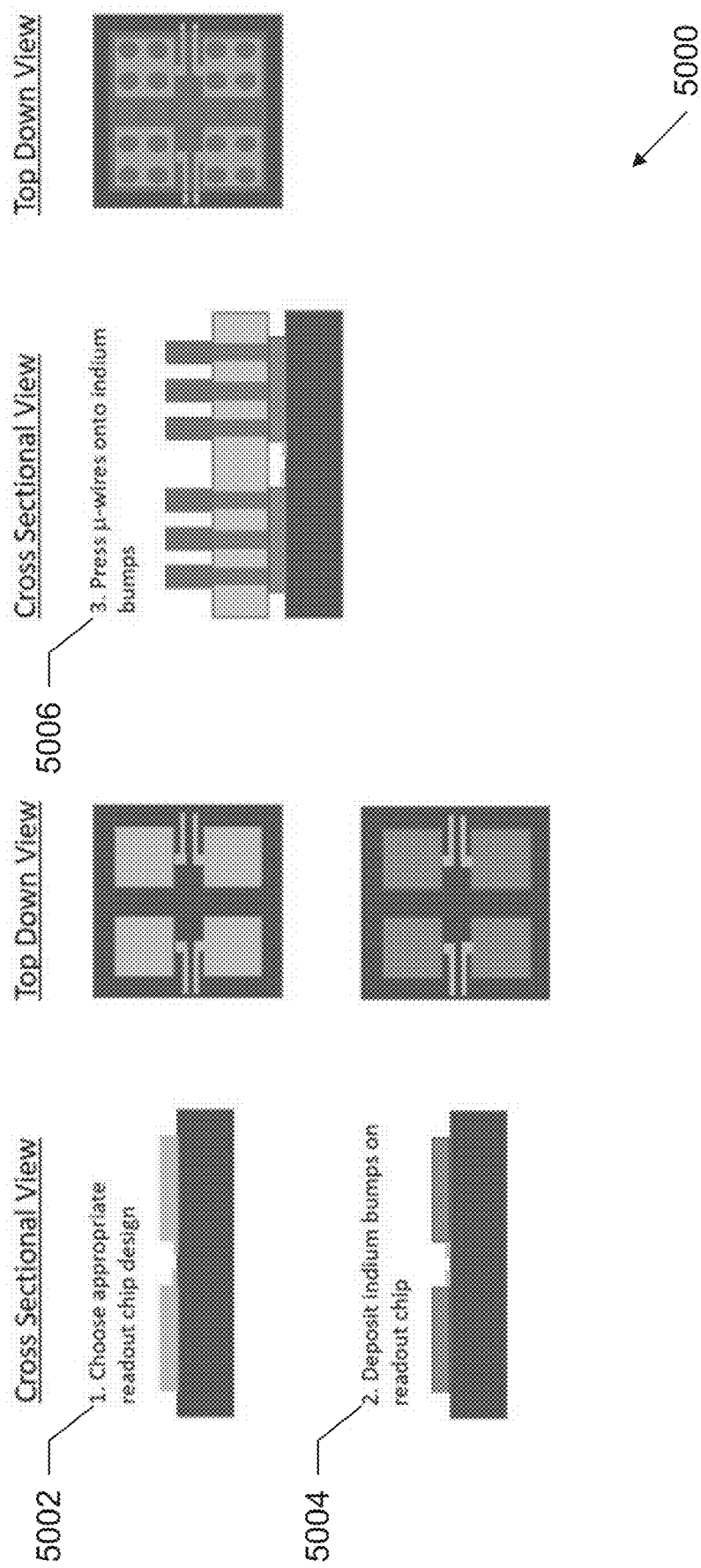
FIG. 50 is an exemplary process diagram of an embodiment of a process of fabrication of CNT implant devices.

An example of a process 5000, which is of a portion of a process of fabrication of CNT implant devices, is shown in FIG. 50. In this example, the MGA/CNT-based microelectrodes may be hybridized to an electrical readout chip providing for a parallel neural-electronic interface to the brain. A primary function of the device may be to stimulate and read localized neuron activity. Using already established hybridization techniques commonly found in focal plane arrays, the MGA/CNT-based microelectrodes may be hybridized to an electrical readout chip, thus, allowing for a massively parallel neural-electronic interface to the brain.

Process 5000 may begin with 5002, in which an appropriate readout chip design may be selected. At 5004, metal bumps, such as indium, may be deposited on the contacts of the readout chip. At 5006, the micro wires that were exposed on the backside at 4912 in FIG. 49 may be pressed onto the metal bumps, creating electrical contact with the readout chip.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A method for detection of neurodegenerative disease comprising:
   measuring functioning of the motor system, including measuring functioning of upper limb and shoulder movement, cognitive function, including measuring cognitive function during combined physical motion and speech, and brain activity of a subject during everyday life, wherein measuring functioning of the motor system comprises:
   placing a wearable body sensor system on the subject, the wearable body sensor system adapted to measure movements and object interaction of the subject in everyday living situations, the wearable body sensor system comprising an Integrated Clothing Sensing System, an Inertial Measurement Unit, an optical marker tracking system, acceleration sensors, and a Hydrocele Geodesic Sensor Net, and gathering movement data with the wearable body sensor system, wherein a measuring functioning of the cognitive function comprises:
   gathering cognitive function data comprising everyday speech data gathered using an audio capture device, and wherein measuring brain activity comprises:
   gathering brain activity data comprising neuronal signals obtained using an implantable probe comprising a microelectrode array of carbon nanotube connections between electronic circuitry and in-vivo human neural tissue;
   and determining, at a computer system comprising a processor, memory accessible by the processor, and computer program instructions stored in the memory and executable by the processor, the presence of an abnormal condition based on the gathered at least one motor system data, cognitive function data, and brain activity data of the subject, wherein analyzing the gathered motor system data comprises:
   analyzing the gathered movement data to differentiate between movement conditions using wavelet analysis, and generating information indicating movement conditions, wherein analyzing the gathered cognitive function data comprises:
   analyzing the gathered speech data for motor and non-motor correlations related to severity of the neurodegenerative disease data, including determining inability to control voice tone based on jitter of the speech data and determining lack of normal voice modulation based on shimmer of the speech data, and generating information indicating severity of the neurodegenerative disease and the measured motor and non-motor aspects;
   and wherein analyzing the gathered brain activity comprises:
   analyzing the gathered neural oscillation detection data related to severity of the neurodegenerative disease, including determining spindles in the neural oscillation detection data based on a frequency spectrum of the neural oscillation detection data, and generating information indicating severity of the neurodegenerative disease;
   and outputting, from the computer system, information indicating severity of the neurodegenerative disease based on the generated information.

2. A computer program product for detection of neurodegenerative disease, the computer program product comprising a non-transitory computer readable storage having program instructions embodied therewith, the program instructions executable by a computer, to cause the computer to perform a method comprising:
   receiving data measuring functioning of at least one of the motor system, cognitive function, and brain activity of a subject during everyday life, wherein measuring functioning of the motor system comprises:
   placing a wearable body sensor system on the subject, the wearable body sensor system adapted to measure movements and object interaction of the subject in everyday living situations, the wearable body sensor system comprising at least two sensor systems selected from a group comprising an Integrated Clothing Sensing System, an Inertial Measurement Unit, an optical marker tracking system, acceleration sensors, and a Hydrocele Geodesic Sensor Net, and gathering movement data with the wearable body sensor system, wherein measuring functioning of the cognitive function comprises:
   gathering cognitive function data comprising everyday speech data gathered using an audio capture device, and wherein measuring brain activity comprises:
   gathering brain activity data comprising neuronal signals obtained using an implantable probe comprising a microelectrode array of carbon nanotube connections between electronic circuitry and in-vivo human neural tissue;
   and determining the presence of an abnormal condition based on the gathered at least one motor system data, cognitive function data, and brain activity data of the subject, wherein analyzing the gathered motor system data comprises:
   analyzing the gathered movement data to differentiate between movement conditions using wavelet analysis, and generating information indicating movement conditions, wherein analyzing the gathered cognitive function data comprises:
   analyzing the gathered speech data for motor and non-motor correlations related to severity of the neurodegenerative disease data, including determining inability to control voice tone based on jitter of the speech data and determining lack of normal voice modulation based on shimmer of the speech data, and generating information indicating severity of the neurodegenerative disease and the measured motor and non-motor aspects, and wherein analyzing the gathered brain activity comprises:

analyzing the gathered neural oscillation detection data related to severity of the neurodegenerative disease, including determining spindles in the neural oscillation detection data based on a frequency spectrum of the neural oscillation detection data, and generating information indicating severity of the neurodegenerative disease;

and outputting information indicating severity of the neurodegenerative disease based on the generated information.

3. A system for detection of neurodegenerative disease, the system comprising:

at least one of a wearable body sensor system, apparatus for gathering everyday speech data, apparatus for neural oscillation detection, and an electro-encephalogram apparatus;

a processor;

memory accessible by the processor;

computer program instructions stored m the memory and executable by the processor to perform:

receiving data measuring functioning of at least one of the motor system, cognitive function, and brain activity of a subject during everyday life, wherein measuring functioning of the motor system comprises:

placing a wearable body sensor system on the subject, the wearable body sensor system adapted to measure movements and object interaction of the subject in everyday living situations, the wearable body sensor system comprising at least two sensor systems selected from a group comprising an Integrated Clothing Sensing System, an Inertial Measurement Unit, an optical marker tracking system, acceleration sensors, and a Hydrocele Geodesic Sensor Net, and gathering movement data with the wearable body sensor system, wherein measuring functioning of the cognitive function comprises:

gathering cognitive function data comprising everyday speech data gathered using an audio capture device, and wherein measuring brain activity comprises:

gathering brain activity data comprising neuronal signals obtained using an implantable probe comprising a microelectrode array of carbon nanotube connections between electronic circuitry and in-vivo human neural tissue;

and determining the presence of an abnormal condition based on the gathered at least one motor system data, cognitive function data, and brain activity data of the subject, wherein analyzing the gathered motor system data comprises:

analyzing the gathered movement data to differentiate between movement conditions using wavelet analysis, and generating information indicating movement conditions, wherein analyzing the gathered cognitive function data comprises:

analyzing the gathered speech data for motor and non-motor correlations related to severity of the neurodegenerative disease data, including determining inability to control voice tone based on jitter of the speech data and determining lack of normal voice modulation based on shimmer of the speech data, and generating information indicating severity of the neurodegenerative disease and the measured motor and non-motor aspects, and wherein analyzing the gathered brain activity comprises:

analyzing the gathered neural oscillation detection data related to severity of the neurodegenerative disease, including determining spindles in the neural oscillation detection data based on a frequency spectrum of the neural oscillation detection data, and generating information indicating severity of the neurodegenerative disease;

and outputting information indicating severity of the neurodegenerative disease based on the generated information.

\* \* \* \* \*